United States Patent
Keck et al.

(10) Patent No.: US 6,273,598 B1
(45) Date of Patent: *Aug. 14, 2001

(54) COMPUTER SYSTEM AND METHODS FOR PRODUCING MORPHOGEN ANALOGS OF HUMAN OP-1

(75) Inventors: Peter C. Keck, Millbury; Diana L. Griffith; William D. Carlson, both of Weston; David C. Rueger, Hopkinton; Kuber T. Sampath, Medway, all of MA (US)

(73) Assignee: Creative BioMolecules, Inc., Boston, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 08/786,284

(22) Filed: Jan. 22, 1997

Related U.S. Application Data

(63) Continuation-in-part of application No. 08/589,552, filed on Jan. 22, 1996, now abandoned.

(51) Int. Cl.[7] .............................. G06G 7/48; G01N 15/00; G01N 23/207; G06F 17/00
(52) U.S. Cl. ....................... 364/578; 364/496; 364/497; 364/499; 702/19; 702/22; 702/27; 378/73
(58) Field of Search .................................. 364/496–499, 364/578; 702/19, 22, 27; 378/73

(56) References Cited

U.S. PATENT DOCUMENTS

| | | | |
|---|---|---|---|
| 4,881,175 | 11/1989 | Ladner | 364/496 |
| 4,908,773 | 3/1990 | Pantoliano et al. | 364/496 |
| 5,061,786 | 10/1991 | Burnier et al. | 530/326 |
| 5,118,791 | 6/1992 | Burnier et al. | 530/326 |
| 5,322,933 | 6/1994 | Davies et al. | 530/399 |
| 5,331,573 | 7/1994 | Balaji et al. | 364/500 |
| 5,353,236 | 10/1994 | Subbiah | 364/499 |
| 5,453,937 | 9/1995 | Srinivasan et al. | 364/496 |
| 5,579,250 | 11/1996 | Balaji et al. | 364/496 |
| 5,581,476 | * 12/1996 | Osslund . | |

FOREIGN PATENT DOCUMENTS

| | | |
|---|---|---|
| 0 535 804 A1 | 4/1993 | (EP) . |
| 0 646 599 A2 | 4/1994 | (EP) . |
| WO 89/09788 | 10/1989 | (WO) . |
| WO92/01933 | 2/1992 | (WO) . |
| WO 92/07073 | 4/1992 | (WO) . |
| WO93/02209 | 2/1993 | (WO) . |
| WO92/04914 | 4/1994 | (WO) . |
| WO94/18236 | 8/1994 | (WO) . |
| WO95/01800 | 1/1995 | (WO) . |
| WO95/05394 | 2/1995 | (WO) . |
| WO95/07093 | 3/1995 | (WO) . |
| WO95/14791 | 6/1995 | (WO) . |

OTHER PUBLICATIONS http://www.pdb.bnl.gov Griffith et al., Bone Morphogenetic–7, Dec. 14, 1995.*

Hol (1986), "Protein Crystallography and Computer Graphics—Toward Rational Drug Design," *Angew. Chem. Int. Ed. Engagement.* 25 No. 9:767–778.

Martin (1991), "Computer–Assisted Rational Drug Design," *Meth. Enzymol.* 203:587–613.

Dixon (1992), "Computer–Aided Drug Design: Getting The Best Results," *TIBTECH* 10:357–363.

Bowen et al. (1993), "Computer–Assisted Molecular Modeling: Indispensible Tools For Molecular Pharmacology," *J. Clin. Pharmacol.* 33:1149–1164.

Tschinke et al. (1993), "The NEWLEAD Program: A New Method For The Design Of Candidate Structures From Pharmacophoric Hypotheses," *J. Med. Chem.* 36, No. 24:3863–3870.

Eisen et al. (1994), "HOOK: A Program For Finding Novel Molecular Architectures That Satisfy The Chemical And Steric Requirements Of A Macromolecule Binding Site," *Proteins: Structure, Function, and Genetics* 19:199–221.

Tomioka et al. (1994), "GREEN: A Program Package For Docking Studies In Rational Drug Design," *J. Computer–Aided Mol. Design* 8:347–366.

Waskowycz et al. (1994), "PRO LIGAND: An Approach To de Novo Molecular Design. 2. Design of Novel Molecules From Molecular Field Analysis (MFA) Models and Pharmacophores," *J. Med. Chem.* 37, No. 23:3994–4002.

(List continued on next page.)

Primary Examiner—Kenneth R. Horlick
Assistant Examiner—Jeffrey Siew
(74) Attorney, Agent, or Firm—Ivor R. Elrifi; Michel Morency; Mintz, Levin, Cohn, Ferris, Glovsky & Popeo, PC

(57) ABSTRACT

The invention disclosed herein provides methods and compositions for the computer-assisted design of morphogen analogs. Practice of the invention is enabled by the use of at least a portion of the atomic co-ordinates defining the three-dimensional structure of human osteogenic protein-1 (hOP-1) as a starting point in the design of the morphogen analogs. In addition, the invention provides methods for producing morphogen analogs of interest, and methods for testing whether the resulting analogs mimic or agonize human OP-1-like biological activity. The invention also provides a family of morphogen analogs produced by such methods.

21 Claims, 98 Drawing Sheets

OTHER PUBLICATIONS

Desjarlais et al. (1995), "De Novo Design Of The Hydrophobic Cores Of Proteins," *Protein Science* 4:2006–2018.

Struthers et al. (1996), "Design of a Monomeric 23–Residue Polypeptide With Defined Tertiary Structure," *Science* 271:342–344.

Bartlett et al. (1989) "CAVEAT: A Program To Facilitate The Structure–Derived Design of Biologically Active Molecules," *In Molecular Recognition: Chemical and Biological Problems (Roberts ed.)* 182–196.

Helder et al., "Expression Pattern of Osteogenic Protein–1 (Bone Morphogenetic Protein–7) in Human and Mouse Development," *J. Histochem. Cytochem.*, 43:1035–1044 (1995).

Schlunegger et al., "An unusual feature revealed by the crystal structure at 2.2Å resolution of human tranforming growth factor–$\beta 2$," *Nature*, 358:430–434 (1992).

Daopin et al., "Crystal Structure of Transforming Growth Factor–$\beta 2$: An Unusual Fold for the Superfamily," *Science*, 257:369–373 (1992).

Griffith et al., "Three–dimensional structure of recombinant human osteogenic proteins 1; structural paradigm for the transforming growth factor beta superfamily," *Proceedings of the National Academy of Sciences of USA*, 93(2); 878–883 (1996).

Griffith et al., "Crystallization and Preliminary Crystallographic Data of Recominant Human Osteogenic Protein–1 (hOP–1)," *J. Mol. Biol.*, 244:657–658 (1994).

Griffith et al., "Crystal Structure of Recombinant Human Osteogenic Protein–1 (BMP–7)," *J. of Bone and Mineral Research*, vol. 10, Supplement 1, Abstract T 394, Seventeenth Annual Meeting of the American Society for Bone and Mineral Research, Sep. 9–13, 1995, 1st International Conference On Bone Morphogenetic Proteins, Jun. 8–11, 1994, Baltimore, Maryland.

\* cited by examiner

```
                                                                                 FINGER 1
         40         50            60             70
         v          v             v              v
OP-1   CKKHELYVSFR-DLGWQDWIIAPEGYAAYYCEGEC
TGF-β2 CCLRPLYIDFKRDLGW-KWIHEPKGYNANFCAGAC
         ^          ^              ^
         20         30             40

HEEL
         80             90             100
         v              v              v
OP-1   AFPPLNSYMNATNHAIVQTLVNSVNSKIPKACCVPTELSAISMLYLDENEKVVLKNYQDMVVEGCGCR
TGF-β2 PYLWS--SDTQHSRVLSLYNTINPEASASPCC
         ^              ^
         50             60             70

FINGER 2
         110           120          130
         v             v            v                                             v
OP-1   A--PTQLNAISVLYFDDSSNVILKKYRNMVVRACGCH
TGF-β2 V--SQDLEPLTILYYIG-KTPKIEQLSNMIVKSCKCS
         ^             ^            ^                                             ^
         80            90           100                                           110
```

| RESIDUE | | MONOMER % AREA | DIMER % AREA | HIDDEN % AREA | EPITOPE RESIDUES | SURFACE MODIFIABLE | MODIFIABLE 0 IMPROVE SOLUBILITY |
|---|---|---|---|---|---|---|---|
| 36 | GLN | 71.89 | 71.89 | 0.00 | | | |
| 37 | ALA | 52.51 | 52.51 | 0.00 | | | |
| 39 | LYS | 62.19 | 62.19 | 0.00 | EPITOPE | | |
| 40 | LYS | 39.26 | 39.26 | 0.00 | EPITOPE | | |
| 41 | HIS | 27.13 | 27.13 | 0.00 | | * | |
| 42 | GLU | 79.09 | 79.09 | 0.00 | EPITOPE | | |
| 43 | LEU | 51.26 | 11.83 | -39.43 | | | |
| 44 | TYR | 50.51 | 50.51 | 0.00 | EPITOPE | | |
| 45 | VAL | 15.22 | 0.51 | -14.71 | | | |
| 46 | SER | 23.02 | 23.02 | 0.00 | | * | |
| 47 | PHE | 3.26 | 3.26 | 0.00 | | | |
| 48 | ARG | 76.89 | 76.89 | 0.00 | EPITOPE | | |
| 49 | ASP | 68.71 | 52.15 | -16.56 | EPITOPE | | |
| 50 | LEU | 37.77 | 0.00 | -37.77 | | | |
| 51 | GLY | 0.00 | 0.00 | 0.00 | | | |
| 52 | TRP | 40.99 | 34.53 | -6.46 | | * | * |
| 53 | GLN | 54.47 | 54.47 | 0.00 | EPITOPE | | |
| 54 | ASP | 54.22 | 54.22 | 0.00 | EPITOPE | | |
| 55 | TRP | 62.99 | 62.99 | 0.00 | EPITOPE | | |
| 56 | ILE | 9.68 | 9.68 | 0.00 | | | |
| 57 | ILE | 33.58 | 33.58 | 0.00 | EPITOPE | | |
| 58 | ALA | 0.00 | 0.00 | 0.00 | | | |
| 59 | PRO | 34.01 | 34.01 | 0.00 | EPITOPE | | |
| 60 | GLU | 60.90 | 60.90 | 0.00 | EPITOPE | | |
| 61 | GLY | 0.00 | 0.00 | 0.00 | | | |
| 62 | TYR | 8.93 | 2.09 | -6.84 | | | |
| 63 | ALA | 39.31 | 39.31 | 0.00 | | * | * |

Fig. 8.1

| RESIDUE | | MONOMER % AREA | DIMER % AREA | HIDDEN % AREA | EPITOPE RESIDUES | SURFACE MODIFIABLE | MODIFIABLE 0 IMPROVE SOLUBILITY |
|---|---|---|---|---|---|---|---|
| 64 | ALA | 14.78 | 0.00 | -14.78 | | | |
| 65 | TYR | 26.22 | 26.22 | 0.00 | | * | * |
| 66 | TYR | 48.32 | 15.41 | -32.91 | | | |
| 67 | CYS | 1.67 | 1.67 | 0.00 | | | |
| 68 | GLU | 59.70 | 43.27 | -16.43 | EPITOPE | | |
| 69 | GLY | 0.00 | 0.00 | 0.00 | | | |
| 70 | GLU | 35.82 | 35.82 | 0.00 | EPITOPE | | |
| 71 | CYS | 0.00 | 0.00 | 0.00 | | | |
| 72 | ALA | 43.27 | 43.27 | 0.00 | | * | * |
| 73 | PHE | 39.54 | 39.54 | 0.00 | EPITOPE | | |
| 74 | PRO | 96.68 | 96.68 | 0.00 | EPITOPE | | |
| 75 | LEU | 1.72 | 1.72 | 0.00 | | | |
| 76 | ASN | 60.54 | 60.54 | 0.00 | EPITOPE | | |
| 77 | SER | 73.24 | 73.24 | 0.00 | EPITOPE | | |
| 78 | TYR | 104.34 | 104.34 | 0.00 | EPITOPE | | |
| 79 | MET | 12.40 | 12.40 | 0.00 | | | |
| 80 | ASN | 46.31 | 46.31 | 0.00 | | * | |
| 81 | ALA | 32.45 | 32.45 | 0.00 | | * | * |
| 82 | THR | 34.63 | 5.99 | -28.64 | | | |
| 83 | ASN | 84.54 | 38.00 | -46.54 | | | |
| 84 | HIS | 71.01 | 0.26 | -70.75 | | | |
| 85 | ALA | 0.00 | 0.00 | 0.00 | | | |
| 86 | ILE | 46.99 | 46.93 | -0.06 | | * | * |
| 87 | VAL | 64.29 | 1.95 | -62.34 | | | |
| 88 | GLN | 18.05 | 4.31 | -13.74 | | | |
| 89 | THR | 4.29 | 4.29 | 0.00 | | | |
| 90 | LEU | 50.95 | 29.43 | -21.52 | | | |
| 91 | VAL | 39.39 | 8.51 | -30.88 | | | |
| 92 | HIS | 26.42 | 26.42 | 0.00 | | * | |

Fig. 8.2

| RESIDUE | | MONOMER % AREA | DIMER % AREA | HIDDEN % AREA | EPITOPE RESIDUES | SURFACE MODIFIABLE | MODIFIABLE 0 IMPROVE SOLUBILITY |
|---|---|---|---|---|---|---|---|
| 93 | PHE | 73.77 | 73.77 | 0.00 | EPITOPE | | |
| 94 | ILE | 57.23 | 32.03 | -25.20 | EPITOPE | | |
| 95 | ASN | 43.23 | 43.23 | 0.00 | EPITOPE | | |
| 96 | PRO | 66.64 | 66.64 | 0.00 | EPITOPE | | |
| 97 | GLU | 88.25 | 88.25 | 0.00 | EPITOPE | | |
| 98 | THR | 52.59 | 48.71 | -3.88 | EPITOPE | | |
| 99 | VAL | 25.83 | 0.00 | -25.83 | | | |
| 100 | PRO | 89.22 | 30.78 | -58.44 | | | |
| 101 | LYS | 35.15 | 35.15 | 0.00 | | * | |
| 102 | PRO | 0.00 | 0.00 | 0.00 | | | |
| 103 | CYS | 79.14 | 27.13 | -52.01 | | | |
| 104 | CYS | 5.39 | 5.39 | 0.00 | | | |
| 105 | ALA | 44.46 | 5.15 | -39.31 | | | |
| 106 | PRO | 11.24 | 2.30 | -8.94 | | | |
| 107 | THR | 21.76 | 21.76 | 0.00 | | * | |
| 108 | GLN | 53.40 | 53.40 | 0.00 | EPITOPE | | |
| 109 | LEU | 29.98 | 87.79 | -22.19 | | | |
| 110 | ASN | 35.00 | 35.00 | 0.00 | | * | |
| 111 | ALA | 23.61 | 23.61 | 0.00 | | * | * |
| 112 | ILE | 22.72 | 22.72 | 0.00 | | * | * |
| 113 | SER | 38.55 | 38.55 | 0.00 | | * | |
| 114 | VAL | 1.15 | 1.15 | 0.00 | | | |
| 115 | LEU | 36.05 | 36.05 | 0.00 | EPITOPE | | |
| 116 | TYR | 18.62 | 18.62 | 0.00 | | | |
| 117 | PHE | 46.55 | 46.55 | 0.00 | EPITOPE | | |
| 118 | ASP | 32.53 | 32.53 | 0.00 | EPITOPE | | |
| 119 | ASP | 84.02 | 84.02 | 0.00 | EPITOPE | | |
| 120 | SER | 48.35 | 48.35 | 0.00 | EPITOPE | | |
| 121 | SER | 68.39 | 68.39 | 0.00 | EPITOPE | | |

Fig. 8.3

| RESIDUE | | MONOMER % AREA | DIMER % AREA | HIDDEN % AREA | EPITOPE RESIDUES | SURFACE MODIFIABLE | MODIFIABLE 0 IMPROVE SOLUBILITY |
|---|---|---|---|---|---|---|---|
| 122 | ASN | 63.15 | 63.15 | 0.00 | EPITOPE | | |
| 123 | VAL | 41.27 | 41.27 | 0.00 | EPITOPE | | |
| 124 | ILE | 34.51 | 34.51 | 0.00 | EPITOPE | | |
| 125 | LEU | 63.34 | 63.34 | 0.00 | EPITOPE | | |
| 126 | LYS | 54.81 | 54.81 | 0.00 | EPITOPE | | |
| 127 | LYS | 48.78 | 48.78 | 0.00 | EPITOPE | | |
| 128 | TYR | 34.23 | 32.55 | -1.68 | | * | * |
| 129 | ARG | 63.25 | 62.85 | -0.40 | EPITOPE | | |
| 130 | ASN | 62.31 | 40.62 | -21.69 | | | |
| 131 | MET | 32.35 | 7.44 | -24.91 | | | |
| 132 | VAL | 16.38 | 16.38 | 0.00 | | | |
| 133 | VAL | 7.50 | 0.07 | -7.43 | | | |
| 134 | ARG | 65.10 | 65.10 | 0.00 | | | |
| 135 | ALA | 47.10 | 47.10 | 0.00 | | * | * |
| 136 | CYS | 0.29 | 0.29 | 0.00 | | | |
| 137 | GLY | 0.00 | 0.00 | 0.00 | | | |
| 138 | CYS | 0.00 | 0.00 | 0.00 | | | |
| 139 | HIS | 47.68 | 18.94 | -28.74 | | | |

Fig. 8.4

| RIDGE RESIDUES | | RECEPTOR SITES | |
|---|---|---|---|
| B90 | Leu | Heel | |
| B91 | Val | Heel | |
| B92 | His | Heel | |
| B93 | Phe | Heel | * |
| B94 | Ile | Heel | |
| B95 | Asn | Heel | * |
| B96 | Pro | Heel | * |
| B97 | Glu | Heel | * |
| B98 | Thr | Heel | * |
| A48 | Arg | Finger 1 | * |
| A49 | Asp | Finger 1 | |
| A50 | Leu | Finger 1 | |
| A51 | Gly | Finger 1 | |
| A52 | Trp | Finger 1 | |
| A53 | Gln | Finger 1 | * |
| A54 | Asp | Finger 1 | |
| A55 | Trp | Finger 1 | |
| A56 | Ile | Finger 1 | |
| A57 | Ile | Finger 1 | |
| A58 | Ala | Finger 1 | |
| A59 | Pro | Finger 1 | |
| A60 | Glu | Finger 1 | * |
| A116 | Tyr | Finger 2 | |
| A117 | Phe | Finger 2 | * |
| A118 | Asp | Finger 2 | |
| A119 | Asp | Finger 2 | * |
| A120 | Ser | Finger 2 | * |
| A121 | Ser | Finger 2 | * |
| A122 | Asn | Finger 2 | * |
| A123 | Val | Finger 2 | |
| A124 | Ile | Finger 2 | |
| A125 | Leu | Finger 2 | |
| A126 | Lys | Finger 2 | |
| A127 | Lys | Finger 2 | * |
| A128 | Tyr | Finger 2 | |
| A129 | Arg | Finger 2 | * |

Fig. 9

| RESIDUE IN 1st CHAIN | RESIDUE IN 2nd CHAIN | DISTANCE (A) |
|---|---|---|
| Ala-105 | Ala-105 | 3.61 |
| Cys-103 | Cys-103 | 3.95 |
| Asn-83 | Asn-130 | 4.01 |
| Thr-82 | Asn-130 | 4.20 |

Fig. 11A

| RESIDUE IN FINGER 1 | RESIDUE IN FINGER 2 | DISTANCE (A) |
|---|---|---|
| Ala-58 | Val-114 | 3.30 |
| Tyr-65 | Val-133 | 3.93 |
| Ala-58 | Leu-115 | 3.98 |
| Ile-57 | Leu-115 | 4.62 |
| Ile-56 | Tyr-116 | 4.54 |
| Trp-55 | Tyr-116 | 4.74 |

Fig. 11B

| ATOM | | RESIDUE | | CHAIN | X | Y | Z |
|---|---|---|---|---|---|---|---|
| 1 | N | GLN | 36 | A | 3.543 | -13.365 | 11.899 |
| 2 | CA | GLN | 36 | A | 2.246 | -13.227 | 11.283 |
| 3 | C | GLN | 36 | A | 2.601 | -12.220 | 10.237 |
| 4 | O | GLN | 36 | A | 2.736 | -11.030 | 10.439 |
| 5 | CB | GLN | 36 | A | 1.233 | -12.644 | 12.291 |
| 6 | CG | GLN | 36 | A | 1.403 | -11.130 | 12.646 |
| 7 | CD | GLN | 36 | A | 2.684 | -10.667 | 13.351 |
| 8 | OE1 | GLN | 36 | A | 3.651 | -11.405 | 13.452 |
| 9 | NE2 | GLN | 36 | A | 2.743 | -9.471 | 13.880 |
| 10 | N | ALA | 37 | A | 2.753 | -12.854 | 9.097 |
| 11 | CA | ALA | 37 | A | 3.663 | -12.466 | 8.044 |
| 12 | C | ALA | 37 | A | 2.836 | -11.639 | 7.174 |
| 13 | O | ALA | 37 | A | 1.660 | -11.899 | 7.227 |
| 14 | CB | ALA | 37 | A | 4.126 | -13.708 | 7.294 |
| 15 | N | CYS | 38 | A | 3.205 | -10.694 | 6.369 |
| 16 | CA | CYS | 38 | A | 2.177 | -9.971 | 5.682 |
| 17 | C | CYS | 38 | A | 1.538 | -10.860 | 4.675 |
| 18 | O | CYS | 38 | A | 2.249 | -11.266 | 3.753 |
| 19 | CB | CYS | 38 | A | 2.821 | -8.791 | 5.057 |
| 20 | SG | CYS | 38 | A | 1.945 | -8.415 | 3.597 |
| 21 | N | LYS | 39 | A | 0.235 | -11.141 | 4.862 |
| 22 | CA | LYS | 39 | A | -0.586 | -11.883 | 3.903 |
| 23 | C | LYS | 39 | A | -1.990 | -11.277 | 3.660 |
| 24 | O | LYS | 39 | A | -2.443 | -10.382 | 4.358 |
| 25 | CB | LYS | 39 | A | -0.753 | -13.348 | 4.365 |
| 26 | CG | LYS | 39 | A | -0.858 | -13.470 | 5.883 |
| 27 | CD | LYS | 39 | A | -1.201 | -14.824 | 6.505 |
| 28 | CE | LYS | 39 | A | -0.991 | -14.585 | 8.025 |
| 29 | NZ | LYS | 39 | A | -1.199 | -15.799 | 8.829 |
| 30 | N | LYS | 40 | A | -2.728 | -11.748 | 2.658 |
| 31 | CA | LYS | 40 | A | -4.076 | -11.299 | 2.397 |
| 32 | C | LYS | 40 | A | -4.987 | -11.916 | 3.394 |
| 33 | O | LYS | 40 | A | -4.652 | -12.991 | 3.851 |
| 34 | CB | LYS | 40 | A | -4.574 | -11.743 | 1.058 |
| 35 | CG | LYS | 40 | A | -5.826 | -11.024 | 0.591 |
| 36 | CD | LYS | 40 | A | -6.625 | -11.965 | -0.285 |
| 37 | CE | LYS | 40 | A | -5.763 | -12.585 | -1.352 |
| 38 | NZ | LYS | 40 | A | -6.552 | -13.536 | -2.104 |
| 39 | N | HIS | 41 | A | -6.124 | -11.330 | 3.782 |
| 40 | CA | HIS | 41 | A | -7.047 | -11.957 | 4.717 |
| 41 | C | HIS | 41 | A | -8.465 | -11.660 | 4.308 |
| 42 | O | HIS | 41 | A | -8.676 | -10.901 | 3.384 |
| 43 | CB | HIS | 41 | A | -6.945 | -11.406 | 6.101 |
| 44 | CG | HIS | 41 | A | -5.626 | -11.606 | 6.758 |
| 45 | ND1 | HIS | 41 | A | -5.353 | -12.221 | 7.907 |

Fig. 15.1

| ATOM | | RESIDUE | CHAIN | X | Y | Z |
|---|---|---|---|---|---|---|
| 46 | CD2 | HIS 41 | A | -4.544 | -10.869 | 6.408 |
| 47 | CE1 | HIS 41 | A | -4.173 | -11.833 | 8.293 |
| 48 | NE2 | HIS 41 | A | -3.705 | -11.017 | 7.380 |
| 49 | N | GLU 42 | A | -9.516 | -12.183 | 4.920 |
| 50 | CA | GLU 42 | A | -10.858 | -12.077 | 4.368 |
| 51 | C | GLU 42 | A | -11.642 | -10.923 | 4.856 |
| 52 | O | GLU 42 | A | -11.379 | -10.417 | 5.925 |
| 53 | CB | GLU 42 | A | -11.639 | -13.320 | 4.667 |
| 54 | CG | GLU 42 | A | -11.132 | -14.387 | 3.691 |
| 55 | CD | GLU 42 | A | -12.251 | -15.373 | 3.342 |
| 56 | OE1 | GLU 42 | A | -11.923 | -16.555 | 3.062 |
| 57 | OE2 | GLU 42 | A | -13.443 | -14.955 | 3.347 |
| 58 | N | LEU 43 | A | -12.631 | -10.414 | 4.163 |
| 59 | CA | LEU 43 | A | -13.426 | -9.333 | 4.751 |
| 60 | C | LEU 43 | A | -14.554 | -9.413 | 3.765 |
| 61 | O | LEU 43 | A | -14.352 | -9.107 | 2.600 |
| 62 | CB | LEU 43 | A | -12.846 | -7.946 | 4.589 |
| 63 | CG | LEU 43 | A | -12.886 | -6.923 | 5.690 |
| 64 | CD1 | LEU 43 | A | -13.082 | -5.561 | 5.031 |
| 65 | CD2 | LEU 43 | A | -13.968 | -7.216 | 6.695 |
| 66 | N | TYR 44 | A | -15.723 | -9.818 | 4.196 |
| 67 | CA | TYR 44 | A | -16.879 | -9.800 | 3.365 |
| 68 | C | TYR 44 | A | -17.493 | -8.484 | 3.638 |
| 69 | O | TYR 44 | A | -17.838 | -8.320 | 4.790 |
| 70 | CB | TYR 44 | A | -17.749 | -10.903 | 3.800 |
| 71 | CG | TYR 44 | A | -18.836 | -11.049 | 2.820 |
| 72 | CD1 | TYR 44 | A | -20.055 | -10.566 | 3.189 |
| 73 | CD2 | TYR 44 | A | -18.610 | -11.580 | 1.592 |
| 74 | CE1 | TYR 44 | A | -21.079 | -10.473 | 2.308 |
| 75 | CE2 | TYR 44 | A | -19.633 | -11.489 | 0.699 |
| 76 | CZ | TYR 44 | A | -20.825 | -10.877 | 1.042 |
| 77 | OH | TYR 44 | A | -21.774 | -10.553 | 0.068 |
| 78 | N | VAL 45 | A | -17.673 | -7.514 | 2.740 |
| 79 | CA | VAL 45 | A | -18.427 | -6.338 | 3.122 |
| 80 | C | VAL 45 | A | -19.847 | -6.545 | 2.610 |
| 81 | O | VAL 45 | A | -20.040 | -6.909 | 1.461 |
| 82 | CB | VAL 45 | A | -17.796 | -5.139 | 2.507 |
| 83 | CG1 | VAL 45 | A | -18.457 | -3.857 | 2.960 |
| 84 | CG2 | VAL 45 | A | -16.348 | -5.147 | 2.939 |
| 85 | N | SER 46 | A | -20.877 | -6.334 | 3.431 |
| 86 | CA | SER 46 | A | -22.255 | -6.548 | 3.059 |
| 87 | C | SER 46 | A | -22.799 | -5.210 | 2.818 |
| 88 | O | SER 46 | A | -22.704 | -4.398 | 3.707 |
| 89 | CB | SER 46 | A | -23.054 | -7.160 | 4.179 |
| 90 | OG | SER 46 | A | -24.417 | -7.335 | 3.799 |

Fig. 15.2

| ATOM | | RESIDUE | | CHAIN | X | Y | Z |
|---|---|---|---|---|---|---|---|
| 91 | N | PHE | 47 | A | -23.389 | -4.851 | 1.705 |
| 92 | CA | PHE | 47 | A | -23.751 | -3.481 | 1.472 |
| 93 | C | PHE | 47 | A | -24.740 | -2.959 | 2.450 |
| 94 | O | PHE | 47 | A | -24.979 | -1.770 | 2.498 |
| 95 | CB | PHE | 47 | A | -24.352 | -3.321 | 0.142 |
| 96 | CG | PHE | 47 | A | -23.337 | -3.619 | -0.910 |
| 97 | CD1 | PHE | 47 | A | -22.233 | -2.845 | -1.022 |
| 98 | CD2 | PHE | 47 | A | -23.634 | -4.545 | -1.868 |
| 99 | CE1 | PHE | 47 | A | -21.486 | -2.920 | -2.152 |
| 100 | CE2 | PHE | 47 | A | -22.889 | -4.598 | -3.018 |
| 101 | CZ | PHE | 47 | A | -21.825 | -3.765 | -3.173 |
| 102 | N | ARG | 48 | A | -25.371 | -3.781 | 3.275 |
| 103 | CA | ARG | 48 | A | -26.102 | -3.279 | 4.414 |
| 104 | C | ARG | 48 | A | -25.162 | -2.527 | 5.278 |
| 105 | O | ARG | 48 | A | -25.411 | -1.399 | 5.572 |
| 106 | CB | ARG | 48 | A | -26.719 | -4.406 | 5.231 |
| 107 | CG | ARG | 48 | A | -27.809 | -5.147 | 4.442 |
| 108 | CD | ARG | 48 | A | -28.661 | -6.042 | 5.341 |
| 109 | NE | ARG | 48 | A | -29.918 | -6.386 | 4.698 |
| 110 | CZ | ARG | 48 | A | -30.415 | -7.627 | 4.795 |
| 111 | NH1 | ARG | 48 | A | -29.715 | -8.597 | 5.456 |
| 112 | NH2 | ARG | 48 | A | -31.623 | -7.961 | 4.241 |
| 113 | N | ASP | 49 | A | -24.037 | -3.036 | 5.731 |
| 114 | CA | ASP | 49 | A | -23.280 | -2.378 | 6.778 |
| 115 | C | ASP | 49 | A | -22.753 | -1.006 | 6.372 |
| 116 | O | ASP | 49 | A | -22.313 | -0.188 | 7.168 |
| 117 | CB | ASP | 49 | A | -22.095 | -3.224 | 7.190 |
| 118 | CG | ASP | 49 | A | -22.486 | -4.646 | 7.506 |
| 119 | OD1 | ASP | 49 | A | -21.605 | -5.482 | 7.303 |
| 120 | OD2 | ASP | 49 | A | -23.619 | -4.962 | 7.924 |
| 121 | N | LEU | 50 | A | -22.770 | -0.677 | 5.092 |
| 122 | CA | LEU | 50 | A | -22.319 | 0.638 | 4.686 |
| 123 | C | LEU | 50 | A | -23.510 | 1.477 | 4.402 |
| 124 | O | LEU | 50 | A | -23.448 | 2.588 | 3.870 |
| 125 | CB | LEU | 50 | A | -21.468 | 0.539 | 3.582 |
| 127 | CD1 | LEU | 50 | A | -20.061 | -1.030 | 2.227 |
| 128 | CD2 | LEU | 50 | A | -19.052 | 0.319 | 4.121 |
| 129 | N | GLY | 51 | A | -24.651 | 0.915 | 4.749 |
| 130 | CA | GLY | 51 | A | -25.907 | 1.551 | 4.454 |
| 131 | C | GLY | 51 | A | -26.245 | 1.497 | 2.985 |
| 132 | O | GLY | 51 | A | -27.355 | 1.857 | 2.609 |
| 133 | N | TRP | 52 | A | -25.389 | 1.072 | 2.054 |
| 134 | CA | TRP | 52 | A | -25.828 | 1.011 | 0.660 |
| 135 | C | TRP | 52 | A | -27.045 | 0.114 | 0.381 |

Fig. 15.3

| ATOM | | RESIDUE | | CHAIN | X | Y | Z |
|---|---|---|---|---|---|---|---|
| 136 | O | TRP | 52 | A | -27.129 | -0.483 | -0.668 |
| 137 | CB | TRP | 52 | A | -24.614 | 0.556 | -0.189 |
| 138 | CG | TRP | 52 | A | -23.484 | 1.602 | -0.152 |
| 139 | CD1 | TRP | 52 | A | -23.615 | 2.896 | 0.315 |
| 140 | CD2 | TRP | 52 | A | -22.092 | 1.295 | -0.610 |
| 141 | NE1 | TRP | 52 | A | -22.430 | 3.454 | 0.213 |
| 142 | CE2 | TRP | 52 | A | -21.489 | 2.641 | -0.293 |
| 143 | CE3 | TRP | 52 | A | -21.262 | 0.304 | -1.105 |
| 144 | CZ2 | TRP | 52 | A | -20.133 | 2.852 | -0.442 |
| 145 | CZ3 | TRP | 52 | A | -19.913 | 0.575 | -1.247 |
| 146 | CH2 | TRP | 52 | A | -19.360 | 1.810 | -0.907 |
| 147 | N | GLN | 53 | A | -28.072 | -0.088 | 1.197 |
| 148 | CA | GLN | 53 | A | -28.758 | -1.377 | 1.098 |
| 149 | C | GLN | 53 | A | -29.798 | -1.458 | 0.072 |
| 150 | O | GLN | 53 | A | -30.460 | -2.475 | -0.062 |
| 151 | CB | GLN | 53 | A | -29.504 | -1.835 | 2.360 |
| 152 | CG | GLN | 53 | A | -29.756 | -0.759 | 3.403 |
| 153 | CD | GLN | 53 | A | -31.038 | -1.078 | 4.192 |
| 154 | OE1 | GLN | 53 | A | -31.953 | -0.232 | 4.230 |
| 155 | NE2 | GLN | 53 | A | -31.163 | -2.269 | 4.840 |
| 156 | N | ASP | 54 | A | -29.992 | -0.405 | -0.689 |
| 157 | CA | ASP | 54 | A | -31.357 | 0.003 | -0.992 |
| 158 | C | ASP | 54 | A | -31.136 | 0.729 | -2.255 |
| 159 | O | ASP | 54 | A | -31.000 | 1.942 | -2.119 |
| 160 | CB | ASP | 54 | A | -31.873 | 0.982 | 0.073 |
| 161 | CG | ASP | 54 | A | -30.722 | 1.807 | 0.710 |
| 162 | OD1 | ASP | 54 | A | -30.861 | 2.211 | 1.892 |
| 163 | OD2 | ASP | 54 | A | -29.698 | 2.012 | 0.027 |
| 164 | N | TRP | 55 | A | -31.067 | 0.175 | -3.470 |
| 165 | CA | TRP | 55 | A | -30.322 | 0.915 | -4.515 |
| 166 | C | TRP | 55 | A | -29.770 | -0.083 | -5.462 |
| 167 | O | TRP | 55 | A | -29.915 | 0.104 | -6.662 |
| 168 | CB | TRP | 55 | A | -29.011 | 1.599 | -4.158 |
| 169 | CG | TRP | 55 | A | -29.091 | 3.035 | -3.787 |
| 170 | CD1 | TRP | 55 | A | -30.088 | 3.925 | -4.101 |
| 171 | CD2 | TRP | 55 | A | -27.886 | 3.623 | -3.134 |
| 172 | NE1 | TRP | 55 | A | -29.608 | 5.108 | -3.722 |
| 173 | CE2 | TRP | 55 | A | -28.348 | 5.080 | -3.173 |
| 174 | CE3 | TRP | 55 | A | -26.706 | 3.288 | -2.489 |
| 175 | CZ2 | TRP | 55 | A | -27.508 | 6.047 | -2.602 |
| 176 | CZ3 | TRP | 55 | A | -25.932 | 4.297 | -1.921 |
| 177 | CH2 | TRP | 55 | A | -26.304 | 5.642 | -1.988 |
| 178 | N | ILE | 56 | A | -29.151 | -1.108 | -4.812 |
| 179 | CA | ILE | 56 | A | -28.323 | -2.142 | -5.400 |
| 190 | C | ILE | 56 | A | -29.209 | -3.352 | -5.699 |

Fig. 15.4

| ATOM | RESIDUE | | CHAIN | X | Y | Z |
|---|---|---|---|---|---|---|
| 181 | O | ILE 56 | A | -29.900 | -3.795 | -4.792 |
| 182 | CB | ILE 56 | A | -27.221 | -2.452 | -4.390 |
| 183 | CG1 | ILE 56 | A | -25.998 | -1.743 | -4.815 |
| 184 | CG2 | ILE 56 | A | -26.917 | -3.924 | -4.291 |
| 185 | CD1 | ILE 56 | A | -25.964 | -0.422 | -4.122 |
| 186 | N | ILE 57 | A | -29.260 | -3.924 | -6.907 |
| 187 | CA | ILE 57 | A | -29.961 | -5.182 | -7.093 |
| 188 | C | ILE 57 | A | -28.927 | -6.288 | -6.809 |
| 189 | O | ILE 57 | A | -29.163 | -7.475 | -6.713 |
| 190 | CB | ILE 57 | A | -30.481 | -5.241 | -8.549 |
| 191 | CG1 | ILE 57 | A | -31.405 | -4.079 | -8.780 |
| 192 | CG2 | ILE 57 | A | -31.273 | -6.511 | -8.844 |
| 193 | CD1 | ILE 57 | A | -31.745 | -4.110 | -10.274 |
| 194 | N | ALA 58 | A | -27.684 | -5.914 | -6.623 |
| 195 | CA | ALA 58 | A | -26.550 | -6.030 | -7.556 |
| 196 | C | ALA 58 | A | -25.789 | -7.248 | -7.200 |
| 197 | O | ALA 58 | A | -26.272 | -8.230 | -7.747 |
| 198 | CB | ALA 58 | A | -25.682 | -4.813 | -7.386 |
| 199 | N | PRO 59 | A | -24.748 | -7.272 | -6.411 |
| 200 | CA | PRO 59 | A | -24.570 | -8.349 | -5.438 |
| 201 | C | PRO 59 | A | -25.086 | -7.952 | -4.063 |
| 202 | O | PRO 59 | A | -25.265 | -6.789 | -3.797 |
| 203 | CB | PRO 59 | A | -23.068 | -8.697 | -5.439 |
| 204 | CG | PRO 59 | A | -22.447 | -7.366 | -5.730 |
| 205 | CD | PRO 59 | A | -23.408 | -6.817 | -6.757 |
| 206 | N | GLU 60 | A | -25.376 | -8.795 | -3.088 |
| 207 | CA | GLU 60 | A | -25.696 | -8.242 | -1.777 |
| 208 | C | GLU 60 | A | -24.492 | -7.832 | -0.980 |
| 209 | O | GLU 60 | A | -24.571 | -7.233 | 0.078 |
| 210 | CB | GLU 60 | A | -26.502 | -9.249 | -0.927 |
| 211 | CG | GLU 60 | A | -25.753 | -10.380 | -0.180 |
| 212 | CD | GLU 60 | A | -24.990 | -9.971 | 1.084 |
| 213 | OE1 | GLU 60 | A | -25.319 | -8.939 | 1.717 |
| 214 | OE2 | GLU 60 | A | -24.089 | -10.738 | 1.457 |
| 215 | N | GLY 61 | A | -23.307 | -8.146 | -1.448 |
| 216 | CA | GLY 61 | A | -22.099 | -7.722 | -0.784 |
| 217 | C | GLY 61 | A | -21.009 | -8.349 | -1.571 |
| 218 | O | GLY 61 | A | -21.289 | -8.862 | -2.648 |
| 219 | N | TYR 62 | A | -19.777 | -8.343 | -1.088 |
| 220 | CA | TYR 62 | A | -18.689 | -8.872 | -1.879 |
| 221 | C | TYR 62 | A | -17.524 | -9.144 | -0.981 |
| 222 | O | TYR 62 | A | -17.554 | -8.747 | 0.169 |
| 223 | CB | TYR 62 | A | -18.362 | -7.838 | -2.934 |
| 224 | CG | TYR 62 | A | -17.588 | -6.667 | -2.413 |
| 225 | CD1 | TYR 62 | A | -18.181 | -5.490 | -1.956 |

Fig. 15.5

| ATOM | RESIDUE | CHAIN | X | Y | Z |
|---|---|---|---|---|---|
| 226 | CD2 | TYR 62 | A | -16.236 | -6.785 | -2.513 |
| 227 | CE1 | TYR 62 | A | -17.379 | -4.412 | -1.599 |
| 228 | CS2 | TYR 62 | A | -15.447 | -5.739 | -2.169 |
| 229 | CZ | TYR 62 | A | -16.004 | -4.571 | -1.715 |
| 230 | OH | TYR 62 | A | -15.097 | -3.565 | -1.383 |
| 231 | N | ALA 63 | A | -16.476 | -9.808 | -1.456 |
| 232 | CA | ALA 63 | A | -15.231 | -9.961 | -0.740 |
| 233 | C | ALA 63 | A | -14.242 | -8.820 | -0.961 |
| 234 | O | ALA 63 | A | -13.659 | -8.712 | -2.023 |
| 235 | CB | ALA 63 | A | -14.655 | -11.248 | -1.205 |
| 236 | N | ALA 64 | A | -14.020 | -7.948 | 0.007 |
| 237 | CA | ALA 64 | A | -13.051 | -6.893 | -0.114 |
| 238 | C | ALA 64 | A | -11.606 | -7.304 | 0.192 |
| 239 | O | ALA 64 | A | -10.608 | -6.800 | -0.298 |
| 240 | CB | ALA 64 | A | -13.454 | -5.781 | 0.832 |
| 241 | N | TYR 65 | A | -11.469 | -8.294 | 1.060 |
| 242 | CA | TYR 65 | A | -10.215 | -8.675 | 1.672 |
| 243 | C | TYR 65 | A | -9.503 | -7.544 | 2.281 |
| 244 | O | TYR 65 | A | -9.863 | -6.400 | 2.147 |
| 245 | CB | TYR 65 | A | -9.290 | -9.333 | 0.678 |
| 246 | CG | TYR 65 | A | -9.846 | -10.614 | 0.126 |
| 247 | CD1 | TYR 65 | A | -10.300 | -11.608 | 0.939 |
| 248 | CD2 | TYR 65 | A | -9.927 | -10.753 | -1.219 |
| 249 | CE1 | TYR 65 | A | -10.905 | -12.716 | 0.405 |
| 250 | CE2 | TYR 65 | A | -10.526 | -11.847 | -1.767 |
| 251 | CZ | TYR 65 | A | -11.039 | -12.799 | -0.951 |
| 252 | OH | TYR 65 | A | -11.729 | -13.859 | -1.515 |
| 253 | N | TYR 66 | A | -8.459 | -7.830 | 2.998 |
| 254 | CA | TYR 66 | A | -7.615 | -6.771 | 3.442 |
| 255 | C | TYR 66 | A | -6.303 | -7.401 | 3.710 |
| 256 | O | TYR 66 | A | -6.198 | -8.619 | 3.836 |
| 257 | CB | TYR 66 | A | -8.154 | -6.109 | 4.712 |
| 258 | CG | TYR 66 | A | -8.091 | -6.906 | 5.984 |
| 259 | CD1 | TYR 66 | A | -8.948 | -7.941 | 6.159 |
| 260 | CD2 | TYR 66 | A | -7.215 | -6.546 | 6.978 |
| 261 | CE1 | TYR 66 | A | -8.929 | -8.634 | 7.333 |
| 262 | CE2 | TYR 66 | A | -7.183 | -7.227 | 8.155 |
| 263 | CZ | TYR 66 | A | -8.041 | -8.273 | 8.310 |
| 264 | OH | TYR 66 | A | -8.024 | -9.037 | 9.472 |
| 265 | N | CYS 67 | A | -5.286 | -6.571 | 3.812 |
| 266 | CA | CYS 67 | A | -3.921 | -7.055 | 3.949 |
| 267 | C | CYS 67 | A | -3.364 | -6.825 | 5.358 |
| 268 | O | CYS 67 | A | -3.426 | -5.705 | 5.888 |
| 269 | CB | CYS 67 | A | -2.971 | -6.328 | 3.056 |
| 270 | SG | CYS 67 | A | -3.158 | -6.344 | 1.310 |

Fig. 15.6

| ATOM | | RESIDUE | | CHAIN | X | Y | Z |
|---|---|---|---|---|---|---|---|
| 271 | N | GLU | 68 | A | -2.792 | -7.828 | 6.031 |
| 272 | CA | GLU | 68 | A | -2.322 | -7.457 | 7.318 |
| 273 | C | GLU | 68 | A | -1.275 | -8.383 | 7.726 |
| 274 | O | GLU | 68 | A | -1.438 | -9.577 | 7.481 |
| 275 | CB | GLU | 68 | A | -3.408 | -7.534 | 8.334 |
| 276 | CG | GLU | 68 | A | -3.092 | -6.620 | 9.488 |
| 277 | CD | GLU | 68 | A | -3.797 | -7.134 | 10.693 |
| 278 | OE1 | GLU | 68 | A | -3.899 | -6.397 | 11.674 |
| 279 | OE2 | GLU | 68 | A | -4.246 | -8.282 | 10.661 |
| 280 | N | GLY | 69 | A | -0.219 | -7.857 | 8.348 |
| 281 | CA | GLY | 69 | A | 0.772 | -8.701 | 8.979 |
| 282 | C | GLY | 69 | A | 2.107 | -7.997 | 8.920 |
| 283 | O | GLY | 69 | A | 2.212 | -6.844 | 8.501 |
| 284 | N | GLU | 70 | A | 3.192 | -8.624 | 9.316 |
| 285 | CA | GLU | 70 | A | 4.349 | -7.810 | 9.600 |
| 286 | C | GLU | 70 | A | 5.364 | -7.795 | 8.496 |
| 287 | O | GLU | 70 | A | 5.603 | -8.818 | 7.881 |
| 288 | CB | GLU | 70 | A | 4.996 | -8.309 | 10.865 |
| 289 | CG | GLU | 70 | A | 5.202 | -7.080 | 11.735 |
| 290 | CD | GLU | 70 | A | 6.392 | -7.339 | 12.618 |
| 291 | OE1 | GLU | 70 | A | 7.092 | -6.368 | 12.941 |
| 292 | OE2 | GLU | 70 | A | 6.637 | -8.516 | 12.968 |
| 293 | N | CYS | 71 | A | 5.988 | -6.666 | 8.222 |
| 294 | CA | CYS | 71 | A | 7.049 | -6.657 | 7.253 |
| 295 | C | CYS | 71 | A | 8.436 | -6.637 | 7.832 |
| 296 | O | CYS | 71 | A | 8.961 | -5.627 | 8.241 |
| 297 | CB | CYS | 71 | A | 6.787 | -5.467 | 6.371 |
| 298 | SG | CYS | 71 | A | 5.598 | -5.970 | 5.102 |
| 299 | N | ALA | 72 | A | 9.141 | -7.740 | 7.914 |
| 300 | CA | ALA | 72 | A | 10.322 | -7.789 | 8.729 |
| 301 | C | ALA | 72 | A | 11.166 | -8.899 | 8.174 |
| 302 | O | ALA | 72 | A | 10.670 | -9.710 | 7.406 |
| 303 | CB | ALA | 72 | A | 9.874 | -8.066 | 10.139 |
| 304 | N | PHE | 73 | A | 12.457 | -9.057 | 8.463 |
| 305 | CA | PHE | 73 | A | 13.195 | -10.119 | 7.773 |
| 306 | C | PHE | 73 | A | 12.738 | -11.435 | 8.328 |
| 307 | O | PHE | 73 | A | 12.521 | -11.454 | 9.530 |
| 308 | CB | PHE | 73 | A | 14.723 | -9.995 | 7.990 |
| 309 | CG | PHE | 73 | A | 15.255 | -8.809 | 7.230 |
| 310 | CD1 | PHE | 73 | A | 15.243 | -8.804 | 5.868 |
| 311 | CD2 | PHE | 73 | A | 15.746 | -7.737 | 7.919 |
| 312 | CE1 | PHE | 73 | A | 15.709 | -7.716 | 5.190 |
| 313 | CE2 | PHE | 73 | A | 16.225 | -6.647 | 7.217 |
| 314 | CZ | PHE | 73 | A | 16.203 | -6.634 | 5.857 |
| 315 | N | PRO | 74 | A | 12.570 | -12.531 | 7.695 |

Fig. 15.7

| ATOM | | RESIDUE | | CHAIN | X | Y | Z |
|---|---|---|---|---|---|---|---|
| 316 | CA | PRO | 74 | A | 12.982 | -12.802 | 6.339 |
| 317 | C | PRO | 74 | A | 11.990 | -12.148 | 5.485 |
| 318 | O | PRO | 74 | A | 10.891 | -12.643 | 5.423 |
| 319 | CB | PRO | 74 | A | 12.945 | -14.284 | 6.176 |
| 320 | CG | PRO | 74 | A | 12.664 | -14.772 | 7.587 |
| 321 | CD | PRO | 74 | A | 11.893 | -13.668 | 8.292 |
| 322 | N | LEU | 75 | A | 12.254 | -11.051 | 4.786 |
| 323 | CA | LEU | 75 | A | 11.328 | -10.466 | 3.831 |
| 324 | C | LEU | 75 | A | 11.299 | -11.508 | 2.762 |
| 325 | O | LEU | 75 | A | 11.992 | -11.532 | 1.756 |
| 326 | CB | LEU | 75 | A | 11.912 | -9.144 | 3.346 |
| 327 | CG | LEU | 75 | A | 10.922 | -8.023 | 3.399 |
| 328 | CD1 | LEU | 75 | A | 9.924 | -8.232 | 4.514 |
| 329 | CD2 | LEU | 75 | A | 11.680 | -6.741 | 3.622 |
| 330 | N | ASN | 76 | A | 10.419 | -12.442 | 3.038 |
| 331 | CA | ASN | 76 | A | 10.337 | -13.665 | 2.288 |
| 332 | C | ASN | 76 | A | 9.758 | -13.535 | 0.863 |
| 333 | O | ASN | 76 | A | 8.766 | -14.166 | 0.569 |
| 334 | CB | ASN | 76 | A | 9.548 | -14.511 | 3.229 |
| 335 | CG | ASN | 76 | A | 9.704 | -15.945 | 2.935 |
| 336 | OD1 | ASN | 76 | A | 9.686 | -16.766 | 3.862 |
| 337 | ND2 | ASN | 76 | A | 9.760 | -16.324 | 1.643 |
| 338 | N | SER | 77 | A | 10.263 | -12.752 | -0.109 |
| 339 | CA | SER | 77 | A | 9.917 | -12.843 | -1.545 |
| 340 | C | SER | 77 | A | 8.445 | -12.920 | -1.915 |
| 341 | O | SER | 77 | A | 7.832 | -11.897 | -2.284 |
| 342 | CB | SER | 77 | A | 10.599 | -14.059 | -2.195 |
| 343 | OG | SER | 77 | A | 10.201 | -15.273 | -1.560 |
| 344 | N | TYR | 78 | A | 7.776 | -14.081 | -1.847 |
| 345 | CA | TYR | 78 | A | 6.343 | -13.977 | -1.994 |
| 346 | C | TYR | 78 | A | 5.734 | -13.258 | -0.792 |
| 347 | O | TYR | 78 | A | 4.827 | -13.833 | -0.216 |
| 348 | CB | TYR | 78 | A | 5.683 | -15.337 | -2.079 |
| 349 | CG | TYR | 78 | A | 5.162 | -15.723 | -3.465 |
| 350 | CD1 | TYR | 78 | A | 4.144 | -16.681 | -3.432 |
| 351 | CD2 | TYR | 78 | A | 5.865 | -15.473 | -4.665 |
| 352 | CE1 | TYR | 78 | A | 3.985 | -17.578 | -4.480 |
| 353 | CE2 | TYR | 78 | A | 5.706 | -16.377 | -5.729 |
| 354 | CZ | TYR | 78 | A | 4.859 | -17.489 | -5.557 |
| 355 | OH | TYR | 78 | A | 4.965 | -18.610 | -6.363 |
| 356 | N | MET | 79 | A | 6.220 | -12.058 | -0.418 |
| 357 | CA | MET | 79 | A | 5.629 | -11.035 | 0.425 |
| 358 | C | MET | 79 | A | 5.931 | -9.703 | -0.270 |
| 359 | O | MET | 79 | A | 5.976 | -8.606 | 0.269 |
| 360 | CB | MET | 79 | A | 6.271 | -10.880 | 1.754 |

Fig. 15.8

| ATOM | RESIDUE | CHAIN | X | Y | Z |
|---|---|---|---|---|---|
| 361 CG | MET 79 | A | 6.288 | -12.036 | 2.716 |
| 362 SD | MET 79 | A | 6.974 | -11.247 | 4.193 |
| 363 CE | MET 79 | A | 7.145 | -12.664 | 5.230 |
| 364 N | ASN 80 | A | 6.171 | -9.795 | -1.562 |
| 365 CA | ASN 80 | A | 6.444 | -8.675 | -2.417 |
| 366 C | ASN 80 | A | 7.324 | -7.534 | -1.973 |
| 367 O | ASN 80 | A | 7.169 | -6.458 | -2.499 |
| 368 CB | ASN 80 | A | 5.129 | -8.059 | -2.909 |
| 369 CG | ASN 80 | A | 5.403 | -7.179 | -4.135 |
| 370 OD1 | ASN 80 | A | 5.383 | -5.934 | -4.172 |
| 371 ND2 | ASN 80 | A | 5.792 | -7.856 | -5.212 |
| 372 N | ALA 81 | A | 8.295 | -7.505 | -1.068 |
| 373 CA | ALA 81 | A | 9.543 | -6.854 | -1.431 |
| 374 C | ALA 81 | A | 9.731 | -5.440 | -1.931 |
| 375 O | ALA 81 | A | 10.248 | -4.546 | -1.301 |
| 376 CB | ALA 81 | A | 10.249 | -7.718 | -2.461 |
| 377 N | THR 82 | A | 9.352 | -5.062 | -3.108 |
| 378 CA | THR 82 | A | 10.122 | -4.047 | -3.818 |
| 379 C | THR 82 | A | 11.649 | -4.060 | -3.652 |
| 380 O | TER 82 | A | 12.323 | -4.730 | -4.441 |
| 381 CB | THR 82 | A | 9.752 | -2.568 | -3.534 |
| 382 OG1 | THR 82 | A | 9.779 | -2.312 | -2.158 |
| 383 CG2 | THR 82 | A | 8.458 | -2.245 | -4.220 |
| 384 N | ASN 83 | A | 12.288 | -3.380 | -2.692 |
| 385 CA | ASN 83 | A | 13.708 | -3.070 | -2.868 |
| 386 C | ASN 83 | A | 13.915 | -1.957 | -1.951 |
| 387 O | ASN 83 | A | 14.715 | -1.956 | -1.057 |
| 388 CB | ASN 83 | A | 14.082 | -2.493 | -4.184 |
| 389 CG | ASN 83 | A | 14.958 | -3.390 | -4.974 |
| 390 OD1 | ASN 83 | A | 15.593 | -2.957 | -5.919 |
| 391 ND2 | ASN 83 | A | 14.990 | -4.682 | -4.709 |
| 392 N | HIS 84 | A | 13.196 | -0.870 | -2.081 |
| 393 CA | HIS 84 | A | 13.067 | 0.094 | -1.008 |
| 394 C | HIS 84 | A | 12.526 | -0.632 | 0.181 |
| 395 O | HIS 84 | A | 12.864 | -0.201 | 1.261 |
| 396 CB | HIS 84 | A | 12.095 | 1.187 | -1.379 |
| 397 CG | HIS 84 | A | 12.020 | 2.264 | -0.350 |
| 398 ND1 | HIS 84 | A | 11.255 | 2.299 | 0.730 |
| 399 CD2 | HIS 84 | A | 12.640 | 3.478 | -0.465 |
| 400 CE1 | HIS 84 | A | 11.393 | 3.487 | 1.258 |
| 401 NE2 | HIS 84 | A | 12.201 | 4.192 | 0.533 |
| 402 N | ALA 85 | A | 11.706 | -1.690 | 0.180 |
| 403 CA | ALA 85 | A | 11.398 | -2.240 | 1.463 |
| 404 C | ALA 85 | A | 12.553 | -3.020 | 1.972 |
| 405 O | ALA 85 | A | 12.626 | -3.221 | 3.161 |

Fig. 15.9

| ATOM | | RESIDUE | | CHAIN | X | Y | Z |
|---|---|---|---|---|---|---|---|
| 406 | CB | ALA | 85 | A | 10.199 | -3.130 | 1.402 |
| 407 | N | ILE | 86 | A | 13.538 | -3.522 | 1.249 |
| 408 | CA | ILE | 86 | A | 14.606 | -4.201 | 1.925 |
| 409 | C | ILE | 86 | A | 15.457 | -3.071 | 2.472 |
| 410 | O | ILE | 86 | A | 15.835 | -3.146 | 3.602 |
| 411 | CB | ILE | 86 | A | 15.300 | -5.078 | 0.903 |
| 412 | CG1 | ILE | 86 | A | 14.276 | -6.058 | 0.301 |
| 413 | CG2 | ILE | 86 | A | 16.470 | -5.804 | 1.570 |
| 414 | CD1 | ILE | 86 | A | 14.811 | -7.212 | -0.547 |
| 415 | N | VAL | 87 | A | 15.835 | -1.962 | 1.844 |
| 416 | CA | VAL | 87 | A | 16.554 | -0.892 | 2.511 |
| 417 | C | VAL | 87 | A | 15.798 | -0.836 | 3.762 |
| 418 | O | VAL | 87 | A | 16.284 | -0.769 | 4.847 |
| 419 | CB | VAL | 87 | A | 16.672 | 0.325 | 1.574 |
| 420 | CG1 | VAL | 87 | A | 16.890 | 1.606 | 2.333 |
| 421 | CG2 | VAL | 87 | A | 17.858 | 0.133 | 0.660 |
| 422 | N | GLN | 88 | A | 14.596 | 0.026 | 3.752 |
| 423 | CA | GLN | 88 | A | 13.942 | 0.411 | 4.993 |
| 424 | C | GLN | 88 | A | 13.900 | -0.690 | 6.037 |
| 425 | O | GLN | 88 | A | 14.176 | -0.400 | 7.186 |
| 426 | CB | GLN | 88 | A | 12.531 | 0.829 | 4.715 |
| 427 | CG | GLN | 88 | A | 12.099 | 2.208 | 5.146 |
| 428 | CD | GLN | 88 | A | 10.634 | 2.123 | 5.038 |
| 429 | OE1 | GLN | 88 | A | 9.852 | 2.201 | 5.962 |
| 430 | NE2 | GLN | 88 | A | 10.159 | 1.742 | 3.868 |
| 431 | N | THR | 89 | A | 13.582 | -1.949 | 5.766 |
| 432 | CA | THR | 89 | A | 13.633 | -2.920 | 6.799 |
| 433 | C | THR | 89 | A | 15.038 | -3.073 | 7.309 |
| 434 | O | THR | 89 | A | 15.197 | -3.213 | 8.509 |
| 435 | CB | THR | 89 | A | 13.156 | -4.198 | 6.275 |
| 436 | OG1 | THR | 89 | A | 11.863 | -3.908 | 5.883 |
| 437 | CG2 | THR | 89 | A | 12.973 | -5.302 | 7.272 |
| 438 | N | LEU | 90 | A | 16.122 | -3.061 | 6.519 |
| 439 | CA | LEU | 90 | A | 17.492 | -3.003 | 7.017 |
| 440 | C | LEU | 90 | A | 17.782 | -1.770 | 7.832 |
| 441 | O | LEU | 90 | A | 18.260 | -1.850 | 8.947 |
| 442 | CB | LEU | 90 | A | 18.454 | -3.009 | 5.868 |
| 443 | CG | LEU | 90 | A | 19.904 | -3.128 | 6.174 |
| 444 | CD1 | LEU | 90 | A | 20.166 | -4.389 | 6.967 |
| 445 | CD2 | LEU | 90 | A | 20.641 | -3.116 | 4.854 |
| 446 | N | VAL | 91 | A | 17.528 | -0.569 | 7.354 |
| 447 | CA | VAL | 91 | A | 17.690 | 0.623 | 8.155 |
| 448 | C | VAL | 91 | A | 16.866 | 0.546 | 9.409 |
| 449 | O | VAL | 91 | A | 17.188 | 1.150 | 10.422 |
| 450 | CB | VAL | 91 | A | 17.282 | 1.803 | 7.334 |

Fig. 15.10

| ATOM | | RESIDUE | | CHAIN | X | Y | Z |
|---|---|---|---|---|---|---|---|
| 451 | CG1 | VAL | 91 | A | 17.149 | 3.078 | 8.140 |
| 452 | CG2 | VAL | 91 | A | 18.356 | 1.954 | 6.278 |
| 453 | N | HIS | 92 | A | 15.762 | -0.193 | 9.453 |
| 454 | CA | HIS | 92 | A | 15.046 | -0.309 | 10.719 |
| 455 | C | HIS | 92 | A | 15.946 | -0.915 | 11.723 |
| 456 | O | HIS | 92 | A | 16.085 | -0.444 | 12.816 |
| 457 | CB | HIS | 92 | A | 13.805 | -1.224 | 10.633 |
| 458 | CG | HIS | 92 | A | 12.902 | -1.039 | 11.826 |
| 459 | ND1 | HIS | 92 | A | 12.332 | -1.848 | 12.711 |
| 460 | CD2 | HIS | 92 | A | 12.540 | 0.216 | 12.159 |
| 461 | CE1 | HIS | 92 | A | 11.678 | -1.086 | 13.538 |
| 462 | NE2 | HIS | 92 | A | 11.826 | 0.165 | 13.212 |
| 463 | N | PHE | 93 | A | 16.591 | -1.984 | 11.374 |
| 464 | CA | PHE | 93 | A | 17.374 | -2.777 | 12.262 |
| 465 | C | PHE | 93 | A | 18.620 | -2.032 | 12.652 |
| 466 | O | PHE | 93 | A | 19.005 | -1.893 | 13.796 |
| 467 | CB | PHE | 93 | A | 17.592 | -4.024 | 11.472 |
| 468 | CG | PHE | 93 | A | 18.741 | -4.858 | 11.921 |
| 469 | CD1 | PHE | 93 | A | 20.039 | -4.461 | 11.662 |
| 470 | CD2 | PHE | 93 | A | 18.474 | -6.111 | 12.455 |
| 471 | CE1 | PHE | 93 | A | 21.058 | -5.341 | 11.903 |
| 472 | CE2 | PHE | 93 | A | 19.507 | -6.993 | 12.676 |
| 473 | CZ | PHE | 93 | A | 20.790 | -6.600 | 12.394 |
| 474 | N | ILE | 94 | A | 19.399 | -1.476 | 11.751 |
| 475 | CA | ILE | 94 | A | 20.477 | -0.592 | 12.182 |
| 476 | C | ILE | 94 | A | 19.938 | 0.454 | 13.131 |
| 477 | O | ILE | 94 | A | 20.706 | 1.117 | 13.787 |
| 478 | CB | ILE | 94 | A | 21.036 | -0.005 | 10.907 |
| 479 | CG1 | ILE | 94 | A | 21.808 | -1.156 | 10.367 |
| 480 | CG2 | ILE | 94 | A | 21.876 | 1.246 | 11.008 |
| 481 | CD1 | ILE | 94 | A | 22.103 | -0.863 | 8.903 |
| 482 | N | ASN | 95 | A | 18.635 | 0.704 | 13.302 |
| 483 | CA | ASN | 95 | A | 18.237 | 1.955 | 13.901 |
| 484 | C | ASN | 95 | A | 16.753 | 2.185 | 14.183 |
| 485 | O | ASN | 95 | A | 16.082 | 3.112 | 13.702 |
| 486 | CB | ASN | 95 | A | 18.719 | 3.074 | 13.024 |
| 487 | CG | ASN | 95 | A | 18.887 | 4.221 | 13.977 |
| 488 | OD1 | ASN | 95 | A | 18.243 | 4.291 | 15.040 |
| 489 | ND2 | ASN | 95 | A | 19.771 | 5.172 | 13.602 |
| 490 | N | PRO | 96 | A | 16.204 | 1.357 | 15.006 |
| 491 | CA | PRO | 96 | A | 14.787 | 1.108 | 15.108 |
| 492 | C | PRO | 96 | A | 13.919 | 2.281 | 15.324 |
| 493 | O | PRO | 96 | A | 12.713 | 2.226 | 15.089 |
| 494 | CB | PRO | 96 | A | 14.647 | 0.084 | 16.217 |
| 495 | CG | PRO | 96 | A | 16.039 | -0.490 | 16.300 |

Fig. 15.11

| ATOM | | RESIDUE | | CHAIN | X | Y | Z |
|---|---|---|---|---|---|---|---|
| 496 | CD | PRO | 96 | A | 16.846 | 0.801 | 16.173 |
| 497 | N | GLU | 97 | A | 14.559 | 3.336 | 15.774 |
| 498 | CA | GLU | 97 | A | 13.846 | 4.558 | 15.992 |
| 499 | C | GLU | 97 | A | 14.019 | 5.333 | 14.722 |
| 500 | O | GLU | 97 | A | 13.031 | 5.781 | 14.197 |
| 501 | CB | GLU | 97 | A | 14.429 | 5.329 | 17.184 |
| 502 | CG | GLU | 97 | A | 13.550 | 5.172 | 18.453 |
| 503 | CD | GLU | 97 | A | 13.769 | 3.807 | 19.163 |
| 504 | OE1 | GLU | 97 | A | 14.723 | 3.749 | 19.999 |
| 505 | OE2 | GLU | 97 | A | 12.998 | 2.824 | 18.896 |
| 506 | N | THR | 98 | A | 15.145 | 5.584 | 14.080 |
| 507 | CA | THR | 98 | A | 15.073 | 6.445 | 12.897 |
| 508 | C | THR | 98 | A | 14.148 | 6.043 | 11.715 |
| 509 | O | THR | 98 | A | 14.015 | 6.906 | 10.851 |
| 510 | CB | THR | 98 | A | 16.514 | 6.624 | 12.388 |
| 511 | OG1 | THR | 98 | A | 17.067 | 5.331 | 12.373 |
| 512 | CG2 | THR | 98 | A | 17.451 | 7.417 | 13.322 |
| 513 | N | VAL | 99 | A | 13.482 | 4.877 | 11.518 |
| 514 | CA | VAL | 99 | A | 12.654 | 4.635 | 10.334 |
| 515 | C | VAL | 99 | A | 11.675 | 3.508 | 10.660 |
| 516 | O | VAL | 99 | A | 12.183 | 2.611 | 11.310 |
| 517 | CB | VAL | 99 | A | 13.546 | 4.251 | 9.139 |
| 518 | CG1 | VAL | 99 | A | 13.636 | 2.753 | 8.774 |
| 519 | CG2 | VAL | 99 | A | 12.902 | 4.955 | 7.978 |
| 520 | N | PRO | 100 | A | 10.408 | 3.461 | 10.322 |
| 521 | CA | PRO | 100 | A | 9.442 | 2.427 | 10.687 |
| 522 | C | PRO | 100 | A | 9.639 | 1.132 | 10.021 |
| 523 | O | PRO | 100 | A | 10.611 | 1.033 | 9.342 |
| 524 | CB | PRO | 100 | A | 8.119 | 3.003 | 10.359 |
| 525 | CG | PRO | 100 | A | 8.348 | 4.485 | 10.464 |
| 526 | CD | PRO | 100 | A | 9.713 | 4.645 | 9.854 |
| 527 | N | LYS | 101 | A | 8.889 | 0.042 | 10.071 |
| 528 | CA | LYS | 101 | A | 9.245 | -1.083 | 9.226 |
| 529 | C | LYS | 101 | A | 8.344 | -0.893 | 8.022 |
| 530 | O | LYS | 101 | A | 7.361 | -0.183 | 8.151 |
| 531 | CB | LYS | 101 | A | 8.901 | -2.426 | 9.859 |
| 532 | CG | LYS | 101 | A | 8.737 | -2.477 | 11.364 |
| 533 | CD | LYS | 101 | A | 8.039 | -3.748 | 11.889 |
| 534 | CE | LYS | 101 | A | 6.454 | -3.645 | 12.044 |
| 535 | NZ | LYS | 101 | A | 5.616 | -3.935 | 10.845 |
| 536 | N | PRO | 102 | A | 8.452 | -1.381 | 6.846 |
| 537 | CA | PRO | 102 | A | 7.556 | -1.032 | 5.775 |
| 538 | C | PRO | 102 | A | 6.203 | -1.549 | 6.093 |
| 539 | O | PRO | 102 | A | 6.087 | -2.464 | 6.892 |
| 540 | CB | PRO | 102 | A | 8.171 | -1.646 | 4.535 |

Fig. 15.12

| ATOM | | RESIDUE | | CHAIN | X | Y | Z |
|---|---|---|---|---|---:|---:|---:|
| 541 | CG | PRO | 102 | A | 8.812 | -2.855 | 5.077 |
| 542 | CD | PRO | 102 | A | 9.333 | -2.458 | 6.451 |
| 543 | N | CYS | 103 | A | 5.086 | -1.078 | 5.549 |
| 544 | CA | CYS | 103 | A | 3.887 | -1.780 | 5.921 |
| 545 | C | CYS | 103 | A | 3.229 | -2.407 | 4.753 |
| 546 | O | CYS | 103 | A | 3.592 | -2.289 | 3.598 |
| 547 | CB | CYS | 103 | A | 2.930 | -0.840 | 6.599 |
| 548 | SG | CYS | 103 | A | 2.131 | -0.050 | 5.233 |
| 549 | N | CYS | 104 | A | 2.191 | -3.102 | 5.117 |
| 550 | CA | CYS | 104 | A | 1.736 | -4.199 | 4.338 |
| 551 | C | CYS | 104 | A | 0.466 | -3.786 | 3.641 |
| 552 | O | CYS | 104 | A | -0.555 | -3.520 | 4.240 |
| 553 | CB | CYS | 104 | A | 1.633 | -5.221 | 5.372 |
| 554 | SG | CYS | 104 | A | 0.823 | -6.586 | 4.674 |
| 555 | N | ALA | 105 | A | 0.490 | -3.719 | 2.337 |
| 556 | CA | ALA | 105 | A | -0.396 | -2.886 | 1.605 |
| 557 | C | ALA | 105 | A | -0.839 | -3.742 | 0.482 |
| 558 | O | ALA | 105 | A | -0.170 | -4.745 | 0.282 |
| 559 | CB | ALA | 105 | A | 0.400 | -1.708 | 1.149 |
| 560 | N | PRO | 106 | A | -1.857 | -3.510 | -0.271 |
| 561 | CA | PRO | 106 | A | -2.156 | -4.293 | 1.435 |
| 562 | C | PRO | 106 | A | -1.352 | -3.905 | -2.675 |
| 563 | O | PRO | 106 | A | -1.065 | -2.765 | -2.987 |
| 564 | CB | PRO | 106 | A | -3.647 | -4.136 | -1.574 |
| 565 | CG | PRO | 106 | A | -3.879 | -2.759 | -1.095 |
| 566 | CD | PRO | 106 | A | -3.107 | -2.927 | 0.186 |
| 567 | N | THR | 107 | A | -0.999 | -4.955 | -3.391 |
| 568 | CA | THR | 107 | A | -0.073 | -4.974 | -4.479 |
| 569 | C | THR | 107 | A | -1.001 | -4.913 | -5.659 |
| 570 | O | THR | 107 | A | -0.955 | -3.955 | -6.424 |
| 571 | CB | THR | 107 | A | 0.666 | -6.265 | -4.172 |
| 572 | OG1 | THR | 107 | A | 1.728 | -5.736 | -3.391 |
| 573 | CG2 | THR | 107 | A | 1.115 | -7.153 | -5.311 |
| 574 | N | GLN | 108 | A | -1.900 | -5.847 | -5.940 |
| 575 | CA | GLN | 108 | A | -2.913 | -5.442 | -6.865 |
| 576 | C | GLN | 108 | A | -4.352 | -5.682 | -6.500 |
| 577 | O | GLN | 108 | A | -4.739 | -6.674 | -5.905 |
| 578 | CB | GLN | 108 | A | -2.460 | -6.080 | -8.189 |
| 579 | CG | GLN | 108 | A | -2.948 | -7.440 | -8.663 |
| 580 | CD | GLN | 108 | A | -2.234 | -8.459 | -7.886 |
| 581 | OE1 | GLN | 108 | A | -1.660 | -8.222 | -6.832 |
| 582 | NE2 | GLN | 108 | A | -2.298 | -9.656 | -8.471 |
| 583 | N | LEU | 109 | A | -5.100 | -4.662 | -6.917 |
| 584 | CA | LEU | 109 | A | -6.522 | -4.430 | -6.644 |
| 585 | C | LEU | 109 | A | -7.495 | -4.780 | -7.798 |

Fig. 15.13

| ATOM | RESIDUE | CHAIN | X | Y | Z |
|---|---|---|---|---|---|
| 586 O | LEU 109 | A | -7.256 | -4.573 | -8.986 |
| 587 CB | LEU 109 | A | -6.694 | -2.932 | -6.225 |
| 588 CG | LEU 109 | A | -6.102 | -2.671 | -4.830 |
| 589 CD1 | LEU 109 | A | -6.012 | -1.216 | -4.502 |
| 590 CD2 | LEU 109 | A | -7.022 | -3.304 | -3.811 |
| 591 N | ASN 110 | A | -8.659 | -5.343 | -7.521 |
| 592 CA | ASN 110 | A | -9.570 | -5.629 | -8.584 |
| 593 C | ASN 110 | A | -10.824 | -4.870 | -8.418 |
| 594 O | ASN 110 | A | -10.985 | -4.117 | -7.471 |
| 595 CB | ASN 110 | A | -9.945 | -7.054 | -8.620 |
| 596 CG | ASN 110 | A | -8.771 | -7.863 | -9.017 |
| 597 OD1 | ASN 110 | A | -8.810 | -9.080 | -8.781 |
| 598 ND2 | ASN 110 | A | -7.687 | -7.281 | -9.560 |
| 599 N | ALA 111 | A | -11.767 | -5.052 | -9.338 |
| 600 CA | ALA 111 | A | -12.876 | -4.131 | -9.476 |
| 601 C | ALA 111 | A | -14.026 | -4.974 | -9.121 |
| 602 O | ALA 111 | A | -13.880 | -6.178 | -9.058 |
| 603 CB | ALA 111 | A | -12.993 | -3.615 | -10.928 |
| 604 N | ILE 112 | A | -15.182 | -4.401 | -8.876 |
| 605 CA | ILE 112 | A | -16.371 | -5.172 | -8.539 |
| 606 C | ILE 112 | A | -17.371 | -4.462 | -9.404 |
| 607 O | ILE 112 | A | -17.265 | -3.251 | -9.506 |
| 608 CB | ILE 112 | A | -16.583 | -5.062 | -6.980 |
| 609 CG1 | ILE 112 | A | -16.477 | -6.535 | -6.632 |
| 610 CG2 | ILE 112 | A | -17.869 | -4.480 | -6.379 |
| 611 CD1 | ILE 112 | A | -17.762 | -7.334 | -6.966 |
| 612 N | SER 113 | A | -18.320 | -5.126 | -10.037 |
| 613 CA | SER 113 | A | -19.389 | -4.403 | -10.673 |
| 614 C | SER 113 | A | -20.670 | -4.529 | -9.920 |
| 615 O | SER 113 | A | -20.965 | -5.655 | -9.564 |
| 616 CB | SER 113 | A | -19.576 | -4.919 | -12.074 |
| 617 OG | SER 113 | A | -18.826 | -4.052 | -12.946 |
| 618 N | VAL 114 | A | -21.472 | -3.484 | -9.631 |
| 619 CA | VAL 114 | A | -22.751 | -3.722 | -8.970 |
| 620 C | VAL 114 | A | -23.830 | -3.148 | -9.882 |
| 621 O | VAL 114 | A | -23.658 | -2.119 | -10.522 |
| 622 CB | VAL 114 | A | -22.897 | -3.057 | -7.536 |
| 623 CG1 | VAL 114 | A | -21.637 | -3.226 | -6.742 |
| 624 CG2 | VAL 114 | A | -23.194 | -1.588 | -7.611 |
| 625 N | LEU 115 | A | -24.960 | -3.847 | -9.955 |
| 626 CA | LEU 115 | A | -26.160 | -3.492 | -10.709 |
| 627 C | LEU 115 | A | -27.151 | -2.699 | -9.903 |
| 628 O | LEU 115 | A | -27.603 | -3.173 | -8.860 |
| 629 CB | LEU 115 | A | -26.840 | -4.789 | -11.194 |
| 630 CG | LEU 115 | A | -28.187 | -4.790 | -11.902 |

Fig. 15.14

| ATOM | | RESIDUE | | CHAIN | X | Y | Z |
|---|---|---|---|---|---|---|---|
| 631 | CD1 | LEU | 115 | A | -28.011 | -4.403 | -13.339 |
| 632 | CD2 | LEU | 115 | A | -28.797 | -6.184 | -11.806 |
| 633 | N | TYR | 116 | A | -27.598 | -1.505 | -10.254 |
| 634 | CA | TYR | 116 | A | -28.495 | -0.859 | -9.329 |
| 635 | C | TYR | 116 | A | -29.472 | 0.124 | -9.908 |
| 636 | O | TYR | 116 | A | -29.241 | 0.596 | -11.014 |
| 637 | CB | TYR | 116 | A | -27.619 | -0.201 | -8.316 |
| 638 | CG | TYR | 116 | A | -26.890 | 0.935 | -8.941 |
| 639 | CD1 | TYR | 116 | A | -25.664 | 0.712 | -9.513 |
| 640 | CD2 | TYR | 116 | A | -27.474 | 2.166 | -8.888 |
| 641 | CE1 | TYR | 116 | A | -25.034 | 1.750 | -10.131 |
| 642 | CE2 | TYR | 116 | A | -26.850 | 3.205 | -9.502 |
| 643 | CZ | TYR | 116 | A | -25.669 | 2.961 | -10.141 |
| 644 | OH | TYR | 116 | A | -25.140 | 3.965 | -10.902 |
| 645 | N | PHE | 117 | A | -30.566 | 0.506 | -9.242 |
| 646 | CA | PHE | 117 | A | -31.478 | 1.445 | -9.867 |
| 647 | C | PHE | 117 | A | -30.914 | 2.785 | -9.556 |
| 648 | O | PHE | 117 | A | -30.775 | 3.080 | -8.381 |
| 649 | CB | PHE | 117 | A | -32.882 | 1.514 | -9.284 |
| 650 | G | PHE | 117 | A | -33.447 | 0.159 | -8.982 |
| 651 | CD1 | PHE | 117 | A | -33.259 | -0.395 | -7.738 |
| 652 | CD2 | PHE | 117 | A | -34.137 | -0.534 | -9.952 |
| 653 | CE1 | PHE | 117 | A | -33.750 | -1.660 | -7.482 |
| 654 | CE2 | PHE | 117 | A | -34.618 | -1.807 | -9.709 |
| 655 | CZ | PHE | 117 | A | -34.419 | -2.373 | -8.466 |
| 656 | N | ASP | 118 | A | -30.555 | 3.683 | -10.458 |
| 657 | CA | ASP | 118 | A | -30.375 | 5.050 | -9.964 |
| 658 | C | ASP | 118 | A | -31.794 | 5.566 | -9.803 |
| 659 | O | ASP | 118 | A | -32.746 | 4.804 | -9.876 |
| 660 | CB | ASP | 118 | A | -29.612 | 5.972 | -10.973 |
| 661 | CG | ASP | 118 | A | -30.317 | 5.985 | -12.316 |
| 662 | OD1 | ASP | 118 | A | -29.855 | 6.724 | -13.211 |
| 663 | OD2 | ASP | 118 | A | -31.322 | 5.245 | -12.467 |
| 664 | N | ASP | 119 | A | -31.939 | 6.868 | -9.594 |
| 665 | CA | ASP | 119 | A | -33.218 | 7.509 | -9.718 |
| 666 | C | ASP | 119 | A | -33.915 | 7.160 | -11.070 |
| 667 | O | ASP | 119 | A | -33.359 | 6.483 | -11.946 |
| 668 | CB | ASP | 119 | A | -33.033 | 9.030 | -9.618 |
| 669 | CG | ASP | 119 | A | -31.942 | 9.455 | -10.598 |
| 670 | OD1 | ASP | 119 | A | -31.911 | 8.877 | -11.719 |
| 671 | OD2 | ASP | 119 | A | -31.115 | 10.325 | -10.232 |
| 672 | N | SER | 120 | A | -35.161 | 7.670 | -11.218 |
| 673 | CA | SER | 120 | A | -36.125 | 7.119 | -12.146 |
| 674 | C | SER | 120 | A | -36.295 | 5.699 | -11.621 |
| 675 | O | SER | 120 | A | -36.515 | 5.484 | -10.431 |

Fig. 15.15

| ATOM | | RESIDUE | | CHAIN | X | Y | Z |
|---|---|---|---|---|---|---|---|
| 676 | CB | SER | 120 | A | -35.506 | 7.257 | -13.534 |
| 677 | OG | SER | 120 | A | -35.100 | 6.005 | -14.079 |
| 678 | N | SER | 121 | A | -36.217 | 4.669 | -12.388 |
| 679 | CA | SER | 121 | A | -35.537 | 3.572 | -11.785 |
| 680 | C | SER | 121 | A | -34.705 | 3.104 | -12.949 |
| 681 | O | SER | 121 | A | -34.958 | 2.007 | -13.464 |
| 682 | CB | SER | 121 | A | -36.551 | 2.525 | -11.340 |
| 683 | OG | SER | 121 | A | -37.674 | 3.246 | -10.810 |
| 684 | N | ASN | 122 | A | -33.701 | 3.800 | -13.473 |
| 685 | CA | ASN | 122 | A | -32.990 | 3.100 | -14.519 |
| 686 | C | ASN | 122 | A | -32.307 | 1.922 | -13.858 |
| 687 | O | ASN | 122 | A | -31.660 | 2.138 | -12.857 |
| 688 | CB | ASN | 122 | A | -31.913 | 3.941 | -15.157 |
| 689 | CG | ASN | 122 | A | -32.456 | 4.847 | -16.232 |
| 690 | OD1 | ASN | 122 | A | -33.543 | 5.397 | -16.193 |
| 691 | ND2 | ASN | 122 | A | -31.577 | 5.040 | -17.223 |
| 692 | N | VAL | 123 | A | -32.362 | 0.675 | -14.271 |
| 693 | CA | VAL | 123 | A | -31.447 | -0.312 | -13.748 |
| 694 | C | VAL | 123 | A | -30.061 | -0.155 | -14.305 |
| 695 | O | VAL | 123 | A | -29.858 | -0.450 | -15.460 |
| 696 | CB | VAL | 123 | A | -31.992 | -1.647 | -14.081 |
| 697 | CG1 | VAL | 123 | A | -31.033 | -2.769 | -13.818 |
| 698 | CG2 | VAL | 123 | A | -33.230 | -1.785 | -13.234 |
| 699 | N | ILE | 124 | A | -29.010 | 0.291 | -13.637 |
| 700 | CA | ILE | 124 | A | -27.704 | 0.244 | -14.288 |
| 701 | C | ILE | 124 | A | -26.583 | -0.682 | -13.814 |
| 702 | O | ILE | 124 | A | -26.689 | -1.441 | -12.866 |
| 703 | CB | ILE | 124 | A | -27.187 | 1.630 | -14.333 |
| 704 | CG1 | ILE | 124 | A | -27.086 | 2.273 | -13.025 |
| 705 | CG2 | ILE | 124 | A | -28.198 | 2.409 | -15.116 |
| 706 | CD1 | ILE | 124 | A | -26.681 | 3.705 | -13.362 |
| 707 | N | LEU | 125 | A | -25.411 | -0.711 | -14.431 |
| 708 | CA | LEU | 125 | A | -24.372 | -1.639 | -13.989 |
| 709 | C | LEU | 125 | A | -23.210 | -0.681 | -13.840 |
| 710 | O | LEU | 125 | A | -22.730 | -0.263 | -14.888 |
| 711 | CB | LEU | 125 | A | -24.075 | -2.659 | -15.069 |
| 712 | CG | LEU | 125 | A | -23.261 | -3.900 | -14.761 |
| 713 | CD1 | LEU | 125 | A | -23.927 | -4.875 | -13.791 |
| 714 | CD2 | LEU | 125 | A | -23.108 | -4.618 | -16.093 |
| 715 | N | LYS | 126 | A | -22.754 | -0.305 | -12.615 |
| 716 | CA | LYS | 126 | A | -21.529 | 0.463 | -12.487 |
| 717 | C | LYS | 126 | A | -20.416 | -0.467 | -12.106 |
| 718 | O | LYS | 126 | A | -20.595 | -1.572 | -11.608 |
| 719 | CB | LYS | 126 | A | -21.624 | 1.556 | -11.437 |
| 720 | CG | LYS | 126 | A | -20.629 | 2.603 | -12.021 |

Fig. 15.16

| ATOM | | RESIDUE | | CHAIN | X | Y | Z |
|---|---|---|---|---|---|---|---|
| 721 | CD | LYS | 126 | A | -20.367 | 3.908 | -11.203 |
| 722 | CE | LYS | 126 | A | -19.079 | 4.686 | -11.635 |
| 723 | NZ | LYS | 126 | A | -17.843 | 3.882 | -11.529 |
| 724 | N | LYS | 127 | A | -19.199 | -0.029 | -12.352 |
| 725 | CA | LYS | 127 | A | -18.017 | -0.835 | -12.143 |
| 726 | C | LYS | 127 | A | -17.282 | 0.026 | -11.185 |
| 727 | O | LYS | 127 | A | -17.184 | 1.224 | -11.370 |
| 728 | CB | LYS | 127 | A | -17.097 | -0.968 | -13.339 |
| 729 | CG | LYS | 127 | A | -16.235 | -2.196 | -13.072 |
| 730 | CD | LYS | 127 | A | -15.334 | -2.558 | -14.231 |
| 731 | CE | LYS | 127 | A | -14.497 | -1.365 | -14.645 |
| 732 | NZ | LYS | 127 | A | -13.360 | -1.909 | -15.350 |
| 733 | N | TYR | 128 | A | -16.763 | -0.565 | -10.145 |
| 734 | CA | TYR | 128 | A | -16.120 | 0.206 | -9.143 |
| 735 | C | TYR | 128 | A | -14.784 | -0.346 | -9.316 |
| 736 | O | TYR | 128 | A | -14.664 | -1.559 | -9.483 |
| 737 | CB | TYR | 128 | A | -16.692 | -0.131 | -7.789 |
| 738 | CG | TYR | 128 | A | -17.935 | 0.643 | -7.636 |
| 739 | CD1 | TYR | 128 | A | -19.083 | 0.008 | -7.229 |
| 740 | CD2 | TYR | 128 | A | -17.936 | 1.966 | -7.982 |
| 741 | CE1 | TYR | 128 | A | -20.272 | 0.703 | -7.216 |
| 742 | CE2 | TYR | 128 | A | -19.101 | 2.672 | -7.977 |
| 743 | CZ | TYR | 128 | A | -20.270 | 2.038 | -7.613 |
| 744 | OS | TYR | 128 | A | -21.474 | 2.754 | -7.674 |
| 745 | N | ARG | 129 | A | -13.741 | 0.463 | -9.292 |
| 746 | CA | ARG | 129 | A | -12.483 | -0.169 | -9.488 |
| 747 | C | ARG | 129 | A | -11.895 | -0.158 | -8.145 |
| 748 | O | ARG | 129 | A | -12.287 | 0.615 | -7.288 |
| 749 | CB | ARG | 129 | A | -11.616 | 0.626 | -10.404 |
| 750 | CG | ARG | 129 | A | -12.191 | 1.806 | -11.208 |
| 751 | CD | ARG | 129 | A | -11.134 | 2.214 | -12.267 |
| 752 | NE | ARG | 129 | A | -10.607 | 1.001 | -12.893 |
| 753 | CZ | ARG | 129 | A | -11.262 | 0.401 | -13.888 |
| 754 | NH1 | ARG | 129 | A | -12.339 | 0.985 | -14.529 |
| 755 | NH2 | ARG | 129 | A | -10.849 | -0.846 | -14.242 |
| 756 | N | ASN | 130 | A | -10.935 | -1.039 | -7.949 |
| 757 | CA | ASN | 130 | A | -10.085 | -1.012 | -6.790 |
| 758 | C | ASN | 130 | A | -10.851 | -1.277 | -5.599 |
| 759 | O | ASN | 130 | A | -10.708 | -0.669 | -4.572 |
| 760 | CB | ASN | 130 | A | -9.393 | 0.323 | -6.609 |
| 761 | CG | ASN | 130 | A | -8.261 | 0.341 | -7.600 |
| 762 | OD1 | ASN | 130 | A | -7.739 | -0.694 | -7.981 |
| 763 | ND2 | ASN | 130 | A | -7.853 | 1.492 | -8.122 |
| 764 | N | MET | 131 | A | -11.728 | -2.248 | -5.704 |
| 765 | CA | MET | 131 | A | -12.531 | -2.586 | -4.577 |

Fig. 15.17

| ATOM | | RESIDUE | | CHAIN | X | Y | Z |
|---|---|---|---|---|---|---|---|
| 766 | C | MET | 131 | A | -12.155 | -3.895 | -3.926 |
| 767 | O | MET | 131 | A | -12.642 | -4.228 | -2.858 |
| 768 | CB | MET | 131 | A | -13.944 | -2.576 | -5.083 |
| 769 | CG | MET | 131 | A | -14.347 | -1.149 | -5.256 |
| 770 | SD | MET | 131 | A | -15.527 | -0.836 | -3.944 |
| 771 | CE | MET | 131 | A | -14.884 | 0.789 | -3.671 |
| 772 | N | VAL | 132 | A | -11.291 | -4.690 | -4.521 |
| 773 | CA | VAL | 132 | A | -11.025 | -6.042 | -4.048 |
| 774 | C | VAL | 132 | A | -9.531 | -6.189 | -3.925 |
| 775 | O | VAL | 132 | A | -8.827 | -5.797 | -4.819 |
| 776 | CB | VAL | 132 | A | -11.556 | -7.015 | -5.070 |
| 777 | CG1 | VAL | 132 | A | -11.478 | -8.446 | -4.622 |
| 778 | CG2 | VAL | 132 | A | -13.002 | -6.636 | -5.321 |
| 779 | N | VAL | 133 | A | -8.890 | -6.710 | -2.915 |
| 780 | CA | VAL | 133 | A | -7.469 | -6.920 | -2.922 |
| 781 | C | VAL | 133 | A | -7.287 | -8.237 | -3.624 |
| 782 | O | VAL | 133 | A | -8.076 | -9.130 | -3.369 |
| 783 | CB | VAL | 133 | A | -7.014 | -6.965 | -1.472 |
| 784 | CG1 | VAL | 133 | A | -5.786 | -7.825 | -1.195 |
| 785 | CG2 | VAL | 133 | A | -6.799 | -5.522 | -1.123 |
| 786 | N | ARG | 134 | A | -6.278 | -8.372 | -4.493 |
| 787 | CA | ARG | 134 | A | -5.826 | -9.648 | -5.013 |
| 788 | C | ARG | 134 | A | -4.558 | -10.087 | -4.286 |
| 789 | O | ARG | 134 | A | -4.366 | -11.235 | -3.880 |
| 790 | CB | ARG | 134 | A | -5.517 | -9.521 | -6.505 |
| 791 | CG | ARG | 134 | A | -6.403 | -10.251 | -7.540 |
| 792 | CD | ARG | 134 | A | -5.677 | -10.152 | -8.920 |
| 793 | NE | ARG | 134 | A | -6.330 | -10.776 | -10.106 |
| 794 | CZ | ARG | 134 | A | -6.819 | -12.047 | -10.211 |
| 795 | NH1 | ARG | 134 | A | -7.257 | -12.490 | -11.438 |
| 796 | NH2 | ARG | 134 | A | -6.948 | -12.890 | -9.134 |
| 797 | N | ALA | 135 | A | -3.591 | -9.198 | -4.086 |
| 798 | CA | ALA | 135 | A | -2.487 | -9.628 | -3.277 |
| 799 | C | ALA | 135 | A | -1.918 | -8.469 | -2.523 |
| 800 | O | ALA | 135 | A | -2.177 | -7.321 | -2.854 |
| 801 | CB | ALA | 135 | A | -1.466 | -10.268 | -4.196 |
| 802 | N | CYS | 136 | A | -1.126 | -8.787 | -1.485 |
| 803 | CA | CYS | 136 | A | -0.495 | -7.839 | -0.552 |
| 804 | C | CYS | 136 | A | 1.009 | -8.034 | -0.432 |
| 805 | O | CYS | 136 | A | 1.465 | -9.160 | -0.589 |
| 806 | CB | CYS | 136 | A | -0.883 | -7.996 | 0.872 |
| 807 | SG | CYS | 136 | A | -2.530 | -8.641 | 1.107 |
| 808 | N | GLY | 137 | A | 1.790 | -7.010 | -0.149 |
| 809 | CA | GLY | 137 | A | 3.125 | -7.303 | 0.230 |
| 810 | C | GLY | 137 | A | 3.304 | -6.043 | 0.544 |

Fig. 15.18

| ATOM | | RESIDUE | | CHAIN | X | Y | Z |
|---|---|---|---|---|---|---|---|
| 811 | O | GLY | 137 | A | 3.166 | -5.012 | 0.413 |
| 812 | N | CYS | 138 | A | 5.077 | -6.032 | 0.947 |
| 813 | CA | CYS | 138 | A | 5.617 | -4.923 | 1.740 |
| 814 | C | CYS | 138 | A | 6.031 | -3.785 | 0.894 |
| 815 | O | CYS | 138 | A | 6.745 | -4.136 | -0.019 |
| 816 | CB | CYS | 138 | A | 6.815 | -5.368 | 2.504 |
| 817 | SG | CYS | 138 | A | 6.442 | -7.019 | 3.133 |
| 818 | N | HIS | 139 | A | 5.732 | -2.511 | 1.016 |
| 819 | CA | HIS | 139 | A | 6.451 | -1.586 | 0.176 |
| 820 | C | HIS | 139 | A | 6.716 | -0.472 | 1.145 |
| 821 | O | HIS | 139 | A | 5.993 | -0.333 | 2.154 |
| 822 | CB | HIS | 139 | A | 5.651 | -1.066 | -1.031 |
| 823 | CG | HIS | 139 | A | 5.126 | -2.180 | -1.889 |
| 824 | ND1 | HIS | 139 | A | 4.592 | -3.381 | -1.428 |
| 825 | CD2 | HIS | 139 | A | 5.565 | -2.289 | -3.201 |
| 826 | CE1 | HIS | 139 | A | 4.749 | -4.140 | -2.529 |
| 827 | NE2 | HIS | 139 | A | 5.322 | -3.570 | -3.624 |
| 828 | OXT | HIS | 139 | A | 7.321 | 0.362 | 0.777 |
| 829 | N | GLN | 36 | B | -1.316 | 13.234 | 11.930 |
| 830 | CA | GLN | 36 | B | -0.019 | 13.097 | 11.315 |
| 831 | C | GLN | 36 | B | -0.372 | 12.092 | 10.267 |
| 832 | O | GLN | 36 | B | -0.507 | 10.903 | 10.466 |
| 833 | CB | GLN | 36 | B | 0.994 | 12.511 | 12.324 |
| 834 | CG | GLN | 36 | B | 0.822 | 10.996 | 12.674 |
| 835 | CD | GLN | 36 | B | -0.460 | 10.531 | 13.376 |
| 836 | OE1 | GLN | 36 | B | -1.426 | 11.270 | 13.478 |
| 837 | NE2 | GLN | 36 | B | -0.520 | 9.334 | 13.901 |
| 838 | N | ALA | 37 | B | -0.523 | 12.730 | 9.128 |
| 839 | CA | ALA | 37 | B | -1.432 | 12.344 | 8.073 |
| 840 | C | ALA | 37 | B | -0.603 | 11.520 | 7.202 |
| 841 | O | ALA | 37 | B | 0.573 | 11.779 | 7.257 |
| 842 | CB | ALA | 37 | B | -1.894 | 13.588 | 7.326 |
| 843 | N | CYS | 38 | B | -0.971 | 10.577 | 6.394 |
| 844 | CA | CYS | 38 | B | 0.057 | 9.856 | 5.706 |
| 845 | C | CYS | 38 | B | 0.697 | 10.748 | 4.703 |
| 846 | O | CYS | 38 | B | -0.011 | 11.155 | 3.781 |
| 847 | CB | CYS | 38 | B | -0.585 | 8.677 | 5.078 |
| 848 | SG | CYS | 38 | B | 0.292 | 8.306 | 3.618 |
| 849 | N | LYS | 39 | B | 2.000 | 11.027 | 4.892 |
| 850 | CA | LYS | 39 | B | 2.823 | 11.772 | 3.937 |
| 851 | C | LYS | 39 | B | 4.228 | 11.167 | 3.694 |
| 852 | O | LYS | 39 | B | 4.679 | 10.270 | 4.389 |
| 853 | CB | LYS | 39 | B | 2.990 | 13.236 | 4.403 |
| 854 | CG | LYS | 39 | B | 3.093 | 13.354 | 5.921 |
| 855 | CD | LYS | 39 | B | 3.434 | 14.707 | 6.546 |

Fig. 15.19

| ATOM | | RESIDUE | | CHAIN | X | Y | Z |
|---|---|---|---|---|---|---|---|
| 856 | CE | LYS | 39 | B | 3.222 | 14.463 | 8.066 |
| 857 | NZ | LYS | 39 | B | 3.429 | 15.675 | 8.873 |
| 858 | N | LYS | 40 | B | 4.966 | 11.640 | 2.693 |
| 859 | CA | LYS | 40 | B | 6.314 | 11.192 | 2.434 |
| 860 | C | LYS | 40 | B | 7.224 | 11.807 | 3.433 |
| 861 | O | LYS | 40 | B | 6.889 | 12.880 | 3.892 |
| 862 | CB | LYS | 40 | B | 6.814 | 11.640 | 1.096 |
| 863 | CG | LYS | 40 | B | 8.068 | 10.922 | 0.629 |
| 864 | CD | LYS | 40 | B | 8.867 | 11.865 | -0.243 |
| 865 | CE | LYS | 40 | B | 8.006 | 12.488 | -1.310 |
| 866 | NZ | LYS | 40 | B | 8.797 | 13.441 | -2.059 |
| 867 | N | HIS | 41 | B | 8.361 | 11.220 | 3.821 |
| 868 | CA | HIS | 41 | B | 9.283 | 11.844 | 4.760 |
| 869 | C | HIS | 41 | B | 10.701 | 11.549 | 4.352 |
| 870 | O | HIS | 41 | B | 10.914 | 10.791 | 3.425 |
| 871 | CB | HIS | 41 | B | 9.179 | 11.290 | 6.141 |
| 872 | CG | HIS | 41 | B | 7.860 | 11.488 | 6.797 |
| 873 | ND1 | HIS | 41 | B | 7.584 | 12.100 | 7.948 |
| 874 | CD2 | HIS | 41 | B | 6.778 | 10.752 | 6.444 |
| 875 | CE1 | HIS | 41 | B | 6.404 | 11.711 | 8.330 |
| 876 | NE2 | HIS | 41 | B | 5.937 | 10.898 | 7.415 |
| 877 | N | GLU | 42 | B | 11.751 | 12.069 | 4.966 |
| 878 | CA | GLU | 42 | B | 13.094 | 11.965 | 4.415 |
| 879 | C | GLU | 42 | B | 13.878 | 10.810 | 4.901 |
| 880 | O | GLU | 42 | B | 13.613 | 10.301 | 5.969 |
| 881 | CB | GLU | 42 | B | 13.875 | 13.207 | 4.718 |
| 882 | CG | GLU | 42 | B | 13.369 | 14.277 | 3.745 |
| 883 | CD | GLU | 42 | B | 14.490 | 15.264 | 3.400 |
| 884 | OE1 | GLU | 42 | B | 14.161 | 16.446 | 3.123 |
| 885 | OE2 | GLU | 42 | B | 15.681 | 14.846 | 3.405 |
| 886 | N | LEU | 43 | B | 14.868 | 10.303 | 4.208 |
| 887 | CA | LEU | 43 | B | 15.662 | 9.220 | 4.794 |
| 888 | C | LEU | 43 | B | 16.791 | 9.303 | 3.810 |
| 889 | O | LEU | 43 | B | 16.590 | 9.000 | 2.644 |
| 890 | CB | LEU | 43 | B | 15.082 | 7.834 | 4.628 |
| 891 | CG | LEU | 43 | B | 15.121 | 6.808 | 5.726 |
| 892 | CD1 | LEU | 43 | B | 15.317 | 5.447 | 5.064 |
| 893 | CD2 | LEU | 43 | B | 16.201 | 7.098 | 6.734 |
| 894 | N | TYR | 44 | B | 17.960 | 9.706 | 4.244 |
| 895 | CA | TYR | 44 | B | 19.116 | 9.691 | 3.414 |
| 896 | C | TYR | 44 | B | 19.731 | 8.374 | 3.684 |
| 897 | O | TYR | 44 | B | 20.074 | 8.206 | 4.838 |
| 898 | CB | TYR | 44 | B | 19.987 | 10.792 | 3.853 |
| 899 | CG | TYR | 44 | B | 21.075 | 10.941 | 2.875 |
| 900 | CD1 | TYR | 44 | B | 22.293 | 10.457 | 3.244 |

Fig. 15.20

| ATOM | | RESIDUE | CHAIN | X | Y | Z |
|---|---|---|---|---|---|---|
| 901 | CD2 | TYR | 44 | B | 20.850 | 11.476 | 1.648 |
| 902 | CE1 | TYR | 44 | B | 23.318 | 10.366 | 2.365 |
| 903 | CE2 | TYR | 44 | B | 21.874 | 11.387 | 0.757 |
| 904 | CZ | TYR | 44 | B | 23.066 | 10.774 | 1.099 |
| 905 | OH | TYR | 44 | B | 24.015 | 10.452 | 0.125 |
| 906 | N | VAL | 45 | B | 19.912 | 7.407 | 2.784 |
| 907 | CA | VAL | 45 | B | 20.665 | 6.229 | 3.164 |
| 908 | C | VAL | 45 | B | 22.087 | 6.437 | 2.654 |
| 909 | O | VAL | 45 | B | 22.279 | 6.805 | 1.507 |
| 910 | CB | VAL | 45 | B | 20.035 | 5.032 | 2.545 |
| 911 | CG1 | VAL | 45 | B | 20.695 | 3.749 | 2.995 |
| 912 | CG2 | VAL | 45 | B | 18.586 | 5.039 | 2.976 |
| 913 | N | SER | 46 | B | 23.114 | 6.225 | 3.477 |
| 914 | CA | SER | 46 | B | 24.493 | 6.439 | 3.107 |
| 915 | C | SER | 46 | B | 25.038 | 5.102 | 2.862 |
| 916 | O | SER | 46 | B | 24.941 | 4.287 | 3.750 |
| 917 | CB | SER | 46 | B | 25.291 | 7.048 | 4.229 |
| 918 | OG | SER | 46 | B | 26.655 | 7.224 | 3.852 |
| 919 | N | PHE | 47 | B | 25.629 | 4.746 | 1.749 |
| 920 | CA | PHE | 47 | B | 25.991 | 3.376 | 1.514 |
| 921 | C | PRE | 47 | B | 26.978 | 2.852 | 2.491 |
| 922 | O | PHE | 47 | B | 27.217 | 1.663 | 2.537 |
| 923 | CB | PHE | 47 | B | 26.594 | 3.221 | 0.184 |
| 924 | CG | PHE | 47 | B | 25.580 | 3.521 | -0.868 |
| 925 | CD1 | PHE | 47 | B | 24.477 | 2.747 | -0.984 |
| 926 | CD2 | PHE | 47 | B | 25.878 | 4.449 | -1.823 |
| 927 | CE1 | PHE | 47 | B | 23.731 | 2.826 | -2.115 |
| 928 | CE2 | PHE | 47 | B | 25.135 | 4.505 | -2.974 |
| 929 | CZ | PHE | 47 | B | 24.071 | 3.673 | -3.132 |
| 930 | N | ARG | 48 | B | 27.608 | 3.672 | 3.320 |
| 931 | CA | ARG | 48 | B | 28.339 | 3.167 | 4.458 |
| 932 | C | ARG | 48 | B | 27.398 | 2.413 | 5.320 |
| 933 | O | ARG | 48 | B | 27.646 | 1.284 | 5.611 |
| 934 | CB | ARG | 48 | B | 28.954 | 4.292 | 5.278 |
| 935 | CG | ARG | 48 | B | 30.046 | 5.035 | 4.494 |
| 936 | CD | ARG | 48 | B | 30.896 | 5.928 | 5.396 |
| 937 | NE | ARG | 48 | B | 32.154 | 6.274 | 4.756 |
| 938 | CZ | ARG | 48 | B | 32.651 | 7.514 | 4.856 |
| 939 | NH1 | ARG | 48 | B | 31.950 | 8.482 | 5.519 |
| 940 | NH2 | ARG | 48 | B | 33.859 | 7.849 | 4.304 |
| 941 | N | ASP | 49 | B | 26.272 | 2.920 | 5.771 |
| 942 | CA | ASP | 49 | B | 25.514 | 2.260 | 6.816 |
| 943 | C | ASP | 49 | B | 24.987 | 0.889 | 6.405 |
| 944 | O | ASP | 49 | B | 24.545 | 0.069 | 7.199 |
| 945 | CB | ASP | 49 | B | 24.328 | 3.105 | 7.229 |

Fig. 15.21

| ATOM | | RESIDUE | | CHAIN | X | Y | Z |
|---|---|---|---|---|---|---|---|
| 946 | CG | ASP | 49 | B | 24.718 | 4.526 | 7.549 |
| 947 | OD1 | ASP | 49 | B | 23.837 | 5.362 | 7.347 |
| 948 | OD2 | ASP | 49 | B | 25.851 | 4.840 | 7.969 |
| 949 | N | LEU | 50 | B | 25.005 | 0.563 | 5.125 |
| 950 | CA | LEU | 50 | B | 24.555 | -0.751 | 4.716 |
| 951 | C | LEU | 50 | B | 25.746 | -1.589 | 4.430 |
| 952 | O | LEU | 50 | B | 25.685 | -2.699 | 3.895 |
| 953 | CB | LEU | 50 | B | 23.706 | -0.649 | 3.461 |
| 954 | CG | LEU | 50 | B | 22.524 | 0.294 | 3.611 |
| 955 | CD1 | LEU | 50 | B | 22.301 | 0.924 | 2.257 |
| 956 | CD2 | LEU | 50 | B | 21.289 | -0.430 | 4.147 |
| 957 | N | GLY | 51 | B | 26.887 | -1.028 | 4.780 |
| 958 | CA | GLY | 51 | B | 28.143 | -1.664 | 4.485 |
| 959 | C | GLY | 51 | B | 28.483 | -1.605 | 3.017 |
| 960 | O | GLY | 51 | B | 29.593 | -1.964 | 2.642 |
| 961 | N | TRP | 52 | B | 27.628 | -1.178 | 2.086 |
| 962 | CA | TRP | 52 | B | 28.069 | -1.113 | 0.692 |
| 963 | C | TRP | 52 | B | 29.287 | -0.215 | 0.418 |
| 964 | O | TRP | 52 | B | 29.372 | 0.385 | -0.629 |
| 965 | CB | TRP | 52 | B | 26.856 | -0.656 | -0.156 |
| 966 | CG | TRP | 52 | B | 25.726 | -1.702 | -0.123 |
| 967 | CD1 | TRP | 52 | B | 25.857 | -2.997 | 0.341 |
| 968 | CD2 | TRP | 52 | B | 24.335 | -1.394 | -0.582 |
| 969 | NE1 | TRP | 52 | B | 24.672 | -3.554 | 0.236 |
| 970 | CE2 | TRP | 52 | B | 23.731 | -2.740 | -0.270 |
| 971 | CE3 | TRP | 52 | B | 23.505 | -0.402 | -1.076 |
| 972 | CZ2 | TRP | 52 | B | 22.376 | -2.951 | -0.421 |
| 973 | CZ3 | TRP | 52 | B | 22.157 | -0.672 | -1.220 |
| 974 | CH2 | TRP | 52 | B | 21.604 | -1.908 | -0.885 |
| 975 | N | GLN | 53 | B | 30.313 | -0.015 | 1.236 |
| 976 | CA | GLN | 53 | B | 30.998 | 1.273 | 1.141 |
| 977 | C | GLN | 53 | B | 32.040 | 1.358 | 0.116 |
| 978 | O | GLN | 53 | B | 32.702 | 2.374 | -0.014 |
| 979 | CB | GLN | 53 | B | 31.742 | 1.728 | 2.405 |
| 980 | CG | GLN | 53 | B | 31.993 | 0.649 | 3.446 |
| 981 | CD | GLN | 53 | B | 33.274 | 0.967 | 4.237 |
| 982 | OE1 | GLN | 53 | B | 34.189 | 0.121 | 4.274 |
| 983 | NE2 | GLN | 53 | B | 33.399 | 2.156 | 4.889 |
| 984 | N | ASP | 54 | B | 32.235 | 0.306 | -0.647 |
| 985 | CA | ASP | 54 | B | 33.600 | -0.101 | -0.948 |
| 986 | C | ASP | 54 | B | 33.381 | -0.824 | -2.214 |
| 987 | O | ASP | 54 | B | 33.245 | -2.036 | -2.082 |
| 988 | CB | ASP | 54 | B | 34.116 | -1.083 | 0.114 |
| 989 | CG | ASP | 54 | B | 32.963 | -1.909 | 0.747 |
| 990 | OD1 | ASP | 54 | B | 33.101 | -2.317 | 1.928 |

Fig. 15.22

| ATOM | RESIDUE | CHAIN | X | Y | Z |
|---|---|---|---|---|---|
| 991 | OD2 | ASP 54 | B | 31.940 | -2.112 | 0.062 |
| 992 | N | TRP 55 | B | 33.314 | -0.266 | -3.427 |
| 993 | CA | TRP 55 | B | 32.570 | -1.004 | -4.476 |
| 994 | C | TRP 55 | B | 32.019 | -0.003 | -5.421 |
| 995 | O | TRP 55 | B | 32.165 | -0.187 | -6.621 |
| 996 | CB | TRP 55 | B | 31.258 | -1.689 | -4.123 |
| 997 | CG | TRP 55 | B | 31.339 | -3.126 | -3.756 |
| 998 | CD1 | TRP 55 | B | 32.336 | -4.015 | -4.070 |
| 999 | CD2 | TRP 55 | B | 30.132 | -3.715 | -3.105 |
| 1000 | NE1 | TRP 55 | B | 31.855 | -5.199 | -3.695 |
| 1001 | CE2 | TRP 55 | B | 30.594 | -5.172 | -3.148 |
| 1002 | CE3 | TRP 55 | B | 28.951 | -3.382 | -2.460 |
| 1003 | CZ2 | TRP 55 | B | 29.753 | -6.141 | -2.581 |
| 1004 | CZ3 | TRP 55 | B | 28.177 | -4.393 | -1.896 |
| 1005 | CH2 | TRP 55 | B | 28.549 | -5.738 | -1.967 |
| 1006 | N | ILE 56 | B | 31.399 | 1.020 | -4.769 |
| 1007 | CA | ILE 56 | B | 30.572 | 2.056 | -5.356 |
| 1008 | C | ILE 56 | B | 31.459 | 3.266 | -5.650 |
| 1009 | O | ILE 56 | B | 32.148 | 3.707 | -4.741 |
| 1010 | CB | ILE 56 | B | 29.469 | 2.363 | -4.346 |
| 1011 | CG1 | ILE 56 | B | 28.247 | 1.655 | -4.774 |
| 1012 | CG2 | ILE 56 | B | 29.164 | 3.835 | -4.244 |
| 1013 | CD1 | ILE 56 | B | 28.212 | 0.333 | -4.085 |
| 1014 | N | ILE 57 | B | 31.511 | 3.841 | -6.857 |
| 1015 | CA | ILE 57 | B | 32.213 | 5.100 | -7.039 |
| 1016 | C | ILE 57 | B | 31.178 | 6.206 | -6.753 |
| 1017 | O | ILE 57 | B | 31.414 | 7.392 | -6.654 |
| 1018 | CB | ILE 57 | B | 32.735 | 5.162 | -8.493 |
| 1019 | CG1 | ILE 57 | B | 33.659 | 4.001 | -8.726 |
| 1020 | CG2 | ILE 57 | B | 33.527 | 6.433 | -8.784 |
| 1021 | CD1 | ILE 57 | B | 34.001 | 4.036 | -10.220 |
| 1022 | N | ALA 58 | B | 29.934 | 5.831 | -6.570 |
| 1023 | CA | ALA 58 | B | 28.802 | 5.950 | -7.504 |
| 1024 | C | ALA 58 | B | 28.040 | 7.166 | -7.145 |
| 1025 | O | ALA 58 | B | 28.524 | 8.150 | -7.690 |
| 1026 | CB | ALA 58 | B | 27.934 | 4.732 | -7.338 |
| 1027 | N | PRO 59 | B | 26.999 | 7.188 | -6.358 |
| 1028 | CA | PRO 59 | B | 26.820 | 8.263 | -5.382 |
| 1029 | C | PRO 59 | B | 27.333 | 7.862 | -4.008 |
| 1030 | O | PRO 59 | B | 27.512 | 6.698 | -3.744 |
| 1031 | CB | PRO 59 | B | 25.317 | 8.611 | -5.384 |
| 1032 | CG | PRO 59 | B | 24.697 | 7.280 | -5.680 |
| 1033 | CD | PRO 59 | B | 25.659 | 6.734 | -6.707 |
| 1034 | N | GLU 60 | B | 27.622 | 8.703 | -3.030 |
| 1035 | CA | GLU 60 | B | 27.941 | 8.146 | -1.719 |

Fig. 15.23

| ATOM | RESIDUE | CHAIN | X | Y | Z |
|---|---|---|---|---|---|
| 1036 C | GLU 60 | B | 26.735 | 7.734 | -0.926 |
| 1037 O | GLU 60 | B | 26.813 | 7.132 | 0.131 |
| 1038 CB | GLU 60 | B | 28.74S | 9.151 | -0.867 |
| 1039 CG | GLU 60 | B | 27.995 | 10.280 | -0.117 |
| 1040 CD | GLU 60 | B | 27.231 | 9.868 | 1.144 |
| 1041 OE1 | GLU 60 | B | 27.559 | 8.834 | 1.775 |
| 1042 OE2 | GLU 60 | B | 26.329 | 10.634 | 1.518 |
| 1043 N | GLY 61 | B | 25.552 | 8.049 | -1.395 |
| 1044 CA | GLY 61 | B | 24.342 | 7.623 | -0.733 |
| 1045 C | GLY 61 | B | 23.253 | 8.252 | -1.519 |
| 1046 O | GLY 61 | B | 23.535 | 8.769 | -2.595 |
| 1047 N | TYR 62 | B | 22.021 | 8.246 | -1.038 |
| 1048 CA | TYR 62 | B | 20.934 | 8.777 | -1.830 |
| 1049 C | TYR 62 | B | 19.767 | 9.046 | -0.932 |
| 1050 O | TYR 62 | B | 19.796 | 8.647 | 0.217 |
| 1051 CB | TYR 62 | B | 20.608 | 7.745 | -2.889 |
| 1052 CG | TYR 62 | B | 19.833 | 6.572 | -2.370 |
| 1053 CD1 | TYR 62 | B | 20.425 | 5.395 | -1.917 |
| 1054 CD2 | TYR 62 | B | 18.481 | 6.692 | -2.472 |
| 1055 CE1 | TYR 62 | B | 19.624 | 4.316 | -1.563 |
| 1056 CE2 | TYR 62 | B | 17.692 | 5.644 | -2.132 |
| 1057 CZ | TYR 62 | B | 18.249 | 4.475 | -1.681 |
| 1058 OH | TYR 62 | B | 17.341 | 3.468 | -1.352 |
| 1059 N | ALA 63 | B | 18.720 | 9.711 | -1.407 |
| 1060 CA | ALA 63 | B | 17.474 | 9.863 | -0.693 |
| 1061 C | ALA 63 | B | 16.485 | 8.722 | -0.918 |
| 1062 O | ALA 63 | B | 15.903 | 8.617 | -1.981 |
| 1063 CB | ALA 63 | B | 16.899 | 11.151 | -1.155 |
| 1064 N | ALA 64 | B | 16.262 | 7.847 | 0.047 |
| 1065 CA | ALA 64 | B | 15.293 | 6.793 | -0.077 |
| 1066 C | ALA 64 | B | 13.847 | 7.203 | 0.227 |
| 1067 O | ALA 64 | B | 12.851 | 6.701 | -0.265 |
| 1068 CB | ALA 64 | B | 15.695 | 5.679 | 0.866 |
| 1069 N | TYR 65 | B | 13.710 | 8.191 | 1.098 |
| 1070 CA | TYR 65 | B | 12.454 | 8.570 | 1.709 |
| 1071 C | TYR 65 | B | 11.742 | 7.437 | 2.314 |
| 1072 O | TYR 65 | B | 12.101 | 6.294 | 2.178 |
| 1073 CB | TYR 65 | B | 11.531 | 9.231 | 0.716 |
| 1074 CG | TYR 65 | B | 12.088 | 10.513 | 0.168 |
| 1075 CD1 | TYR 65 | B | 12.540 | 11.505 | 0.984 |
| 1076 CD2 | TYR 65 | B | 12.170 | 10.655 | -1.176 |
| 1077 CE1 | TYR 65 | B | 13.147 | 12.614 | 0.454 |
| 1078 CE2 | TYR 65 | B | 12.771 | 11.751 | -1.721 |
| 1079 CZ | TYR 65 | B | 13.282 | 12.701 | -0.902 |
| 1080 OH | TYR 65 | B | 13.974 | 13.762 | -1.462 |

Fig. 15.24

| ATOM | | RESIDUE | CHAIN | X | Y | Z |
|---|---|---|---|---|---|---|
| 1081 | N | TYR 66 | B | 10.697 | 7.722 | 3.031 |
| 1082 | CA | TYR 66 | B | 9.852 | 6.661 | 3.471 |
| 1083 | C | TYR 66 | B | 8.541 | 7.291 | 3.740 |
| 1084 | O | TYR 66 | B | 8.435 | 8.508 | 3.867 |
| 1085 | CB | TYR 66 | B | 10.389 | 5.996 | 4.739 |
| 1086 | CG | TYR 66 | B | 10.325 | 6.790 | 6.014 |
| 1087 | CD1 | TYR 66 | B | 11.182 | 7.824 | 6.193 |
| 1088 | CD2 | TYR 66 | B | 9.448 | 6.427 | 7.006 |
| 1089 | CE1 | TYR 66 | B | 11.162 | 8.514 | 7.369 |
| 1090 | CE2 | TYR 66 | B | 9.415 | 7.105 | 8.185 |
| 1091 | CZ | TYR 66 | B | 10.273 | 8.151 | 8.343 |
| 1092 | OR | TYR 66 | B | 10.254 | 8.912 | 9.507 |
| 1093 | N | CYS 67 | B | 7.523 | 6.461 | 3.838 |
| 1094 | CA | CYS 67 | B | 6.157 | 6.944 | 3.974 |
| 1095 | C | CYS 67 | B | 5.600 | 6.711 | 5.382 |
| 1096 | O | CYS 67 | B | 5.660 | 5.589 | 5.909 |
| 1097 | CB | CYS 67 | B | 5.210 | 6.219 | 3.078 |
| 1098 | SG | CYS 67 | B | 5.398 | 6.240 | 1.331 |
| 1099 | N | GLU 68 | B | 5.026 | 7.712 | 6.056 |
| 1100 | CA | GLU 68 | B | 4.554 | 7.337 | 7.342 |
| 1101 | C | GLU 68 | B | 3.507 | 8.263 | 7.751 |
| 1102 | O | GLU 68 | B | 3.670 | 9.457 | 7.509 |
| 1103 | CB | GLU 68 | B | 5.639 | 7.411 | 8.360 |
| 1104 | CG | GLU 68 | B | 5.322 | 6.494 | 9.510 |
| 1105 | CD | GLU 68 | B | 6.024 | 7.006 | 10.718 |
| 1106 | OE1 | GLU 68 | B | 6.127 | 6.266 | 11.697 |
| 1107 | OE2 | GLU 68 | B | 6.475 | 8.154 | 10.689 |
| 1108 | N | GLY 69 | B | 2.450 | 7.734 | 8.369 |
| 1109 | CA | GLY 69 | B | 1.458 | 8.577 | 9.002 |
| 1110 | C | GLY 69 | B | 0.123 | 7.873 | 8.939 |
| 1111 | O | GLY 69 | B | 0.019 | 6.722 | 8.517 |
| 1112 | N | GLU 70 | B | -0.962 | 8.499 | 9.336 |
| 1113 | CA | GLU 70 | B | -2.120 | 7.685 | 9.616 |
| 1114 | C | GLU 70 | B | -3.133 | 7.672 | 8.511 |
| 1115 | O | GLU 70 | B | -3.372 | 8.697 | 7.898 |
| 1116 | CB | GLU 70 | B | -2.769 | 8.180 | 10.882 |
| 1117 | CG | GLU 70 | B | -2.975 | 6.949 | 11.748 |
| 1118 | CD | GLU 70 | B | -4.167 | 7.206 | 12.630 |
| 1119 | OE1 | GLU 70 | B | -4.866 | 6.234 | 12.949 |
| 1120 | OE2 | GLU 70 | B | -4.412 | 8.381 | 12.984 |
| 1121 | N | CYS 71 | B | -3.757 | 6.544 | 8.233 |
| 1122 | CA | CYS 71 | B | -4.817 | 6.538 | 7.262 |
| 1123 | C | CYS 71 | B | -6.205 | 6.516 | 7.840 |
| 1124 | O | CYS 71 | B | -6.730 | 5.505 | 8.245 |
| 1125 | CB | CYS 71 | B | -4.553 | 5.350 | 6.377 |

Fig. 15.25

| ATOM | RESIDUE | CHAIN | X | Y | Z |
|---|---|---|---|---|---|
| 1126 SG | CYS 71 | B | -3.363 | 5.857 | 5.112 |
| 1127 N | ALA 72 | B | -6.909 | 7.619 | 7.924 |
| 1128 CA | ALA 72 | B | -8.091 | 7.666 | 8.737 |
| 1129 C | ALA 72 | B | -8.935 | 8.777 | 8.184 |
| 1130 O | ALA 72 | B | -8.438 | 9.590 | 7.418 |
| 1131 CB | ALA 72 | B | -7.646 | 7.939 | 10.149 |
| 1132 N | PHE 73 | B | -10.225 | 8.934 | 8.471 |
| 1133 CA | PHE 73 | B | -10.963 | 9.998 | 7.782 |
| 1134 C | PHE 73 | B | -10.507 | 11.313 | 8.342 |
| 1135 O | PHE 73 | B | -10.291 | 11.328 | 9.544 |
| 1136 CB | PHE 73 | B | -12.492 | 9.874 | 7.997 |
| 1137 CG | PHE 73 | B | -13.023 | 8.690 | 7.235 |
| 1138 CD1 | PHE 73 | B | -13.009 | 8.688 | 5.873 |
| 1139 CD2 | PHE 73 | B | -13.514 | 7.616 | 7.919 |
| 1140 CE1 | PHE 73 | B | -13.473 | 7.602 | 5.190 |
| 1141 CE2 | PHE 73 | B | -13.992 | 6.528 | 7.214 |
| 1142 CZ | PHE 73 | B | -13.969 | 6.518 | 5.854 |
| 1143 N | PRO 74 | B | -10.337 | 12.410 | 7.712 |
| 1144 CA | PRO 74 | B | -10.748 | 12.685 | 6.357 |
| 1145 C | PRO 74 | B | -9.754 | 12.033 | 5.502 |
| 1146 O | PRO 74 | B | -8.656 | 12.529 | 5.443 |
| 1147 CB | PRO 74 | B | -10.712 | 14.168 | 6.197 |
| 1148 CG | PRO 74 | B | -10.432 | 14.652 | 7.611 |
| 1149 CD | PRO 74 | B | -9.662 | 13.546 | 8.313 |
| 1150 N | LEU 75 | B | -10.018 | 10.938 | 4.799 |
| 1151 CA | LEU 75 | B | -9.091 | 10.355 | 3.845 |
| 1152 C | LEU 75 | B | -9.061 | 11.400 | 2.779 |
| 1153 O | LEU 75 | B | -9.752 | 11.427 | 1.772 |
| 1154 CB | LEU 75 | B | -9.674 | 9.034 | 3.355 |
| 1155 CG | LEU 75 | B | -8.684 | 7.913 | 3.407 |
| 1156 CD1 | LEU 75 | B | -7.689 | 8.120 | 4.525 |
| 1157 CD2 | LEU 75 | B | -9.442 | 6.631 | 3.626 |
| 1158 N | ASN 76 | B | -8.181 | 12.333 | 3.059 |
| 1159 CA | ASN 76 | B | -8.098 | 13.558 | 2.311 |
| 1160 C | ASN 76 | B | -7.517 | 13.432 | 0.887 |
| 1161 O | ASN 76 | B | -6.525 | 14.065 | 0.596 |
| 1162 CB | ASN 76 | B | -7.310 | 14.402 | 3.255 |
| 1163 CG | ASN 76 | B | -7.466 | 15.837 | 2.965 |
| 1164 OD1 | ASN 76 | B | -7.449 | 16.655 | 3.894 |
| 1165 ND2 | ASN 76 | B | -7.521 | 16.219 | 1.674 |
| 1166 N | SER 77 | B | -8.021 | 12.652 | -0.088 |
| 1167 CA | SER 77 | B | -7.673 | 12.747 | -1.523 |
| 1168 C | SER 77 | B | -6.200 | 12.824 | -1.891 |
| 1169 O | SER 77 | B | -5.587 | 11.803 | -2.261 |
| 1170 CB | SER 77 | B | -8.354 | 13.964 | -2.171 |

Fig. 15.26

| ATOM | RESIDUE | CHAIN | X | Y | Z |
|---|---|---|---|---|---|
| 1171 OG | SER 77 | B | -7.957 | 15.177 | -1.532 |
| 1172 N | TYR 78 | B | -5.531 | 13.986 | -1.819 |
| 1173 CA | TYR 78 | B | -4.098 | 13.882 | -1.965 |
| 1174 C | TYR 78 | B | -3.490 | 13.159 | -0.764 |
| 1175 O | TYR 78 | B | -2.585 | 13.733 | -0.185 |
| 1176 CB | TYR 78 | B | -3.438 | 15.241 | -2.045 |
| 1177 CG | TYR 78 | B | -2.916 | 15.632 | -3.429 |
| 1178 CD1 | TYR 78 | B | -1.897 | 16.590 | -3.392 |
| 1179 CD2 | TYR 78 | B | -3.617 | 15.385 | -4.630 |
| 1180 CE1 | TYR 78 | B | -1.737 | 17.490 | -4.438 |
| 1181 CE2 | TYR 78 | B | -3.456 | 16.292 | -5.692 |
| 1182 CZ | TYR 78 | B | -2.610 | 17.403 | -5.516 |
| 1183 OH | TYR 78 | B | -2.715 | 18.527 | -6.319 |
| 1184 N | MET 79 | B | -3.978 | 11.959 | -0.393 |
| 1185 CA | MET 79 | B | -3.388 | 10.933 | 0.448 |
| 1186 C | MET 79 | B | -3.689 | 9.603 | -0.251 |
| 1187 O | MET 79 | B | -3.734 | 8.505 | 0.285 |
| 1188 CB | MET 79 | B | -4.031 | 10.775 | 1.776 |
| 1189 CG | MET 79 | B | -4.050 | 11.928 | 2.741 |
| 1190 SD | MET 79 | B | -4.737 | 11.135 | 4.215 |
| 1191 CE | MET 79 | B | -4.910 | 12.550 | 5.255 |
| 1192 N | ASN 80 | B | -3.926 | 9.699 | -1.544 |
| 1193 CA | ASN 80 | B | -4.199 | 8.581 | -2.401 |
| 1194 C | ASN 80 | B | -5.079 | 7.439 | -1.962 |
| 1195 O | ASN 80 | B | -4.924 | 6.364 | -2.490 |
| 1196 CB | ASN 80 | B | -2.883 | 7.967 | -2.894 |
| 1197 CG | ASN 80 | B | -3.155 | 7.090 | -4.121 |
| 1198 OD1 | ASN 80 | B | -3.135 | 5.844 | -4.162 |
| 1199 ND2 | ASN 80 | B | -3.543 | 7.769 | -5.198 |
| 1200 N | ALA 81 | B | -6.051 | 7.407 | -1.058 |
| 1201 CA | ALA 81 | B | -7.299 | 6.757 | -1.424 |
| 1202 C | ALA 81 | B | -7.486 | 5.344 | -1.928 |
| 1203 O | ALA 81 | B | -8.004 | 4.449 | -1.302 |
| 1204 CB | ALA 81 | B | -8.004 | 7.624 | -2.452 |
| 1205 N | THR 82 | B | -7.106 | 4.970 | -3.106 |
| 1206 CA | THR 82 | B | -7.875 | 3.957 | -3.819 |
| 1207 C | THR 82 | B | -9.402 | 3.970 | -3.655 |
| 1208 O | THR 82 | B | -10.075 | 4.641 | -4.444 |
| 1209 CB | THR 82 | B | -7.505 | 2.477 | -3.539 |
| 1210 OG1 | THR 82 | B | -7.534 | 2.217 | -2.163 |
| 1211 CG2 | THR 82 | B | -6.211 | 2.155 | -4.224 |
| 1212 N | ASN 83 | B | -10.043 | 3.286 | -2.697 |
| 1213 CA | ASN 83 | B | -11.462 | 2.977 | -2.877 |
| 1214 C | ASN 83 | B | -11.670 | 1.861 | -1.963 |
| 1215 O | ASN 83 | B | -12.472 | 1.858 | -1.070 |

Fig. 15.27

| ATOM | | RESIDUE | CHAIN | X | Y | Z |
|---|---|---|---|---|---|---|
| 1216 | CB | ASN 83 | B | -11.835 | 2.404 | -4.195 |
| 1217 | CG | ASN 83 | B | -12.710 | 3.302 | -4.983 |
| 1218 | OD1 | ASN 83 | B | -13.343 | 2.872 | -5.931 |
| 1219 | ND2 | ASN 83 | B | -12.741 | 4.594 | -4.715 |
| 1220 | N | HIS 84 | B | -10.950 | 0.775 | -2.095 |
| 1221 | CA | HIS 84 | B | -10.823 | -0.192 | -1.024 |
| 1222 | C | HIS 84 | B | -10.284 | 0.531 | 0.167 |
| 1223 | O | HIS 84 | B | -10.623 | 0.097 | 1.245 |
| 1224 | CB | HIS 84 | B | -9.851 | -1.284 | -1.397 |
| 1225 | CG | HIS 84 | B | -9.778 | -2.364 | -0.370 |
| 1226 | ND1 | HIS 84 | B | -9.014 | -2.402 | 0.711 |
| 1227 | CD2 | HIS 84 | B | -10.397 | -3.578 | -0.489 |
| 1228 | CE1 | HIS 84 | B | -9.153 | -3.590 | 1.235 |
| 1229 | NE2 | HIS 84 | B | -9.960 | -4.294 | 0.507 |
| 1230 | N | ALA 85 | B | -9.464 | 1.589 | 0.169 |
| 1231 | CA | ALA 85 | B | -9.158 | 2.136 | 1.455 |
| 1232 | C | ALA 85 | B | -10.314 | 2.915 | 1.965 |
| 1233 | O | ALA 85 | B | -10.388 | 3.113 | 3.155 |
| 1234 | CB | ALA 85 | B | -7.958 | 3.026 | 1.398 |
| 1235 | N | ILE 86 | B | -11.298 | 3.418 | 1.242 |
| 1236 | CA | ILE 86 | B | -12.366 | 4.096 | 1.919 |
| 1237 | C | ILE 86 | B | -13.219 | 2.964 | 2.461 |
| 1238 | O | ILE 86 | B | -13.597 | 3.036 | 3.590 |
| 1239 | CB | ILE 86 | B | -13.058 | 4.975 | 0.897 |
| 1240 | CG1 | ILE 86 | B | -12.035 | 5.957 | 0.299 |
| 1241 | CG2 | ILE 86 | B | -14.230 | 5.699 | 1.565 |
| 1242 | CD1 | ILE 86 | B | -12.568 | 7.113 | -0.547 |
| 1243 | N | VAL 87 | B | -13.596 | 1.857 | 1.829 |
| 1244 | CA | VAL 87 | B | -14.315 | 0.785 | 2.493 |
| 1245 | C | VAL 87 | B | -13.560 | 0.425 | 3.744 |
| 1246 | O | VAL 87 | B | -14.049 | 0.656 | 4.828 |
| 1247 | CB | VAL 87 | B | -14.432 | -0.429 | 1.553 |
| 1248 | CG1 | VAL 87 | B | -14.652 | -1.712 | 2.308 |
| 1249 | CG2 | VAL 87 | B | -15.617 | -0.236 | 0.637 |
| 1250 | N | GLN 88 | B | -12.358 | -0.137 | 3.734 |
| 1251 | CA | GLN 88 | B | -11.706 | -0.524 | 4.975 |
| 1252 | C | GLN 88 | B | -11.666 | 0.574 | 6.022 |
| 1253 | O | GLN 88 | B | -11.943 | 0.280 | 7.170 |
| 1254 | CB | GLN 88 | B | -10.295 | -0.941 | 4.697 |
| 1255 | CG | GLN 88 | B | -9.864 | -2.322 | 5.125 |
| 1256 | CD | GLN 88 | B | -8.398 | -2.237 | 5.020 |
| 1257 | OE1 | GLN 88 | B | -7.618 | -2.317 | 5.944 |
| 1258 | NE2 | GLN 88 | B | -7.922 | -1.853 | 3.852 |
| 1259 | N | THR 89 | B | -11.347 | 1.833 | 5.754 |
| 1260 | CA | THR 89 | B | -11.401 | 2.802 | 6.790 |

Fig. 15.28

| ATOM | RESIDUE | CHAIN | X | Y | Z |
|---|---|---|---|---|---|
| 1261 C | THR 89 | B | -12.805 | 2.953 | 7.298 |
| 1262 O | THR 89 | B | -12.966 | 3.090 | 8.499 |
| 1263 CB | THR 89 | B | -10.923 | 4.081 | 6.270 |
| 1264 OG1 | THR 89 | B | -9.628 | 3.792 | 5.879 |
| 1265 CG2 | THR 89 | B | -10.741 | 5.183 | 7.270 |
| 1266 N | LEU 90 | B | -13.888 | 2.943 | 6.506 |
| 1267 CA | LEU 90 | B | -15.260 | 2.885 | 7.003 |
| 1268 C | LEU 90 | B | -15.550 | 1.649 | 7.814 |
| 1269 O | LEU 90 | B | -16.030 | 1.727 | 8.929 |
| 1270 CB | LEU 90 | B | -16.220 | 2.893 | 5.853 |
| 1271 CG | LEU 90 | B | -17.670 | 3.011 | 6.158 |
| 1272 CD1 | LEU 90 | B | -17.933 | 4.270 | 6.954 |
| 1273 CD2 | LEU 90 | B | -18.406 | 3.003 | 4.837 |
| 1274 N | VAL 91 | B | -15.296 | 0.449 | 7.333 |
| 1275 CA | VAL 91 | B | -15.459 | -0.745 | 8.132 |
| 1276 C | VAL 91 | B | -14.637 | -0.671 | 9.387 |
| 1277 O | VAL 91 | B | -14.959 | -1.278 | 10.398 |
| 1278 CB | VAL 91 | B | -15.049 | -1.923 | 7.308 |
| 1279 CG1 | VAL 91 | B | -14.917 | -3.200 | 8.111 |
| 1280 CG2 | VAL 91 | B | -16.122 | -2.071 | 6.250 |
| 1281 N | HIS 92 | B | -13.533 | 0.068 | 9.434 |
| 1282 CA | HIS 92 | B | -12.818 | 0.180 | 10.702 |
| 1283 C | HIS 92 | B | -13.719 | 0.784 | 11.705 |
| 1284 O | HIS 92 | B | -13.859 | 0.310 | 12.797 |
| 1285 CB | HIS 92 | B | -11.577 | 1.095 | 10.619 |
| 1286 CG | HIS 92 | B | -10.675 | 0.908 | 11.812 |
| 1287 ND1 | HIS 92 | B | -10.106 | 1.714 | 12.701 |
| 1288 CD2 | HIS 92 | B | -10.314 | -0.348 | 12.142 |
| 1289 CE1 | HIS 92 | B | -9.454 | 0.950 | 13.527 |
| 1290 NE2 | HIS 92 | B | -9.602 | -0.300 | 13.197 |
| 1291 N | PHE 93 | B | -14.364 | 1.854 | 11.358 |
| 1292 CA | PHE 93 | B | -15.148 | 2.645 | 12.248 |
| 1293 C | PHE 93 | B | -16.394 | 1.899 | 12.634 |
| 1294 O | PHE 93 | B | -16.782 | 1.756 | 13.777 |
| 1295 CB | PHE 93 | B | -15.365 | 3.894 | 11.461 |
| 1296 CG | PHE 93 | B | -16.515 | 4.726 | 11.911 |
| 1297 CD1 | PHE 93 | B | -17.812 | 4.330 | 11.649 |
| 1298 CD2 | PHE 93 | B | -16.248 | 5.977 | 12.448 |
| 1299 CE1 | PHE 93 | B | -18.832 | 5.210 | 11.890 |
| 1300 CE2 | PHE 93 | B | -17.282 | 6.860 | 12.670 |
| 1301 CZ | PHE 93 | B | -18.564 | 6.467 | 12.386 |
| 1302 N | ILE 94 | B | -17.172 | 1.345 | 11.730 |
| 1303 CA | ILE 94 | B | -18.251 | 0.460 | 12.158 |
| 1304 C | ILE 94 | B | -17.714 | -0.589 | 13.105 |
| 1305 O | ILE 94 | B | -18.482 | -1.254 | 13.758 |

Fig. 15.29

| ATOM | RESIDUE | CHAIN | X | Y | Z |
|---|---|---|---|---|---|
| 1306 CB | ILE 94 | B | -18.808 | -0.124 | 10.880 |
| 1307 CG1 | ILE 94 | B | -19.580 | 1.028 | 10.342 |
| 1308 CG2 | ILE 94 | B | -19.648 | -1.375 | 10.977 |
| 1309 CD1 | ILE 94 | B | -19.872 | 0.740 | 8.877 |
| 1310 N | ASN 95 | B | -16.410 | -0.839 | 13.277 |
| 1311 CA | ASN 95 | B | -16.013 | -2.092 | 13.873 |
| 1312 C | ASN 95 | B | -14.529 | -2.322 | 14.157 |
| 1313 O | ASN 95 | B | -13.858 | -3.248 | 13.673 |
| 1314 CB | ASN 95 | B | -16.495 | -3.208 | 12.993 |
| 1315 CG | ASN 95 | B | -16.663 | -4.358 | 13.942 |
| 1316 OD1 | ASN 95 | B | -16.021 | -4.431 | 15.007 |
| 1317 ND2 | ASN 95 | B | -17.547 | -5.309 | 13.564 |
| 1318 N | PRO 96 | B | -13.981 | -1.497 | 14.982 |
| 1319 CA | PRO 96 | B | -12.565 | -1.248 | 15.087 |
| 1320 C | PRO 96 | B | -11.697 | -2.421 | 15.300 |
| 1321 O | PRO 96 | B | -10.491 | -2.366 | 15.067 |
| 1322 CB | PRO 96 | B | -12.426 | -0.227 | 16.199 |
| 1323 CG | PRO 96 | B | -13.819 | 0.347 | 16.282 |
| 1324 CD | PRO 96 | B | -14.625 | -0.944 | 16.151 |
| 1325 N | GLU 97 | B | -12.338 | -3.478 | 15.747 |
| 1326 CA | GLU 97 | B | -11.625 | -4.700 | 15.963 |
| 1327 C | GLU 97 | B | -11.796 | -5.472 | 14.691 |
| 1328 O | GLU 97 | B | -10.808 | -5.919 | 14.166 |
| 1329 CB | GLU 97 | B | -12.209 | -5.474 | 17.153 |
| 1330 CG | GLU 97 | B | -11.332 | -5.321 | 18.423 |
| 1331 CD | GLU 97 | B | -11.552 | -3.957 | 19.136 |
| 1332 OE1 | GLU 97 | B | -12.507 | -3.902 | 19.971 |
| 1333 OE2 | GLU 97 | B | -10.781 | -2.974 | 18.873 |
| 1334 N | THR 98 | a | -12.921 | -5.722 | 14.047 |
| 1335 CA | THR 98 | B | -12.848 | -6.579 | 12.862 |
| 1336 C | THR 98 | B | -11.921 | -6.174 | 11.682 |
| 1337 O | THR 98 | B | -11.787 | -7.035 | 10.815 |
| 1338 CB | THR 98 | B | -14.289 | -6.757 | 12.349 |
| 1339 OG1 | THR 98 | B | -14.841 | -5.463 | 12.337 |
| 1340 CG2 | THR 98 | B | -15.226 | -7.552 | 13.281 |
| 1341 N | VAL 99 | B | -11.255 | -5.008 | 11.488 |
| 1342 CA | VAL 99 | B | -10.426 | -4.763 | 10.307 |
| 1343 C | VAL 99 | B | -9.447 | -3.636 | 10.637 |
| 1344 O | VAL 99 | B | -9.956 | -2.741 | 11.289 |
| 1345 CB | VAL 99 | B | -11.316 | -4.375 | 9.112 |
| 1346 CG1 | VAL 99 | B | -11.405 | -2.876 | 8.750 |
| 1347 CG2 | VAL 99 | B | -10.670 | -5.076 | 7.950 |
| 1348 N | PRO 100 | B | -8.179 | -3.588 | 10.300 |
| 1349 CA | PRO 100 | B | -7.213 | -2.555 | 10.669 |
| 1350 C | PRO 100 | B | -7 409 | -1.258 | 10.007 |

Fig. 15.30

| ATOM | RESIDUE | CHAIN | X | Y | Z |
|---|---|---|---|---|---|
| 1351 O | PRO 100 | B | -8.381 | -1.158 | 9.326 |
| 1352 CB | PRO 100 | B | -5.890 | -3.130 | 10.342 |
| 1353 CG | PRO 100 | B | -6.120 | -4.613 | 10.443 |
| 1354 CD | PRO 100 | B | -7.484 | -4.771 | 9.830 |
| 1355 N | LYS 101 | B | -6.660 | -0.169 | 10.060 |
| 1356 CA | LYS 101 | B | -7.015 | 0.958 | 9.218 |
| 1357 C | LYS 101 | B | -6.112 | 0.771 | 8.015 |
| 1358 O | LYS 101 | B | -5.130 | 0.061 | 8.142 |
| 1359 CB | LYS 101 | B | -6.671 | 2.300 | 9.855 |
| 1360 CG | LYS 101 | B | -6.510 | 2.347 | 11.360 |
| 1361 CD | LYS 101 | B | -5.813 | 3.616 | 11.889 |
| 1362 CE | LYS 101 | B | -4.227 | 3.513 | 12.046 |
| 1363 NZ | LYS 101 | B | -3.387 | 3.806 | 10.849 |
| 1364 N | PRO 102 | B | -6.219 | 1.262 | 6.840 |
| 1365 CA | PRO 102 | B | -5.321 | 0.916 | 5.769 |
| 1366 C | PRO 102 | B | -3.970 | 1.433 | 6.090 |
| 1367 O | PRO 102 | B | -3.853 | 2.346 | 6.892 |
| 1368 CB | PRO 102 | B | -5.934 | 1.534 | 4.529 |
| 1369 CG | PRO 102 | B | -6.576 | 2.741 | 5.074 |
| 1370 CD | PRO 102 | B | -7.100 | 2.341 | 6.447 |
| 1371 N | CYS 103 | B | -2.852 | 0.963 | 5.547 |
| 1372 CA | CYS 103 | B | -1.653 | 1.665 | 5.922 |
| 1373 C | CYS 103 | B | -0.993 | 2.294 | 4.757 |
| 1374 O | CYS 103 | B | -1.354 | 2.179 | 3.600 |
| 1375 CB | CYS 103 | B | -0.697 | 0.722 | 6.598 |
| 1376 SG | CYS 103 | B | 0.104 | -0.064 | 5.231 |
| 1377 N | CYS 104 | B | 0.044 | 2.988 | 5.123 |
| 1378 CA | CYS 104 | B | 0.501 | 4.087 | 4.348 |
| 1379 C | CYS 104 | B | 1.771 | 3.676 | 3.652 |
| 1380 O | CYS 104 | B | 2.791 | 3.408 | 4.251 |
| 1381 CB | CYS 104 | B | 0.602 | 5.107 | 5.385 |
| 1382 SG | CYS 104 | B | 1.414 | 6.474 | 4.692 |
| 1383 N | ALA 105 | B | 1.749 | 3.613 | 2.347 |
| 1384 CA | ALA 105 | B | 2.637 | 2.781 | 1.614 |
| 1385 C | ALA 105 | B | 3.081 | 3.640 | 0.494 |
| 1386 O | ALA 105 | B | 2.412 | 4.644 | 0.296 |
| 1387 CB | ALA 105 | B | 1.841 | 1.604 | 1.154 |
| 1388 N | PRO 106 | B | 4.100 | 3.411 | -0.258 |
| 1389 CA | PRO 106 | B | 4.400 | 4.197 | -1.420 |
| 1390 C | PRO 106 | B | 3.597 | 3.811 | -2.662 |
| 1391 O | PRO 106 | B | 3.311 | 2.672 | -2.978 |
| 1392 CB | PRO 106 | B | 5.891 | 4.039 | -1.557 |
| 1393 CG | PRO 106 | B | 6.123 | 2.662 | -1.081 |
| 1394 CD | PRO 106 | B | 5.349 | 2.826 | 0.199 |
| 1395 N | THR 107 | B | 3.246 | 4.864 | -3.375 |

Fig. 15.31

| ATOM | RESIDUE | CHAIN | X | Y | Z |
|---|---|---|---|---|---|
| 1396 CA | THR 107 | B | 2.321 | 4.885 | -4.464 |
| 1397 C | THR 107 | B | 3.250 | 4.827 | -5.644 |
| 1398 O | THR 107 | B | 3.206 | 3.871 | -6.411 |
| 1399 CB | THR 107 | B | 1.582 | 6.175 | -4.155 |
| 1400 OG1 | THR 107 | B | 0.518 | 5.644 | -3.377 |
| 1401 CG2 | THR 107 | B | 1.134 | 7.066 | -5.292 |
| 1402 N | GLN 108 | B | 4.151 | 5.763 | -5.922 |
| 1403 CA | GLN 108 | B | 5.164 | 5.360 | -6.846 |
| 1404 C | GLN 108 | B | 6.603 | 5.599 | -6.478 |
| 1405 O | GLN 108 | B | 6.989 | 6.589 | -5.880 |
| 1406 CB | GLN 108 | B | 4.712 | 6.001 | -8.168 |
| 1407 CG | GLN 108 | B | 5.202 | 7.362 | -8.639 |
| 1408 CD | GLN 108 | B | 4.487 | 8.380 | -7.859 |
| 1409 OE1 | GLN 108 | B | 3.911 | 8.140 | -6.806 |
| 1410 NE2 | GLN 108 | B | 4.552 | 9.578 | -8.441 |
| 1411 N | LEU 109 | B | 7.351 | 4.579 | -6.896 |
| 1412 CA | LEU 109 | B | 8.773 | 4.347 | -6.622 |
| 1413 C | LEU 109 | B | 9.747 | 4.700 | -7.774 |
| 1414 O | LEU 109 | B | 9.510 | 4.496 | -8.963 |
| 1415 CB | LEU 109 | B | 8.945 | 2.848 | -6.208 |
| 1416 CG | LEU 109 | B | 8.351 | 2.584 | -4.813 |
| 1417 CD1 | LEU 109 | B | 8.260 | 1.128 | -4.489 |
| 1418 CD2 | LEU 109 | B | 9.269 | 3.213 | -3.792 |
| 1419 N | ASN 110 | B | 10.911 | 5.262 | -7.494 |
| 1420 CA | ASN 110 | B | 11.823 | 5.551 | -8.555 |
| 1421 C | ASN 110 | B | 13.077 | 4.792 | -8.391 |
| 1422 O | ASN 110 | B | 13.238 | 4.036 | -7.445 |
| 1423 CB | ASN 110 | B | 12.199 | 6.976 | -8.586 |
| 1424 CG | ASN 110 | B | 11.025 | 7.786 | -8.983 |
| 1425 OD1 | ASN 110 | B | 11.064 | 9.002 | -8.744 |
| 1426 ND2 | ASN 110 | B | 9.942 | 7.206 | -9.529 |
| 1427 N | ALA 111 | B | 14.021 | 4.976 | -9.308 |
| 1428 CA | ALA 111 | B | 15.130 | 4.055 | -9.447 |
| 1429 C | ALA 111 | B | 16.280 | 4.897 | -9.088 |
| 1430 O | ALA 111 | B | 16.134 | 6.101 | -9.021 |
| 1431 CB | ALA 111 | B | 15.249 | 3.543 | -10.900 |
| 1432 N | ILE 112 | B | 17.436 | 4.324 | -8.843 |
| 1433 CA | ILE 112 | B | 18.624 | 5.094 | -8.502 |
| 1434 C | ILE 112 | B | 19.626 | 4.386 | -9.369 |
| 1435 O | ILE 112 | B | 19.520 | 3.175 | -9.473 |
| 1436 CB | ILE 112 | B | 18.834 | 4.979 | -6.944 |
| 1437 CG1 | ILE 112 | B | 18.727 | 6.452 | -6.591 |
| 1438 CG2 | ILE 112 | B | 20.119 | 4.396 | -6.342 |
| 1439 CD1 | ILE 112 | B | 20.014 | 7.252 | -6.922 |
| 1440 N | SER 113 | B | 20.575 | 5.052 | -9.998 |

Fig. 15.32

| ATOM | RESIDUE | CHAIN | X | Y | Z |
|---|---|---|---|---|---|
| 1441 CA | SER 113 | B | 21.646 | 4.330 | -10.635 |
| 1442 C | SER 113 | B | 22.926 | 4.454 | -9.879 |
| 1443 O | SER 113 | B | 23.220 | 5.579 | -9.520 |
| 1444 CB | SER 113 | B | 21.834 | 4.850 | -12.034 |
| 1445 OG | SER 113 | B | 21.085 | 3.985 | -12.909 |
| 1446 N | VAL 114 | B | 23.726 | 3.408 | -9.592 |
| 1447 CA | VAL 114 | B | 25.005 | 3.645 | -8.929 |
| 1448 C | VAL 114 | B | 26.085 | 3.074 | -9.841 |
| 1449 O | VAL 114 | B | 25.914 | 2.046 | -10.484 |
| 1450 CB | VAL 114 | B | 25.150 | 2.977 | -7.496 |
| 1451 CG1 | VAL 114 | B | 23.888 | 3.143 | -6.703 |
| 1452 CG2 | VAL 114 | B | 25.446 | 1.508 | -7.575 |
| 1453 N | LEU 115 | B | 27.215 | 3.773 | -9.911 |
| 1454 CA | LEU 115 | B | 28.417 | 3.420 | -10.663 |
| 1455 C | LEU 115 | B | 29.406 | 2.624 | -9.859 |
| 1456 O | LEU 115 | B | 29.857 | 3.095 | -8.814 |
| 1457 CB | LEU 115 | B | 29.096 | 4.718 | -11.145 |
| 1458 CG | LEU 115 | B | 30.445 | 4.721 | -11.850 |
| 1459 CD1 | LEU 115 | B | 30.271 | 4.338 | -13.289 |
| 1460 CD2 | LEU 115 | B | 31.054 | 6.115 | -11.750 |
| 1461 N | TYR 116 | B | 29.854 | 1.432 | -10.212 |
| 1462 CA | TYR 116 | B | 30.750 | 0.783 | -9.287 |
| 1463 C | TYR 116 | B | 31.728 | -0.199 | -9.868 |
| 1464 O | TYR 116 | B | 31.498 | -0.667 | -10.976 |
| 1465 CB | TYR 116 | B | 29.872 | 0.123 | -8.278 |
| 1466 CG | TYR 116 | B | 29.144 | -1.012 | -8.907 |
| 1467 CD1 | TYR 116 | B | 27.919 | -0.788 | -9.480 |
| 1468 CD2 | TYR 116 | B | 29.728 | -2.243 | -8.856 |
| 1469 CE1 | TYR 116 | B | 27.289 | -1.824 | -10.101 |
| 1470 CE2 | TYR 116 | B | 29.105 | -3.280 | -9.474 |
| 1471 CZ | TYR 116 | B | 27.925 | -3.035 | -10.113 |
| 1472 OH | TYR 116 | B | 27.396 | -4.037 | -10.879 |
| 1473 N | PHE 117 | B | 32.820 | -0.583 | -9.201 |
| 1474 CA | PHE 117 | B | 33.733 | -1.520 | -9.828 |
| 1475 C | PHE 117 | B | 33.168 | -2.861 | -9.521 |
| 1476 O | PHE 117 | B | 33.029 | -3.159 | -8.347 |
| 1477 CB | PHE 117 | B | 35.137 | -1.590 | -9.242 |
| 1478 CG | PHE 117 | B | 35.701 | -0.236 | -8.937 |
| 1479 CD1 | PHE 117 | B | 35.512 | 0.315 | -7.691 |
| 1480 CD2 | PHE 117 | B | 36.392 | 0.459 | -9.903 |
| 1481 CE1 | PHE 117 | B | 36.002 | 1.579 | -7.433 |
| 1482 CE2 | PHE 117 | B | 36.872 | 1.732 | -9.656 |
| 1483 CZ | PHE 117 | B | 36.672 | 2.294 | -8.412 |
| 1484 N | ASP 118 | B | 32.811 | -3.756 | -10.426 |
| 1485 CA | ASP 118 | B | 32.630 | -5.124 | -9.935 |

Fig. 15.33

| ATOM | RESIDUE | CHAIN | X | Y | Z |
|---|---|---|---|---|---|
| 1486 C | ASP 118 | B | 34.049 | -5.641 | -9.774 |
| 1487 O | ASP 118 | B | 35.001 | -4.878 | -9.844 |
| 1488 CB | ASP 118 | B | 31.868 | -6.043 | -10.948 |
| 1489 CG | ASP 118 | B | 32.575 | -6.053 | -12.291 |
| 1490 OD1 | ASP 118 | B | 32.115 | -6.790 | -13.188 |
| 1491 OD2 | ASP 118 | B | 33.580 | -5.313 | -12.438 |
| 1492 N | ASP 119 | B | 34.193 | -6.943 | -9.569 |
| 1493 CA | ASP 119 | B | 35.472 | -7.584 | -9.692 |
| 1494 C | ASP 119 | B | 36.172 | -7.231 | -11.043 |
| 1495 O | ASP 119 | B | 35.617 | -6.552 | -11.918 |
| 1496 CB | ASP 119 | B | 35.288 | -9.105 | -9.596 |
| 1497 CG | ASP 119 | B | 34.198 | -9.528 | -10.579 |
| 1498 OD1 | ASP 119 | B | 34.168 | -8.947 | -11.699 |
| 1499 OD2 | ASP 119 | B | 33.370 | -10.399 | -10.216 |
| 1500 N | SER 120 | B | 37.418 | -7.741 | -11.190 |
| 1501 CA | SER 120 | B | 38.384 | -7.188 | -12.116 |
| 1502 C | SER 120 | B | 38.552 | -5.769 | -11.587 |
| 1503 O | SER 120 | B | 38.771 | -5.557 | -10.396 |
| 1504 CB | SER 120 | B | 37.765 | -7.322 | -13.505 |
| 1505 OG | SER 120 | B | 37.361 | -6.068 | -14.048 |
| 1506 N | SER 121 | B | 38.475 | -4.737 | -12.351 |
| 1507 CA | SER 121 | B | 37.795 | -3.641 | -11.746 |
| 1508 C | SER 121 | B | 36.964 | -3.170 | -12.910 |
| 1509 O | SER 121 | B | 37.218 | -2.073 | -13.421 |
| 1510 CB | SER 121 | B | 38.808 | -2.596 | -11.297 |
| 1511 OG | SER 121 | B | 39.930 | -3.318 | -10.767 |
| 1512 N | ASN 122 | B | 35.961 | -3.865 | -13.437 |
| 1513 CA | ASN 122 | B | 35.251 | -3.163 | -14.482 |
| 1514 C | ASN 122 | B | 34.567 | -1.986 | -13.818 |
| 1515 O | ASN 122 | B | 33.919 | -2.205 | -12.820 |
| 1516 CB | ASN 122 | B | 34.175 | -4.002 | -15.124 |
| 1517 CG | ASN 122 | B | 34.720 | -4.905 | -16.200 |
| 1518 OD1 | ASN 122 | B | 35.807 | -5.455 | -16.161 |
| 1519 ND2 | ASN 122 | B | 33.842 | -5.095 | -17.193 |
| 1520 N | VAL 123 | B | 34.623 | -0.738 | -14.229 |
| 1521 CA | VAL 123 | B | 33.707 | 0.247 | -13.704 |
| 1522 C | VAL 123 | B | 32.323 | 0.092 | -14.263 |
| 1523 O | VAL 123 | B | 32.121 | 0.390 | -15.418 |
| 1524 CB | VAL 123 | B | 34.253 | 1.583 | -14.033 |
| 1525 CG1 | VAL 123 | B | 33.293 | 2.705 | -13.768 |
| 1526 CG2 | VAL 123 | B | 35.490 | 1.719 | -13.184 |
| 1527 N | ILE 124 | B | 31.270 | -0.356 | -13.598 |
| 1528 CA | ILE 124 | B | 29.966 | -0.307 | -14.250 |
| 1529 C | ILE 124 | B | 28.844 | 0.618 | -13.776 |
| 1530 O | ILE 124 | B | 28.948 | 1.374 | -12.826 |

Fig. 15.34

| ATOM | RESIDUE | CHAIN | X | Y | Z |
|---|---|---|---|---|---|
| 1531 CB | ILE 124 | B | 29.448 | -1.693 | -14.301 |
| 1532 CG1 | ILE 124 | B | 29.346 | -2.339 | -12.994 |
| 1533 CG2 | ILE 124 | B | 30.460 | -2.470 | -15.084 |
| 1534 CD1 | ILE 124 | B | 28.941 | -3.771 | -13.335 |
| 1535 N | LEU 125 | B | 27.672 | 0.649 | -14.394 |
| 1536 CA | LEU 125 | B | 26.633 | 1.575 | -13.951 |
| 1537 C | LEU 125 | B | 25.470 | 0.617 | -13.807 |
| 1538 O | LEU 125 | B | 24.992 | 0.201 | -14.856 |
| 1539 CB | LEU 125 | B | 26.338 | 2.598 | -15.029 |
| 1540 CG | LEU 125 | B | 25.522 | 3.838 | -14.719 |
| 1541 CD1 | LEU 125 | B | 26.188 | 4.811 | -13.745 |
| 1542 CD2 | LEU 125 | B | 25.371 | 4.560 | -16.049 |
| 1543 N | LYS 126 | B | 25.012 | 0.237 | -12.583 |
| 1544 CA | LYS 126 | B | 23.788 | -0.531 | -12.459 |
| 1545 C | LYS 126 | B | 22.674 | 0.399 | -12.077 |
| 1546 O | LYS 126 | B | 22.853 | 1.502 | -11.576 |
| 1547 CB | LYS 126 | B | 23.882 | -1.627 | -11.411 |
| 1548 CG | LYS 126 | B | 22.887 | -2.671 | -12.000 |
| 1549 CD | LYS 126 | B | 22.624 | -3.980 | -11.185 |
| 1550 CE | LYS 126 | B | 21.336 | -4.756 | -11.620 |
| 1551 NZ | LYS 126 | B | 20.100 | -3.953 | -11.514 |
| 1552 N | LYS 127 | B | 21.457 | -0.039 | -12.325 |
| 1553 CA | LYS 127 | B | 20.275 | 0.766 | -12.115 |
| 1554 C | LYS 127 | B | 19.538 | -0.097 | -11.161 |
| 1555 O | LYS 127 | B | 19.442 | -1.295 | -11.349 |
| 1556 CB | LYS 127 | B | 19.357 | 0.902 | -13.313 |
| 1557 CG | LYS 127 | B | 18.494 | 2.130 | -13.043 |
| 1558 CD | LYS 127 | B | 17.595 | 2.495 | -14.203 |
| 1559 CE | LYS 127 | B | 16.759 | 1.303 | -14.621 |
| 1560 NZ | LYS 127 | B | 15.623 | 1.849 | -15.326 |
| 1561 N | TYR 128 | B | 19.018 | 0.491 | -10.119 |
| 1562 CA | TYR 128 | B | 18.374 | -0.282 | -9.120 |
| 1563 C | TYR 128 | B | 17.039 | 0.270 | -9.294 |
| 1564 O | TYR 128 | B | 16.919 | 1.484 | -9.458 |
| 1565 CB | TYR 128 | B | 18.944 | 0.051 | -7.765 |
| 1566 CG | TYR 128 | B | 20.187 | -0.723 | -7.613 |
| 1567 CD1 | TYR 128 | B | 21.334 | -0.090 | -7.202 |
| 1568 CD2 | TYR 128 | B | 20.189 | -2.046 | -7.962 |
| 1569 CE1 | TYR 128 | B | 22.524 | -0.785 | -7.189 |
| 1570 CE2 | TYR 128 | B | 21.354 | -2.752 | -7.957 |
| 1571 CZ | TYR 128 | B | 22.522 | -2.118 | -7.590 |
| 1572 OH | TYR 128 | B | 23.726 | -2.834 | -7.651 |
| 1573 N | ARG 129 | B | 15.995 | -0.539 | -9.273 |
| 1574 CA | ARG 129 | B | 14.738 | 0.093 | -9.471 |
| 1575 C | ARG 129 | B | 54.148 | 0.079 | -8.127 |

Fig. 15.35

| ATOM | RESIDUE | CHAIN | X | Y | Z |
|---|---|---|---|---|---|
| 1576 O | ARG 129 | B | 14.539 | -0.696 | -7.272 |
| 1577 CB | ARG 129 | B | 13.872 | -0.699 | -10.389 |
| 1578 CG | ARG 129 | B | 14.448 | -1.877 | -11.194 |
| 1579 CD | ARG 129 | B | 13.392 | -2.283 | -12.257 |
| 1580 NE | ARG 129 | B | 12.867 | -1.068 | -12.880 |
| 1581 CZ | ARG 129 | B | 13.523 | -0.465 | -13.872 |
| 1582 NH1 | ARG 129 | B | 14.600 | -1.048 | -14.514 |
| 1583 NH2 | ARG 129 | B | 13.110 | 0.783 | -14.224 |
| 1584 N | ASN 130 | B | 13.187 | 0.959 | -7.931 |
| 1585 CA | ASN 130 | B | 12.337 | 0.930 | -6.773 |
| 1586 C | ASN 130 | B | 13.101 | 1.191 | -5.580 |
| 1587 O | ASN 130 | B | 12.956 | 0.581 | -4.555 |
| 1588 CB | ASN 130 | B | 11.644 | -0.406 | -6.596 |
| 1589 CG | ASN 130 | B | 10.513 | -0.422 | -7.589 |
| 1590 OD1 | ASN 130 | B | 9.991 | 0.615 | -7.968 |
| 1591 ND2 | ASN 130 | B | 10.106 | -1.571 | -8.113 |
| 1592 N | MET 131 | B | 13.978 | 2.163 | -5.682 |
| 1593 CA | MET 131 | B | 14.779 | 2.497 | -4.552 |
| 1594 C | MET 131 | B | 14.403 | 3.805 | -3.898 |
| 1595 O | MET 131 | B | 14.888 | 4.135 | -2.829 |
| 1596 CB | MET 131 | B | 16.193 | 2.489 | -5.056 |
| 1597 CG | MET 131 | B | 16.596 | 1.063 | -5.233 |
| 1598 SD | MET 131 | B | 17.774 | 0.746 | -3.920 |
| 1599 CE | MET 131 | B | 17.131 | -0.880 | -3.651 |
| 1600 N | VAL 132 | B | 13.540 | 4.602 | -4.492 |
| 1601 CA | VAL 132 | B | 13.272 | 5.952 | -4.016 |
| 1602 C | VAL 132 | B | 11.778 | 6.099 | -3.895 |
| 1603 O | VAL 132 | B | 11.075 | 5.709 | -4.791 |
| 1604 CB | VAL 132 | B | 13.804 | 6.928 | -5.035 |
| 1605 CG1 | VAL 132 | B | 13.726 | 8.358 | -4.584 |
| 1606 CG2 | VAL 132 | B | 15.252 | 6.549 | -5.285 |
| 1607 N | VAL 133 | B | 11.136 | 6.617 | -2.884 |
| 1608 CA | VAL 133 | B | 9.714 | 6.827 | -2.893 |
| 1609 C | VAL 133 | B | 9.534 | 8.146 | -3.591 |
| 1610 O | VAL 133 | B | 10.322 | 9.039 | -3.333 |
| 1611 CB | VAL 133 | B | 9.257 | 6.869 | -1.443 |
| 1612 CG1 | VAL 133 | B | 8.030 | 7.727 | -1.166 |
| 1613 CG2 | VAL 133 | B | 9.043 | 5.425 | -1.098 |
| 1614 N | ARG 134 | B | 8.526 | 8.283 | -4.462 |
| 1615 CA | ARG 134 | B | 8.074 | 9.561 | -4.979 |
| 1616 C | ARG 134 | B | 6.805 | 9.998 | -4.253 |
| 1617 O | ARG 134 | B | 6.613 | 11.145 | -3.844 |
| 1618 CB | ARG 134 | B | 7.767 | 9.438 | -6.471 |
| 1619 CG | ARG 134 | B | 8.655 | 10.170 | -7.503 |
| 1620 CD | ARG 134 | B | 7.931 | 10.074 | -8.884 |

Fig. 15.36

| ATOM | RESIDUE | CHAIN | X | Y | Z |
|---|---|---|---|---|---|
| 1621 NE | ARG 134 | B | 8.585 | 10.702 | -10.068 |
| 1622 CZ | ARG 134 | B | 9.074 | 11.973 | -10.169 |
| 1623 NH1 | ARG 134 | B | 9.514 | 12.419 | -11.395 |
| 1624 NH2 | ARG 134 | B | 9.202 | 12.813 | -9.089 |
| 1625 N | ALA 135 | B | 5.839 | 9.108 | -4.056 |
| 1626 CA | ALA 135 | B | 4.734 | 9.536 | -3.247 |
| 1627 C | ALA 135 | B | 4.163 | 8.375 | -2.497 |
| 1628 O | ALA 135 | B | 4.422 | 7.228 | -2.831 |
| 1629 CB | ALA 135 | B | 3.713 | 10.178 | -4.165 |
| 1630 N | CYS 136 | B | 3.370 | 8.691 | -1.459 |
| 1631 CA | CYS 136 | B | 2.737 | 7.740 | -0.529 |
| 1632 C | CYS 136 | B | 1.234 | 7.935 | -0.411 |
| 1633 O | CYS 136 | B | 0.778 | 9.062 | -0.565 |
| 1634 CB | CYS 136 | B | 3.124 | 7.893 | 0.896 |
| 1635 SG | CYS 136 | B | 4.770 | 8.538 | 1.134 |
| 1636 N | GLY 137 | B | 0.452 | 6.910 | -0.132 |
| 1637 CA | GLY 137 | B | -0.882 | 7.202 | 0.246 |
| 1638 C | GLY 137 | B | -1.562 | 5.941 | 0.556 |
| 1639 O | GLY 137 | B | -0.925 | 4.911 | 0.422 |
| 1640 N | CYS 138 | B | -2.836 | 5.929 | 0.957 |
| 1641 CA | CYS 138 | B | -3.377 | 4.818 | 1.746 |
| 1642 C | CYS 138 | B | -3.790 | 3.683 | 0.897 |
| 1643 O | CYS 138 | B | -4.502 | 4.036 | -0.016 |
| 1644 CB | CYS 138 | B | -4.575 | 5.261 | 2.510 |
| 1645 SG | CYS 138 | B | -4.204 | 6.910 | 3.144 |
| 1646 N | HIS 139 | B | -3.491 | 2.408 | 1.017 |
| 1647 CA | HIS 139 | B | -4.209 | 1.485 | 0.173 |
| 1648 C | HIS 139 | B | -4.475 | 0.369 | 1.139 |
| 1649 O | HIS 139 | B | -3.753 | 0.227 | 2.148 |
| 1650 CB | HIS 139 | B | -3.407 | 0.969 | -1.034 |
| 1651 CG | HIS 139 | B | -2.881 | 2.085 | -1.888 |
| 1652 ND1 | HIS 139 | B | -2.348 | 3.285 | -1.424 |
| 1653 CD2 | HIS 139 | B | -3.320 | 2.198 | -3.200 |
| 1654 CE1 | HIS 139 | B | -2.505 | 4.047 | -2.523 |
| 1655 NE2 | HIS 139 | B | -3.077 | 3.480 | -3.620 |
| 1656 OT | HIS 139 | B | -5.079 | -0.465 | 0.767 |

Fig. 15.37

| ATOM | RESIDUE | | CHAIN | X | Y | Z | δ |
|---|---|---|---|---|---|---|---|
| 1 | CB | GLN 36 | A | 34.688 | 54.268 | 11.979 | 0.80 |
| 2 | CG | GLN 36 | A | 34.454 | 55.622 | 11.327 | 0.98 |
| 3 | CD | GLN 36 | A | 35.339 | 55.912 | 10.142 | 1.07 |
| 4 | OE1 | GLN 36 | A | 36.525 | 55.589 | 10.061 | 0.98 |
| 5 | NE2 | GLN 36 | A | 34.724 | 56.519 | 9.123 | 1.05 |
| 6 | C | GLN 36 | A | 33.292 | 52.214 | 11.583 | 0.62 |
| 7 | O | GLN 36 | A | 33.249 | 52.268 | 10.349 | 0.67 |
| 8 | N | GLN 36 | A | 33.249 | 53.240 | 13.781 | 0.82 |
| 9 | CA | GLN 36 | A | 33.430 | 53.511 | 12.360 | 0.72 |
| 10 | N | ALA 37 | A | 33.283 | 51.110 | 12.314 | 0.65 |
| 11 | CA | ALA 37 | A | 33.203 | 49.784 | 11.644 | 0.64 |
| 12 | CB | ALA 37 | A | 33.628 | 48.665 | 12.576 | 0.58 |
| 13 | C | ALA 37 | A | 31.758 | 49.525 | 11.201 | 0.62 |
| 14 | O | ALA 37 | A | 30.825 | 49.957 | 11.868 | 0.67 |
| 15 | N | CYS 38 | A | 31.645 | 48.593 | 10.285 | 0.64 |
| 16 | CA | CYS 38 | A | 30.373 | 48.172 | 9.714 | 0.53 |
| 17 | C | CYS 38 | A | 29.433 | 47.699 | 10.797 | 0.63 |
| 18 | O | CYS 38 | A | 29.746 | 46.761 | 11.527 | 0.66 |
| 19 | CB | CYS 38 | A | 30.559 | 47.212 | 8.582 | 0.58 |
| 20 | SG | CYS 38 | A | 29.056 | 46.598 | 7.828 | 0.63 |
| 21 | N | LYS 39 | A | 28.382 | 48.487 | 11.010 | 0.63 |
| 22 | CA | LYS 39 | A | 27.261 | 48.136 | 11.860 | 0.50 |
| 23 | CB | LYS 39 | A | 27.365 | 48.642 | 13.296 | 0.56 |
| 24 | CG | LYS 39 | A | 28.183 | 49.898 | 13.549 | 0.69 |
| 25 | CD | LYS 39 | A | 27.844 | 50.564 | 14.870 | 0.62 |
| 26 | CE | LYS 39 | A | 26.701 | 49.872 | 15.592 | 0.92 |
| 27 | NZ | LYS 39 | A | 26.052 | 50.747 | 16.607 | 0.92 |
| 28 | C | LYS 39 | A | 25.926 | 48.637 | 11.262 | 0.50 |
| 29 | O | LYS 39 | A | 25.872 | 49.334 | 10.242 | 0.49 |
| 30 | N | LYS 40 | A | 24.890 | 48.324 | 11.988 | 0.59 |
| 31 | CA | LYS 40 | A | 23.483 | 48.556 | 11.659 | 0.64 |
| 32 | CB | LYS 40 | A | 22.606 | 47.362 | 12.132 | 0.61 |
| 33 | CG | LYS 40 | A | 21.167 | 47.575 | 11.621 | 0.60 |
| 34 | CD | LYS 40 | A | 20.283 | 46.452 | 12.085 | 0.48 |
| 35 | CE | LYS 40 | A | 19.989 | 46.487 | 13.565 | 0.60 |
| 36 | NZ | LYS 40 | A | 19.214 | 45.258 | 13.873 | 0.73 |
| 37 | C | LYS 40 | A | 23.019 | 49.744 | 12.504 | 0.63 |
| 38 | O | LYS 40 | A | 23.463 | 49.862 | 13.659 | 0.61 |
| 39 | N | HIS 41 | A | 22.524 | 50.763 | 11.826 | 0.65 |
| 40 | CA | HIS 41 | A | 22.150 | 51.977 | 12.590 | 0.58 |
| 41 | CB | HIS 41 | A | 22.881 | 53.195 | 12.011 | 0.57 |
| 42 | CG | HIS 41 | A | 24.359 | 52.907 | 11.899 | 0.60 |
| 43 | CD2 | HIS 41 | A | 25.094 | 52.514 | 10.838 | 0.63 |
| 44 | ND1 | HIS 41 | A | 25.270 | 53.346 | 12.835 | 0.61 |
| 45 | CE1 | HIS 41 | A | 26.482 | 53.207 | 12.338 | 0.63 |

Fig. 16.1

| ATOM | | RESIDUE | | CHAIN | X | Y | Z | δ |
|---|---|---|---|---|---|---|---|---|
| 46 | NE2 | HIS | 41 | A | 26.411 | 52.515 | 11.217 | 0.67 |
| 47 | C | HIS | 41 | A | 20.645 | 52.146 | 12.505 | 0.58 |
| 48 | O | HIS | 41 | A | 19.994 | 51.655 | 11.564 | 0.60 |
| 49 | N | GLU | 42 | A | 20.173 | 53.007 | 13.373 | 0.63 |
| 50 | CA | GLU | 42 | A | 18.747 | 53.323 | 13.460 | 0.65 |
| 51 | CB | GLU | 42 | A | 18.389 | 53.683 | 14.894 | 0.67 |
| 52 | CG | GLU | 42 | A | 17.998 | 52.443 | 15.724 | 0.61 |
| 53 | CD | GLU | 42 | A | 17.770 | 52.760 | 17.171 | 0.80 |
| 54 | OE1 | GLU | 42 | A | 18.180 | 52.068 | 18.082 | 0.89 |
| 55 | OE2 | GLU | 42 | A | 17.221 | 53.875 | 17.309 | 0.92 |
| 56 | C | GLU | 42 | A | 18.296 | 54.397 | 12.507 | 0.63 |
| 57 | O | GLU | 42 | A | 19.083 | 55.313 | 12.261 | 0.68 |
| 58 | N | LEU | 43 | A | 17.163 | 54.191 | 11.858 | 0.57 |
| 59 | CA | LEU | 43 | A | 16.444 | 55.149 | 11.012 | 0.57 |
| 60 | CB | LEU | 43 | A | 16.827 | 54.887 | 9.561 | 0.56 |
| 61 | CG | LEU | 43 | A | 16.795 | 55.850 | 8.455 | 0.65 |
| 62 | CD1 | LEU | 43 | A | 16.623 | 55.408 | 7.043 | 0.59 |
| 63 | CD2 | LEU | 43 | A | 16.638 | 57.296 | 8.715 | 0.64 |
| 64 | C | LEU | 43 | A | 14.940 | 54.753 | 11.210 | 0.63 |
| 65 | O | LEU | 43 | A | 14.568 | 53.682 | 10.710 | 0.62 |
| 66 | N | TYR | 44 | A | 14.119 | 55.703 | 11.580 | 0.58 |
| 67 | CA | TYR | 44 | A | 12.646 | 55.504 | 11.590 | 0.54 |
| 68 | CB | TYR | 44 | A | 12.117 | 56.253 | 12.845 | 0.52 |
| 69 | CG | TYR | 44 | A | 10.648 | 55.954 | 13.022 | 0.63 |
| 70 | CD1 | TYR | 44 | A | 9.663 | 56.853 | 12.620 | 0.50 |
| 71 | CE1 | TYR | 44 | A | 8.318 | 56.490 | 12.742 | 0.58 |
| 72 | CD2 | TYR | 44 | A | 10.267 | 54.766 | 13.634 | 0.52 |
| 73 | CE2 | TYR | 44 | A | 8.957 | 54.379 | 13.694 | 0.56 |
| 74 | CZ | TYR | 44 | A | 7.976 | 55.253 | 13.235 | 0.69 |
| 75 | OH | TYR | 44 | A | 6.668 | 54.894 | 13.434 | 0.81 |
| 76 | C | TYR | 44 | A | 12.114 | 56.295 | 10.395 | 0.51 |
| 77 | O | TYR | 44 | A | 12.538 | 57.447 | 10.316 | 0.63 |
| 78 | N | VAL | 45 | A | 11.336 | 55.713 | 9.534 | 0.53 |
| 79 | CA | VAL | 45 | A | 10.722 | 56.389 | 8.368 | 0.53 |
| 80 | CB | VAL | 45 | A | 10.910 | 55.465 | 7.148 | 0.56 |
| 81 | CG1 | VAL | 45 | A | 10.355 | 56.000 | 5.844 | 0.47 |
| 82 | CG2 | VAL | 45 | A | 12.346 | 54.969 | 7.035 | 0.52 |
| 83 | C | VAL | 45 | A | 9.220 | 56.590 | 8.673 | 0.55 |
| 84 | O | VAL | 45 | A | 8.585 | 55.655 | 9.193 | 0.53 |
| 85 | N | SER | 46 | A | 8.851 | 57.845 | 8.765 | 0.59 |
| 86 | CA | SER | 46 | A | 7.518 | 58.414 | 8.858 | 0.52 |
| 87 | CB | SER | 46 | A | 7.518 | 59.907 | 9.287 | 0.46 |
| 88 | OG | SER | 46 | A | 6.397 | 60.090 | 10.135 | 0.69 |
| 89 | C | SER | 46 | A | 6.883 | 58.405 | 7.482 | 0.52 |
| 90 | O | SER | 46 | A | 7.484 | 58.947 | 6.553 | 0.56 |

Fig. 16.2

| ATOM | RESIDUE | | CHAIN | X | Y | Z | δ |
|---|---|---|---|---|---|---|---|
| 91 | N | PHE 47 | A | 5.713 | 57.819 | 7.380 | 0.59 |
| 92 | CA | PHE 47 | A | 5.009 | 57.837 | 6.069 | 0.57 |
| 93 | CB | PHE 47 | A | 3.844 | 56.851 | 6.088 | 0.53 |
| 94 | CG | PHE 47 | A | 4.154 | 55.395 | 6.174 | 0.55 |
| 95 | CD1 | PHE 47 | A | 5.279 | 54.859 | 5.517 | 0.45 |
| 96 | CD2 | PHE 47 | A | 3.287 | 54.509 | 6.818 | 0.54 |
| 97 | CE1 | PHE 47 | A | 5.580 | 53.514 | 5.633 | 0.71 |
| 98 | CE2 | PHE 47 | A | 3.618 | 53.164 | 7.010 | 0.56 |
| 99 | CZ | PHE 47 | A | 4.739 | 52.644 | 6.313 | 0.60 |
| 100 | C | PHE 47 | A | 4.737 | 59.281 | 5.648 | 0.49 |
| 101 | O | PHE 47 | A | 4.748 | 59.578 | 4.426 | 0.61 |
| 102 | N | ARG 48 | A | 4.422 | 60.187 | 6.541 | 0.51 |
| 103 | CA | ARG 48 | A | 4.356 | 61.641 | 6.314 | 0.57 |
| 104 | CB | ARG 48 | A | 4.183 | 62.463 | 7.564 | 0.49 |
| 105 | CG | ARG 48 | A | 3.277 | 62.040 | 8.662 | 0.74 |
| 106 | CD | ARG 48 | A | 2.096 | 62.917 | 8.844 | 0.83 |
| 107 | NE | ARG 48 | A | 2.148 | 63.816 | 9.964 | 0.71 |
| 108 | CZ | ARG 48 | A | 1.255 | 64.003 | 10.923 | 0.66 |
| 109 | NH1 | ARG 48 | A | -0.043 | 63.685 | 10.831 | 0.68 |
| 110 | NH2 | ARG 48 | A | 1.739 | 64.330 | 12.123 | 0.61 |
| 111 | C | ARG 48 | A | 5.516 | 62.216 | 5.517 | 0.64 |
| 112 | O | ARG 48 | A | 5.342 | 62.761 | 4.397 | 0.69 |
| 113 | N | ASP 49 | A | 6.737 | 61.953 | 5.977 | 0.60 |
| 114 | CA | ASP 49 | A | 7.962 | 62.298 | 5.274 | 0.57 |
| 115 | CB | ASP 49 | A | 9.205 | 61.850 | 6.047 | 0.68 |
| 116 | CG | ASP 49 | A | 9.188 | 62.342 | 7.481 | 0.80 |
| 117 | OD1 | ASP 49 | A | 10.062 | 61.939 | 8.272 | 0.89 |
| 118 | OD2 | ASP 49 | A | 8.235 | 63.099 | 7.801 | 0.83 |
| 119 | C | ASP 49 | A | 7.998 | 61.913 | 3.814 | 0.66 |
| 120 | O | ASP 49 | A | 8.811 | 62.490 | 3.062 | 0.72 |
| 121 | N | LEU 50 | A | 7.456 | 60.746 | 3.465 | 0.70 |
| 122 | CA | LEU 50 | A | 7.487 | 60.243 | 2.086 | 0.60 |
| 123 | CB | LEU 50 | A | 7.446 | 58.703 | 2.187 | 0.62 |
| 124 | CG | LEU 50 | A | 8.580 | 58.098 | 3.022 | 0.69 |
| 125 | CD1 | LEU 50 | A | 8.786 | 56.662 | 2.544 | 0.66 |
| 126 | CD2 | LEU 50 | A | 9.836 | 58.911 | 2.667 | 0.66 |
| 127 | C | LEU 50 | A | 6.275 | 60.748 | 1.275 | 0.62 |
| 128 | O | LEU 50 | A | 6.080 | 60.203 | 0.167 | 0.69 |
| 129 | N | GLY 51 | A | 5.315 | 61.265 | 2.005 | 0.62 |
| 130 | CA | GLY 51 | A | 3.950 | 61.540 | 1.563 | 0.59 |
| 131 | C | GLY 51 | A | 3.215 | 60.231 | 1.303 | 0.68 |
| 132 | O | GLY 51 | A | 2.960 | 59.916 | 0.130 | 0.73 |
| 133 | N | TRP 52 | A | 3.076 | 59.385 | 2.325 | 0.60 |
| 134 | CA | TRP 52 | A | 2.385 | 58.104 | 2.063 | 0.63 |
| 135 | CB | TRP 52 | A | 3.281 | 56.916 | 2.022 | 0.76 |

Fig. 16.3

| ATOM | RESIDUE | CHAIN | X | Y | Z | δ |
|---|---|---|---|---|---|---|
| 136 | CG | TRP 52 | A | 4.282 | 56.698 | 0.951 | 0.80 |
| 137 | CD2 | TRP 52 | A | 5.364 | 55.744 | 1.004 | 0.74 |
| 138 | CE2 | TRP 52 | A | 5.991 | 55.750 | -0.263 | 0.92 |
| 139 | CE3 | TRP 52 | A | 5.811 | 54.835 | 1.963 | 1.01 |
| 140 | CD1 | TRP 52 | A | 4.256 | 57.163 | -0.333 | 0.82 |
| 141 | NE1 | TRP 52 | A | 5.315 | 56.649 | -1.050 | 0.73 |
| 142 | CZ2 | TRP 52 | A | 7.038 | 54.881 | -0.576 | 0.75 |
| 143 | CZ3 | TRP 52 | A | 6.886 | 54.012 | 1.684 | 0.68 |
| 144 | CH2 | TRP 52 | A | 7.495 | 54.041 | 0.428 | 0.80 |
| 145 | C | TRP 52 | A | 1.218 | 57.994 | 3.046 | 0.72 |
| 146 | O | TRP 52 | A | 0.425 | 57.045 | 2.965 | 0.78 |
| 147 | N | GLN 53 | A | 1.009 | 59.076 | 3.769 | 0.64 |
| 148 | CA | GLN 53 | A | 0.000 | 59.125 | 4.822 | 0.74 |
| 149 | CB | GLN 53 | A | 0.235 | 60.290 | 5.798 | 0.68 |
| 150 | CG | GLN 53 | A | 0.108 | 61.647 | 5.138 | 0.56 |
| 151 | CD | GLN 53 | A | 1.210 | 62.152 | 4.268 | 0.78 |
| 152 | OE1 | GLN 53 | A | 1.734 | 61.501 | 3.363 | 0.75 |
| 153 | NE2 | GLN 53 | A | 1.476 | 63.465 | 4.447 | 0.80 |
| 154 | C | GLN 53 | A | -1.419 | 59.100 | 4.280 | 0.74 |
| 155 | O | GLN 53 | A | -2.376 | 59.017 | 5.080 | 0.83 |
| 156 | N | ASP 54 | A | -1.613 | 59.500 | 3.040 | 0.77 |
| 157 | CA | ASP 54 | A | -2.945 | 59.676 | 2.432 | 0.76 |
| 158 | CB | ASP 54 | A | -2.747 | 60.190 | 1.004 | 0.92 |
| 159 | CG | ASP 54 | A | -2.418 | 61.667 | 0.920 | 0.92 |
| 160 | OD1 | ASP 54 | A | -2.672 | 62.439 | 1.863 | 0.96 |
| 161 | OD2 | ASP 54 | A | -2.074 | 62.062 | -0.217 | 0.75 |
| 162 | C | ASP 54 | A | -3.808 | 58.408 | 2.491 | 0.80 |
| 163 | O | ASP 54 | A | -4.988 | 58.426 | 2.898 | 0.82 |
| 164 | N | TRP 55 | A | -3.265 | 57.334 | 1.953 | 0.72 |
| 165 | CA | TRP 55 | A | -3.905 | 56.052 | 1.723 | 0.78 |
| 166 | CB | TRP 55 | A | -3.527 | 55.614 | 0.293 | 0.69 |
| 167 | CG | TRP 55 | A | -3.900 | 56.679 | -0.691 | 0.80 |
| 168 | CD2 | TRP 55 | A | -4.955 | 57.641 | -0.465 | 0.76 |
| 169 | CE2 | TRP 55 | A | -4.935 | 58.522 | -1.569 | 0.85 |
| 170 | CE3 | TRP 55 | A | -6.064 | 57.611 | 0.374 | 0.87 |
| 171 | CD1 | TRP 55 | A | -3.230 | 57.113 | -1.796 | 0.74 |
| 172 | NE1 | TRP 55 | A | -3.835 | 58.229 | -2.337 | 0.76 |
| 173 | CZ2 | TRP 55 | A | -5.913 | 59.493 | -1.745 | 0.78 |
| 174 | CZ3 | TRP 55 | A | -7.074 | 58.520 | 0.151 | 0.88 |
| 175 | CH2 | TRP 55 | A | -7.012 | 59.424 | -0.905 | 0.82 |
| 176 | C | TRP 55 | A | -3.640 | 54.977 | 2.770 | 0.84 |
| 177 | O | TRP 55 | A | -4.364 | 53.952 | 2 758 | 0.77 |
| 178 | N | ILE 56 | A | -2.653 | 55.170 | 3.642 | 0.83 |
| 179 | CA | ILE 56 | A | -2.272 | 54.240 | 4.693 | 0.78 |
| 180 | CB | ILE 56 | A | -0.750 | 54.279 | 5.076 | 0.77 |

Fig. 16.4

| ATOM | | RESIDUE | | CHAIN | X | Y | Z | δ |
|---|---|---|---|---|---|---|---|---|
| 181 | CG2 | ILE | 56 | A | -0.539 | 54.069 | 6.606 | 0.71 |
| 182 | CG1 | ILE | 56 | A | -0.007 | 53.147 | 4.316 | 0.82 |
| 183 | CD | ILE | 56 | A | 1.044 | 53.678 | 3.298 | 0.90 |
| 184 | C | ILE | 56 | A | -3.122 | 54.432 | 5.944 | 0.74 |
| 185 | O | ILE | 56 | A | -3.277 | 55.575 | 6.388 | 0.80 |
| 186 | N | ILE | 57 | A | -3.481 | 53.314 | 6.567 | 0.68 |
| 187 | CA | ILE | 57 | A | -4.235 | 53.305 | 7.822 | 0.64 |
| 188 | CB | ILE | 57 | A | -5.462 | 52.319 | 7.725 | 0.65 |
| 189 | CG2 | ILE | 57 | A | -6.003 | 51.940 | 9.109 | 0.55 |
| 190 | CG1 | ILE | 57 | A | -6.532 | 52.829 | 6.736 | 0.64 |
| 191 | CD | ILE | 57 | A | -7.736 | 51.860 | 6.540 | 0.62 |
| 192 | C | ILE | 57 | A | -3.350 | 52.989 | 9.020 | 0.60 |
| 193 | O | ILE | 57 | A | -3.634 | 53.435 | 10.145 | 0.62 |
| 194 | N | ALA | 58 | A | -2.432 | 52.035 | 8.834 | 0.58 |
| 195 | CA | ALA | 58 | A | -1.568 | 51.588 | 9.967 | 0.49 |
| 196 | CB | ALA | 58 | A | -2.381 | 50.553 | 10.789 | 0.55 |
| 197 | C | ALA | 58 | A | -0.372 | 50.826 | 9.376 | 0.46 |
| 198 | O | ALA | 58 | A | -0.718 | 50.311 | 8.302 | 0.49 |
| 199 | N | PRO | 59 | A | 0.849 | 51.149 | 9.744 | 0.53 |
| 200 | CD | PRO | 59 | A | 2.056 | 50.542 | 9.192 | 0.46 |
| 201 | CA | PRO | 59 | A | 1.271 | 52.004 | 10.870 | 0.45 |
| 202 | CB | PRO | 59 | A | 2.504 | 51.340 | 11.429 | 0.47 |
| 203 | CG | PRO | 59 | A | 3.139 | 50.681 | 10.217 | 0.43 |
| 204 | C | PRO | 59 | A | 1.496 | 53.434 | 10.384 | 0.53 |
| 205 | O | PRO | 59 | A | 1.157 | 53.822 | 9.239 | 0.55 |
| 206 | N | GLU | 60 | A | 2.009 | 54.297 | 11.255 | 0.49 |
| 207 | CA | GLU | 60 | A | 2.315 | 55.678 | 10.776 | 0.58 |
| 208 | CB | GLU | 60 | A | 1.953 | 56.668 | 11.906 | 0.64 |
| 209 | CG | GLU | 60 | A | 0.536 | 57.221 | 11.886 | 0.77 |
| 210 | CD | GLU | 60 | A | -0.327 | 57.374 | 13.082 | 0.79 |
| 211 | OE1 | GLU | 60 | A | -1.419 | 56.801 | 13.170 | 0.84 |
| 212 | OE2 | GLU | 60 | A | 0.122 | 58.112 | 13.997 | 0.61 |
| 213 | C | GLU | 60 | A | 3.778 | 55.806 | 10.374 | 0.53 |
| 214 | O | GLU | 60 | A | 4.180 | 56.692 | 9.605 | 0.52 |
| 215 | N | GLY | 61 | A | 4.521 | 54.712 | 10.496 | 0.52 |
| 216 | CA | GLY | 61 | A | 5.866 | 54.512 | 9.965 | 0.54 |
| 217 | C | GLY | 61 | A | 6.549 | 53.304 | 10.585 | 0.58 |
| 218 | O | GLY | 61 | A | 5.879 | 52.548 | 11.298 | 0.55 |
| 219 | N | TYR | 62 | A | 7.807 | 53.047 | 10.231 | 0.55 |
| 220 | CA | TYR | 62 | A | 8.462 | 51.838 | 10.845 | 0.54 |
| 221 | CB | TYR | 62 | A | 8.178 | 50.656 | 9.853 | 0.38 |
| 222 | CG | TYR | 62 | A | 8.980 | 50.842 | 8.558 | 0.47 |
| 223 | CD1 | TYR | 62 | A | 8.538 | 51.787 | 7.649 | 0.47 |
| 224 | CE1 | TYR | 62 | A | 9.247 | 52.151 | 6.499 | 0.51 |
| 225 | CD2 | TYR | 62 | A | 10.091 | 50.092 | 8.201 | 0.45 |

Fig. 16.5

| ATOM | | RESIDUE | | CHAIN | X | Y | Z | δ |
|---|---|---|---|---|---|---|---|---|
| 226 | CE2 | TYR | 62 | A | 10.662 | 50.225 | 6.912 | 0.35 |
| 227 | CZ | TYR | 62 | A | 10.294 | 51.305 | 6.115 | 0.51 |
| 228 | OH | TYR | 62 | A | 10.785 | 51.429 | 4.839 | 0.65 |
| 229 | C | TYR | 62 | A | 9.960 | 52.092 | 10.973 | 0.59 |
| 230 | O | TYR | 62 | A | 10.580 | 52.978 | 10.330 | 0.55 |
| 231 | N | ALA | 63 | A | 10.590 | 51.236 | 11.731 | 0.54 |
| 232 | CA | ALA | 63 | A | 12.067 | 51.311 | 11.984 | 0.49 |
| 233 | CB | ALA | 63 | A | 12.243 | 50.507 | 13.282 | 0.58 |
| 234 | C | ALA | 63 | A | 12.734 | 50.563 | 10.845 | 0.51 |
| 235 | O | ALA | 63 | A | 12.508 | 49.358 | 10.665 | 0.58 |
| 236 | N | ALA | 64 | A | 13.289 | 51.297 | 9.895 | 0.54 |
| 237 | CA | ALA | 64 | A | 13.878 | 50.657 | 8.735 | 0.53 |
| 238 | CB | ALA | 64 | A | 13.779 | 51.617 | 7.550 | 0.53 |
| 239 | C | ALA | 64 | A | 15.319 | 50.155 | 8.972 | 0.52 |
| 240 | O | ALA | 64 | A | 15.797 | 49.399 | 8.091 | 0.54 |
| 241 | N | TYR | 65 | A | 16.092 | 50.933 | 9.671 | 0.51 |
| 242 | CA | TYR | 65 | A | 17.512 | 50.804 | 9.978 | 0.54 |
| 243 | CB | TYR | 65 | A | 17.944 | 49.390 | 10.438 | 0.47 |
| 244 | CG | TYR | 65 | A | 17.297 | 49.063 | 11.777 | 0.47 |
| 245 | CD1 | TYR | 65 | A | 17.763 | 49.564 | 12.974 | 0.44 |
| 246 | CE1 | TYR | 65 | A | 17.164 | 49.219 | 14.190 | 0.47 |
| 247 | CD2 | TYR | 65 | A | 15.978 | 48.600 | 11.756 | 0.61 |
| 248 | CE2 | TYR | 65 | A | 15.250 | 48.484 | 12.922 | 0.44 |
| 249 | CZ | TYR | 65 | A | 15.849 | 48.733 | 14.139 | 0.67 |
| 250 | OH | TYR | 65 | A | 15.077 | 48.514 | 15.253 | 0.70 |
| 251 | C | TYR | 65 | A | 18.332 | 51.188 | 8.752 | 0.51 |
| 252 | O | TYR | 65 | A | 17.714 | 51.205 | 7.664 | 0.49 |
| 253 | N | TYR | 66 | A | 19.638 | 51.001 | 8.928 | 0.52 |
| 254 | CA | TYR | 66 | A | 20.521 | 51.078 | 7.729 | 0.50 |
| 255 | CB | TYR | 66 | A | 20.564 | 52.484 | 7.126 | 0.60 |
| 256 | CG | TYR | 66 | A | 21.276 | 53.507 | 7.983 | 0.59 |
| 257 | CD1 | TYR | 66 | A | 20.563 | 54.255 | 8.917 | 0.59 |
| 258 | CE1 | TYR | 66 | A | 21.155 | 55.260 | 9.659 | 0.53 |
| 259 | CD2 | TYR | 66 | A | 22.592 | 53.893 | 7.721 | 0.53 |
| 260 | CE2 | TYR | 66 | A | 23.149 | 55.001 | 8.335 | 0.47 |
| 261 | CZ | TYR | 66 | A | 22.511 | 55.532 | 9.448 | 0.58 |
| 262 | OH | TYR | 66 | A | 23.095 | 56.600 | 10.066 | 0.70 |
| 263 | C | TYR | 66 | A | 21.939 | 50.673 | 8.166 | 0.51 |
| 264 | O | TYR | 66 | A | 22.223 | 50.678 | 9.351 | 0.52 |
| 265 | N | CYS | 67 | A | 22 764 | 50.444 | 7.173 | 0.58 |
| 266 | CA | CYS | 67 | A | 24.127 | 49.897 | 7.372 | 0.57 |
| 267 | C | CYS | 67 | A | 25.134 | 50.997 | 7.066 | 0.52 |
| 268 | O | CYS | 67 | A | 25.035 | 51.589 | 5.968 | 0.48 |
| 269 | CB | CYS | 67 | A | 24.270 | 48.712 | 6.413 | 0.54 |
| 270 | SG | CYS | 67 | A | 23.285 | 47.244 | 6.831 | 0.64 |

Fig. 16.6

| ATOM | RESIDUE | CHAIN | X | Y | Z | δ |
|---|---|---|---|---|---|---|
| 271 | N | GLU | 68 | A | 26.124 | 51.140 | 7.930 | 0.56 |
| 272 | CA | GLU | 68 | A | 27.251 | 52.049 | 7.617 | 0.47 |
| 273 | CB | GLU | 68 | A | 26.880 | 53.495 | 7.993 | 0.68 |
| 274 | CG | GLU | 68 | A | 27.575 | 54.628 | 7.264 | 0.53 |
| 275 | CD | GLU | 68 | A | 27.058 | 56.019 | 7.510 | 0.67 |
| 276 | OE1 | GLU | 68 | A | 27.235 | 56.925 | 6.720 | 0.64 |
| 277 | OE2 | GLU | 68 | A | 26.696 | 56.240 | 8.687 | 0.63 |
| 278 | C | GLU | 68 | A | 28.467 | 51.725 | 8.485 | 0.43 |
| 279 | O | GLU | 68 | A | 28.311 | 51.441 | 9.663 | 0.42 |
| 280 | N | GLY | 69 | A | 29.646 | 52.013 | 7.922 | 0.48 |
| 281 | CA | GLY | 69 | A | 30.920 | 51.860 | 8.669 | 0.44 |
| 282 | C | GLY | 69 | A | 31.899 | 51.218 | 7.670 | 0.51 |
| 283 | O | GLY | 69 | A | 31.525 | 50.790 | 6.563 | 0.53 |
| 284 | N | GLU | 70 | A | 33.165 | 51.150 | 8.048 | 0.57 |
| 285 | CA | GLU | 70 | A | 34.166 | 50.669 | 7.116 | 0.63 |
| 286 | CB | GLU | 70 | A | 35.428 | 51.440 | 6.924 | 0.74 |
| 287 | CG | GLU | 70 | A | 36.419 | 51.567 | 8.062 | 0.77 |
| 288 | CD | GLU | 70 | A | 37.808 | 51.898 | 7.554 | 1.02 |
| 289 | OE1 | GLU | 70 | A | 38.022 | 52.115 | 6.372 | 0.84 |
| 290 | OE2 | GLU | 70 | A | 38.665 | 51.734 | 8.441 | 0.95 |
| 291 | C | GLU | 70 | A | 34.384 | 49.172 | 7.133 | 0.44 |
| 292 | O | GLU | 70 | A | 34.224 | 48.564 | 8.186 | 0.42 |
| 293 | N | CYS | 71 | A | 34.793 | 48.707 | 5.962 | 0.50 |
| 294 | CA | CYS | 71 | A | 35.136 | 47.281 | 5.805 | 0.62 |
| 295 | C | CYS | 71 | A | 36.652 | 47.128 | 5.637 | 0.54 |
| 296 | O | CYS | 71 | A | 37.173 | 47.188 | 4.547 | 0.51 |
| 297 | CB | CYS | 71 | A | 34.283 | 46.609 | 4.771 | 0.62 |
| 298 | SG | CYS | 71 | A | 32.525 | 46.435 | 5.196 | 0.57 |
| 299 | N | ALA | 72 | A | 37.345 | 47.031 | 6.745 | 0.50 |
| 300 | CA | ALA | 72 | A | 38.781 | 47.033 | 6.862 | 0.61 |
| 301 | CB | ALA | 72 | A | 39.243 | 48.414 | 7.425 | 0.61 |
| 302 | C | ALA | 72 | A | 39.174 | 45.969 | 7.903 | 0.62 |
| 303 | O | ALA | 72 | A | 38.444 | 45.747 | 8.880 | 0.59 |
| 304 | N | PHE | 73 | A | 40.472 | 45.646 | 7.785 | 0.59 |
| 305 | CA | PHE | 73 | A | 41.088 | 44.789 | 8.805 | 0.46 |
| 306 | CB | PHE | 73 | A | 42.425 | 44.197 | 8.472 | 0.54 |
| 307 | CG | PHE | 73 | A | 42.433 | 43.361 | 7.198 | 0.45 |
| 308 | CD1 | PHE | 73 | A | 41.659 | 42.210 | 7.129 | 0.43 |
| 309 | CD2 | PHE | 73 | A | 43.175 | 43.752 | 6.117 | 0.45 |
| 310 | CE1 | PHE | 73 | A | 41.516 | 41.496 | 5.935 | 0.34 |
| 311 | CE2 | PHE | 73 | A | 43.202 | 42.987 | 4.959 | 0.37 |
| 312 | CZ | PHE | 73 | A | 42.340 | 41.869 | 4.895 | 0.33 |
| 313 | C | PHE | 73 | A | 40.895 | 45.531 | 10.083 | 0.52 |
| 314 | O | PHE | 73 | A | 41.336 | 46.672 | 9.925 | 0.54 |
| 315 | N | PRO | 74 | A | 40.737 | 44.872 | 11.197 | 0.57 |

Fig. 16.7

| ATOM | | RESIDUE | | CHAIN | X | Y | Z | δ |
|---|---|---|---|---|---|---|---|---|
| 316 | CD  | PRO | 74 | A | 40.751 | 45.550 | 12.495 | 0.57 |
| 317 | CA  | PRO | 74 | A | 40.171 | 43.560 | 11.370 | 0.56 |
| 318 | CB  | PRO | 74 | A | 40.235 | 43.204 | 12.832 | 0.52 |
| 319 | CG  | PRO | 74 | A | 40.362 | 44.522 | 13.519 | 0.54 |
| 320 | C   | PRO | 74 | A | 38.776 | 43.425 | 10.805 | 0.66 |
| 321 | O   | PRO | 74 | A | 37.919 | 44.259 | 11.112 | 0.74 |
| 322 | N   | LEU | 75 | A | 38.607 | 42.334 | 10.090 | 0.58 |
| 323 | CA  | LEU | 75 | A | 37.302 | 41.889 | 9.627  | 0.61 |
| 324 | CB  | LEU | 75 | A | 37.400 | 41.397 | 8.209  | 0.63 |
| 325 | CG  | LEU | 75 | A | 37.038 | 42.169 | 7.006  | 0.60 |
| 326 | CD1 | LEU | 75 | A | 36.742 | 43.625 | 7.025  | 0.57 |
| 327 | CD2 | LEU | 75 | A | 37.596 | 41.719 | 5.703  | 0.49 |
| 328 | C   | LEU | 75 | A | 36.805 | 40.946 | 10.726 | 0.68 |
| 329 | O   | LEU | 75 | A | 36.983 | 39.722 | 10.655 | 0.72 |
| 330 | N   | ASN | 76 | A | 36.381 | 41.589 | 11.802 | 0.68 |
| 331 | CA  | ASN | 76 | A | 35.736 | 40.919 | 12.939 | 0.66 |
| 332 | CB  | ASN | 76 | A | 35.320 | 41.901 | 14.028 | 0.62 |
| 333 | CG  | ASN | 76 | A | 36.481 | 42.611 | 14.697 | 0.83 |
| 334 | OD1 | ASN | 76 | A | 37.623 | 42.110 | 14.677 | 0.97 |
| 335 | ND2 | ASN | 76 | A | 36.246 | 43.740 | 15.370 | 0.81 |
| 336 | C   | ASN | 76 | A | 34.658 | 39.972 | 12.449 | 0.67 |
| 337 | O   | ASN | 76 | A | 34.194 | 39.990 | 11.281 | 0.73 |
| 338 | N   | SER | 77 | A | 34.415 | 38.958 | 13.260 | 0.73 |
| 339 | CA  | SER | 77 | A | 33.432 | 37.909 | 12.886 | 0.74 |
| 340 | CB  | SER | 77 | A | 33.434 | 36.747 | 13.894 | 0.54 |
| 341 | OG  | SER | 77 | A | 33.117 | 35.573 | 13.128 | 0.96 |
| 342 | C   | SER | 77 | A | 32.033 | 38.539 | 12.767 | 0.62 |
| 343 | O   | SER | 77 | A | 31.287 | 38.245 | 11.835 | 0.66 |
| 344 | N   | TYR | 78 | A | 31.705 | 39.321 | 13.767 | 0.63 |
| 345 | CA  | TYR | 78 | A | 30.579 | 40.220 | 13.850 | 0.75 |
| 346 | CB  | TYR | 78 | A | 30.615 | 41.057 | 15.137 | 0.63 |
| 347 | CG  | TYR | 78 | A | 30.922 | 42.527 | 14.976 | 0.91 |
| 348 | CD1 | TYR | 78 | A | 32.115 | 43.118 | 15.447 | 0.81 |
| 349 | CE1 | TYR | 78 | A | 32.383 | 44.471 | 15.228 | 0.88 |
| 350 | CD2 | TYR | 78 | A | 29.929 | 43.382 | 14.494 | 0.98 |
| 351 | CE2 | TYR | 78 | A | 30.178 | 44.734 | 14.265 | 0.99 |
| 352 | CZ  | TYR | 78 | A | 31.402 | 45.277 | 14.640 | 0.94 |
| 353 | OH  | TYR | 78 | A | 31.541 | 46.629 | 14.483 | 0.97 |
| 354 | C   | TYR | 78 | A | 30.340 | 41.045 | 12.592 | 0.78 |
| 355 | O   | TYR | 78 | A | 29.244 | 41.627 | 12.487 | 0.79 |
| 356 | N   | MET | 79 | A | 31.322 | 41.194 | 11.719 | 0.74 |
| 357 | CA  | MET | 79 | A | 31.228 | 41.956 | 10.475 | 0.62 |
| 358 | CB  | MET | 79 | A | 32.506 | 42.736 | 10.191 | 0.68 |
| 359 | CG  | MET | 79 | A | 32.600 | 43.844 | 11.207 | 0.51 |
| 360 | SD  | MET | 79 | A | 34.243 | 44.508 | 11.149 | 0.67 |

Fig. 16.8

| ATOM | | RESIDUE | | CHAIN | X | Y | Z | δ |
|---|---|---|---|---|---|---|---|---|
| 361 | CE | MET | 79 | A | 34.390 | 45.358 | 9.625 | 0.53 |
| 362 | C | MET | 79 | A | 30.807 | 41.104 | 9.309 | 0.58 |
| 363 | O | MET | 79 | A | 30.601 | 41.571 | 8.186 | 0.61 |
| 364 | N | ASN | 80 | A | 30.496 | 39.834 | 9.575 | 0.55 |
| 365 | CA | ASN | 80 | A | 30.017 | 39.029 | 8.431 | 0.54 |
| 366 | CB | ASN | 80 | A | 28.501 | 38.847 | 8.469 | 0.86 |
| 367 | CG | ASN | 80 | A | 27.937 | 38.129 | 7.244 | 1.05 |
| 368 | OD1 | ASN | 80 | A | 28.023 | 38.584 | 6.079 | 0.95 |
| 369 | ND2 | ASN | 80 | A | 27.180 | 37.052 | 7.518 | 0.86 |
| 370 | C | ASN | 80 | A | 30.573 | 39.451 | 7.091 | 0.57 |
| 371 | O | ASN | 80 | A | 29.821 | 39.382 | 6.054 | 0.67 |
| 372 | N | ALA | 81 | A | 31.852 | 39.123 | 6.890 | 0.60 |
| 373 | CA | ALA | 81 | A | 32.527 | 39.331 | 5.577 | 0.52 |
| 374 | CB | ALA | 81 | A | 34.012 | 39.611 | 5.894 | 0.53 |
| 375 | C | ALA | 81 | A | 32.276 | 38.077 | 4.802 | 0.53 |
| 376 | O | ALA | 81 | A | 32.376 | 37.027 | 5.445 | 0.60 |
| 377 | N | THR | 82 | A | 32.057 | 38.098 | 3.500 | 0.54 |
| 378 | CA | THR | 82 | A | 32.162 | 36.889 | 2.680 | 0.44 |
| 379 | CB | THR | 82 | A | 31.426 | 37.170 | 1.326 | 0.45 |
| 380 | OG1 | THR | 82 | A | 32.057 | 38.409 | 0.821 | 0.49 |
| 381 | CG2 | THR | 82 | A | 29.937 | 37.606 | 1.601 | 0.58 |
| 382 | C | THR | 82 | A | 33.652 | 36.578 | 2.443 | 0.67 |
| 383 | O | THR | 82 | A | 34.576 | 37.324 | 2.852 | 0.55 |
| 384 | N | ASN | 83 | A | 33.946 | 35.396 | 1.913 | 0.61 |
| 385 | CA | ASN | 83 | A | 35.352 | 35.123 | 1.529 | 0.56 |
| 386 | CB | ASN | 83 | A | 35.532 | 33.739 | 0.901 | 0.53 |
| 387 | CG | ASN | 83 | A | 35.404 | 32.602 | 1.900 | 0.48 |
| 388 | OD1 | ASN | 83 | A | 35.542 | 32.820 | 3.108 | 0.55 |
| 389 | ND2 | ASN | 83 | A | 34.880 | 31.483 | 1.410 | 0.55 |
| 390 | C | ASN | 83 | A | 35.756 | 36.228 | 0.535 | 0.55 |
| 391 | O | ASN | 83 | A | 36.971 | 36.442 | 0.428 | 0.54 |
| 392 | N | HIS | 84 | A | 35.021 | 36.349 | -0.569 | 0.55 |
| 393 | CA | HIS | 84 | A | 35.225 | 37.440 | -1.518 | 0.41 |
| 394 | CB | HIS | 84 | A | 34.045 | 37.721 | -2.462 | 0.58 |
| 395 | CG | HIS | 84 | A | 34.351 | 38.672 | -3.572 | 0.40 |
| 396 | CD2 | HIS | 84 | A | 34.775 | 38.378 | -4.809 | 0.29 |
| 397 | ND1 | HIS | 84 | A | 34.471 | 40.064 | -3.426 | 0.22 |
| 398 | CE1 | HIS | 84 | A | 34.778 | 40.549 | -4.612 | 0.18 |
| 399 | NE2 | HIS | 84 | A | 34.912 | 39.565 | -5.513 | 0.31 |
| 400 | C | HIS | 84 | A | 35.639 | 38.754 | -0.878 | 0.47 |
| 401 | O | HIS | 84 | A | 36.412 | 39.493 | -1.484 | 0.50 |
| 402 | N | ALA | 85 | A | 35.014 | 39.218 | 0.190 | 0.52 |
| 403 | CA | ALA | 85 | A | 35.340 | 40.514 | 0.773 | 0.53 |
| 404 | CB | ALA | 85 | A | 34.341 | 40.834 | 1.868 | 0.48 |
| 405 | C | ALA | 85 | A | 36.756 | 40.456 | 1.388 | 0.57 |

Fig. 16.9

| ATOM | | RESIDUE | CHAIN | X | Y | Z | δ |
|---|---|---|---|---|---|---|---|
| 406 | O | ALA | 85 | A | 37.222 | 41.564 | 1.781 | 0.55 |
| 407 | N | ILE | 86 | A | 37.011 | 39.347 | 2.095 | 0.50 |
| 408 | CA | ILE | 86 | A | 38.305 | 39.171 | 2.783 | 0.52 |
| 409 | CB | ILE | 86 | A | 38.390 | 37.738 | 3.425 | 0.57 |
| 410 | CG2 | ILE | 86 | A | 39.877 | 37.505 | 3.912 | 0.42 |
| 411 | CG1 | ILE | 86 | A | 37.435 | 37.747 | 4.652 | 0.40 |
| 412 | CD | ILE | 86 | A | 37.270 | 36.306 | 5.234 | 0.49 |
| 413 | C | ILE | 86 | A | 39.432 | 39.316 | 1.751 | 0.45 |
| 414 | O | ILE | 86 | A | 40.345 | 40.113 | 1.894 | 0.58 |
| 415 | N | VAL | 87 | A | 39.232 | 38.678 | 0.618 | 0.49 |
| 416 | CA | VAL | 87 | A | 40.135 | 38.769 | -0.517 | 0.42 |
| 417 | CB | VAL | 87 | A | 39.663 | 37.786 | -1.570 | 0.43 |
| 418 | CG1 | VAL | 87 | A | 40.259 | 38.002 | -2.950 | 0.39 |
| 419 | CG2 | VAL | 87 | A | 39.952 | 36.365 | -1.097 | 0.50 |
| 420 | C | VAL | 87 | A | 40.276 | 40.212 | -0.984 | 0.52 |
| 421 | O | VAL | 87 | A | 41.217 | 40.442 | -1.765 | 0.57 |
| 422 | N | GLN | 88 | A | 39.086 | 40.754 | -1.301 | 0.64 |
| 423 | CA | GLN | 88 | A | 38.956 | 42.130 | -1.773 | 0.50 |
| 424 | CB | GLN | 88 | A | 37.685 | 42.583 | -2.372 | 0.54 |
| 425 | CG | GLN | 88 | A | 37.381 | 44.072 | -2.355 | 0.50 |
| 426 | CD | GLN | 88 | A | 36.114 | 44.340 | -3.126 | 0.53 |
| 427 | OE1 | GLN | 88 | A | 35.371 | 43.417 | -3.448 | 0.63 |
| 428 | NE2 | GLN | 88 | A | 35.759 | 45.595 | -3.183 | 0.42 |
| 429 | C | GLN | 88 | A | 39.679 | 43.085 | -0.867 | 0.42 |
| 430 | O | GLN | 88 | A | 40.292 | 44.052 | -1.314 | 0.52 |
| 431 | N | THR | 89 | A | 39.512 | 42.927 | 0.420 | 0.52 |
| 432 | CA | THR | 89 | A | 40.198 | 43.702 | 1.434 | 0.51 |
| 433 | CB | THR | 89 | A | 39.557 | 43.573 | 2.830 | 0.44 |
| 434 | OG1 | THR | 89 | A | 38.120 | 43.824 | 2.666 | 0.58 |
| 435 | CG2 | THR | 89 | A | 40.094 | 44.473 | 3.906 | 0.28 |
| 436 | C | THR | 89 | A | 41.709 | 43.490 | 1.437 | 0.60 |
| 437 | O | THR | 89 | A | 42.412 | 44.454 | 1.772 | 0.60 |
| 438 | N | LEU | 90 | A | 42.218 | 42.388 | 0.944 | 0.60 |
| 439 | CA | LEU | 90 | A | 43.647 | 42.052 | 0.965 | 0.54 |
| 440 | CB | LEU | 90 | A | 43.888 | 40.582 | 1.267 | 0.64 |
| 441 | CG | LEU | 90 | A | 45.291 | 40.015 | 1.078 | 0.62 |
| 442 | CD1 | LEU | 90 | A | 46.152 | 40.465 | 2.272 | 0.49 |
| 443 | CD2 | LEU | 90 | A | 45.199 | 38.484 | 1.213 | 0.62 |
| 444 | C | LEU | 90 | A | 44.288 | 42.626 | -0.279 | 0.47 |
| 445 | O | LEU | 90 | A | 45.284 | 43.352 | -0.185 | 0.63 |
| 446 | N | VAL | 91 | A | 43.579 | 42.594 | -1.376 | 0.43 |
| 447 | CA | VAL | 91 | A | 43.901 | 43.242 | -2.618 | 0.40 |
| 448 | CB | VAL | 91 | A | 42.933 | 42.872 | -3.726 | 0.35 |
| 449 | CG1 | VAL | 91 | A | 43.378 | 43.386 | -5.070 | 0.33 |
| 450 | CG2 | VAL | 91 | A | 42.991 | 41.354 | -3.941 | 0.47 |

Fig. 16.10

| ATOM | | RESIDUE | | CHAIN | X | Y | Z | δ |
|---|---|---|---|---|---|---|---|---|
| 451 | C | VAL | 91 | A | 44.178 | 44.727 | -2.505 | 0.49 |
| 452 | O | VAL | 91 | A | 44.650 | 45.311 | -3.477 | 0.59 |
| 453 | N | HIS | 92 | A | 43.441 | 45.341 | -1.635 | 0.51 |
| 454 | CA | HIS | 92 | A | 43.261 | 46.741 | -1.409 | 0.56 |
| 455 | CB | HIS | 92 | A | 41.870 | 47.044 | -0.770 | 0.55 |
| 456 | CG | HIS | 92 | A | 41.747 | 48.505 | -0.469 | 0.52 |
| 457 | CD2 | HIS | 92 | A | 42.030 | 49.193 | 0.668 | 0.36 |
| 458 | ND1 | HIS | 92 | A | 41.469 | 49.429 | -1.483 | 0.42 |
| 459 | CE1 | HIS | 92 | A | 41.437 | 50.616 | -0.876 | 0.49 |
| 460 | NE2 | HIS | 92 | A | 41.799 | 50.525 | 0.379 | 0.43 |
| 461 | C | HIS | 92 | A | 44.394 | 47.223 | -0.492 | 0.50 |
| 462 | O | HIS | 92 | A | 45.068 | 48.210 | -0.766 | 0.62 |
| 463 | N | PHE | 93 | A | 44.696 | 46.435 | 0.494 | 0.52 |
| 464 | CA | PHE | 93 | A | 45.853 | 46.579 | 1.335 | 0.62 |
| 465 | CB | PHE | 93 | A | 45.848 | 45.644 | 2.519 | 0.52 |
| 466 | CG | PHE | 93 | A | 47.210 | 45.573 | 3.167 | 0.65 |
| 467 | CD1 | PHE | 93 | A | 48.069 | 44.545 | 2.795 | 0.60 |
| 468 | CD2 | PHE | 93 | A | 47.593 | 46.500 | 4.135 | 0.66 |
| 469 | CE1 | PHE | 93 | A | 49.393 | 44.536 | 3.237 | 0.64 |
| 470 | CE2 | PHE | 93 | A | 48.928 | 46.509 | 4.580 | 0.66 |
| 471 | CZ | PHE | 93 | A | 49.711 | 45.369 | 4.295 | 0.51 |
| 472 | C | PHE | 93 | A | 47.144 | 46.550 | 0.506 | 0.66 |
| 473 | O | PHE | 93 | A | 47.943 | 47.489 | 0.617 | 0.73 |
| 474 | N | ILE | 94 | A | 47.331 | 45.557 | -0.315 | 0.64 |
| 475 | CA | ILE | 94 | A | 48.423 | 45.367 | -1.252 | 0.61 |
| 476 | CB | ILE | 94 | A | 48.402 | 43.957 | -1.897 | 0.63 |
| 477 | CG2 | ILE | 94 | A | 49.466 | 43.645 | -2.972 | 0.63 |
| 478 | CG1 | ILE | 94 | A | 48.404 | 42.831 | -0.814 | 0.51 |
| 479 | CD | ILE | 94 | A | 48.147 | 41.476 | -1.602 | 0.63 |
| 480 | C | ILE | 94 | A | 48.550 | 46.477 | -2.289 | 0.70 |
| 481 | O | ILE | 94 | A | 49.659 | 46.609 | -2.824 | 0.75 |
| 482 | N | ASN | 95 | A | 47.465 | 46.873 | -2.923 | 0.74 |
| 483 | CA | ASN | 95 | A | 47.356 | 47.921 | -3.913 | 0.64 |
| 484 | CB | ASN | 95 | A | 47.834 | 47.543 | -5.288 | 0.70 |
| 485 | CG | ASN | 95 | A | 48.029 | 48.754 | -6.197 | 0.86 |
| 486 | OD1 | ASN | 95 | A | 47.797 | 49.907 | -5.782 | 0.79 |
| 487 | ND2 | ASN | 95 | A | 48.255 | 48.499 | -7.487 | 0.87 |
| 488 | C | ASN | 95 | A | 46.014 | 48.658 | -3.867 | 0.65 |
| 489 | O | ASN | 95 | A | 45.144 | 48.489 | -4.746 | 0.65 |
| 490 | N | PRO | 96 | A | 46.039 | 49.731 | -3.096 | 0.64 |
| 491 | CD | PRO | 96 | A | 47.201 | 50.067 | -2.228 | 0.68 |
| 492 | CA | PRO | 96 | A | 44.914 | 50.589 | -2.805 | 0.65 |
| 493 | CB | PRO | 96 | A | 45.500 | 51.713 | -1.943 | 0.69 |
| 494 | CG | PRO | 96 | A | 46.582 | 50.992 | -1.180 | 0.72 |
| 495 | C | PRO | 96 | A | 44.106 | 51.115 | -3.961 | 0.72 |

Fig. 16.11

| ATOM | RESIDUE | | CHAIN | X | Y | Z | δ |
|---|---|---|---|---|---|---|---|
| 496 | O | PRO 96 | A | 42.930 | 51.520 | -3.812 | 0.73 |
| 497 | N | GLU 97 | A | 44.662 | 50.992 | -5.140 | 0.72 |
| 498 | CA | GLU 97 | A | 44.135 | 51.677 | -6.338 | 0.70 |
| 499 | CB | GLU 97 | A | 45.301 | 52.282 | -7.121 | 0.84 |
| 500 | CG | GLU 97 | A | 45.685 | 53.733 | -7.069 | 0.80 |
| 501 | CD | GLU 97 | A | 45.275 | 54.630 | -5.952 | 1.11 |
| 502 | OE1 | GLU 97 | A | 44.477 | 55.564 | -6.044 | 1.13 |
| 503 | OE2 | GLU 97 | A | 46.026 | 54.515 | -4.948 | 1.11 |
| 504 | C | GLU 97 | A | 43.468 | 50.625 | -7.224 | 0.72 |
| 505 | O | GLU 97 | A | 42.759 | 50.951 | -8.192 | 0.74 |
| 506 | N | THR 98 | A | 43.863 | 49.373 | -7.015 | 0.69 |
| 507 | CA | THR 98 | A | 43.305 | 48.280 | -7.830 | 0.67 |
| 508 | CB | THR 98 | A | 44.071 | 46.915 | -7.570 | 0.65 |
| 509 | OG1 | THR 98 | A | 45.398 | 47.345 | -7.123 | 0.77 |
| 510 | CG2 | THR 98 | A | 44.197 | 46.102 | -8.854 | 0.78 |
| 511 | C | THR 98 | A | 41.817 | 48.097 | -7.527 | 0.63 |
| 512 | O | THR 98 | A | 41.046 | 47.740 | -8.443 | 0.67 |
| 513 | N | VAL 99 | A | 41.488 | 48.234 | -6.249 | 0.57 |
| 514 | CA | VAL 99 | A | 40.083 | 47.984 | -5.846 | 0.52 |
| 515 | CB | VAL 99 | A | 39.921 | 46.444 | -5.871 | 0.56 |
| 516 | CG1 | VAL 99 | A | 40.467 | 45.868 | -4.573 | 0.44 |
| 517 | CG2 | VAL 99 | A | 38.532 | 45.932 | -6.138 | 0.62 |
| 518 | C | VAL 99 | A | 39.813 | 48.669 | -4.532 | 0.52 |
| 519 | O | VAL 99 | A | 40.679 | 48.871 | -3.666 | 0.53 |
| 520 | N | PRO 100 | A | 38.557 | 49.141 | -4.403 | 0.53 |
| 521 | CD | PRO 100 | A | 37.460 | 48.923 | -5.352 | 0.54 |
| 522 | CA | PRO 100 | A | 38.083 | 49.661 | -3.125 | 0.49 |
| 523 | CB | PRO 100 | A | 36.659 | 50.149 | -3.411 | 0.50 |
| 524 | CG | PRO 100 | A | 36.231 | 49.470 | -4.666 | 0.47 |
| 525 | C | PRO 100 | A | 38.085 | 48.608 | -2.041 | 0.41 |
| 526 | O | PRO 100 | A | 37.913 | 47.407 | -2.250 | 0.58 |
| 527 | N | LYS 101 | A | 37.739 | 49.029 | -0.836 | 0.48 |
| 528 | CA | LYS 101 | A | 37.365 | 48.136 | 0.241 | 0.40 |
| 529 | CB | LYS 101 | A | 37.549 | 48.844 | 1.590 | 0.58 |
| 530 | CG | LYS 101 | A | 38.756 | 48.257 | 2.367 | 0.69 |
| 531 | CD | LYS 101 | A | 39.462 | 49.214 | 3.271 | 0.65 |
| 532 | CE | LYS 101 | A | 38.839 | 50.616 | 3.297 | 0.61 |
| 533 | NZ | LYS 101 | A | 39.223 | 51.248 | 4.589 | 0.76 |
| 534 | C | LYS 101 | A | 35.850 | 47.825 | 0.048 | 0.56 |
| 535 | O | LYS 101 | A | 35.301 | 48.383 | -0.922 | 0.54 |
| 536 | N | PRO 102 | A | 35.434 | 46.638 | 0.475 | 0.57 |
| 537 | CD | PRO 102 | A | 36.255 | 45.605 | 1.164 | 0.48 |
| 538 | CA | PRO 102 | A | 34.017 | 46.290 | 0.428 | 0.59 |
| 539 | CB | PRO 102 | A | 33.921 | 44.912 | 1.028 | 0.43 |
| 540 | CG | PRO 102 | A | 35.209 | 44.663 | 1.736 | 0.64 |

Fig. 16.12

| ATOM | | RESIDUE | | CHAIN | X | Y | Z | δ |
|---|---|---|---|---|---|---|---|---|
| 541 | C | PRO | 102 | A | 33.146 | 47.342 | 1.076 | 0.56 |
| 542 | O | PRO | 102 | A | 33.527 | 48.083 | 2.006 | 0.63 |
| 543 | N | CYS | 103 | A | 31.861 | 47.298 | 0.744 | 0.58 |
| 544 | CA | CYS | 103 | A | 30.857 | 48.177 | 1.400 | 0.48 |
| 545 | CB | CYS | 103 | A | 30.152 | 49.052 | 0.384 | 0.75 |
| 546 | SG | CYS | 103 | A | 28.673 | 48.328 | -0.344 | 0.81 |
| 547 | C | CYS | 103 | A | 29.943 | 47.435 | 2.355 | 0.55 |
| 548 | O | CYS | 103 | A | 29.809 | 46.208 | 2.353 | 0.53 |
| 549 | N | CYS | 104 | A | 29.644 | 48.101 | 3.461 | 0.32 |
| 550 | CA | CYS | 104 | A | 28.717 | 47.709 | 4.468 | 0.48 |
| 551 | C | CYS | 104 | A | 27.265 | 47.729 | 3.963 | 0.60 |
| 552 | O | CYS | 104 | A | 26.729 | 48.760 | 3.570 | 0.60 |
| 553 | CB | CYS | 104 | A | 28.932 | 48.683 | 5.594 | 0.32 |
| 554 | SG | CYS | 104 | A | 28.146 | 48.223 | 7.124 | 0.54 |
| 555 | N | ALA | 105 | A | 26.605 | 46.583 | 4.024 | 0.51 |
| 556 | CA | ALA | 105 | A | 25.412 | 46.300 | 3.222 | 0.51 |
| 557 | CB | ALA | 105 | A | 25.801 | 45.889 | 1.838 | 0.51 |
| 558 | C | ALA | 105 | A | 24.633 | 45.240 | 4.017 | 0.51 |
| 559 | O | ALA | 105 | A | 25.189 | 44.843 | 5.068 | 0.57 |
| 560 | N | PRO | 106 | A | 23.328 | 45.294 | 3.866 | 0.59 |
| 561 | CD | PRO | 106 | A | 22.564 | 46.026 | 2.822 | 0.51 |
| 562 | CA | PRO | 106 | A | 22.416 | 44.526 | 4.739 | 0.59 |
| 563 | CB | PRO | 106 | A | 21.014 | 45.021 | 4.321 | 0.54 |
| 564 | CG | PRO | 106 | A | 21.235 | 46.282 | 3.559 | 0.50 |
| 565 | C | PRO | 106 | A | 22.577 | 43.053 | 4.332 | 0.58 |
| 566 | O | PRO | 106 | A | 22.779 | 42.755 | 3.154 | 0.54 |
| 567 | N | THR | 107 | A | 22.616 | 42.182 | 5.306 | 0.60 |
| 568 | CA | THR | 107 | A | 22.791 | 40.733 | 4.913 | 0.65 |
| 569 | CB | THR | 107 | A | 23.831 | 40.113 | 5.928 | 0.45 |
| 570 | OG1 | THR | 107 | A | 23.141 | 40.103 | 7.208 | 0.68 |
| 571 | CG2 | THR | 107 | A | 25.153 | 40.852 | 6.091 | 0.56 |
| 572 | C | THR | 107 | A | 21.417 | 40.091 | 5.133 | 0.68 |
| 573 | O | THR | 107 | A | 21.037 | 39.069 | 4.543 | 0.68 |
| 574 | N | GLN | 108 | A | 20.597 | 40.806 | 5.902 | 0.67 |
| 575 | CA | GLN | 108 | A | 19.208 | 40.371 | 6.067 | 0.64 |
| 576 | CB | GLN | 108 | A | 19.029 | 39.316 | 7.105 | 0.58 |
| 577 | CG | GLN | 108 | A | 19.016 | 39.718 | 8.547 | 0.70 |
| 578 | CD | GLN | 108 | A | 18.119 | 38.791 | 9.358 | 0.99 |
| 579 | OE1 | GLN | 108 | A | 17.035 | 38.401 | 8.916 | 0.83 |
| 580 | NE2 | GLN | 108 | A | 18.624 | 38.356 | 10.508 | 0.94 |
| 581 | C | GLN | 108 | A | 18.217 | 41.519 | 6.135 | 0.63 |
| 582 | O | GLN | 108 | A | 18.323 | 42.360 | 7.047 | 0.64 |
| 583 | N | LEU | 109 | A | 17.213 | 41.401 | 5.288 | 0.60 |
| 584 | CA | LEU | 109 | A | 15.994 | 42.229 | 5.307 | 0.65 |
| 585 | CB | LEU | 109 | A | 15.882 | 42.694 | 3.831 | 0.55 |

Fig. 16.13

| ATOM | RESIDUE | | CHAIN | X | Y | Z | δ |
|---|---|---|---|---|---|---|---|
| 586 | CG | LEU 109 | A | 17.101 | 43.501 | 3.407 | 0.59 |
| 587 | CD1 | LEU 109 | A | 17.359 | 43.341 | 1.936 | 0.68 |
| 588 | CD2 | LEU 109 | A | 16.896 | 44.975 | 3.746 | 0.56 |
| 589 | C | LEU 109 | A | 14.740 | 41.492 | 5.774 | 0.70 |
| 590 | O | LEU 109 | A | 14.393 | 40.460 | 5.142 | 0.75 |
| 591 | N | ASN 110 | A | 13.876 | 42.190 | 6.507 | 0.67 |
| 592 | CA | ASN 110 | A | 12.512 | 41.767 | 6.849 | 0.65 |
| 593 | CB | ASN 110 | A | 12.192 | 41.773 | 8.350 | 0.59 |
| 594 | CG | ASN 110 | A | 13.043 | 40.783 | 9.115 | 0.79 |
| 595 | OD1 | ASN 110 | A | 13.197 | 40.850 | 10.340 | 0.90 |
| 596 | ND2 | ASN 110 | A | 13.591 | 39.872 | 8.302 | 0.79 |
| 597 | C | ASN 110 | A | 11.441 | 42.589 | 6.116 | 0.65 |
| 598 | O | ASN 110 | A | 11.655 | 43.703 | 5.641 | 0.61 |
| 599 | N | ALA 111 | A | 10.255 | 41.992 | 6.127 | 0.68 |
| 600 | CA | ALA 111 | A | 9.062 | 42.537 | 5.489 | 0.64 |
| 601 | CB | ALA 111 | A | 8.158 | 41.466 | 4.906 | 0.59 |
| 602 | C | ALA 111 | A | 8.315 | 43.435 | 6.467 | 0.57 |
| 603 | O | ALA 111 | A | 8.500 | 43.354 | 7.697 | 0.54 |
| 604 | N | ILE 112 | A | 7.548 | 44.344 | 5.879 | 0.54 |
| 605 | CA | ILE 112 | A | 6.518 | 45.030 | 6.743 | 0.47 |
| 606 | CB | ILE 112 | A | 6.821 | 46.531 | 6.985 | 0.63 |
| 607 | CG2 | ILE 112 | A | 7.990 | 46.879 | 7.923 | 0.68 |
| 608 | CG1 | ILE 112 | A | 6.825 | 47.379 | 5.712 | 0.56 |
| 609 | CD | ILE 112 | A | 6.369 | 48.858 | 5.888 | 0.64 |
| 610 | C | ILE 112 | A | 5.183 | 44.777 | 5.997 | 0.45 |
| 611 | O | ILE 112 | A | 5.166 | 44.766 | 4.747 | 0.54 |
| 612 | N | SER 113 | A | 4.150 | 44.802 | 6.770 | 0.44 |
| 613 | CA | SER 113 | A | 2.734 | 44.868 | 6.330 | 0.61 |
| 614 | CB | SER 113 | A | 1.946 | 43.791 | 7.102 | 0.63 |
| 615 | OG | SER 113 | A | 2.163 | 42.503 | 6.515 | 0.62 |
| 616 | C | SER 113 | A | 2.172 | 46.244 | 6.694 | 0.53 |
| 617 | O | SER 113 | A | 2.299 | 46.730 | 7.828 | 0.52 |
| 618 | N | VAL 114 | A | 1.400 | 46.804 | 5.778 | 0.55 |
| 619 | CA | VAL 114 | A | 0.651 | 48.025 | 6.121 | 0.58 |
| 620 | CB | VAL 114 | A | 1.371 | 49.244 | 5.514 | 0.64 |
| 621 | CG1 | VAL 114 | A | 2.885 | 49.190 | 5.667 | 0.49 |
| 622 | CG2 | VAL 114 | A | 0.949 | 49.424 | 4.094 | 0.55 |
| 623 | C | VAL 114 | A | -0.813 | 47.879 | 5.686 | 0.60 |
| 624 | O | VAL 114 | A | -1.189 | 47.327 | 4.637 | 0.51 |
| 625 | N | LEU 115 | A | -1.652 | 48.484 | 6.510 | 0.49 |
| 626 | CA | LEU 115 | A | -3.116 | 48.419 | 6.182 | 0.58 |
| 627 | CB | LEU 115 | A | -3.789 | 48.328 | 7.603 | 0.55 |
| 628 | CG | LEU 115 | A | -5.284 | 47.999 | 7.568 | 0.57 |
| 629 | CD1 | LEU 115 | A | -5.523 | 46.603 | 7.036 | 0.59 |
| 630 | CO2 | LEU 115 | A | -5.943 | 48.190 | 8.975 | 0.52 |

Fig. 16.14

| ATOM | RESIDUE | | CHAIN | X | Y | Z | δ |
|---|---|---|---|---|---|---|---|
| 631 | C | LEU 115 | A | -3.421 | 49.685 | 5.403 | 0.47 |
| 632 | O | LEU 115 | A | -3.244 | 50.761 | 5.955 | 0.57 |
| 633 | N | TYR 116 | A | -3.971 | 49.616 | 4.196 | 0.57 |
| 634 | CA | TYR 116 | A | -4.302 | 50.847 | 3.479 | 0.69 |
| 635 | CB | TYR 116 | A | -3.192 | 51.211 | 2.480 | 0.70 |
| 636 | CG | TYR 116 | A | -3.119 | 50.316 | 1.269 | 0.46 |
| 637 | CD1 | TYR 116 | A | -2.487 | 49.097 | 1.272 | 0.57 |
| 638 | CE1 | TYR 116 | A | -2.542 | 48.256 | 0.154 | 0.66 |
| 639 | CD2 | TYR 116 | A | -3.584 | 50.775 | 0.050 | 0.57 |
| 640 | CE2 | TYR 116 | A | -3.689 | 49.971 | -1.067 | 0.52 |
| 641 | CZ | TYR 116 | A | -3.151 | 48.697 | -1.016 | 0.76 |
| 642 | OH | TYR 116 | A | -3.119 | 47.979 | -2.184 | 0.78 |
| 643 | C | TYR 116 | A | -5.692 | 50.766 | 2.849 | 0.69 |
| 644 | O | TYR 116 | A | -6.250 | 49.665 | 2.752 | 0.69 |
| 645 | N | PHE 117 | A | -6.209 | 51.919 | 2.485 | 0.56 |
| 646 | CA | PHE 117 | A | -7.443 | 52.158 | 1.793 | 0.60 |
| 647 | CB | PHE 117 | A | -8.462 | 53.064 | 2.413 | 0.64 |
| 648 | CG | PHE 117 | A | -8.074 | 54.254 | 3.206 | 0.82 |
| 649 | CD1 | PHE 117 | A | -8.221 | 54.256 | 4.599 | 0.91 |
| 650 | CD2 | PHE 117 | A | -7.813 | 55.472 | 2.561 | 1.11 |
| 651 | CE1 | PHE 117 | A | -7.964 | 55.401 | 5.343 | 1.12 |
| 652 | CE2 | PHE 117 | A | -7.547 | 56.638 | 3.292 | 1.03 |
| 653 | CZ | PHE 117 | A | -7.638 | 56.601 | 4.697 | 1.02 |
| 654 | C | PHE 117 | A | -7.240 | 52.362 | 0.315 | 0.62 |
| 655 | O | PHE 117 | A | -6.666 | 53.381 | -0.059 | 0.72 |
| 656 | N | ASP 118 | A | -7.607 | 51.365 | -0.474 | 0.67 |
| 657 | CA | ASP 118 | A | -7.388 | 51.415 | -1.922 | 0.67 |
| 658 | CB | ASP 118 | A | -7.342 | 50.074 | -2.610 | 0.73 |
| 659 | CG | ASP 118 | A | -8.694 | 49.558 | -3.079 | 0.82 |
| 660 | OD1 | ASP 118 | A | -8.748 | 48.554 | -3.798 | 0.72 |
| 661 | OD2 | ASP 118 | A | -9.705 | 50.249 | -2.831 | 0.60 |
| 662 | C | ASP 118 | A | -8.337 | 52.433 | -2.526 | 0.68 |
| 663 | O | ASP 118 | A | -9.108 | 53.096 | -1.826 | 0.75 |
| 664 | N | ASP 119 | A | -8.344 | 52.429 | -3.851 | 0.76 |
| 665 | CA | ASP 119 | A | -9.035 | 53.486 | -4.614 | 0.83 |
| 666 | CB | ASP 119 | A | -8.356 | 53.711 | -5.961 | 0.94 |
| 667 | CG | ASP 119 | A | -7.989 | 52.393 | -6.634 | 1.08 |
| 668 | OD1 | ASP 119 | A | -8.883 | 51.605 | -6.991 | 1.04 |
| 669 | OD2 | ASP 119 | A | -6.773 | 52.103 | -6.627 | 1.06 |
| 670 | C | ASP 119 | A | -10.531 | 53.204 | -4.673 | 0.87 |
| 671 | O | ASP 119 | A | -11.339 | 54.138 | -4.854 | 0.90 |
| 672 | N | SER 120 | A | -10.886 | 51.946 | -4.448 | 0.85 |
| 673 | CA | SER 120 | A | -12.314 | 51.574 | -4.389 | 0.80 |
| 674 | CB | SER 120 | A | -12.618 | 50.258 | -5.030 | 0.83 |
| 675 | OG | SER 120 | A | -11.534 | 49.729 | -5.781 | 1.02 |

Fig. 16.15

| ATOM | RESIDUE | | CHAIN | X | Y | Z | δ |
|---|---|---|---|---|---|---|---|
| 676 | C | SER 120 | A | -12.796 | 51.719 | -2.957 | 0.80 |
| 677 | O | SER 120 | A | -14.013 | 51.770 | -2.686 | 0.83 |
| 678 | N | SER 121 | A | -11.823 | 51.902 | -2.064 | 0.73 |
| 679 | CA | SER 121 | A | -12.197 | 52.163 | -0.653 | 0.69 |
| 680 | CB | SER 121 | A | -13.578 | 52.816 | -0.607 | 0.66 |
| 681 | OG | SER 121 | A | -13.479 | 54.163 | -1.016 | 0.85 |
| 682 | C | SER 121 | A | -12.186 | 50.879 | 0.163 | 0.63 |
| 683 | O | SER 121 | A | -12.564 | 50.874 | 1.332 | 0.69 |
| 684 | N | ASN 122 | A | -11.745 | 49.825 | -0.477 | 0.65 |
| 685 | CA | ASN 122 | A | -11.388 | 48.578 | 0.218 | 0.63 |
| 686 | CB | ASN 122 | A | -11.103 | 47.558 | -0.897 | 0.69 |
| 687 | CG | ASN 122 | A | -12.211 | 47.680 | -1.955 | 0.73 |
| 688 | OD1 | ASN 122 | A | -13.370 | 47.437 | -1.597 | 0.73 |
| 689 | ND2 | ASN 122 | A | -11.867 | 47.636 | -3.240 | 0.75 |
| 690 | C | ASN 122 | A | -10.237 | 48.837 | 1.176 | 0.67 |
| 691 | O | ASN 122 | A | -9.323 | 49.604 | 0.852 | 0.63 |
| 692 | N | VAL 123 | A | -10.305 | 48.227 | 2.346 | 0.66 |
| 693 | CA | VAL 123 | A | -9.252 | 48.270 | 3.360 | 0.61 |
| 694 | CB | VAL 123 | A | -9.927 | 48.279 | 4.744 | 0.58 |
| 695 | CG1 | VAL 123 | A | -8.929 | 47.747 | 5.758 | 0.59 |
| 696 | CG2 | VAL 123 | A | -10.405 | 49.677 | 5.089 | 0.56 |
| 697 | C | VAL 123 | A | -8.351 | 47.044 | 3.220 | 0.63 |
| 698 | O | VAL 123 | A | -8.901 | 45.942 | 3.098 | 0.65 |
| 699 | N | ILE 124 | A | -7.133 | 47.256 | 2.758 | 0.70 |
| 700 | CA | ILE 124 | A | -6.224 | 46.189 | 2.302 | 0.65 |
| 701 | CB | ILE 124 | A | -5.819 | 46.559 | 0.813 | 0.67 |
| 702 | CG2 | ILE 124 | A | -4.839 | 45.531 | 0.198 | 0.67 |
| 703 | CG1 | ILE 124 | A | -7.136 | 46.616 | 0.011 | 0.66 |
| 704 | CD | ILE 124 | A | -7.044 | 46.191 | -1.468 | 0.84 |
| 705 | C | ILE 124 | A | -4.998 | 46.057 | 3.208 | 0.67 |
| 706 | O | ILE 124 | A | -4.326 | 47.034 | 3.582 | 0.63 |
| 707 | N | LEU 125 | A | -4.598 | 44.815 | 3.448 | 0.63 |
| 708 | CA | LEU 125 | A | -3.323 | 44.541 | 4.140 | 0.69 |
| 709 | CB | LEU 125 | A | -3.602 | 43.477 | 5.187 | 0.67 |
| 710 | CG | LEU 125 | A | -2.441 | 43.036 | 6.067 | 0.64 |
| 711 | CD1 | LEU 125 | A | -2.163 | 44.105 | 7.130 | 0.49 |
| 712 | CD2 | LEU 125 | A | -2.977 | 41.760 | 6.750 | 0.48 |
| 713 | C | LEU 125 | A | -2.249 | 44.132 | 3.135 | 0.67 |
| 714 | O | LEU 125 | A | -2.431 | 43.103 | 2.470 | 0.66 |
| 715 | N | LYS 126 | A | -1.263 | 44.993 | 2.961 | 0.66 |
| 716 | CA | LYS 126 | A | -0.174 | 44.777 | 2.001 | 0.59 |
| 717 | CB | LYS 126 | A | -0.157 | 45.640 | 0.788 | 0.61 |
| 718 | CG | LYS 126 | A | 1.066 | 45.500 | -0.128 | 0.78 |
| 719 | CD | LYS 126 | A | 0.687 | 45.478 | -1.601 | 0.91 |
| 720 | CE | LYS 126 | A | 1.833 | 45.164 | -2.543 | 0.82 |

Fig. 16.16

| ATOM | | RESIDUE | | CHAIN | X | Y | Z | δ |
|---|---|---|---|---|---|---|---|---|
| 721 | NZ  | LYS | 126 | A | 1.346  | 44.434 | -3.746 | 0.86 |
| 722 | C   | LYS | 126 | A | 1.173  | 44.619 | 2.669  | 0.50 |
| 723 | O   | LYS | 126 | A | 1.398  | 44.978 | 3.845  | 0.57 |
| 724 | N   | LYS | 127 | A | 1.836  | 43.565 | 2.204  | 0.61 |
| 725 | CA  | LYS | 127 | A | 3.124  | 43.060 | 2.664  | 0.60 |
| 726 | CB  | LYS | 127 | A | 3.188  | 41.534 | 2.620  | 0.58 |
| 727 | CG  | LYS | 127 | A | 4.330  | 40.965 | 3.471  | 0.57 |
| 728 | CD  | LYS | 127 | A | 4.828  | 39.671 | 2.833  | 0.62 |
| 729 | CE  | LYS | 127 | A | 5.639  | 38.881 | 3.845  | 0.76 |
| 730 | NZ  | LYS | 127 | A | 5.283  | 39.360 | 5.208  | 0.83 |
| 731 | C   | LYS | 127 | A | 4.245  | 43.589 | 1.755  | 0.60 |
| 732 | O   | LYS | 127 | A | 4.058  | 43.699 | 0.521  | 0.49 |
| 733 | N   | TYR | 128 | A | 5.136  | 44.302 | 2.424  | 0.56 |
| 734 | CA  | TYR | 128 | A | 6.222  | 44.975 | 1.669  | 0.50 |
| 735 | CB  | TYR | 128 | A | 6.302  | 46.457 | 2.089  | 0.77 |
| 736 | CG  | TYR | 128 | A | 5.310  | 47.284 | 1.298  | 0.64 |
| 737 | CD1 | TYR | 128 | A | 4.269  | 47.954 | 1.935  | 0.68 |
| 738 | CE1 | TYR | 128 | A | 3.320  | 48.646 | 1.174  | 0.68 |
| 739 | CD2 | TYR | 128 | A | 5.280  | 47.163 | -0.085 | 0.72 |
| 740 | CE2 | TYR | 128 | A | 4.318  | 47.820 | -0.857 | 0.77 |
| 741 | CZ  | TYR | 128 | A | 3.268  | 48.459 | -0.200 | 0.89 |
| 742 | OH  | TYR | 128 | A | 2.279  | 49.021 | -0.961 | 0.90 |
| 743 | C   | TYR | 128 | A | 7.527  | 44.284 | 2.110  | 0.46 |
| 744 | O   | TYR | 128 | A | 7.781  | 44.139 | 3.308  | 0.59 |
| 745 | N   | ARG | 129 | A | 7.978  | 43.511 | 1.150  | 0.56 |
| 746 | CA  | ARG | 129 | A | 9.194  | 42.698 | 1.396  | 0.61 |
| 747 | CB  | ARG | 129 | A | 9.175  | 41.646 | 0.273  | 0.74 |
| 748 | CG  | ARG | 129 | A | 8.115  | 40.550 | 0.447  | 0.74 |
| 749 | CD  | ARG | 129 | A | 8.486  | 39.314 | -0.337 | 0.61 |
| 750 | NE  | ARG | 129 | A | 9.295  | 38.414 | 0.488  | 1.06 |
| 751 | CZ  | ARG | 129 | A | 10.599 | 38.183 | 0.310  | 1.07 |
| 752 | NH1 | ARG | 129 | A | 11.211 | 38.363 | -0.861 | 0.91 |
| 753 | NH2 | ARG | 129 | A | 11.370 | 37.849 | 1.349  | 0.87 |
| 754 | C   | ARG | 129 | A | 10.405 | 43.636 | 1.302  | 0.54 |
| 755 | O   | ARG | 129 | A | 10.406 | 44.605 | 0.522  | 0.55 |
| 756 | N   | ASN | 130 | A | 11.403 | 43.372 | 2.095  | 0.60 |
| 757 | CA  | ASN | 130 | A | 12.792 | 43.856 | 2.013  | 0.59 |
| 758 | CB  | ASN | 130 | A | 13.359 | 43.611 | 0.610  | 0.52 |
| 759 | CG  | ASN | 130 | A | 13.760 | 42.157 | 0.392  | 0.63 |
| 760 | OD1 | ASN | 130 | A | 14.053 | 41.398 | 1.318  | 0.58 |
| 761 | ND2 | ASN | 130 | A | 13.517 | 41.609 | -0.782 | 0.55 |
| 762 | C   | ASN | 130 | A | 12.807 | 45.343 | 2.380  | 0.55 |
| 763 | O   | ASN | 130 | A | 13.426 | 46.094 | 1.648  | 0.48 |
| 764 | N   | MET | 131 | A | 12.267 | 45.671 | 3.520  | 0.54 |
| 765 | CA  | MET | 131 | A | 11.990 | 47.026 | 3.974  | 0.51 |

Fig. 16.17

| ATOM | | RESIDUE | | CHAIN | X | Y | Z | δ |
|---|---|---|---|---|---|---|---|---|
| 766 | CB | MET | 131 | A | 10.470 | 47.189 | 4.327 | 0.54 |
| 767 | CG | MET | 131 | A | 9.590 | 47.290 | 3.137 | 0.44 |
| 768 | SD | MET | 131 | A | 9.927 | 48.720 | 2.052 | 0.61 |
| 769 | CE | MET | 131 | A | 8.873 | 49.928 | 2.915 | 0.60 |
| 770 | C | MET | 131 | A | 12.790 | 47.266 | 5.256 | 0.52 |
| 771 | O | MET | 131 | A | 13.048 | 48.429 | 5.570 | 0.59 |
| 772 | N | VAL | 132 | A | 12.997 | 46.230 | 6.055 | 0.59 |
| 773 | CA | VAL | 132 | A | 13.670 | 46.399 | 7.359 | 0.60 |
| 774 | CB | VAL | 132 | A | 12.807 | 46.001 | 8.517 | 0.52 |
| 775 | CG1 | VAL | 132 | A | 13.412 | 46.036 | 9.898 | 0.48 |
| 776 | CG2 | VAL | 132 | A | 11.331 | 46.318 | 8.485 | 0.66 |
| 777 | C | VAL | 132 | A | 15.035 | 45.704 | 7.308 | 0.69 |
| 778 | O | VAL | 132 | A | 15.148 | 44.495 | 7.012 | 0.63 |
| 779 | N | VAL | 133 | A | 16.039 | 46.488 | 7.668 | 0.65 |
| 780 | CA | VAL | 133 | A | 17.424 | 45.971 | 7.709 | 0.62 |
| 781 | CB | VAL | 133 | A | 18.486 | 47.081 | 7.591 | 0.56 |
| 782 | CG1 | VAL | 133 | A | 19.842 | 46.568 | 8.105 | 0.53 |
| 783 | CG2 | VAL | 133 | A | 18.577 | 47.505 | 6.128 | 0.39 |
| 784 | C | VAL | 133 | A | 17.542 | 45.241 | 9.052 | 0.62 |
| 785 | O | VAL | 133 | A | 17.392 | 45.958 | 10.044 | 0.54 |
| 786 | N | ARG | 134 | A | 17.821 | 43.930 | 8.941 | 0.53 |
| 787 | CA | ARG | 134 | A | 17.924 | 43.188 | 10.208 | 0.56 |
| 788 | CB | ARG | 134 | A | 17.114 | 41.877 | 10.158 | 0.68 |
| 789 | CG | ARG | 134 | A | 15.779 | 41.942 | 10.908 | 0.80 |
| 790 | CD | ARG | 134 | A | 15.932 | 41.805 | 12.379 | 0.79 |
| 791 | NE | ARG | 134 | A | 15.072 | 40.814 | 12.976 | 1.02 |
| 792 | CZ | ARG | 134 | A | 15.265 | 39.514 | 13.159 | 1.10 |
| 793 | NH1 | ARG | 134 | A | 16.185 | 38.783 | 12.533 | 1.08 |
| 794 | NH2 | ARG | 134 | A | 14.403 | 38.858 | 13.952 | 1.09 |
| 795 | C | ARG | 134 | A | 19.370 | 42.957 | 10.622 | 0.57 |
| 796 | O | ARG | 134 | A | 19.660 | 42.742 | 11.813 | 0.61 |
| 797 | N | ALA | 135 | A | 20.282 | 42.931 | 9.659 | 0.53 |
| 798 | CA | ALA | 135 | A | 21.722 | 42.782 | 9.986 | 0.49 |
| 799 | CB | ALA | 135 | A | 22.059 | 41.272 | 9.934 | 0.64 |
| 800 | C | ALA | 135 | A | 22.466 | 43.400 | 8.774 | 0.42 |
| 801 | O | ALA | 135 | A | 21.937 | 43.282 | 7.673 | 0.49 |
| 802 | N | CYS | 136 | A | 23.726 | 43.635 | 9.022 | 0.59 |
| 803 | CA | CYS | 136 | A | 24.682 | 44.274 | 8.089 | 0.67 |
| 804 | C | CYS | 136 | A | 25.954 | 43.443 | 7.969 | 0.61 |
| 805 | O | CYS | 136 | A | 26.383 | 42.850 | 8.985 | 0.59 |
| 806 | CB | CYS | 136 | A | 25.073 | 45.641 | 8.701 | 0.61 |
| 807 | SG | CYS | 136 | A | 23.632 | 46.772 | 8.673 | 0.61 |
| 808 | N | GLY | 137 | A | 26.579 | 43.476 | 6.808 | 0.59 |
| 809 | CA | GLY | 137 | A | 27.915 | 42.790 | 6.772 | 0.59 |
| 810 | C | GLY | 137 | A | 28.804 | 43.523 | 5.787 | 0.52 |

Fig. 16.18

| ATOM | | RESIDUE | | CHAIN | X | Y | Z | δ |
|------|------|------|-----|---|--------|--------|---------|------|
| 811 | O | GLY | 137 | A | 28.249 | 44.112 | 4.845 | 0.49 |
| 812 | N | CYS | 138 | A | 30.019 | 43.036 | 5.634 | 0.57 |
| 813 | CA | CYS | 138 | A | 30.912 | 43.537 | 4.545 | 0.48 |
| 814 | C | CYS | 138 | A | 30.845 | 42.606 | 3.369 | 0.56 |
| 815 | O | CYS | 138 | A | 31.335 | 41.457 | 3.446 | 0.55 |
| 816 | CB | CYS | 138 | A | 32.348 | 43.567 | 5.123 | 0.38 |
| 817 | SG | CYS | 138 | A | 32.401 | 44.877 | 6.428 | 0.57 |
| 818 | N | HIS | 139 | A | 30.522 | 43.184 | 2.210 | 0.63 |
| 819 | CA | HIS | 139 | A | 30.557 | 42.395 | 0.970 | 0.54 |
| 820 | CB | HIS | 139 | A | 29.665 | 41.188 | 0.842 | 0.88 |
| 821 | CG | HIS | 139 | A | 28.437 | 41.289 | 1.707 | 0.94 |
| 822 | CD2 | HIS | 139 | A | 27.571 | 42.337 | 1.811 | 0.79 |
| 823 | ND1 | HIS | 139 | A | 28.113 | 40.406 | 2.706 | 0.91 |
| 824 | CE1 | HIS | 139 | A | 27.001 | 40.825 | 3.288 | 0.97 |
| 825 | NE2 | HIS | 139 | A | 26.665 | 41.993 | 2.774 | 0.96 |
| 826 | C | HIS | 139 | A | 30.936 | 43.135 | -0.264 | 0.58 |
| 827 | OT1 | HIS | 139 | A | 31.164 | 42.426 | -1.268 | 0.75 |
| 828 | OT2 | HIS | 139 | A | 31.123 | 44.371 | -0.256 | 0.79 |
| 829 | CB | GLN | 36 | B | 29.653 | 57.175 | -11.979 | 0.80 |
| 830 | CG | GLN | 36 | B | 30.943 | 57.649 | -11.327 | 0.98 |
| 831 | CD | GLN | 36 | B | 30.751 | 58.560 | -10.142 | 1.07 |
| 832 | OE1 | GLN | 36 | B | 29.879 | 59.426 | -10.061 | 0.98 |
| 833 | NE2 | GLN | 36 | B | 31.585 | 58.331 | -9.123 | 1.05 |
| 834 | C | GLN | 36 | B | 28.572 | 54.939 | -11.583 | 0.62 |
| 835 | O | GLN | 36 | B | 28.641 | 54.928 | -10.349 | 0.67 |
| 836 | N | GLN | 36 | B | 29.482 | 55.414 | -13.781 | 0.82 |
| 837 | CA | GLN | 36 | B | 29.627 | 55.707 | -12.360 | 0.72 |
| 838 | N | ALA | 37 | B | 27.621 | 54.379 | -12.314 | 0.65 |
| 839 | CA | ALA | 37 | B | 26.512 | 53.646 | -11.644 | 0.64 |
| 840 | CB | ALA | 37 | B | 25.331 | 53.455 | -12.576 | 0.58 |
| 841 | C | ALA | 37 | B | 27.011 | 52.266 | -11.201 | 0.62 |
| 842 | O | ALA | 37 | B | 27.851 | 51.674 | -11.868 | 0.67 |
| 843 | N | CYS | 38 | B | 26.260 | 51.702 | -10.285 | 0.64 |
| 844 | CA | CYS | 38 | B | 26.531 | 50.390 | -9.714 | 0.53 |
| 845 | C | CYS | 38 | B | 26.592 | 49.339 | -10.797 | 0.63 |
| 846 | O | CYS | 38 | B | 25.623 | 49.141 | -11.527 | 0.66 |
| 847 | CB | CYS | 38 | B | 25.607 | 50.071 | -8.582 | 0.58 |
| 848 | SG | CYS | 38 | B | 25.827 | 48.462 | -7.828 | 0.63 |
| 849 | N | LYS | 39 | B | 27.800 | 48.823 | -11.010 | 0.63 |
| 850 | CA | LYS | 39 | B | 28.056 | 47.677 | -11.860 | 0.50 |
| 851 | CB | LYS | 39 | B | 28.442 | 48.020 | -13.296 | 0.56 |
| 852 | CG | LYS | 39 | B | 29.121 | 49.356 | -13.549 | 0.69 |
| 853 | CD | LYS | 39 | B | 29.867 | 49.395 | -14.870 | 0.62 |
| 854 | CE | LYS | 39 | B | 29.840 | 48.060 | -15.592 | 0.92 |
| 855 | NZ | LYS | 39 | B | 30.922 | 47.935 | -16.607 | 0.92 |

Fig. 16.19

| ATOM | RESIDUE | | CHAIN | X | Y | Z | δ |
|---|---|---|---|---|---|---|---|
| 856 | C | LYS 39 | B | 29.158 | 46.771 | -11.262 | 0.50 |
| 857 | O | LYS 39 | B | 29.788 | 47.073 | -10.242 | 0.49 |
| 858 | N | LYS 40 | B | 29.405 | 45.717 | -11.988 | 0.59 |
| 859 | CA | LYS 40 | B | 30.309 | 44.615 | -11.659 | 0.64 |
| 860 | CB | LYS 40 | B | 29.713 | 43.258 | -12.132 | 0.61 |
| 861 | CG | LYS 40 | B | 30.617 | 42.119 | -11.621 | 0.60 |
| 862 | CD | LYS 40 | B | 30.087 | 40.791 | -12.085 | 0.48 |
| 863 | CE | LYS 40 | B | 30.264 | 40.554 | -13.565 | 0.60 |
| 864 | NZ | LYS 40 | B | 29.587 | 39.269 | -13.873 | 0.73 |
| 865 | C | LYS 40 | B | 31.570 | 44.807 | -12.504 | 0.63 |
| 866 | O | LYS 40 | B | 31.450 | 45.250 | -13.659 | 0.61 |
| 867 | N | HIS 41 | B | 32.700 | 44.888 | -11.826 | 0.65 |
| 868 | CA | HIS 41 | B | 33.938 | 45.171 | -12.590 | 0.58 |
| 869 | CB | HIS 41 | B | 34.627 | 46.413 | -12.011 | 0.57 |
| 870 | CG | HIS 41 | B | 33.639 | 47.549 | -11.899 | 0.60 |
| 871 | CD2 | HIS 41 | B | 32.931 | 47.989 | -10.838 | 0.63 |
| 872 | ND1 | HIS 41 | B | 33.564 | 48.557 | -12.835 | 0.61 |
| 873 | CE1 | HIS 41 | B | 32.837 | 49.537 | -12.338 | 0.63 |
| 874 | NE2 | HIS 41 | B | 32.274 | 49.130 | -11.217 | 0.67 |
| 875 | C | HIS 41 | B | 34.837 | 43.952 | -12.505 | 0.58 |
| 876 | O | HIS 41 | B | 34.737 | 43.143 | -11.564 | 0.60 |
| 877 | N | GLU 42 | B | 35.819 | 43.974 | -13.373 | 0.63 |
| 878 | CA | GLU 42 | B | 36.805 | 42.897 | -13.460 | 0.65 |
| 879 | CB | GLU 42 | B | 37.296 | 42.767 | -14.894 | 0.67 |
| 880 | CG | GLU 42 | B | 36.418 | 41.808 | -15.724 | 0.61 |
| 881 | CD | GLU 42 | B | 36.806 | 41.769 | -17.171 | 0.80 |
| 882 | OE1 | GLU 42 | B | 36.002 | 41.778 | -18.082 | 0.89 |
| 883 | OE2 | GLU 42 | B | 38.046 | 41.851 | -17.309 | 0.92 |
| 884 | C | GLU 42 | B | 37.961 | 43.043 | -12.507 | 0.63 |
| 885 | O | GLU 42 | B | 38.361 | 44.183 | -12.261 | 0.68 |
| 886 | N | LEU 43 | B | 38.349 | 41.959 | -11.858 | 0.57 |
| 887 | CA | LEU 43 | B | 39.538 | 41.815 | -11.012 | 0.57 |
| 888 | CB | LEU 43 | B | 39.120 | 42.016 | -9.561 | 0.56 |
| 889 | CG | LEU 43 | B | 39.970 | 42.470 | -8.455 | 0.65 |
| 890 | CD1 | LEU 43 | B | 39.673 | 42.100 | -7.043 | 0.59 |
| 891 | CD2 | LEU 43 | B | 41.300 | 43.057 | -8.715 | 0.64 |
| 892 | C | LEU 43 | B | 39.947 | 40.315 | -11.210 | 0.63 |
| 893 | O | LEU 43 | B | 39.206 | 39.457 | -10.710 | 0.62 |
| 894 | N | TYR 44 | B | 41.180 | 40.079 | -11.580 | 0.58 |
| 895 | CA | TYR 44 | B | 41.745 | 38.704 | -11.590 | 0.54 |
| 896 | CB | TYR 44 | B | 42.658 | 38.620 | -12.845 | 0.52 |
| 897 | CG | TYR 44 | B | 43.133 | 37.198 | -13.022 | 0.63 |
| 898 | CD1 | TYR 44 | B | 44.404 | 36.795 | -12.620 | 0.50 |
| 899 | CE1 | TYR 44 | B | 44.762 | 35.449 | -12.742 | 0.58 |
| 900 | CD2 | TYR 44 | B | 42.295 | 36.274 | -13.634 | 0.52 |

Fig. 16.20

| ATOM | | RESIDUE | | CHAIN | X | Y | Z | δ |
|---|---|---|---|---|---|---|---|---|
| 901 | CE2 | TYR | 44 | B | 42.615 | 34.946 | -13.694 | 0.56 |
| 902 | CZ | TYR | 44 | B | 43.862 | 34.534 | -13.235 | 0.69 |
| 903 | OH | TYR | 44 | B | 44.205 | 33.222 | -13.434 | 0.81 |
| 904 | C | TYR | 44 | B | 42.696 | 38.638 | -10.395 | 0.51 |
| 905 | O | TYR | 44 | B | 43.481 | 39.582 | -10.316 | 0.63 |
| 906 | N | VAL | 45 | B | 42.581 | 37.674 | -9.534 | 0.53 |
| 907 | CA | VAL | 45 | B | 43.473 | 37.480 | -8.368 | 0.53 |
| 908 | CB | VAL | 45 | B | 42.579 | 37.181 | -7.148 | 0.56 |
| 909 | CG1 | VAL | 45 | B | 43.320 | 36.968 | -5.844 | 0.47 |
| 910 | CG2 | VAL | 45 | B | 41.431 | 38.176 | -7.035 | 0.52 |
| 911 | C | VAL | 45 | B | 44.398 | 36.280 | -8.673 | 0.55 |
| 912 | O | VAL | 45 | B | 43.906 | 3S.262 | -9.193 | 0.53 |
| 913 | N | SER | 46 | B | 45.669 | 36.588 | -8.765 | 0.59 |
| 914 | CA | SER | 46 | B | 46.829 | 35.718 | -8.858 | 0.52 |
| 915 | CB | SER | 46 | B | 48.122 | 36.464 | -9.287 | 0.46 |
| 916 | OG | SER | 46 | B | 48.841 | 35.585 | -10.135 | 0.69 |
| 917 | C | SER | 46 | B | 47.138 | 35.163 | -7.482 | 0.52 |
| 918 | O | SER | 46 | B | 47.307 | 35.955 | -6.553 | 0.56 |
| 919 | N | PHE | 47 | B | 47.216 | 33.857 | -7.380 | 0.59 |
| 920 | CA | PHE | 47 | B | 47.583 | 33.256 | -6.069 | 0.57 |
| 921 | CB | PHE | 47 | B | 47.312 | 31.754 | -6.088 | 0.53 |
| 922 | CG | PHE | 47 | B | 45.896 | 31.295 | -6.174 | 0.55 |
| 923 | CD1 | PHE | 47 | B | 44.869 | 32.001 | -5.517 | 0.45 |
| 924 | CD2 | PHE | 47 | B | 45.562 | 30.101 | -6.818 | 0.54 |
| 925 | CE1 | PHE | 47 | B | 43.554 | 31.589 | -5.633 | 0.71 |
| 926 | CE2 | PHE | 47 | B | 44.232 | 29.715 | -7.010 | 0.56 |
| 927 | CZ | PHE | 47 | B | 43.221 | 30.426 | -6.313 | 0.60 |
| 928 | C | PHE | 47 | B | 48.970 | 33.743 | -5.648 | 0.49 |
| 929 | O | PHE | 47 | B | 49.222 | 33.901 | -4.426 | 0.61 |
| 930 | N | ARG | 48 | B | 49.912 | 33.923 | -6.541 | 0.51 |
| 931 | CA | ARG | 48 | B | 51.204 | 34.593 | -6.314 | 0.57 |
| 932 | CB | ARG | 48 | B | 52.003 | 34.854 | -7.564 | 0.49 |
| 933 | CG | ARG | 48 | B | 52.089 | 33.858 | -8.662 | 0.74 |
| 934 | CD | ARG | 48 | B | 53.439 | 33.274 | -8.844 | 0.83 |
| 935 | NE | ARG | 48 | B | 54.192 | 33.768 | -9.964 | 0.71 |
| 936 | CZ | ARG | 48 | B | 54.800 | 33.088 | -10.923 | 0.66 |
| 937 | NH1 | ARG | 48 | B | 55.174 | 31.805 | -10.831 | 0.68 |
| 938 | NH2 | ARG | 48 | B | 54.842 | 33.671 | -12.123 | 0.61 |
| 939 | C | ARG | 48 | B | 51.122 | 35.885 | -5.517 | 0.64 |
| 940 | O | ARG | 48 | B | 51.681 | 36.007 | -4.397 | 0.69 |
| 941 | N | ASP | 49 | B | 50.284 | 36.811 | -5.977 | 0.60 |
| 942 | CA | ASP | 49 | B | 49.970 | 38.044 | -5.274 | 0.57 |
| 943 | CB | ASP | 49 | B | 48.961 | 38.897 | -6.047 | 0.68 |
| 944 | CG | ASP | 49 | B | 49.395 | 39.128 | -7.481 | 0.80 |
| 945 | OD1 | ASP | 49 | B | 48.609 | 39.683 | -8.272 | 0.89 |

Fig. 16.21

| ATOM | RESIDUE | | CHAIN | X | Y | Z | δ |
|---|---|---|---|---|---|---|---|
| 946 | OD2 | ASP 49 | B | 50.527 | 38.681 | -7.801 | 0.83 |
| 947 | C | ASP 49 | B | 49.619 | 37.883 | -3.814 | 0.66 |
| 948 | O | ASP 49 | B | 49.712 | 38.876 | -3.062 | 0.72 |
| 949 | N | LEU 50 | B | 48.879 | 36.830 | -3.465 | 0.70 |
| 950 | CA | LEU 50 | B | 48.428 | 36.605 | -2.086 | 0.60 |
| 951 | CB | LEU 50 | B | 47.115 | 35.800 | -2.187 | 0.62 |
| 952 | CG | LEU 50 | B | 46.024 | 36.479 | -3.022 | 0.69 |
| 953 | CD1 | LEU 50 | B | 44.677 | 35.940 | -2.544 | 0.66 |
| 954 | CD2 | LEU 50 | B | 46.100 | 37.974 | -2.667 | 0.66 |
| 955 | C | LEU 50 | B | 49.471 | 35.808 | -1.275 | 0.62 |
| 956 | O | LEU 50 | B | 49.097 | 35.367 | -0.167 | 0.69 |
| 957 | N | GLY 51 | B | 50.399 | 35.235 | -2.005 | 0.62 |
| 958 | CA | GLY 51 | B | 51.320 | 34.191 | -1.563 | 0.59 |
| 959 | C | GLY 51 | B | 50.554 | 32.900 | -1.303 | 0.68 |
| 960 | O | GLY 51 | B | 50.408 | 32.521 | -0.130 | 0.73 |
| 961 | N | TRP 52 | B | 49.891 | 32.356 | -2.325 | 0.60 |
| 962 | CA | TRP 52 | B | 49.127 | 31.117 | -2.063 | 0.63 |
| 963 | CB | TRP 52 | B | 47.650 | 31.299 | -2.022 | 0.76 |
| 964 | CG | TRP 52 | B | 46.961 | 32.057 | -0.951 | 0.80 |
| 965 | CD2 | TRP 52 | B | 45.593 | 32.517 | -1.004 | 0.74 |
| 966 | CE2 | TRP 52 | B | 45.285 | 33.063 | 0.263 | 0.92 |
| 967 | CE3 | TRP 52 | B | 44.583 | 32.450 | -1.963 | 1.01 |
| 968 | CD1 | TRP 52 | B | 47.376 | 32.267 | 0.333 | 0.82 |
| 969 | NE1 | TRP 52 | B | 46.402 | 32.927 | 1.050 | 0.73 |
| 970 | CZ2 | TRP 52 | B | 44.009 | 33.536 | 0.576 | 0.75 |
| 971 | CZ3 | TRP 52 | B | 43.332 | 32.969 | -1.684 | 0.68 |
| 972 | CH2 | TRP 52 | B | 43.053 | 33.511 | -0.428 | 0.80 |
| 973 | C | TRP 52 | B | 49.615 | 30.052 | -3.046 | 0.72 |
| 974 | O | TRP 52 | B | 49.190 | 28.891 | -2.965 | 0.78 |
| 975 | N | GLN 53 | B | 50.656 | 30.412 | -3.769 | 0.64 |
| 976 | CA | GLN 53 | B | 51.203 | 29.563 | -4.822 | 0.74 |
| 977 | CB | GLN 53 | B | 52.095 | 30.349 | -5.798 | 0.68 |
| 978 | CG | GLN 53 | B | 53.334 | 30.917 | -5.138 | 0.56 |
| 979 | CD | GLN 53 | B | 53.220 | 32.124 | -4.268 | 0.78 |
| 980 | OE1 | GLN 53 | B | 52.394 | 32.252 | -3.363 | 0.75 |
| 981 | NE2 | GLN 53 | B | 54.224 | 33.011 | -4.447 | 0.80 |
| 982 | C | GLN 53 | B | 51.891 | 28.321 | -4.280 | 0.74 |
| 983 | O | GLN 53 | B | 52.298 | 27.451 | -5.080 | 0.83 |
| 984 | N | ASP 54 | B | 52.335 | 28.353 | -3.040 | 0.77 |
| 985 | CA | ASP 54 | B | 53.153 | 27.288 | -2.432 | 0.76 |
| 986 | CB | ASP 54 | B | 53.499 | 27.716 | -1.004 | 0.92 |
| 987 | CG | ASP 54 | B | 54.614 | 28.739 | -0.920 | 0.92 |
| 988 | OD1 | ASP 54 | B | 55.409 | 28.905 | -1.863 | 0.96 |
| 989 | OD2 | ASP 54 | B | 54.784 | 29.235 | 0.217 | 0.75 |
| 990 | C | ASP 54 | B | 52.486 | 25.906 | -2 491 | 0.80 |

Fig. 16.22

| ATOM | RESIDUE | | CHAIN | X | Y | Z | δ |
|---|---|---|---|---|---|---|---|
| 991 O | ASP | 54 | B | 53.092 | 24.893 | -2.898 | 0.82 |
| 992 N | TRP | 55 | B | 51.285 | 25.839 | -1.953 | 0.72 |
| 993 CA | TRP | 55 | B | 50.495 | 24.644 | -1.723 | 0.78 |
| 994 CB | TRP | 55 | B | 49.926 | 24.753 | -0.293 | 0.69 |
| 995 CG | TRP | 55 | B | 51.035 | 24.962 | 0.691 | 0.80 |
| 996 CD2 | TRP | 55 | B | 52.396 | 24.529 | 0.465 | 0.76 |
| 997 CE2 | TRP | 55 | B | 53.149 | 24.987 | 1.569 | 0.85 |
| 998 CE3 | TRP | 55 | B | 52.924 | 23.554 | -0.374 | 0.87 |
| 999 CD1 | TRP | 55 | B | 51.076 | 25.759 | 1.796 | 0.74 |
| 1000 NE1 | TRP | 55 | B | 52.345 | 25.793 | 2.337 | 0.76 |
| 1001 CZ2 | TRP | 55 | B | 54.479 | 24.626 | 1.745 | 0.78 |
| 1002 CZ3 | TRP | 55 | B | 54.216 | 23.134 | -0.151 | 0.88 |
| 1003 CH2 | TRP | 55 | B | 54.968 | 23.639 | 0.905 | 0.82 |
| 1004 C | TRP | 55 | B | 49.431 | 24.336 | -2.770 | 0.84 |
| 1005 O | TRP | 55 | B | 48.906 | 23.197 | -2.758 | 0.77 |
| 1006 N | ILE | 56 | B | 49.105 | 25.287 | -3.642 | 0.83 |
| 1007 CA | ILE | 56 | B | 48.109 | 25.152 | -4.693 | 0.78 |
| 1008 CB | ILE | 56 | B | 47.382 | 26.490 | -5.076 | 0.77 |
| 1009 CG2 | ILE | 56 | B | 47.094 | 26.568 | -6.606 | 0.71 |
| 1010 CG1 | ILE | 56 | B | 46.030 | 26.567 | -4.316 | 0.82 |
| 1011 CD | ILE | 56 | B | 45.964 | 27.743 | -3.298 | 0.90 |
| 1012 C | ILE | 56 | B | 48.700 | 24.512 | -5.944 | 0.74 |
| 1013 O | ILE | 56 | B | 49.768 | 24.950 | -6.388 | 0.80 |
| 1014 N | ILE | 57 | B | 47.911 | 23.642 | -6.567 | 0.68 |
| 1015 CA | ILE | 57 | B | 48.281 | 22.985 | -7.822 | 0.64 |
| 1016 CB | ILE | 57 | B | 48.040 | 21.429 | -7.725 | 0.65 |
| 1017 CG2 | ILE | 57 | B | 47.983 | 20.771 | -9.109 | 0.55 |
| 1018 CG1 | ILE | 57 | B | 49.017 | 20.758 | -6.736 | 0.64 |
| 1019 CD | ILE | 57 | B | 48.780 | 19.230 | -6.540 | 0.62 |
| 1020 C | ILE | 57 | B | 47.565 | 23.593 | -9.020 | 0.60 |
| 1021 O | ILE | 57 | B | 48.093 | 23.570 | -10.145 | 0.62 |
| 1022 N | ALA | 58 | B | 46.279 | 23.911 | -8.834 | 0.58 |
| 1023 CA | ALA | 58 | B | 45.460 | 24.436 | -9.967 | 0.49 |
| 1024 CB | ALA | 58 | B | 44.970 | 23.215 | -10.789 | 0.55 |
| 1025 C | ALA | 58 | B | 44.202 | 25.091 | -9.376 | 0.46 |
| 1026 O | ALA | 58 | B | 43.929 | 24.534 | -8.302 | 0.49 |
| 1027 N | PRO | 59 | B | 43.872 | 26.310 | -9.744 | 0.53 |
| 1028 CD | PRO | 59 | B | 42.742 | 27.052 | -9.192 | 0.46 |
| 1029 CA | PRO | 59 | B | 44.401 | 27.103 | -10.870 | 0.45 |
| 1030 CB | PRO | 59 | B | 43.209 | 27.839 | -11.429 | 0.47 |
| 1031 CG | PRO | 59 | B | 42.321 | 28.059 | -10.217 | 0.43 |
| 1032 C | PRO | 59 | B | 45.527 | 28.013 | -10.384 | 0.53 |
| 1033 O | PRO | 59 | B | 46.032 | 27.913 | -9.239 | 0.55 |
| 1034 N | GLU | 60 | B | 46.018 | 28.888 | -11.255 | 0.49 |
| 1035 CA | GLU | 60 | B | 47.061 | 29.844 | -10.776 | 0.53 |

Fig. 16.23

| ATOM | RESIDUE | | CHAIN | X | Y | Z | δ |
|---|---|---|---|---|---|---|---|
| 1036 CB | GLU | 60 | B | 48.099 | 30.025 | -11.906 | 0.64 |
| 1037 CG | GLU | 60 | B | 49.287 | 29.075 | -11.886 | 0.77 |
| 1038 CD | GLU | 60 | B | 49.851 | 28.404 | -13.082 | 0.79 |
| 1039 OE1 | GLU | 60 | B | 49.900 | 27.172 | -13.170 | 0.84 |
| 1040 OE2 | GLU | 60 | B | 50.265 | 29.162 | -13.997 | 0.61 |
| 1041 C | GLU | 60 | B | 46.440 | 31.175 | -10.374 | 0.53 |
| 1042 O | GLU | 60 | B | 47.006 | 31.966 | -9.605 | 0.52 |
| 1043 N | GLY | 61 | B | 45.121 | 31.271 | -10.496 | 0.52 |
| 1044 CA | GLY | 61 | B | 44.275 | 32.336 | -9.965 | 0.54 |
| 1045 C | GLY | 61 | B | 42.888 | 32.324 | -10.585 | 0.58 |
| 1046 O | GLY | 61 | B | 42.568 | 31.365 | -11.298 | 0.55 |
| 1047 N | TYR | 62 | B | 42.036 | 33.285 | -10.231 | 0.55 |
| 1048 CA | TYR | 62 | B | 40.662 | 33.247 | -10.845 | 0.54 |
| 1049 CB | TYR | 62 | B | 39.780 | 32.410 | -9.853 | 0.38 |
| 1050 CG | TYR | 62 | B | 39.540 | 33.198 | -8.558 | 0.47 |
| 1051 CD1 | TYR | 62 | B | 40.580 | 33.288 | -7.649 | 0.47 |
| 1052 CE1 | TYR | 62 | B | 40.540 | 34.084 | -6.499 | 0.51 |
| 1053 CD2 | TYR | 62 | B | 38.335 | 33.785 | -8.201 | 0.45 |
| 1054 CE2 | TYR | 62 | B | 38.165 | 34.346 | -6.912 | 0.35 |
| 1055 CZ | TYR | 62 | B | 39.284 | 34.567 | -6.115 | 0.51 |
| 1056 OH | TYR | 62 | B | 39.146 | 35.055 | -4.839 | 0.65 |
| 1057 C | TYR | 62 | B | 40.133 | 34.672 | -10.973 | 0.59 |
| 1058 O | TYR | 62 | B | 40.590 | 35.651 | -10.330 | 0.55 |
| 1059 N | ALA | 63 | B | 39.076 | 34.789 | -11.731 | 0.54 |
| 1060 CA | ALA | 63 | B | 38.403 | 36.106 | -11.984 | 0.49 |
| 1061 CB | ALA | 63 | B | 37.619 | 35.856 | -13.282 | 0.58 |
| 1062 C | ALA | 63 | B | 37.422 | 36.309 | -10.845 | 0.51 |
| 1063 O | ALA | 63 | B | 36.491 | 35.511 | -10.665 | 0.58 |
| 1064 N | ALA | 64 | B | 37.780 | 37.157 | -9.895 | 0.54 |
| 1065 CA | ALA | 64 | B | 36.931 | 37.347 | -8.735 | 0.53 |
| 1066 CB | ALA | 64 | B | 37.812 | 37.741 | -7.550 | 0.53 |
| 1067 C | ALA | 64 | B | 35.776 | 38.344 | -8.972 | 0.52 |
| 1068 O | ALA | 64 | B | 34.882 | 38.380 | -8.091 | 0.54 |
| 1069 N | TYR | 65 | B | 36.063 | 39.402 | -9.671 | 0.51 |
| 1070 CA | TYR | 65 | B | 35.241 | 40.568 | -9.978 | 0.54 |
| 1071 CB | TYR | 65 | B | 33.801 | 40.235 | -10.438 | 0.47 |
| 1072 CG | TYR | 65 | B | 33.841 | 39.511 | -11.777 | 0.47 |
| 1073 CD1 | TYR | 65 | B | 34.042 | 40.165 | -12.974 | 0.44 |
| 1074 CE1 | TYR | 65 | B | 34.043 | 39.474 | -14.190 | 0.47 |
| 1075 CD2 | TYR | 65 | B | 34.100 | 38.137 | -11.756 | 0.61 |
| 1076 CE2 | TYR | 65 | B | 34.363 | 37.449 | -12.922 | 0.44 |
| 1077 CZ | TYR | 65 | B | 34.279 | 38.092 | -14.139 | 0.67 |
| 1078 OH | TYR | 65 | B | 34.476 | 37.314 | -15.253 | 0.70 |
| 1079 C | TYR | 65 | B | 35.164 | 41.470 | -8.752 | 0.51 |
| 1080 O | TYR | 65 | B | 35.488 | 40.943 | -7.664 | 0.49 |

Fig. 16.24

| ATOM | | RESIDUE | CHAIN | X | Y | Z | δ |
|---|---|---|---|---|---|---|---|
| 1081 | N | TYR 66 | B | 34.349 | 42.507 | -8.928 | 0.52 |
| 1082 | CA | TYR 66 | B | 33.974 | 43.311 | -7.729 | 0.50 |
| 1083 | CB | TYR 66 | B | 35.170 | 44.051 | -7.126 | 0.60 |
| 1084 | CG | TYR 66 | B | 35.700 | 45.179 | -7.983 | 0.59 |
| 1085 | CD1 | TYR 66 | B | 36.704 | 44.935 | -8.917 | 0.59 |
| 1086 | CE1 | TYR 66 | B | 37.279 | 45.951 | -9.659 | 0.53 |
| 1087 | CD2 | TYR 66 | B | 35.376 | 46.512 | -7.721 | 0.53 |
| 1088 | CE2 | TYR 66 | B | 36.057 | 47.548 | -8.335 | 0.47 |
| 1089 | CZ | TYR 66 | B | 36.836 | 47.261 | -9.448 | 0.58 |
| 1090 | OH | TYR 66 | B | 37.469 | 48.301 | -10.066 | 0.70 |
| 1091 | C | TYR 66 | B | 32.914 | 44.336 | -8.166 | 0.51 |
| 1092 | O | TYR 66 | B | 32.777 | 44.585 | -9.351 | 0.52 |
| 1093 | N | CYS 67 | B | 32.304 | 44.936 | -7.173 | 0.58 |
| 1094 | CA | CYS 67 | B | 31.148 | 45.843 | -7.372 | 0.57 |
| 1095 | C | CYS 67 | B | 31.597 | 47.265 | -7.066 | 0.52 |
| 1096 | O | CYS 67 | B | 32.160 | 47.475 | -5.968 | 0.48 |
| 1097 | CB | CYS 67 | B | 30.051 | 45.374 | -6.413 | 0.54 |
| 1098 | SG | CYS 67 | B | 29.272 | 43.787 | -6.831 | 0.54 |
| 1099 | N | GLU 68 | B | 31.226 | 48.194 | -7.930 | 0.56 |
| 1100 | CA | GLU 68 | B | 31.450 | 49.624 | -7.617 | 0.47 |
| 1101 | CB | GLU 68 | B | 32.888 | 50.026 | -7.993 | 0.68 |
| 1102 | CG | GLU 68 | B | 33.521 | 51.195 | -7.264 | 0.53 |
| 1103 | CD | GLU 68 | B | 34.985 | 51.442 | -7.510 | 0.67 |
| 1104 | OE1 | GLU 68 | B | 35.681 | 52.049 | -6.720 | 0.64 |
| 1105 | OE2 | GLU 68 | B | 35.357 | 51.239 | -8.687 | 0.63 |
| 1106 | C | GLU 68 | B | 30.561 | 50.515 | -8.485 | 0.43 |
| 1107 | O | GLU 68 | B | 30.393 | 50.238 | -9.663 | 0.42 |
| 1108 | N | GLY 69 | B | 30.221 | 51.681 | -7.922 | 0.48 |
| 1109 | CA | GLY 69 | B | 29.452 | 52.707 | -8.669 | 0.44 |
| 1110 | C | GLY 69 | B | 28.406 | 53.234 | -7.670 | 0.51 |
| 1111 | O | GLY 69 | B | 28.223 | 52.696 | -6.563 | 0.53 |
| 1112 | N | GLU 70 | B | 27.714 | 54.297 | -8.048 | 0.57 |
| 1113 | CA | GLU 70 | 8 | 26.797 | 54.923 | -7.116 | 0.63 |
| 1114 | CB | GLU 70 | B | 26.834 | 56.401 | -6.924 | 0.74 |
| 1115 | CG | GLU 70 | B | 26.449 | 57.323 | -8.062 | 0.77 |
| 1116 | CD | GLU 70 | B | 26.041 | 58.691 | -7.554 | 1.02 |
| 1117 | OE1 | GLU 70 | B | 26.122 | 58.985 | -6.372 | 0.84 |
| 1118 | OE2 | GLU 70 | B | 25.470 | 59.352 | -8.441 | 0.95 |
| 1119 | C | GLU 70 | B | 25.392 | 54.363 | -7.133 | 0.44 |
| 1120 | O | GLU 70 | B | 24.945 | 53.921 | -8.186 | 0.42 |
| 1121 | N | CYS 71 | B | 24.785 | 54.485 | -5.962 | 0.50 |
| 1122 | CA | CYS 71 | B | 23.378 | 54.069 | -5.805 | 0.62 |
| 1123 | C | CYS 71 | B | 22.488 | 55.305 | -5.637 | 0.54 |
| 1124 | O | CYS 71 | B | 22.279 | 55.787 | -4.547 | 0.51 |
| 1125 | CB | CYS 71 | B | 23.223 | 52.994 | -4.771 | 0.62 |

Fig. 16.25

| ATOM | | RESIDUE | CHAIN | X | Y | Z | δ |
|---|---|---|---|---|---|---|---|
| 1126 | SG | CYS 71 | B | 23.951 | 51.385 | -5.196 | 0.57 |
| 1127 | N | ALA 72 | B | 22.057 | 55.857 | -6.745 | 0.50 |
| 1128 | CA | ALA 72 | B | 21.341 | 57.102 | -6.862 | 0.61 |
| 1129 | CB | ALA 72 | B | 22.306 | 58.192 | -7.425 | 0.61 |
| 1130 | C | ALA 72 | B | 20.223 | 56.910 | -7.903 | 0.62 |
| 1131 | O | ALA 72 | B | 20.396 | 56.167 | -8.880 | 0.59 |
| 1132 | N | PHE 73 | B | 19.294 | 57.873 | -7.785 | 0.59 |
| 1133 | CA | PHE 73 | B | 18.244 | 57.978 | -8.805 | 0.46 |
| 1134 | CB | PHE 73 | B | 17.063 | 58.839 | -8.472 | 0.54 |
| 1135 | CG | PHE 73 | B | 16.335 | 58.428 | -7.198 | 0.45 |
| 1136 | CD1 | PHE 73 | B | 15.725 | 57.183 | -7.129 | 0.43 |
| 1137 | CD2 | PHE 73 | B | 16.303 | 59.266 | -6.117 | 0.45 |
| 1138 | CE1 | PHE 73 | B | 15.178 | 56.702 | -5.935 | 0.34 |
| 1139 | CE2 | PHE 73 | B | 15.627 | 58.907 | -4.959 | 0.37 |
| 1140 | CZ | PHE 73 | B | 15.089 | 57.602 | -4.895 | 0.33 |
| 1141 | C | PHE 73 | B | 18.983 | 58.181 | -10.083 | 0.52 |
| 1142 | O | PHE 73 | B | 19.751 | 59.134 | -9.925 | 0.54 |
| 1143 | N | PRO 74 | B | 18.492 | 57.715 | -11.197 | 0.57 |
| 1144 | CD | PRO 74 | B | 19.072 | 58.066 | -12.495 | 0.57 |
| 1145 | CA | PRO 74 | B | 17.638 | 56.569 | -11.370 | 0.56 |
| 1146 | CB | PRO 74 | B | 17.298 | 56.446 | -12.832 | 0.52 |
| 1147 | CG | PRO 74 | B | 18.376 | 57.215 | -13.519 | 0.54 |
| 1148 | C | PRO 74 | B | 18.219 | 55.293 | -10.805 | 0.66 |
| 1149 | O | PRO 74 | B | 19.370 | 54.968 | -11.112 | 0.74 |
| 1150 | N | LEU 75 | B | 17.359 | 54.601 | -10.090 | 0.58 |
| 1151 | CA | LEU 75 | B | 17.626 | 53.249 | -9.627 | 0.61 |
| 1152 | CB | LEU 75 | B | 17.151 | 53.088 | -8.209 | 0.63 |
| 1153 | CG | LEU 75 | B | 18.000 | 53.160 | -7.006 | 0.60 |
| 1154 | CD1 | LEU 75 | B | 19.409 | 53.632 | -7.025 | 0.57 |
| 1155 | CD2 | LEU 75 | B | 17.331 | 53.418 | -5.703 | 0.49 |
| 1156 | C | LEU 75 | B | 17.058 | 52.347 | -10.726 | 0.68 |
| 1157 | O | LEU 75 | B | 15.909 | 51.889 | -10.655 | 0.72 |
| 1158 | N | ASN 76 | B | 17.826 | 52.301 | -11.802 | 0.68 |
| 1159 | CA | ASN 76 | B | 17.569 | 51.408 | -12.939 | 0.66 |
| 1160 | CB | ASN 76 | B | 18.627 | 51.538 | -14.028 | 0.62 |
| 1161 | CG | ASN 76 | B | 18.661 | 52.899 | -14.697 | 0.83 |
| 1162 | OD1 | ASN 76 | B | 17.657 | 53.637 | -14.677 | 0.97 |
| 1163 | ND2 | ASN 76 | B | 19.757 | 53.260 | -15.370 | 0.81 |
| 1164 | C | ASN 76 | B | 17.288 | 50.001 | -12.449 | 0.67 |
| 1165 | O | ASN 76 | B | 17.535 | 49.608 | -11.281 | 0.73 |
| 1166 | N | SER 77 | B | 16.531 | 49.283 | -13.260 | 0.73 |
| 1167 | CA | SER 77 | B | 16.114 | 47.907 | -12.886 | 0.74 |
| 1168 | CB | SER 77 | B | 15.107 | 47.328 | -13.894 | 0.54 |
| 1169 | OG | SER 77 | B | 14.248 | 46.466 | -13.128 | 0.96 |
| 1170 | C | SER 77 | B | 17.359 | 47.011 | -12.767 | 0.62 |

Fig. 16.26

| ATOM | | RESIDUE | | CHAIN | X | Y | Z | δ |
|---|---|---|---|---|---|---|---|---|
| 1171 | O | SER | 77 | B | 17.477 | 46.218 | -11.835 | 0.66 |
| 1172 | N | TYR | 78 | B | 18.200 | 47.118 | -13.767 | 0.63 |
| 1173 | CA | TYR | 78 | B | 19.542 | 46.592 | -13.850 | 0.75 |
| 1174 | CB | TYR | 78 | B | 20.249 | 47.042 | -15.137 | 0.63 |
| 1175 | CG | TYR | 78 | B | 21.368 | 48.043 | -14.976 | 0.91 |
| 1176 | CD1 | TYR | 78 | B | 21.284 | 49.371 | -15.447 | 0.81 |
| 1177 | CE1 | TYR | 78 | B | 22.321 | 50.280 | -15.228 | 0.88 |
| 1178 | CD2 | TYR | 78 | B | 22.605 | 47.610 | -14.494 | 0.98 |
| 1179 | CE2 | TYR | 78 | B | 23.652 | 48.502 | -14.265 | 0.99 |
| 1180 | CZ | TYR | 78 | B | 23.510 | 49.833 | -14.640 | 0.94 |
| 1181 | OH | TYR | 78 | B | 24.611 | 50.630 | -14.483 | 0.97 |
| 1182 | C | TYR | 78 | B | 20.376 | 46.798 | -12.592 | 0.78 |
| 1183 | O | TYR | 78 | B | 21.428 | 46.139 | -12.487 | 0.79 |
| 1184 | N | MET | 79 | B | 20.014 | 47.722 | -11.719 | 0.74 |
| 1185 | CA | MET | 79 | B | 20.721 | 48.022 | -10.475 | 0.62 |
| 1186 | CB | MET | 79 | B | 20.757 | 49.519 | -10.191 | 0.68 |
| 1187 | CG | MET | 79 | B | 21.670 | 50.154 | -11.207 | 0.51 |
| 1188 | SD | MET | 79 | B | 21.423 | 51.909 | -11.149 | 0.67 |
| 1189 | CE | MET | 79 | B | 22.086 | 52.461 | -9.625 | 0.53 |
| 1190 | C | MET | 79 | B | 20.193 | 47.231 | -9.309 | 0.58 |
| 1191 | O | MET | 79 | B | 20.701 | 47.287 | -8.186 | 0.61 |
| 1192 | N | ASN | 80 | B | 19.249 | 46.327 | -9.575 | 0.55 |
| 1193 | CA | ASN | 80 | B | 18.791 | 45.510 | -8.431 | 0.54 |
| 1194 | CB | ASN | 80 | B | 19.392 | 44.106 | -8.469 | 0.86 |
| 1195 | CG | ASN | 80 | B | 19.052 | 43.259 | -7.244 | 1.05 |
| 1196 | OD1 | ASN | 80 | B | 19.403 | 43.560 | -6.079 | 0.95 |
| 1197 | ND2 | ASN | 80 | B | 18.498 | 42.064 | -7.518 | 0.86 |
| 1198 | C | ASN | 80 | B | 18.879 | 46.202 | -7.091 | 0.57 |
| 1199 | O | ASN | 80 | B | 19.195 | 45.517 | -6.054 | 0.67 |
| 1200 | N | ALA | 81 | B | 17.955 | 47.146 | -6.890 | 0.60 |
| 1201 | CA | ALA | 81 | B | 17.798 | 47.835 | -5.577 | 0.52 |
| 1202 | CB | ALA | 81 | B | 17.298 | 49.261 | -5.894 | 0.53 |
| 1203 | C | ALA | 81 | B | 16.837 | 46.990 | -4.802 | 0.53 |
| 1204 | O | ALA | 81 | B | 15.878 | 46.552 | -5.445 | 0.60 |
| 1205 | N | THR | 82 | B | 16.965 | 46.811 | -3.500 | 0.54 |
| 1206 | CA | THR | 82 | B | 15.866 | 46.297 | -2.680 | 0.44 |
| 1207 | CB | THR | 82 | B | 16.477 | 45.801 | -1.326 | 0.45 |
| 1208 | OG1 | THR | 82 | B | 17.234 | 46.967 | -0.821 | 0.49 |
| 1209 | CG2 | THR | 82 | B | 17.599 | 44.729 | -1.601 | 0.58 |
| 1210 | C | THR | 82 | B | 14.851 | 47.432 | -2.443 | 0.67 |
| 1211 | O | THR | 82 | B | 15.035 | 48.606 | -2.852 | 0.55 |
| 1212 | N | ASN | 83 | B | 13.681 | 47.096 | -1.913 | 0.61 |
| 1213 | CA | ASN | 83 | B | 12.741 | 48.177 | -1.529 | 0.56 |
| 1214 | CB | ASN | 83 | B | 11.453 | 47.641 | -0.901 | 0.53 |
| 1215 | CG | ASN | 83 | B | 10.532 | 46.962 | -1.900 | 0.48 |

Fig. 16.27

| ATOM | | RESIDUE | | CHAIN | X | Y | Z | δ |
|---|---|---|---|---|---|---|---|---|
| 1216 | OD1 | ASN | 83 | B | 10.652 | 47.190 | -3.108 | 0.55 |
| 1217 | ND2 | ASN | 83 | B | 9.825 | 45.948 | -1.410 | 0.55 |
| 1218 | C | ASN | 83 | B | 13.496 | 49.079 | -0.535 | 0.55 |
| 1219 | O | ASN | 83 | B | 13.074 | 50.239 | -0.428 | 0.54 |
| 1220 | N | HIS | 84 | B | 13.968 | 48.503 | 0.569 | 0.55 |
| 1221 | CA | HIS | 84 | B | 14.811 | 49.226 | 1.518 | 0.41 |
| 1222 | CB | HIS | 84 | B | 15.645 | 48.344 | 2.462 | 0.58 |
| 1223 | CG | HIS | 84 | B | 16.315 | 49.085 | 3.572 | 0.40 |
| 1224 | CD2 | HIS | 84 | B | 15.849 | 49.305 | 4.809 | 0.29 |
| 1225 | ND1 | HIS | 84 | B | 17.461 | 49.885 | 3.426 | 0.22 |
| 1226 | CE1 | HIS | 84 | B | 17.727 | 50.393 | 4.612 | 0.18 |
| 1227 | NE2 | HIS | 84 | B | 16.808 | 50.017 | 5.513 | 0.31 |
| 1228 | C | HIS | 84 | B | 15.742 | 50.241 | 0.878 | 0.47 |
| 1229 | O | HIS | 84 | B | 15.996 | 51.280 | 1.484 | 0.50 |
| 1230 | N | ALA | 85 | B | 16.457 | 49.932 | -0.190 | 0.52 |
| 1231 | CA | ALA | 85 | B | 17.416 | 50.862 | -0.773 | 0.53 |
| 1232 | CB | ALA | 85 | B | 18.193 | 50.157 | -1.868 | 0.48 |
| 1233 | C | ALA | 85 | B | 16.658 | 52.059 | -1.388 | 0.57 |
| 1234 | O | ALA | 85 | B | 17.384 | 53.017 | -1.781 | 0.55 |
| 1235 | N | ILE | 86 | B | 15.570 | 51.726 | -2.095 | 0.50 |
| 1236 | CA | ILE | 86 | B | 14.770 | 52.758 | -2.783 | 0.52 |
| 1237 | CB | ILE | 86 | B | 13.487 | 52.116 | -3.425 | 0.57 |
| 1238 | CG2 | ILE | 86 | B | 12.542 | 53.287 | -3.912 | 0.42 |
| 1239 | CG1 | ILE | 86 | B | 13.972 | 51.293 | -4.652 | 0.40 |
| 1240 | CD | ILE | 86 | B | 12.807 | 50.430 | -5.234 | 0.49 |
| 1241 | C | ILE | 86 | B | 14.332 | 53.807 | -1.751 | 0.45 |
| 1242 | O | ILE | 86 | B | 14.566 | 54.996 | -1.894 | 0.58 |
| 1243 | N | VAL | 87 | B | 13.880 | 53.315 | -0.618 | 0.49 |
| 1244 | CA | VAL | 87 | B | 13.507 | 54.142 | 0.517 | 0.42 |
| 1245 | CB | VAL | 87 | B | 12.892 | 53.242 | 1.570 | 0.43 |
| 1246 | CG1 | VAL | 87 | B | 12.781 | 53.866 | 2.950 | 0.39 |
| 1247 | CG2 | VAL | 87 | B | 11.517 | 52.782 | 1.097 | 0.50 |
| 1248 | C | VAL | 87 | B | 14.686 | 54.986 | 0.984 | 0.52 |
| 1249 | O | VAL | 87 | B | 14.415 | 55.916 | 1.765 | 0.57 |
| 1250 | N | GLN | 88 | B | 15.751 | 54.226 | 1.301 | 0.64 |
| 1251 | CA | GLN | 88 | B | 17.007 | 54.802 | 1.773 | 0.50 |
| 1252 | CB | GLN | 88 | B | 18.035 | 53.927 | 2.372 | 0.54 |
| 1253 | CG | GLN | 88 | B | 19.477 | 54.409 | 2.355 | 0.50 |
| 1254 | CD | GLN | 88 | B | 20.342 | 53.445 | 3.126 | 0.53 |
| 1255 | OE1 | GLN | 88 | B | 19.914 | 52.340 | 3.448 | 0.63 |
| 1256 | NE2 | GLN | 88 | B | 21.607 | 53.766 | 3.183 | 0.42 |
| 1257 | C | GLN | 88 | B | 17.473 | 55.905 | 0.867 | 0.42 |
| 1258 | O | GLN | 88 | B | 18.004 | 56.920 | 1.314 | 0.52 |
| 1259 | N | THR | 89 | B | 17.420 | 55.682 | -0.420 | 0.52 |
| 1260 | CA | THR | 89 | B | 17.749 | 56.663 | -1.434 | 0.51 |

Fig. 16.28

| ATOM | | RESIDUE | | CHAIN | X | Y | Z | δ |
|---|---|---|---|---|---|---|---|---|
| 1261 | CB | THR | 89 | B | 17.957 | 56.044 | -2.830 | 0.44 |
| 1262 | OG1 | THR | 89 | B | 18.892 | 54.925 | -2.666 | 0.58 |
| 1263 | CG2 | THR | 89 | B | 18.468 | 56.959 | -3.906 | 0.28 |
| 1264 | C | THR | 89 | B | 16.809 | 57.866 | -1.437 | 0.60 |
| 1265 | O | THR | 89 | B | 17.292 | 58.957 | -1.772 | 0.60 |
| 1266 | N | LEU | 90 | B | 15.600 | 57.756 | -0.944 | 0.60 |
| 1267 | CA | LEU | 90 | B | 14.594 | 58.825 | -0.965 | 0.54 |
| 1268 | CB | LEU | 90 | B | 13.201 | 58.299 | -1.267 | 0.64 |
| 1269 | CG | LEU | 90 | B | 12.008 | 59.230 | -1.078 | 0.62 |
| 1270 | CD1 | LEU | 90 | B | 11.967 | 60.201 | -2.272 | 0.49 |
| 1271 | CD2 | LEU | 90 | B | 10.728 | 58.385 | -1.213 | 0.62 |
| 1272 | C | LEU | 90 | B | 14.771 | 59.667 | 0.279 | 0.47 |
| 1273 | O | LEU | 90 | B | 14.902 | 60.893 | 0.185 | 0.63 |
| 1274 | N | VAL | 91 | B | 15.098 | 59.037 | 1.376 | 0.43 |
| 1275 | CA | VAL | 91 | B | 15.498 | 59.640 | 2.618 | 0.40 |
| 1276 | CB | VAL | 91 | B | 15.662 | 58.617 | 3.726 | 0.35 |
| 1277 | CG1 | VAL | 91 | B | 15.884 | 59.259 | 5.070 | 0.33 |
| 1278 | CG2 | VAL | 91 | B | 14.368 | 57.821 | 3.941 | 0.47 |
| 1279 | C | VAL | 91 | B | 16.645 | 60.623 | 2.505 | 0.49 |
| 1280 | O | VAL | 91 | B | 16.915 | 61.323 | 3.477 | 0.59 |
| 1281 | N | HIS | 92 | B | 17.546 | 60.291 | 1.635 | 0.51 |
| 1282 | CA | HIS | 92 | B | 18.848 | 60.835 | 1.409 | 0.56 |
| 1283 | CB | HIS | 92 | B | 19.806 | 59.782 | 0.770 | 0.55 |
| 1284 | CG | HIS | 92 | B | 21.133 | 60.406 | 0.469 | 0.52 |
| 1285 | CD2 | HIS | 92 | B | 21.587 | 60.995 | -0.668 | 0.36 |
| 1286 | ND1 | HIS | 92 | B | 22.072 | 60.627 | 1.483 | 0.42 |
| 1287 | CE1 | HIS | 92 | B | 23.116 | 61.193 | 0.876 | 0.49 |
| 1288 | NE2 | HIS | 92 | B | 22.856 | 61.461 | -0.379 | 0.43 |
| 1289 | C | HIS | 92 | B | 18.699 | 62.058 | 0.492 | 0.50 |
| 1290 | O | HIS | 92 | B | 19.217 | 63.135 | 0.766 | 0.62 |
| 1291 | N | PHE | 93 | B | 17.866 | 61.925 | -0.494 | 0.52 |
| 1292 | CA | PHE | 93 | B | 17.412 | 62.999 | -1.335 | 0.62 |
| 1293 | CB | PHE | 93 | B | 16.605 | 62.527 | -2.519 | 0.52 |
| 1294 | CG | PHE | 93 | B | 15.862 | 63.671 | -3.167 | 0.65 |
| 1295 | CD1 | PHE | 93 | B | 14.542 | 63.901 | -2.795 | 0.60 |
| 1296 | CD2 | PHE | 93 | B | 16.473 | 64.466 | -4.135 | 0.66 |
| 1297 | CE1 | PHE | 93 | B | 13.873 | 65.043 | -3.237 | 0.64 |
| 1298 | CE2 | PHE | 93 | B | 15.814 | 65.627 | -4.580 | 0.66 |
| 1299 | CZ | PHE | 93 | B | 14.435 | 65.735 | -4.295 | 0.51 |
| 1300 | C | PHE | 93 | B | 16.741 | 64.103 | -0.506 | 0.66 |
| 1301 | O | PHE | 93 | B | 17.155 | 65.264 | -0.617 | 0.73 |
| 1302 | N | ILE | 94 | B | 15.788 | 63.768 | 0.315 | 0.64 |
| 1303 | CA | ILE | 94 | B | 15.077 | 64.619 | 1.252 | 0.61 |
| 1304 | CB | ILE | 94 | B | 13.867 | 63.896 | 1.897 | 0.63 |
| 1305 | CG2 | ILE | 94 | B | 13.064 | 64.661 | 2.972 | 0.63 |

Fig. 16.29

| ATOM | RESIDUE | CHAIN | X | Y | Z | δ |
|---|---|---|---|---|---|---|
| 1306 CG1 | ILE 94 | B | 12.891 | 63.334 | 0.814 | 0.51 |
| 1307 CD | ILE 94 | B | 11.846 | 62.434 | 1.602 | 0.63 |
| 1308 C | ILE 94 | B | 15.975 | 65.284 | 2.289 | 0.70 |
| 1309 O | ILE 94 | B | 15.535 | 66.310 | 2.824 | 0.75 |
| 1310 N | ASN 95 | B | 16.860 | 64.542 | 2.923 | 0.74 |
| 1311 CA | ASN 95 | B | 17.823 | 64.972 | 3.913 | 0.64 |
| 1312 CB | ASN 95 | B | 17.256 | 65.197 | 5.288 | 0.70 |
| 1313 CG | ASN 95 | B | 18.207 | 65.971 | 6.197 | 0.86 |
| 1314 OD1 | ASN 95 | B | 19.322 | 66.347 | 5.782 | 0.79 |
| 1315 ND2 | ASN 95 | B | 17.874 | 66.039 | 7.487 | 0.87 |
| 1316 C | ASN 95 | B | 19.132 | 64.178 | 3.867 | 0.65 |
| 1317 O | ASN 95 | B | 19.420 | 63.340 | 4.746 | 0.65 |
| 1318 N | PRO 96 | B | 20.049 | 64.736 | 3.096 | 0.64 |
| 1319 CD | PRO 96 | B | 19.759 | 65.911 | 2.228 | 0.68 |
| 1320 CA | PRO 96 | B | 21.354 | 64.191 | 2.805 | 0.65 |
| 1321 CB | PRO 96 | B | 22.034 | 65.260 | 1.943 | 0.69 |
| 1322 CG | PRO 96 | B | 20.869 | 65.837 | 1.180 | 0.72 |
| 1323 C | PRO 96 | B | 22.214 | 63.754 | 3.961 | 0.72 |
| 1324 O | PRO 96 | B | 23.152 | 62.938 | 3.812 | 0.73 |
| 1325 N | GLU 97 | B | 21.829 | 64.174 | 5.140 | 0.72 |
| 1326 CA | GLU 97 | B | 22.686 | 64.060 | 6.338 | 0.70 |
| 1327 CB | GLU 97 | B | 22.627 | 65.373 | 7.121 | 0.84 |
| 1328 CG | GLU 97 | B | 23.691 | 66.431 | 7.069 | 0.80 |
| 1329 CD | GLU 97 | B | 24.673 | 66.524 | 5.952 | 1.11 |
| 1330 OE1 | GLU 97 | B | 25.881 | 66.300 | 6.044 | 1.13 |
| 1331 OE2 | GLU 97 | B | 24.198 | 67.117 | 4.948 | 1.11 |
| 1332 C | GLU 97 | B | 22.108 | 62.957 | 7.224 | 0.72 |
| 1333 O | GLU 97 | B | 22.745 | 62.506 | 8.192 | 0.74 |
| 1334 N | THR 98 | B | 20.827 | 62.673 | 7.015 | 0.69 |
| 1335 CA | THR 98 | B | 20.159 | 61.643 | 7.830 | 0.67 |
| 1336 CB | THR 98 | B | 18.594 | 61.624 | 7.570 | 0.65 |
| 1337 OG1 | THR 98 | B | 18.303 | 62.988 | 7.123 | 0.77 |
| 1338 CG2 | THR 98 | B | 17.827 | 61.326 | 8.854 | 0.78 |
| 1339 C | THR 98 | B | 20.744 | 60.263 | 7.527 | 0.63 |
| 1340 O | THR 98 | B | 20.821 | 59.417 | 8.443 | 0.67 |
| 1341 N | VAL 99 | B | 21.028 | 60.046 | 6.249 | 0.57 |
| 1342 CA | VAL 99 | B | 21.514 | 58.705 | 5.846 | 0.52 |
| 1343 CB | VAL 99 | B | 20.261 | 57.794 | 5.871 | 0.56 |
| 1344 CG1 | VAL 99 | B | 19.489 | 57.979 | 4.573 | 0.44 |
| 1345 CG2 | VAL 99 | B | 20.512 | 56.335 | 6.138 | 0.62 |
| 1346 C | VAL 99 | B | 22.242 | 58.813 | 4.532 | 0.52 |
| 1347 O | VAL 99 | B | 21.984 | 59.664 | 3.666 | 0.53 |
| 1348 N | PRO 100 | B | 23.279 | 57.962 | 4.403 | 0.53 |
| 1349 CD | PRO 100 | B | 23.638 | 56.903 | 5.352 | 0.54 |
| 1350 CA | PRO 100 | B | 23.966 | 57.811 | 3.125 | 0.49 |

Fig. 16.30

| ATOM | RESIDUE | CHAIN | X | Y | Z | δ |
|---|---|---|---|---|---|---|
| 1351 CB | PRO 100 | B | 25.101 | 56.822 | 3.411 | 0.50 |
| 1352 CG | PRO 100 | B | 24.727 | 56.112 | 4.666 | 0.47 |
| 1353 C | PRO 100 | B | 23.053 | 57.286 | 2.041 | 0.41 |
| 1354 O | PRO 100 | B | 22.099 | 56.537 | 2.250 | 0.58 |
| 1355 N | LYS 101 | B | 23.591 | 57.197 | 0.836 | 0.48 |
| 1356 CA | LYS 101 | B | 23.004 | 56.427 | -0.241 | 0.40 |
| 1357 CB | LYS 101 | B | 23.525 | 56.940 | -1.590 | 0.58 |
| 1358 CG | LYS 101 | B | 22.414 | 57.692 | -2.367 | 0.69 |
| 1359 CD | LYS 101 | B | 22.889 | 58.782 | -3.271 | 0.65 |
| 1360 CE | LYS 101 | B | 24.415 | 58.943 | -3.297 | 0.61 |
| 1361 NZ | LYS 101 | B | 24.770 | 59.592 | -4.589 | 0.76 |
| 1362 C | LYS 101 | B | 23.492 | 54.959 | -0.048 | 0.56 |
| 1363 O | LYS 101 | B | 24.250 | 54.763 | 0.922 | 0.54 |
| 1364 N | PRO 102 | B | 22.672 | 54.006 | -0.475 | 0.57 |
| 1365 CD | PRO 102 | B | 21.367 | 54.200 | -1.164 | 0.48 |
| 1366 CA | PRO 102 | B | 23.080 | 52.604 | -0.428 | 0.59 |
| 1367 CB | PRO 102 | B | 21.934 | 51.832 | -1.028 | 0.43 |
| 1368 CG | PRO 102 | B | 21.075 | 52.823 | -1.736 | 0.54 |
| 1369 C | PRO 102 | B | 24.426 | 52.376 | -1.076 | 0.56 |
| 1370 O | PRO 102 | B | 24.877 | 53.077 | -2.006 | 0.63 |
| 1371 N | CYS 103 | B | 25.031 | 51.241 | -0.744 | 0.58 |
| 1372 CA | CYS 103 | B | 26.294 | 50.811 | -1.400 | 0.48 |
| 1373 CB | CYS 103 | B | 27.404 | 50.638 | -0.384 | 0.75 |
| 1374 SG | CYS 103 | B | 27.517 | 48.995 | 0.344 | 0.81 |
| 1375 C | CYS 103 | B | 26.108 | 49.649 | -2.355 | 0.55 |
| 1376 O | CYS 103 | B | 25.113 | 48.919 | -2.353 | 0.53 |
| 1377 N | CYS 104 | B | 26.834 | 49.723 | -3.461 | 0.32 |
| 1378 CA | CYS 104 | B | 26.958 | 48.724 | -4.468 | 0.48 |
| 1379 C | CYS 104 | B | 27.702 | 47.477 | -3.963 | 0.60 |
| 1380 O | CYS 104 | B | 28.863 | 47.528 | -3.570 | 0.60 |
| 1381 CB | CYS 104 | B | 27.694 | 49.397 | -5.594 | 0.32 |
| 1382 SG | CYS 104 | B | 27.689 | 48.486 | -7.124 | 0.54 |
| 1383 N | ALA 105 | B | 27.039 | 46.332 | -4.024 | 0.51 |
| 1384 CA | ALA 105 | B | 27.391 | 45.157 | -3.222 | 0.51 |
| 1385 CB | ALA 105 | B | 26.840 | 45.289 | -1.838 | 0.51 |
| 1386 C | ALA 105 | B | 26.862 | 43.953 | -4.017 | 0.51 |
| 1387 O | ALA 105 | B | 26.240 | 44.236 | -5.068 | 0.57 |
| 1388 N | PRO 106 | B | 27.562 | 42.850 | -3.866 | 0.59 |
| 1389 CD | PRO 106 | B | 28.577 | 42.554 | -2.822 | 0.51 |
| 1390 CA | PRO 106 | B | 27.352 | 41.676 | -4.739 | 0.59 |
| 1391 CB | PRO 106 | B | 28.482 | 40.709 | -4.321 | 0.54 |
| 1392 CG | PRO 106 | B | 29.464 | 41.531 | -3.559 | 0.50 |
| 1393 C | PRO 106 | B | 25.996 | 41.079 | -4.332 | 0.58 |
| 1394 O | PRO 106 | B | 25.637 | 41.105 | -3.154 | 0.54 |
| 1395 N | THR 107 | B | 25.222 | 40.677 | -5.306 | 0.60 |

Fig. 16.31

| ATOM | RESIDUE | CHAIN | X | Y | Z | δ |
|---|---|---|---|---|---|---|
| 1396 CA | THR 107 | B | 23.880 | 40.104 | -4.913 | 0.65 |
| 1397 CB | THR 107 | B | 22.823 | 40.695 | -5.928 | 0.45 |
| 1398 OG1 | THR 107 | B | 23.160 | 40.092 | -7.208 | 0.68 |
| 1399 CG2 | THR 107 | B | 22.802 | 42.209 | -6.091 | 0.56 |
| 1400 C | THR 107 | B | 24.011 | 38.593 | -5.133 | 0.68 |
| 1401 O | THR 107 | B | 23.316 | 37.753 | -4.543 | 0.68 |
| 1402 N | GLN 108 | B | 25.040 | 38.240 | -5.902 | 0.67 |
| 1403 CA | GLN 108 | B | 25.358 | 36.820 | -6.067 | 0.64 |
| 1404 CB | GLN 108 | B | 24.534 | 36.137 | -7.105 | 0.58 |
| 1405 CG | GLN 108 | B | 24.889 | 36.327 | -8.547 | 0.70 |
| 1406 CD | GLN 108 | B | 24.534 | 35.087 | -9.358 | 0.99 |
| 1407 OE1 | GLN 108 | B | 24.739 | 33.953 | -8.916 | 0.83 |
| 1408 NE2 | GLN 108 | B | 23.905 | 35.307 | -10.508 | 0.94 |
| 1409 C | GLN 108 | B | 26.848 | 36.536 | -6.135 | 0.63 |
| 1410 O | GLN 108 | B | 27.523 | 37.048 | -7.047 | 0.64 |
| 1411 N | LEU 109 | B | 27.248 | 35.607 | -5.288 | 0.60 |
| 1412 CA | LEU 109 | B | 28.574 | 34.966 | -5.307 | 0.65 |
| 1413 CB | LEU 109 | B | 29.033 | 35.101 | -3.831 | 0.55 |
| 1414 CG | LEU 109 | B | 29.122 | 36.560 | -3.407 | 0.59 |
| 1415 CD1 | LEU 109 | B | 28.855 | 36.704 | -1.936 | 0.68 |
| 1416 CD2 | LEU 109 | B | 30.501 | 37.120 | -3.746 | 0.56 |
| 1417 C | LEU 109 | B | 28.563 | 33.511 | -5.774 | 0.70 |
| 1418 O | LEU 109 | B | 27.843 | 32.695 | -5.142 | 0.75 |
| 1419 N | ASN 110 | B | 29.599 | 33.112 | -6.507 | 0.67 |
| 1420 CA | ASN 110 | B | 29.915 | 31.719 | -6.849 | 0.65 |
| 1421 CB | ASN 110 | B | 30.080 | 31.445 | -8.350 | 0.59 |
| 1422 CG | ASN 110 | B | 28.797 | 31.687 | -9.115 | 0.79 |
| 1423 OD1 | ASN 110 | B | 28.778 | 31.854 | -10.340 | 0.90 |
| 1424 ND2 | ASN 110 | B | 27.734 | 31.706 | -8.302 | 0.79 |
| 1425 C | ASN 110 | B | 31.162 | 31.203 | -6.116 | 0.65 |
| 1426 O | ASN 110 | B | 32.020 | 31.945 | -5.641 | 0.61 |
| 1427 N | ALA 111 | B | 31.238 | 29.877 | -6.127 | 0.68 |
| 1428 CA | ALA 111 | B | 32.307 | 29.116 | -5.489 | 0.64 |
| 1429 CB | ALA 111 | B | 31.831 | 27.798 | -4.906 | 0.59 |
| 1430 C | ALA 111 | B | 33.458 | 28.918 | -6.467 | 0.57 |
| 1431 O | ALA 111 | B | 33.295 | 29.038 | -7.697 | 0.54 |
| 1432 N | ILE 112 | B | 34.629 | 28.709 | -5.879 | 0.54 |
| 1433 CA | ILE 112 | B | 35.738 | 28.160 | -6.743 | 0.47 |
| 1434 CB | ILE 112 | B | 36.886 | 29.173 | -6.985 | 0.63 |
| 1435 CG2 | ILE 112 | B | 36.603 | 30.359 | -7.923 | 0.68 |
| 1436 CG1 | ILE 112 | B | 37.619 | 29.600 | -5.712 | 0.56 |
| 1437 CD | ILE 112 | B | 39.128 | 29.945 | -5.888 | 0.64 |
| 1438 C | ILE 112 | B | 36.186 | 26.877 | -5.997 | 0.45 |
| 1439 O | ILE 112 | B | 36.185 | 26.857 | -4.747 | 0.54 |
| 1440 N | SER 113 | B | 36.724 | 25.995 | -6.770 | 0.44 |

Fig. 16.32

| ATOM | RESIDUE | | CHAIN | X | Y | Z | δ |
|---|---|---|---|---|---|---|---|
| 1441 CA | SER | 113 | B | 37.490 | 24.802 | -6.330 | 0.61 |
| 1442 CB | SER | 113 | B | 36.951 | 23.581 | -7.102 | 0.63 |
| 1443 OG | SER | 113 | B | 35.727 | 23.125 | -6.515 | 0.62 |
| 1444 C | SER | 113 | B | 38.962 | 25.003 | -6.694 | 0.53 |
| 1445 O | SER | 113 | B | 39.320 | 25.356 | -7.828 | 0.52 |
| 1446 N | VAL | 114 | B | 39.833 | 24.614 | -5.778 | 0.55 |
| 1447 CA | VAL | 114 | B | 41.265 | 24.576 | -6.121 | 0.58 |
| 1448 CB | VAL | 114 | B | 41.961 | 25.809 | -5.514 | 0.64 |
| 1449 CG1 | VAL | 114 | B | 41.157 | 27.093 | -5.667 | 0.49 |
| 1450 CG2 | VAL | 114 | B | 42.328 | 25.534 | -4.094 | 0.55 |
| 1451 C | VAL | 114 | B | 41.871 | 23.235 | -5.686 | 0.60 |
| 1452 O | VAL | 114 | B | 41.581 | 22.634 | -4.637 | 0.51 |
| 1453 N | LEU | 115 | B | 42.814 | 22.811 | -6.510 | 0.49 |
| 1454 CA | LEU | 115 | B | 43.490 | 21.511 | -6.182 | 0.58 |
| 1455 CB | LEU | 115 | B | 43.748 | 20.883 | -7.603 | 0.55 |
| 1456 CG | LEU | 115 | B | 44.210 | 19.423 | -7.568 | 0.57 |
| 1457 CD1 | LEU | 115 | B | 43.121 | 18.518 | -7.036 | 0.59 |
| 1458 CD2 | LEU | 115 | B | 44.655 | 19.035 | -8.975 | 0.52 |
| 1459 C | LEU | 115 | B | 44.739 | 21.880 | -5.403 | 0.47 |
| 1460 O | LEU | 115 | B | 45.582 | 22.571 | -5.955 | 0.57 |
| 1461 N | TYR | 116 | B | 44.954 | 21.369 | -4.196 | 0.57 |
| 1462 CA | TYR | 116 | B | 46.186 | 21.698 | -3.479 | 0.69 |
| 1463 CB | TYR | 116 | B | 45.946 | 22.841 | -2.480 | 0.70 |
| 1464 CG | TYR | 116 | B | 45.134 | 22.457 | -1.269 | 0.46 |
| 1465 CD1 | TYR | 116 | B | 43.762 | 22.395 | -1.272 | 0.57 |
| 1466 CE1 | TYR | 116 | B | 43.062 | 21.927 | -0.154 | 0.66 |
| 1467 CD2 | TYR | 116 | B | 45.764 | 22.284 | -0.050 | 0.57 |
| 1468 CE2 | TYR | 116 | B | 45.120 | 21.791 | 1.067 | 0.52 |
| 1469 CZ | TYR | 116 | B | 43.748 | 21.620 | 1.016 | 0.76 |
| 1470 OH | TYR | 116 | B | 43.110 | 21.288 | 2.184 | 0.78 |
| 1471 C | TYR | 116 | B | 46.810 | 20.454 | -2.849 | 0.69 |
| 1472 O | TYR | 116 | B | 46.136 | 19.420 | -2.752 | 0.69 |
| 1473 N | PHE | 117 | B | 48.067 | 20.582 | -2.485 | 0.56 |
| 1474 CA | PHE | 117 | B | 48.891 | 19.633 | -1.793 | 0.60 |
| 1475 CB | PHE | 117 | B | 50.185 | 19.204 | -2.413 | 0.64 |
| 1476 CG | PHE | 117 | B | 51.022 | 20.135 | -3.206 | 0.82 |
| 1477 CD1 | PHE | 117 | B | 51.097 | 20.008 | -4.599 | 0.91 |
| 1478 CD2 | PHE | 117 | B | 51.946 | 20.970 | -2.561 | 1.11 |
| 1479 CE1 | PHE | 117 | B | 51.960 | 20.804 | -5.343 | 1.12 |
| 1480 CE2 | PHE | 117 | B | 52.823 | 21.783 | -3.292 | 1.03 |
| 1481 CZ | PHE | 117 | B | 52.837 | 21.686 | -4.697 | 1.02 |
| 1482 C | PHE | 117 | B | 48.967 | 19.911 | -0.315 | 0.62 |
| 1483 O | PHE | 117 | B | 49.562 | 20.918 | 0.059 | 0.72 |
| 1484 N | ASP | 118 | B | 48.287 | 19.095 | 0.474 | 0.67 |
| 1485 CA | ASP | 118 | B | 48.220 | 19.309 | 1.922 | 0.67 |

Fig. 16.33

| ATOM | RESIDUE | CHAIN | X | Y | Z | δ |
|---|---|---|---|---|---|---|
| 1486 CB | ASP 118 | B | 47.036 | 18.679 | 2.610 | 0.73 |
| 1487 CG | ASP 118 | B | 47.265 | 17.250 | 3.079 | 0.82 |
| 1488 OD1 | ASP 118 | B | 46.423 | 16.701 | 3.798 | 0.72 |
| 1489 OD2 | ASP 118 | B | 48.369 | 16.720 | 2.831 | 0.60 |
| 1490 C | ASP 118 | B | 49.577 | 18.996 | 2.526 | 0.68 |
| 1491 O | ASP 118 | B | 50.536 | 18.660 | 1.826 | 0.75 |
| 1492 N | ASP 119 | 9 | 49.577 | 18.988 | 3.851 | 0.76 |
| 1493 CA | ASP 119 | B | 50.837 | 18.919 | 4.614 | 0.83 |
| 1494 CB | ASP 119 | B | 50.693 | 19.619 | 5.961 | 0.94 |
| 1495 CG | ASP 119 | B | 49.368 | 19.278 | 6.634 | 1.08 |
| 1496 OD1 | ASP 119 | B | 49.132 | 18.110 | 6.991 | 1.04 |
| 1497 OD2 | ASP 119 | B | 48.509 | 20.186 | 6.627 | 1.06 |
| 1498 C | ASP 119 | B | 51.341 | 17.482 | 4.673 | 0.87 |
| 1499 O | ASP 119 | B | 52.554 | 17.249 | 4.854 | 0.90 |
| 1500 N | SER 120 | B | 50.429 | 16.546 | 4.448 | 0.85 |
| 1501 CA | SER 120 | B | 50.821 | 15.123 | 4.389 | 0.80 |
| 1502 CB | SER 120 | B | 49.833 | 14.202 | 5.030 | 0.83 |
| 1503 OG | SER 120 | B | 48.833 | 14.876 | 5.781 | 1.02 |
| 1504 C | SER 120 | B | 51.188 | 14.778 | 2.957 | 0.80 |
| 1505 O | SER 120 | B | 51.840 | 13.749 | 2.686 | 0.83 |
| 1506 N | SER 121 | B | 50.860 | 15.712 | 2.064 | 0.73 |
| 1507 CA | SER 121 | B | 51.273 | 15.519 | 0.653 | 0.69 |
| 1508 CB | SER 121 | B | 52.529 | 14.649 | 0.607 | 0.66 |
| 1509 OG | SER 121 | B | 53.646 | 15.408 | 1.016 | 0.85 |
| 1510 C | SER 121 | B | 50.155 | 14.886 | -0.163 | 0.63 |
| 1511 O | SER 121 | B | 50.340 | 14.556 | -1.332 | 0.69 |
| 1512 N | ASN 122 | B | 49.022 | 14.741 | 0.477 | 0.65 |
| 1513 CA | ASN 122 | B | 47.764 | 14.427 | -0.218 | 0.63 |
| 1514 CB | ASN 122 | B | 46.738 | 14.164 | 0.897 | 0.69 |
| 1515 CG | ASN 122 | B | 47.397 | 13.265 | 1.955 | 0.73 |
| 1516 OD1 | ASN 122 | B | 47.766 | 12.140 | 1.597 | 0.73 |
| 1517 ND2 | ASN 122 | B | 47.187 | 13.541 | 3.240 | 0.75 |
| 1518 C | ASN 122 | B | 47.412 | 15.553 | -1.176 | 0.67 |
| 1519 O | ASN 122 | B | 47.620 | 16.728 | -0.852 | 0.63 |
| 1520 N | VAL 123 | B | 46.918 | 15.189 | -2.346 | 0.66 |
| 1521 CA | VAL 123 | B | 46.429 | 16.123 | -3.360 | 0.61 |
| 1522 CB | VAL 123 | B | 46.774 | 15.543 | -4.744 | 0.58 |
| 1523 CG1 | VAL 123 | B | 45.814 | 16.141 | -5.758 | 0.59 |
| 1524 CG2 | VAL 123 | B | 48.224 | 15.828 | -5.089 | 0.56 |
| 1525 C | VAL 123 | B | 44.917 | 16.290 | -3.220 | 0.63 |
| 1526 O | VAL 123 | B | 44.237 | 15.263 | -3.098 | 0.65 |
| 1527 N | ILE 124 | B | 44.491 | 17.451 | -2.758 | 0.70 |
| 1528 CA | ILE 124 | B | 43.113 | 17.704 | -2.302 | 0.65 |
| 1529 CB | ILE 124 | B | 43.231 | 18.240 | -0.813 | 0.67 |
| 1530 CG2 | ITE 124 | B | 41.850 | 18.575 | -0.198 | 0.67 |

Fig. 16.34

| ATOM | | RESIDUE | | CHAIN | X | Y | Z | δ |
|---|---|---|---|---|---|---|---|---|
| 1531 | CG1 | ILE | 124 | B | 43.938 | 17.128 | -0.011 | 0.66 |
| 1532 | CD | ILE | 124 | B | 43.524 | 16.995 | 1.468 | 0.84 |
| 1533 | C | ILE | 124 | B | 42.385 | 18.700 | -3.208 | 0.67 |
| 1534 | O | ILE | 124 | B | 42.895 | 19.771 | -3.582 | 0.63 |
| 1535 | N | LEU | 125 | B | 41.110 | 18.426 | -3.448 | 0.63 |
| 1536 | CA | LEU | 125 | B | 40.235 | 19.393 | -4.140 | 0.69 |
| 1537 | CB | LEU | 125 | B | 39.453 | 18.619 | -5.187 | 0.67 |
| 1538 | CG | LEU | 125 | B | 38.491 | 19.404 | -6.067 | 0.64 |
| 1539 | CD1 | LEU | 125 | B | 39.277 | 20.179 | -7.130 | 0.49 |
| 1540 | CD2 | LEU | 125 | B | 37.653 | 18.302 | -6.750 | 0.48 |
| 1541 | C | LEU | 125 | B | 39.344 | 20.118 | -3.135 | 0.67 |
| 1542 | O | LEU | 125 | B | 38.544 | 19.446 | -2.470 | 0.66 |
| 1543 | N | LYS | 126 | B | 39.596 | 21.403 | -2.961 | 0.66 |
| 1544 | CA | LYS | 126 | B | 38.865 | 22.238 | -2.001 | 0.59 |
| 1545 | CB | LYS | 126 | B | 39.604 | 22.684 | -0.788 | 0.61 |
| 1546 | CG | LYS | 126 | B | 38.871 | 23.673 | 0.128 | 0.78 |
| 1547 | CD | LYS | 126 | B | 39.041 | 23.334 | 1.601 | 0.91 |
| 1548 | CE | LYS | 126 | B | 38.196 | 24.169 | 2.543 | 0.82 |
| 1549 | NZ | LYS | 126 | B | 37.808 | 23.383 | 3.746 | 0.86 |
| 1550 | C | LYS | 126 | B | 38.054 | 23.325 | -2.669 | 0.50 |
| 1551 | O | LYS | 126 | B | 38.253 | 23.700 | -3.845 | 0.57 |
| 1552 | N | LYS | 127 | B | 36.810 | 23.373 | -2.204 | 0.61 |
| 1553 | CA | LYS | 127 | B | 35.729 | 24.235 | -2.664 | 0.60 |
| 1554 | CB | LYS | 127 | B | 34.375 | 23.528 | -2.620 | 0.58 |
| 1555 | CG | LYS | 127 | B | 33.312 | 24.232 | -3.471 | 0.57 |
| 1556 | CD | LYS | 127 | B | 31.942 | 24.017 | -2.833 | 0.62 |
| 1557 | CE | LYS | 127 | B | 30.852 | 24.324 | -3.845 | 0.76 |
| 1558 | NZ | LYS | 127 | B | 31.445 | 24.255 | -5.208 | 0.83 |
| 1559 | C | LYS | 127 | B | 35.626 | 25.471 | -1.755 | 0.60 |
| 1560 | O | LYS | 127 | B | 35.815 | 25.364 | -0.521 | 0.49 |
| 1561 | N | TYR | 128 | B | 35.798 | 26.599 | -2.424 | 0.56 |
| 1562 | CA | TYR | 128 | B | 35.838 | 27.876 | -1.669 | 0.50 |
| 1563 | CB | TYR | 128 | B | 37.082 | 28.686 | -2.089 | 0.77 |
| 1564 | CG | TYR | 128 | B | 38.294 | 28.241 | -1.298 | 0.64 |
| 1565 | CD1 | TYR | 128 | B | 39.395 | 27.674 | -1.935 | 0.68 |
| 1566 | CE1 | TYR | 128 | B | 40.468 | 27.198 | -1.174 | 0.68 |
| 1567 | CD2 | TYR | 128 | B | 38.204 | 28.154 | 0.085 | 0.72 |
| 1568 | CE2 | TYR | 128 | B | 39.254 | 27.649 | 0.857 | 0.77 |
| 1569 | CZ | TYR | 128 | B | 40.332 | 27.060 | 0.200 | 0.89 |
| 1570 | OH | TYR | 128 | B | 41.314 | 26.484 | 0.961 | 0.90 |
| 1571 | C | TYR | 128 | B | 34.587 | 28.661 | -2.110 | 0.46 |
| 1572 | O | TYR | 128 | B | 34.335 | 28.808 | -3.308 | 0.59 |
| 1573 | N | ARG | 129 | B | 33.692 | 28.665 | -1.150 | 0.56 |
| 1574 | CA | ARG | 129 | B | 32.380 | 29.311 | -1.396 | 0.61 |
| 1575 | CB | ARG | 129 | B | 31.479 | 28.769 | -0.273 | 0.74 |

Fig. 16.35

| ATOM | RESIDUE | CHAIN | X | Y | Z | δ |
|---|---|---|---|---|---|---|
| 1576 CG | ARG 129 | B | 31.060 | 27.303 | -0.447 | 0.74 |
| 1577 CD | ARG 129 | B | 29.804 | 27.006 | 0.337 | 0.61 |
| 1578 NE | ARG 129 | B | 28.620 | 27.257 | -0.488 | 1.06 |
| 1579 CZ | ARG 129 | B | 27.768 | 28.270 | -0.310 | 1.07 |
| 1580 NH1 | ARG 129 | B | 27.618 | 28.890 | 0.861 | 0.91 |
| 1581 NH2 | ARG 129 | B | 27.093 | 28.771 | -1.349 | 0.87 |
| 1582 C | ARG 129 | B | 32.587 | 30.829 | -1.302 | 0.54 |
| 1583 O | ARG 129 | B | 33.426 | 31.314 | -0.522 | 0.55 |
| 1584 N | ASN 130 | B | 31.860 | 31.561 | -2.095 | 0.60 |
| 1585 CA | ASN 130 | B | 31.584 | 33.006 | -2.013 | 0.59 |
| 1586 CB | ASN 130 | B | 31.088 | 33.375 | -0.610 | 0.52 |
| 1587 CG | ASN 130 | B | 29.629 | 32.995 | -0.392 | 0.63 |
| 1588 OD1 | ASN 130 | B | 28.825 | 32.869 | -1.318 | 0.58 |
| 1589 ND2 | ASN 130 | B | 29.276 | 32.510 | 0.782 | 0.55 |
| 1590 C | ASN 130 | B | 32.864 | 33.763 | -2.380 | 0.55 |
| 1591 O | ASN 130 | B | 33.205 | 34.674 | -1.648 | 0.48 |
| 1592 N | MET 131 | B | 33.418 | 33.459 | -3.520 | 0.54 |
| 1593 CA | MET 131 | B | 34.730 | 33.897 | -3.974 | 0.51 |
| 1594 CB | MET 131 | B | 35.632 | 32.662 | -4.327 | 0.54 |
| 1595 CG | MET 131 | B | 36.159 | 31.950 | -3.137 | 0.44 |
| 1596 SD | MET 131 | B | 37.229 | 32.957 | -2.052 | 0.61 |
| 1597 CE | MET 131 | B | 38.802 | 32.648 | -2.915 | 0.60 |
| 1598 C | MET 131 | B | 34.538 | 34.709 | -5.256 | 0.52 |
| 1599 O | MET 131 | B | 35.416 | 35.514 | -5.570 | 0.59 |
| 1600 N | VAL 132 | B | 33.538 | 34.371 | -6.055 | 0.59 |
| 1601 CA | VAL 132 | B | 33.347 | 35.038 | -7.359 | 0.60 |
| 1602 CB | VAL 132 | B | 33.434 | 34.092 | -8.517 | 0.52 |
| 1603 CG1 | VAL 132 | B | 33.162 | 34.633 | -9.898 | 0.48 |
| 1604 CG2 | VAL 132 | B | 34.447 | 32.972 | -8.485 | 0.66 |
| 1605 C | VAL 132 | B | 32.063 | 35.873 | -7.308 | 0.69 |
| 1606 O | VAL 132 | B | 30.960 | 35.366 | -7.012 | 0.63 |
| 1607 N | VAL 133 | B | 32.240 | 37.134 | -7.668 | 0.65 |
| 1608 CA | VAL 133 | B | 31.100 | 38.075 | -7.709 | 0.62 |
| 1609 CB | VAL 133 | B | 31.530 | 39.550 | -7.591 | 0.56 |
| 1610 CG1 | VAL 133 | B | 30.408 | 40.468 | -8.105 | 0.53 |
| 1611 CG2 | VAL 133 | B | 31.852 | 39.841 | -6.128 | 0.39 |
| 1612 C | VAL 133 | B | 30.409 | 37.812 | -9.052 | 0.62 |
| 1613 O | VAL 133 | B | 31.105 | 38.041 | -10.044 | 0.54 |
| 1614 N | ARG 134 | B | 29.134 | 37.398 | -8.941 | 0.53 |
| 1615 CA | ARG 134 | B | 28.440 | 37.117 | -10.208 | 0.56 |
| 1616 CB | ARG 134 | B | 27.709 | 35.760 | -10.158 | 0.68 |
| 1617 CG | ARG 134 | B | 28.433 | 34.636 | -10.908 | 0.80 |
| 1618 CD | ARG 134 | B | 28.238 | 34.700 | -12.379 | 0.79 |
| 1619 NE | ARG 134 | B | 27.810 | 33.460 | -12.976 | 1.02 |
| 1620 CZ | ARG 134 | B | 26.587 | 32.977 | -13.159 | 1.18 |

Fig. 16.36

| ATOM | RESIDUE | CHAIN | X | Y | Z | δ |
|---|---|---|---|---|---|---|
| 1621 NH1 | ARG 134 | B | 25.494 | 33.408 | -12.533 | 1.08 |
| 1622 NH2 | ARG 134 | B | 26.450 | 31.902 | -13.952 | 1.09 |
| 1623 C | ARG 134 | B | 27.517 | 38.253 | -10.622 | 0.57 |
| 1624 O | ARG 134 | B | 27.185 | 38.397 | -11.813 | 0.61 |
| 1625 N | ALA 135 | B | 27.038 | 39.030 | -9.659 | 0.53 |
| 1626 CA | ALA 135 | B | 26.189 | 40.203 | -9.986 | 0.49 |
| 1627 CB | ALA 135 | B | 24.713 | 39.740 | -9.934 | 0.64 |
| 1628 C | ALA 135 | B | 26.352 | 41.156 | -8.774 | 0.42 |
| 1629 O | ALA 135 | B | 26.515 | 40.639 | -7.673 | 0.49 |
| 1630 N | CYS 136 | B | 25.926 | 42.365 | -9.022 | 0.59 |
| 1631 CA | CYS 136 | B | 26.001 | 43.512 | -8.089 | 0.67 |
| 1632 C | CYS 136 | B | 24.646 | 44.198 | -7.969 | 0.61 |
| 1633 O | CYS 136 | B | 23.917 | 44.273 | -8.985 | 0.59 |
| 1634 CB | CYS 136 | B | 26.990 | 44.534 | -8.701 | 0.61 |
| 1635 SG | CYS 136 | B | 28.689 | 43.852 | -8.673 | 0.61 |
| 1636 N | GLY 137 | B | 24.362 | 44.756 | -6.808 | 0.59 |
| 1637 CA | GLY 137 | B | 23.099 | 45.570 | -6.772 | 0.59 |
| 1638 C | GLY 137 | B | 23.290 | 46.706 | -5.787 | 0.52 |
| 1639 O | GLY 137 | B | 24.077 | 46.520 | -4.845 | 0.49 |
| 1640 N | CYS 138 | B | 22.261 | 47.515 | -5.634 | 0.57 |
| 1641 CA | CYS 138 | B | 22.248 | 48.539 | -4.545 | 0.48 |
| 1642 C | CYS 138 | B | 21.475 | 48.015 | -3.369 | 0.56 |
| 1643 O | CYS 138 | B | 20.235 | 47.865 | -3.446 | 0.55 |
| 1644 CB | CYS 138 | B | 21.556 | 49.798 | -5.123 | 0.38 |
| 1645 SG | CYS 138 | B | 22.664 | 50.498 | -6.428 | 0.57 |
| 1646 N | HIS 139 | B | 22.137 | 48.025 | -2.210 | 0.63 |
| 1647 CA | HIS 139 | B | 21.436 | 47.660 | -0.970 | 0.54 |
| 1648 CB | HIS 139 | B | 20.837 | 46.284 | -0.842 | 0.88 |
| 1649 CG | HIS 139 | B | 21.539 | 45.272 | -1.707 | 0.94 |
| 1650 CD2 | HIS 139 | B | 22.879 | 45.046 | -1.811 | 0.79 |
| 1651 ND1 | HIS 139 | B | 20.936 | 44.549 | -2.706 | 0.91 |
| 1652 CE1 | HIS 139 | B | 21.855 | 43.796 | -3.288 | 0.97 |
| 1653 NE2 | HIS 139 | B | 23.034 | 44.089 | -2.774 | 0.96 |
| 1654 C | HIS 139 | B | 21.888 | 48.359 | 0.264 | 0.58 |
| 1655 OT1 | HIS 139 | B | 21.160 | 48.202 | 1.268 | 0.75 |
| 1656 OT2 | HIS 139 | B | 22.865 | 49.139 | 0.256 | 0.79 |
| 1657 OT | WAT 201 | A | 31.351 | 45.516 | -2.695 | 0.57 |
| 1658 OT | WAT 202 | A | 10.574 | 42.304 | -3.269 | 0.77 |
| 1659 OT | WAT 203 | A | 41.094 | 47.385 | -10.715 | 0.74 |
| 1660 OT | WAT 204 | A | -6.527 | 46.271 | -4.416 | 0.83 |
| 1661 OT | WAT 205 | A | -7.389 | 42.963 | -2.480 | 0.75 |
| 1662 OT | WAT 206 | A | -5.998 | 42.514 | 2.104 | 0.60 |
| 1663 OT | WAT 207 | A | 25.154 | 37.549 | 3.436 | 0.76 |
| 1664 OT | WAT 208 | A | 31.925 | 33.286 | 2.732 | 0.58 |
| 1665 OT | WAT 209 | A | 32.701 | 43.734 | -4.779 | 0.52 |

Fig. 16.37

| ATOM | RESIDUE | CHAIN | X | Y | Z | δ |
|---|---|---|---:|---:|---:|---:|
| 1666 OT | WAT 210 | A | 15.485 | 51.948 | 13.181 | 0.60 |
| 1667 OT | WAT 211 | A | 9.829 | 38.538 | 6.111 | 0.71 |
| 1668 OT | WAT 212 | A | 11.550 | 40.302 | 3.050 | 0.58 |
| 1669 OT | WAT 213 | A | 42.134 | 46.885 | 5.506 | 0.73 |
| 1670 OT | WAT 214 | A | 37.738 | 52.318 | -0.352 | 0.72 |
| 1671 OT | WAT 215 | A | 40.582 | 52.333 | -4.324 | 0.66 |
| 1672 OT | WAT 216 | A | 22.375 | 54.496 | 15.975 | 0.63 |
| 1673 OT | WAT 217 | A | 49.983 | 39.399 | 2.310 | 0.69 |
| 1674 OT | WAT 218 | A | 5.369 | 58.756 | 12.045 | 0.61 |
| 1675 OT | WAT 219 | A | 0.867 | 40.439 | 5.311 | 0.67 |
| 1676 OT | WAT 220 | A | 25.522 | 37.902 | -0.824 | 0.80 |
| 1677 OT | WAT 221 | A | 12.228 | 59.495 | 7.513 | 0.81 |
| 1678 OT | WAT 222 | A | 10.798 | 47.556 | 11.898 | 0.67 |
| 1679 OT | WAT 223 | A | 0.494 | 40.963 | 0.254 | 0.75 |
| 1680 OT | WAT 224 | A | 33.591 | 41.614 | -1.644 | 0.50 |
| 1681 OT | WAT 225 | A | 24.730 | 59.387 | 8.279 | 0.74 |
| 1682 OT | WAT 226 | A | 17.020 | 38.835 | 3.348 | 0.73 |
| 1683 OT | WAT 227 | A | 34.395 | 49.780 | 3.674 | 0.61 |
| 1684 OT | WAT 228 | A | 6.972 | 43.390 | -2.094 | 0.59 |
| 1685 OT | WAT 229 | A | 25.493 | 43.453 | 12.008 | 0.68 |
| 1686 OT | WAT 230 | A | 31.349 | 49.756 | -3.421 | 0.70 |
| 1687 OT | WAT 231 | A | 2.519 | 49.133 | -4.219 | 0.80 |
| 1688 OT | WAT 232 | A | 24.405 | 52.256 | 3.441 | 0.61 |
| 1689 OT | WAT 233 | A | -0.363 | 65.457 | 3.148 | 0.79 |
| 1690 OT | WAT 201 | B | 23.742 | 49.909 | 2.695 | 0.57 |
| 1691 OT | WAT 202 | B | 31.349 | 30.309 | 3.269 | 0.77 |
| 1692 OT | WAT 203 | B | 20.489 | 59.281 | 10.715 | 0.74 |
| 1693 OT | WAT 204 | B | 43.335 | 17.483 | 4.416 | 0.83 |
| 1694 OT | WAT 205 | B | 40.901 | 15.082 | 2.480 | 0.75 |
| 1695 OT | WAT 206 | B | 39.817 | 16.063 | -2.104 | 0.60 |
| 1696 OT | WAT 207 | B | 19.941 | 40.558 | -3.436 | 0.76 |
| 1697 OT | WAT 208 | B | 12.864 | 44.291 | -2.732 | 0.58 |
| 1698 OT | WAT 209 | B | 21.524 | 50.187 | 4.779 | 0.52 |
| 1699 OT | WAT 210 | B | 37.246 | 39.384 | -13.181 | 0.60 |
| 1700 OT | WAT 211 | B | 28.460 | 27.781 | -6.111 | 0.71 |
| 1701 OT | WAT 212 | B | 29.127 | 30.154 | -3.050 | 0.58 |
| 1702 OT | WAT 213 | B | 19.536 | 59.931 | -5.506 | 0.73 |
| 1703 OT | WAT 214 | B | 26.439 | 58.841 | 0.352 | 0.72 |
| 1704 OT | WAT 215 | B | 25.030 | 61.311 | 4.324 | 0.66 |
| 1705 OT | WAT 216 | B | 36.007 | 46.625 | -15.975 | 0.63 |
| 1706 OT | WAT 217 | B | 9.129 | 62.986 | -2.310 | 0.69 |
| 1707 OT | WAT 218 | B | 48.199 | 34.028 | -12.045 | 0.61 |
| 1708 OT | WAT 219 | B | 34.587 | 20.970 | -5.311 | 0.67 |
| 1709 OT | WAT 220 | B | 20.063 | 41.054 | 0.824 | 0.80 |
| 1710 OT | WAT 221 | B | 45.410 | 40.337 | -7.513 | 0.81 |

Fig. 16.38

| ATOM | RESIDUE | CHAIN | X | Y | Z | $\delta$ |
|---|---|---|---|---|---|---|
| 1711 OT | WAT 222 | B | 35.785 | 33.129 | -11.898 | 0.67 |
| 1712 OT | WAT 223 | B | 35.228 | 20.909 | -0.254 | 0.75 |
| 1713 OT | WAT 224 | B | 19.243 | 49.897 | 1.644 | 0.50 |
| 1714 OT | WAT 225 | B | 39.065 | 51.110 | -8.279 | 0.74 |
| 1715 OT | WAT 226 | B | 25.122 | 34.157 | -3.348 | 0.73 |
| 1716 OT | WAT 227 | B | 25.913 | 54.677 | -3.674 | 0.61 |
| 1717 OT | WAT 228 | B | 34.091 | 27.733 | 2.094 | 0.59 |
| 1718 OT | WAT 229 | B | 24.885 | 43.804 | -12.008 | 0.68 |
| 1719 OT | WAT 230 | B | 27.415 | 52.027 | 3.421 | 0.70 |
| 1720 OT | WAT 231 | B | 41.291 | 26.748 | 4.219 | 0.80 |
| 1721 OT | WAT 232 | B | 33.052 | 47.263 | -3.441 | 0.61 |
| 1722 OT | WAT 233 | B | 56.869 | 32.414 | -3.148 | 0.79 |

Fig. 16.39

SEQUENCE LISTING (1) GENERAL INFORMATION:

(iii) NUMBER OF SEQUENCES: 8

(2) INFORMATION FOR SEQ ID NO:1:

(i) SEQUENCE CHARACTERISTICS:
      (A) LENGTH: 102 amino acids
      (B) TYPE: amino acid
      (C) STRANDEDNESS: single
      (D) TOPOLOGY: linear (ii) MOLECULE TYPE: protein (ix) FEATURE:
      (A) NAME/KEY: Protein
      (B) LOCATION: 1..102
      (D) OTHER INFORMATION: /product= "hOP-1"

(xi) SEQUENCE DESCRIPTION: SEQ ID NO:1:

```
Cys Lys Lys His Glu Leu Tyr Val Ser Phe Arg Asp Leu Gly Trp Gln
1               5                   10                  15

Asp Trp Ile Ile Ala Pro Glu Gly Tyr Ala Ala Tyr Tyr Cys Glu Gly
                20                  25                  30

Glu Cys Ala Phe Pro Leu Asn Ser Tyr Met Asn Ala Thr Asn His Ala
            35                  40                  45

Ile Val Gln Thr Leu Val His Phe Ile Asn Pro Glu Thr Val Pro Lys
        50                  55                  60

Pro Cys Cys Ala Pro Thr Gln Leu Asn Ala Ile Ser Val Leu Tyr Phe
65                  70                  75                  80

Asp Asp Ser Ser Asn Val Ile Leu Lys Lys Tyr Arg Asn Met Val Val
                85                  90                  95

Arg Ala Cys Gly Cys His
            100
```

(2) INFORMATION FOR SEQ ID NO:2:

(i) SEQUENCE CHARACTERISTICS:
      (A) LENGTH: 15 amino acids
      (B) TYPE: amino acid
      (C) STRANDEDNESS: single
      (D) TOPOLOGY: linear (ii) MOLECULE TYPE: peptide (ix) FEATURE:
      (A) NAME/KEY: Peptide (B) LOCATION: 1..15
            (D) OTHER INFORMATION: /product= "PEPTIDE F1-2"

(xi) SEQUENCE DESCRIPTION: SEQ ID NO:2:

Cys Phe Arg Asp Leu Gly Trp Gln Asp Trp Ile Ile Ala Pro Cys
1               5                   10                  15

(2) INFORMATION FOR SEQ ID NO:3:

(i) SEQUENCE CHARACTERISTICS:
            (A) LENGTH: 32 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..32
            (D) OTHER INFORMATION: /product= "PEPTIDE H-1"

(xi) SEQUENCE DESCRIPTION: SEQ ID NO:3:

Cys Ala Phe Pro Leu Asn Ser Tyr Met Asn Ala Thr Asn His Ala Ile
1               5                   10                  15

Val Gln Thr Leu Val His Phe Ile Asn Pro Glu Thr Val Pro Lys Cys
            20                  25                  30

(2) INFORMATION FOR SEQ ID NO:4:

(i) SEQUENCE CHARACTERISTICS:
            (A) LENGTH: 13 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..13
            (D) OTHER INFORMATION: /product= "PEPTIDE H-N2"

(xi) SEQUENCE DESCRIPTION: SEQ ID NO:4:

Cys Leu Asn Ser Tyr Met Asn Ala Thr Asn His Ala Cys
1               5                   10

(2) INFORMATION FOR SEQ ID NO:5:

(i) SEQUENCE CHARACTERISTICS:
            (A) LENGTH: 11 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..11
            (D) OTHER INFORMATION: /product= "PEPTIDE H-C2"

(xi) SEQUENCE DESCRIPTION: SEQ ID NO:5:

Cys Cys Phe Ile Asn Pro Glu Thr Val Cys Cys
1               5                   10

(2) INFORMATION FOR SEQ ID NO:6:

(i) SEQUENCE CHARACTERISTICS:
            (A) LENGTH: 11 amino acids

```
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..11
            (D) OTHER INFORMATION: /product= "PEPTIDE F2-2"

(xi) SEQUENCE DESCRIPTION: SEQ ID NO:6:

Cys Tyr Phe Asp Asp Ser Ser Asn Val Ile Cys
1               5                  10

(2) INFORMATION FOR SEQ ID NO:7:

(i) SEQUENCE CHARACTERISTICS:
            (A) LENGTH: 16 amino acids
            (B) TYPE: amino acid
            (C) STRANDEDNESS: single
            (D) TOPOLOGY: linear (ii) MOLECULE TYPE: peptide (ix) FEATURE:
            (A) NAME/KEY: Peptide
            (B) LOCATION: 1..16
            (D) OTHER INFORMATION: /product= "PEPTIDE F2-3"

(xi) SEQUENCE DESCRIPTION: SEQ ID NO:7:

Cys Tyr Phe Asp Asp Ser Ser Asn Val Ile Cys Lys Lys Tyr Arg Ser
1               5                  10                  15

(2) INFORMATION FOR SEQ ID NO:8:

(i) SEQUENCE CHARACTERISTICS:
            (A) LENGTH: 98 amino acids
            (B) TYPE: amino acid
            (C) STRANDEDNESS: single
            (D) TOPOLOGY: linear (ii) MOLECULE TYPE: protein (ix) FEATURE:
            (A) NAME/KEY: Protein
            (B) LOCATION: 1..98
            (D) OTHER INFORMATION: /product= "TGFB2"

(xi) SEQUENCE DESCRIPTION: SEQ ID NO:8:

Cys Cys Leu Arg Pro Leu Tyr Ile Asp Phe Lys Arg Asp Leu Gly Trp
1               5                  10                  15

Lys Trp Ile His Glu Pro Lys Gly Tyr Asn Ala Asn Phe Cys Ala Gly
            20                  25                  30

Ala Cys Pro Tyr Leu Trp Ser Ser Asp Thr Gln His Ser Arg Val Leu
        35                  40                  45

Ser Leu Tyr Asn Thr Ile Asn Pro Glu Ala Ser Ala Ser Pro Cys Cys
    50                  55                  60

Val Ser Gln Asp Leu Glu Pro Leu Thr Ile Leu Tyr Tyr Ile Gly Lys
65                  70                  75                  80

Thr Pro Lys Ile Glu Gln Leu Ser Asn Met Ile Val Lys Ser Cys Lys
                85                  90                  95

Cys Ser
```

COMPUTER SYSTEM AND METHODS FOR PRODUCING MORPHOGEN ANALOGS OF HUMAN OP-1

RELATED APPLICATIONS

This application is a continuation-in-part of application U.S. Ser. No. 08/589,552, filed Jan. 22, 1996 now abandoned, the disclosure of which is incorporated herein by reference.

FIELD OF THE INVENTION

The present invention relates generally to methods and compositions for designing, identifying, and producing compounds useful as tissue morphogenic protein analogs. More specifically, the invention relates to structure-based methods and compositions useful in designing, identifying, and producing molecules which act as functional mimetics of the tissue morphogenic protein osteogenic protein-1 (OP-1).

BACKGROUND OF THE INVENTION

Cell differentiation is the central characteristic of tissue morphogenesis which initiates during embryogenesis, and continues to various degrees throughout the life of an organism in adult tissue repair and regeneration mechanisms. The degree of morphogenesis in adult tissue varies among different tissues and is related, among other things, to the degree of cell turnover in a given tissue.

The cellular and molecular events which govern the stimulus for differentiation of cells is an area of intensive research. In the medical and veterinary fields, it is anticipated that discovery of the factor or factors which control cell differentiation and tissue morphogenesis will advance significantly the ability to repair and regenerate diseased or damaged mammalian tissues and organs. Particularly useful areas for human and veterinary therapeutics include reconstructive surgery, the treatment of tissue degenerative diseases including, for example, arthritis, emphysema, osteoporosis, cardiomyopathy, cirrhosis, degenerative nerve diseases, inflammatory diseases, and cancer, and in the regeneration of tissues, organs and limbs. In this and related applications, the terms "morphogenetic" and "morphogenic" are used interchangeably.

A number of different factors have been isolated in recent years which appear to play a role in cell differentiation. Recently, a distinct subfamily of the "superfamily" of structurally related proteins referred to in the art as the "transforming growth factor- β (TGF-β) superfamily of proteins" have been identified as true tissue morphogens.

The members of this distinct "subfamily" of true tissue morphogenic proteins share substantial amino acid sequence homology within their morphogenetically active C-terminal domains (at least 50% identity in the C-terminal 102 amino acid sequence), including a conserved six or seven cysteine skeleton, and share the in vivo activity of inducing tissue-specific morphogenesis in a variety of organs and tissues. The proteins apparently contact and interact with progenitor cells e.g., by binding suitable cell surface molecules, predisposing or otherwise stimulating the cells to proliferate and differentiate in a morphogenetically permissive environment. These morphogenic proteins are capable of inducing the developmental cascade of cellular and molecular events that culminate in the formation of new organ-specific tissue, including any vascularization, connective tissue formation, and nerve innervation as required by the naturally occurring tissue. The proteins have been shown to induce morphogenesis of both bone cartilage and bone, as well as periodontal tissues, dentin, liver, and neural tissue, including retinal tissue.

True tissue morphogenic proteins identified to date include proteins originally identified as bone inductive proteins. These include OP-1, (osteogenic protein-i, also referred to in related applications as "OP1"), its Drosophila homolog, 60A, with which it shares 69% identity in the C-terminal "seven cysteine" domain, and the related proteins OP-2 (also referred to in related applications as "OP2") and OP-3, both of which share approximately 65–75% identity with OP-1 in the C-terminal seven cysteine domain, as well as BMP5, BMP6 and its murine homolog, Vgr-1, all of which share greater than 85% identity with OP-1 in the C-terminal seven cysteine domain, and the BMP6 Xenopus homolog, Vgl, which shares approximately 57% identity with OP-1 in the C-terminal seven cysteine domain. Other bone inductive proteins include the CBMP2 proteins (also referred to in the art as BMP2 and BMP4) and their Drosophila homolog, DPP. Another tissue morphogenic protein is GDF-1 (from mouse). See, for example, PCT documents US92/01968 and US92/07358, the disclosures of which are incorporated herein by reference. Members of the BMP/OP subfamily and the amino acid sequence identities (expressed as percentages) between selected members of the TGF-β superfamily are shown in FIG. 6.

As stated above, these true tissue morphogenic proteins are recognized in the art as a distinct subfamily of proteins different from other members of the TGF-β superfamily in that they share a high degree of sequence identity in the C-terminal domain and in that the true tissue morphogenic proteins are able to induce, on their own, the full cascade of events that result in formation of functional tissue rather than merely inducing formation of fibrotic (scar) tissue. Specifically, members of the family of morphogenic proteins are capable of all of the following in a morphogenetically permissive environment: stimulating cell proliferation and cell differentiation, and supporting the growth and maintenance of differentiated cells. The morphogenic proteins apparently also may act as endocrine, paracrine or autocrine factors.

The morphogenic proteins are capable of significant species "crosstalk." That is, xenogenic (foreign species) homologs of these proteins can substitute for one another in functional activity. For example, dpp and 60A, two Drosophila proteins, can substitute for their mammalian homologs, BMP2/4 and OP-1, respectively, and induce endochondral bone formation at a non-bony site in a standard rat bone formation assay. Similarly, BMP2 has been shown to rescue a dpp⁻ mutation in Drosophila. In their native form, however, the proteins appear to be tissue-specific, each protein typically being expressed in or provided to one or only a few tissues or, alternatively, expressed only at particular times during development. For example, GDF-1 appears to be expressed primarily in neural tissue, while OP-2 appears to be expressed at relatively high levels in early (e.g., 8-day) mouse embryos. The endogenous morphogens may be synthesized by the cells on which they act, by neighboring cells, or by cells of a distant tissue, the secreted protein being transported to the cells to be acted on.

A particularly potent tissue morphogenic protein is OP-1. This protein, and its xenogenic homologs, are expressed in a number of tissues, primarily in tissues of urogenital origin, as well as in bone, mammary and salivary gland tissue, reproductive tissues, and gastrointestinal tract tissue. It is expressed also in different tissues during embryogenesis, its presence coincident with the onset of morphogenesis of that tissue.

The morphogenic protein signal transduction across a cell membrane appears to occur as a result of specific binding interaction with one or more cell surface receptors. Recent studies on cell surface receptor binding of various members of the TGF-β protein superfamily suggests that the ligands mediate their activity by interaction with two different receptors, referred to as Type I and Type II receptors to form a hetero-complex. A cell surface bound beta-glycan also may enhance the binding interaction. The Type I and Type II receptors are both serine/threonine kinases, and share similar structures: an intracellular domain that consists essentially of the kinase, a short, extended hydrophobic sequence sufficient to span the membrane one time, and an extracellular domain characterized by a high concentration of conserved cysteines.

Morphogenic proteins are disulfide-linked dimers which are expressed as large precursor polypeptide chains containing a hydrophobic signal sequence, a long and relatively poorly conserved N-terminal pro region of several hundred amino acids, a cleavage site and a mature domain comprising an N-terminal region which varies among the family members and a more highly conserved C-terminal region. The C-terminal region, which is present in the processed mature proteins of all known morphogen family members, contains approximately 100 amino acids with a characteristic motif having a conserved six or seven cysteine skeleton. Each of the morphogenic proteins isolated to date are dimeric structures wherein the monomer subunits are held together by non-covalent interactions or by one or more disulfide bonds. The morphogenic proteins are active as dimeric proteins but are inactive as individual monomer subunits.

As a result of their biological activities, significant effort has been directed toward the development of morphogen-based therapeutics for treating injured or diseased mammalian tissue, including, for example, therapeutic compositions for inducing regenerative healing of bone defects such as fractures, as well as therapeutic compositions for preserving or restoring healthy metabolic properties in diseased bone tissue, e.g., osteopenic bone tissue. Complete descriptions of efforts to develop and characterize morphogen-based therapeutics for non-chondrogenic tissue applications in mammals, particularly humans, are set forth, for example, in: EP 0575,555; WO93/04692; WO93/0575 1; WO94/06399; WO94/03200; WO94/06449; WO94/10203; and WO94/06420, the disclosures of each of which are incorporated herein by reference.

Certain difficulties may be experienced upon administration of naturally isolated or recombinantly produced morphogenic proteins to a mammal. These difficulties may include, for example, loss of morphogenic activity due to disassociation of the biologically active morphogen dimer into its inactive monomer subunits, and/or handling problems due to low solubility under physiological conditions.

Accordingly, a need remains for the identification of morphogen analogs, which mimic or enhance the physiological effects of a morphogenic protein, for example OP-1. The analogs may be modified, morphogenically active hOP-1 protein dimers, or fragments or truncated analogs thereof, peptides or small organic molecules. Preferably the analogs have enhanced therapeutic value, for example, by being more stable and/or more soluble under physiological conditions than naturally occurring hOP-1, or, for example, by having enhanced tissue targeting specificity, enhanced biodistribution or a reduced clearance rate in the body.

It is an object of the present invention to provide a database defining the atomic co-ordinates of the three-dimensional structure of mature hOP-1, all or a portion of which can be used as part of a computer system for designing and/or identifying a functional analog of hOP-1. Another object is to provide means for designing and/or identifying a molecule having enhanced solubility and/or stability under physiological conditions as compared with hOP-1 and which is capable of mimicking or enhancing the biological activity of hOP-1 in a mammal. Another object of the invention is to provide a therapeutic composition comprising an analog designed and/or identified, and produced by the methods of the invention, and suitable for administration to a mammal in need thereof, such as a mammal afflicted with a metabolic bone disease, e.g., a disease characterized by osteopenia. Another object of the invention is to provide methods and compositions useful for designing and/or identifying, and producing an hOP-1 antagonist capable of, for example, competing with hOP-1 for receptor binding, but incapable of inducing a receptor-mediated downstream biological effect.

These and other objects and features of the invention will be apparent from the description, drawings, and claims which follow.

SUMMARY OF THE INVENTION

The present invention is based, in part, upon the X-ray crystallographic determination of the three-dimensional structure of mature, dimeric human osteogenic protein-1 (hOP-1). The three-dimensional structure of hOP-1 has been resolved to 2.3 Å. Provided herein are two sets of atomic X-ray crystallographic co-ordinates for hOP-1, one set defining a hOP-1 structure resolved to a resolution of 2.8 Å, and the other set defining a hOP-1 structure resolved to a resolution of 2.3 Å. With this disclosure, the skilled artisan is provided with sets of atomic co-ordinates for use in conventional computer aided design (CAD) methodologies to identify or design protein or peptide analogs of OP-1, or alternatively, to identify or design small organic molecules that functionally mimic OP-1.

In one aspect, the invention provides a computer system comprising a memory and a processor in electrical communication with the memory. The memory has disposed therein, atomic X-ray crystallographic co-ordinates which together define at least a portion of the three-dimensional structure of hOP-1. In a preferred embodiment, the atomic co-ordinates are defined by either a portion or all of the atomic co-ordinates set forth in FIGS. 15.1–15.7 or FIGS. 16\1–16\39.

The processor, in electrical communication with the memory, comprises a process which generates a molecular model having a three-dimensional shape representative of at least a portion of human OP-1. In a preferred embodiment, the processor is capable of producing a molecular model having, in addition to the three-dimensional shape, a solvent accessible surface representative of at least a portion of human OP-1.

As used herein, the term "computer system" is understood to mean any general or special purpose system which includes a processor in electrical communication with both a memory and at least one input/output device, such as a terminal. Such a system may include, but is not limited to, personal computers, workstations or mainframes. The processor may be a general purpose processor or microprocessor or a specialized processor executing programs located in RAM memory. The programs may be placed in RAM from a storage device, such as a disk or preprogrammed ROM memory. The RAM memory in one embodiment is used both for data storage and program execution. The term computer system also embraces systems where the processor and memory reside in different physical entities but which are in electrical communication by means of a network.

In the present invention, the processor executes a modeling program which accesses data representative of the X-ray crystallographic co-ordinates of hOP-1 thereby to construct a three-dimensional model of the molecule. In addition, the processor also can execute another program, a solvent accessible surface program, which uses the three-dimensional model of hOP-1 to construct a solvent accessible surface of at least a portion of the hOP-1 molecule and optionally calculate the solvent accessible areas of atoms. In one embodiment the solvent accessible surface program and the modeling program are the same program. In another embodiment, the modeling program and the solvent accessible surface program are different programs. In such an embodiment the modeling program may either store the three-dimensional model of hOP-1 in a region of memory accessible both to it and to the solvent accessible surface program, or the three-dimensional model may be written to external storage, such as a disk, CD ROM, or magnetic tape for later access by the solvent accessible surface program.

The memory may have stored therein the entire set of X-ray crystallographic co-ordinates which define mature biologically active human OP-1, or may comprise a subset of such co-ordinates including, for example, one or more of: a finger 1 region; a finger 2 region; and a heel region. The protein structures which correspond to the finger and heel regions are described in detail below.

In another preferred embodiment, the processor also is capable of identifying a morphogen analog, or a morphogen antagonist for example, a protein, peptide or small organic molecule, having a three-dimensional shape and preferably, in addition, a solvent accessible surface corresponding to at least a portion of human OP-1 and competent to mimic an OP-1 specific activity.

As used herein, with respect to OP-1 (or related morphogens), or with respect to a region of OP-1, the phrase "at least a portion of the three-dimensional structure of" or "at least a portion of" is understood to mean a portion of the three-dimensional surface structure of the morphogen, or region of the morphogen, including charge distribution and hydrophilicity/hydrophobicity characteristics, formed by at least three, more preferably at least three to ten, and most preferably at least ten contiguous amino acid residues of the OP-1 monomer or dimer. The contiguous residues forming such a portion may be residues which form a contiguous portion of the primary structure of the OP-1 molecule, residues which form a contiguous portion of the three-dimensional surface of the OP-1 monomer, residues which form a contiguous portion of the three-dimensional surface of the OP-1 dimer, or a combination thereof. Thus, the residues forming a portion of the three-dimensional structure of OP-1 need not be contiguous in the primary sequence of the morphogen but, rather, must form a contiguous portion of the surface of the morphogen monomer or dimer. In particular, such residues may be non-contiguous in the primary structure of a single morphogen monomer or may comprise residues from different monomers in the dimeric form of the morphogen. As used herein, the residues forming "a portion of the three-dimensional structure of" a morphogen, or "a portion of" a morphogen, form a contiguous three-dimensional surface in which each atom or functional group forming the portion of the surface is separated from the nearest atom or functional group forming the portion of the surface by no more than 40 Å, preferably by no more than 20 Å, more preferably by no more than 5–10 Å, and most preferably by no more than 1–5 Å.

As used herein the term "X-ray crystallographic co-ordinates" refers to a series of mathematical co-ordinates (represented as "X", "Y" and "Z" values) that relate to the spatial distribution of reflections produced by the diffraction of a monochromatic beam of X-rays by atoms of an hOP-1 molecule in crystal form. The diffraction data are used to generate electron density maps of the repeating units of a crystal, and the resulting electron density maps are used to define the positions of individual atoms within the unit cell of the crystal.

As will be apparent to those of ordinary skill in the art, the hOP-1 structure presented herein is independent of its orientation, and that the atomic co-ordinates listed in FIGS. 15.1–15.37 and FIGS. 16\1–16\39 merely represent one possible orientation of the hOP-1 structure. It is apparent, therefore, that the atomic co-ordinates listed in FIGS. 15.1–15.37 and FIGS. 16\1–16\39, may be mathematically rotated, translated, scaled, or a combination thereof, without changing the relative positions of atoms or features of the hOP-1 structure. Such mathematical manipulations are intended to be embraced herein. Furthermore, it will be apparent to the skilled artisan that the X-ray atomic co-ordinates defined herein have some degree of uncertainty in location (see, for example, column "δ"in FIG. 16 which shows the thermal uncertainty in location of each atom, as expressed in Å). Accordingly, for purposes of this invention, a preselected protein or peptide having the same amino acid sequence as at least a portion of hOP-1 is considered to have the same structure as the corresponding portion of hOP-1, when a set of atomic co-ordinates defining backbone Cα atoms of the preselected protein or peptide can be superimposed onto the corresponding Cα atoms for hOP-1 (as listed in FIGS. 16\1–16\39) to a root mean square deviation of preferably less than about 1.5 Å, and most preferably less than about 0.75 Å.

As used herein, the term "morphogen analog", is understood to mean any molecule capable of mimicking OP-1's receptor binding activity and/or and inducing a receptor mediated downstream biological effect characteristic of a morphogenic protein. Inducing alkaline phosphatase activity is a characteristic biological effect. The analog may be a protein, peptide, or non-peptidyl based organic molecule. Accordingly, the term morphogen analog embraces any substance having such OP-1 like activity, regardless of the chemical or biochemical nature thereof. The present morphogen analog can be a simple or complex substance produced by a living system or through chemical or biochemical synthetic techniques. It can be a large molecule, e.g., a modified hOP-1 dimer produced by recombinant DNA methodologies, or a small molecule, e.g., an organic molecule prepared de novo according to the principles of rational drug design. It can be a substance which is a mutein (or mutant protein) of hOP-1, a substance that structurally resembles a solvent-exposed surface epitope of hOP-1 and binds an OP-1 specific receptor, or a substance that otherwise stimulates an OP-1 specific receptor displayed on the surface of an OP-1 responsive cell.

As used herein, the terms "OP-1 or OP-1-like biological activity" are understood to mean any biological activities known to be induced or enhanced by OP-1. OP-1 and OP-1-like biological activities include, but are not limited to, stimulating proliferation of progenitor cells; stimulating differentiation of progenitor cells; stimulating proliferation of differentiated cells; and supporting growth and maintenance of differentiated cells. The term "progenitor cells" includes uncommitted cells, preferably of mammalian origin that are competent to differentiate into one or more specific types of differentiated cells, depending on their genomic repertoire and the tissue specificity of the permissive environment where morphogenesis is induced. Specifically, with regard to bone, cartilage, nerve, and liver tissue, the OP-1 stimulated morphogenic cascade culminates in the formation of new or regenerative differentiated tissue appropriate to the selected local environment. OP-1 mediated morphogenesis, therefore, differs significantly from simple reparative healing processes in which scar tissue (e.g., fibrous connective tissue) is formed and fills a lesion or other defect in differentiated functional tissue.

As used herein a "morphogen antagonist" is a molecule competent to mimic OP-1 receptor binding activity but which cannot induce a receptor-mediated downstream effect.

In yet another preferred embodiment, the processor is capable of identifying amino acids defined by the co-ordinates, which upon site-directed modification, either by chemical modification or amino acid substitution, enhance the solubility and/or stability of human OP-1.

In a related aspect, the invention provides a method of producing a morphogen analog that mimics or enhances an OP-1 or OP-1-like biological activity. The method comprises the steps of: (a) providing a molecular model defining a three-dimensional shape representative of at least a portion of human OP-1, (b) identifying a compound having a three-dimensional shape corresponding to the three-dimensional shape representative of at least the portion of human OP-1; and (c) producing the compound identified in step (b). The method can comprise the additional step of testing the compound in a biological system to determine whether the resultant candidate compound mimics or agonizes the biological activity of OP-1. It is contemplated that, in the aforementioned method, step (a) and/or (b) may be performed by means of an electronic processor using commercially available software packages.

It is contemplated that, upon determination of whether the candidate compound modulates OP-1 activity, the candidate compound can be iteratively improved using conventional CAD and/or rational drug design methodologies, well known and thoroughly documented in the art. Furthermore, it is contemplated that the resultant compound identified thus far, may be produced in a commercially useful quantity for administration into a mammal.

In another embodiment, the morphogen analog is created using atomic co-ordinates set forth in either FIGS. 15.1–15.37 or FIGS. 16\1–16\39. By reviewing the atomic co-ordinates set forth in FIGS. 15.1–15.37 and FIGS. 16\1–16\39, the skilled artisan can observe the three-dimensional structure of particular amino acid sequences located in situ within the three-dimensional structure of hOP-1. Preferred amino acid sequences are defined by one or more of the peptides selected from the group consisting of: H1, H-n2, H-c2, F1-2, F2-2 and F2-3, as discussed hereinbelow. The peptides provide templates which can be used in the production of more effective morphogen analogs. In a preferred embodiment, the Cα atoms of amino acid residues in the morphogen analog are located within 6 Å, preferably within 3 Å, and most preferably within 2 Å of the corresponding Co: atom as defined by the respective atomic co-ordinates in FIGS. 15.1–15.37 or FIGS. 16\1–16\39. In another preferred embodiment, the Cα atoms of amino acid residues in the morphogen analog are located within 6 Å, preferably within 3 Å, and most preferably within 2 Å of the corresponding Cα atoms of at least three amino acids in the peptide sequences H1, H-n2, H-c2, F1-2, F2-2 and F23, wherein each of the Cα atoms in the peptides are defined by the respective atomic co-ordinates set forth in FIGS. 15.1–15.37 or FIGS. 16\1–16\39.

In another embodiment, the invention provides morphogen analogs having greater solubility and/or stability in aqueous buffers than native dimeric hOP-1. In yet another embodiment, the invention provides a morphogen analog which is a modified form of dimeric hOP-1, in which the modification eliminates an epitope or region on OP-1 normally recognized by an antibody or by a cellular scavenging protein for clearing OP-1 from the body.

In another embodiment, the invention provides means for creating an analog with altered receptor binding characteristics. For example, provided with the structure, charge distribution, and solvent accessible surface information pertaining to the putative receptor binding site, one can alter or modify receptor binding specificity and avidity. In one embodiment, amino acid replacements in this region are made with reference to the corresponding amino acids of other known morphogens, disclosed for example, in WO94/06449 or WO93/05751.

After having determined the three-dimensional structure of human OP-1, a skilled artisan, in possession of the atomic co-ordinates defining the OP-1 structure is hereby enabled to use conventional CAD and/or rational drug design methodologies to identify or design protein or peptide analogs, or other small organic molecules which, after having been produced using conventional chemistries and methodologies, can be tested either in vitro or in vivo to assess whether they mimic or enhance the biological activity of human OP-1.

The foregoing and other objects, features and advantages of the present invention will be made more apparent from the following detailed description of preferred embodiments of the invention.

BRIEF DESCRIPTION OF THE DRAWINGS

The file of this patent contains at least one drawing executed in color. Copies of this patent with color drawing (s) will be provided by the Patent and Trademark Office upon request and payment of the necessary fee.

The objects and features of the invention may be better understood by reference to the drawings described below, wherein like referenced features identify common features in corresponding figures.

Val 132-His 139 (β8); and the amino acid residues which produce secondary structure in the heel region include: Thr 82-Ile 94(α1).

FIG. 3 is a structure-based sequence alignment of the hOP-1 and TGF-β2 finger-1, heel, and finger-2 regions. Amino acid residues in the heel regions which constitute inter-chain contacts in the dimers of hOP-1 and TGF-β2 are highlighted as white on black. Amino acid residues in the finger-1 and finger-2 regions which contact the other chain are highlighted as black on gray. In hOP-1 and TGF-β2, the amino acids located at the same residue positions constitute the inter-chain contacts.

Figure 4A:
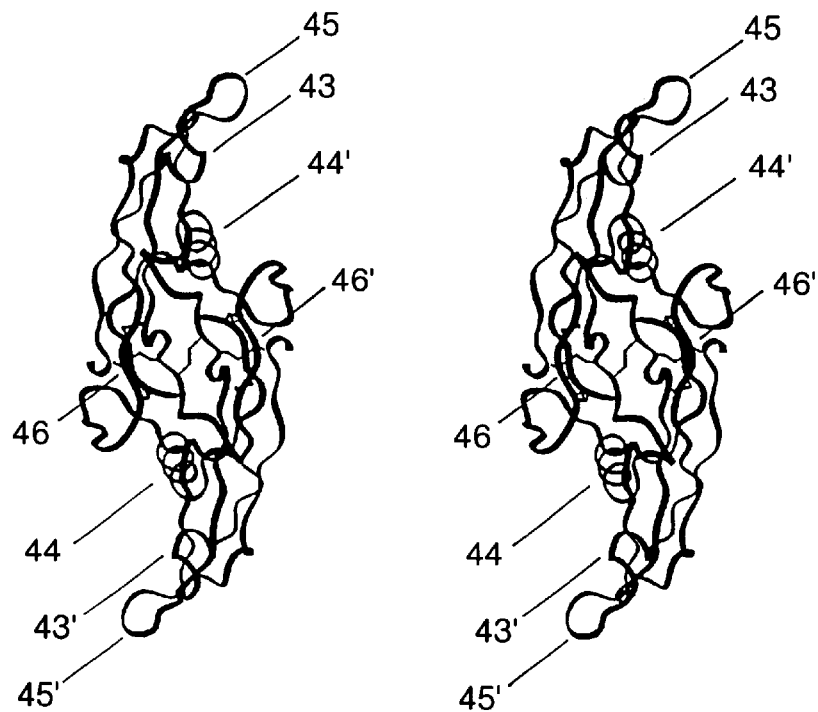
Figure 4B:
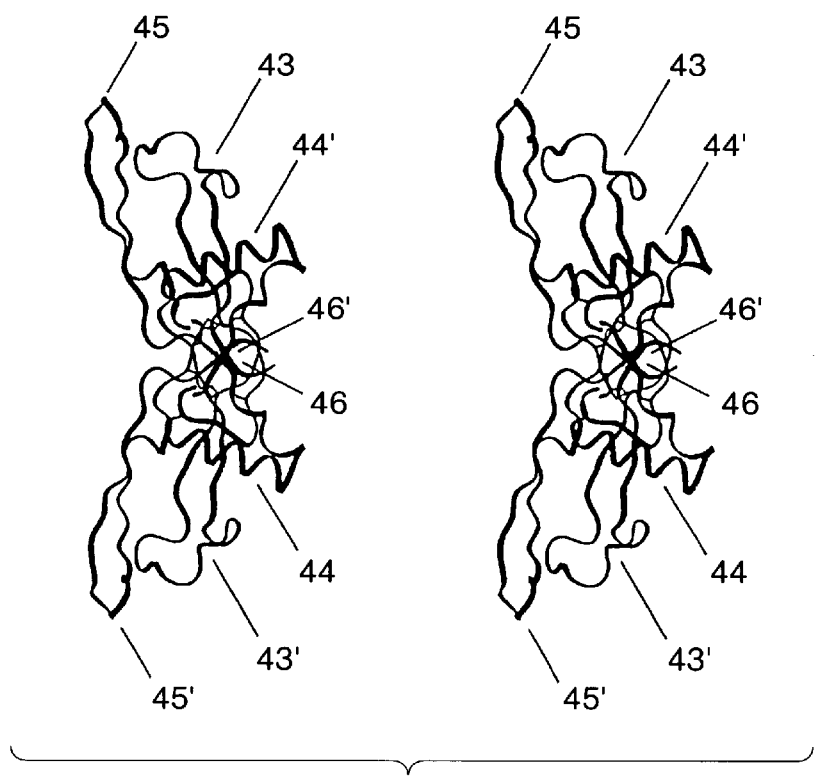

FIGS. 4A and 4B are stereo peptide backbone ribbon trace drawings illustrating the three-dimensional shape of hOP-1: A) from the "top" (down the two-fold axis of symmetry between the subunits) with the axes of the helical heel regions generally normal to the paper and the axes of each of the finger 1 and finger 2 regions generally vertical, and B) from the "side" with the two-fold axis between the subunits in the plane of the paper, with the axes of the heels generally horizontal, and the axes of the fingers generally vertical. The hOP-1 monomer has an accessible non-polar surface area of approximately 4394 Å$^2$, while that for the dimer is approximately 6831 Å$^2$ resulting in a hidden area upon dimerization of approximately 979 Å$^2$ per monomer. The reader is encouraged to view the stereo alpha carbon trace drawings in wall-eyed stereo, for example, using a standard stereo viewer device, to more readily visualize the spatial relationships of amino acids sequences in the morphogen analog design.

Figure 5A:
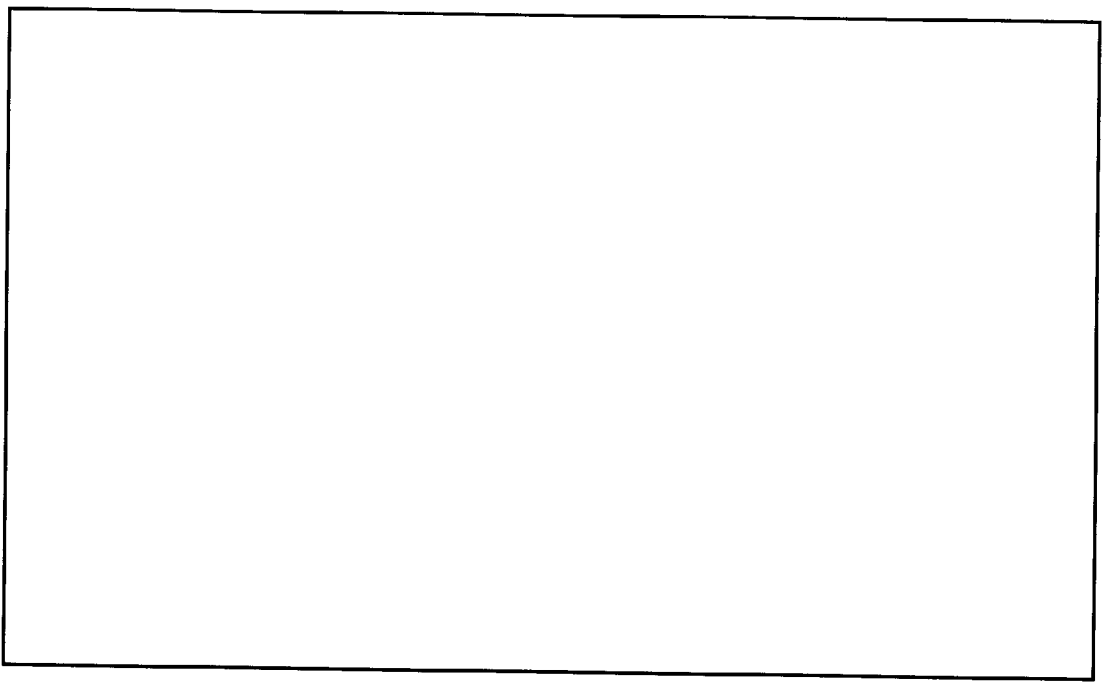

FIG. 5A is a backbone ribbon trace drawing illustrating the hOP-1 dimer comprising the two hOP-1 monomer subunits resolved to 2.8 Å. One monomer subunit is shown in green and the other monomer subunit is shown in gold. Amino acid residues disposed within the purported receptor binding domain having solvent accessible side chains are shown as atomic spheres. The tips of the finger 1 and finger 2 regions of one OP-1 monomeric subunit and a loop at the C-terminal end of the heel of the other OP-1 monomeric subunit are believed to constitute the receptor binding domain. Amino acids located at positions of variable amino acid sequence shown in white while amino acids located at more conserved positions are shown in red.

Figure 5B:
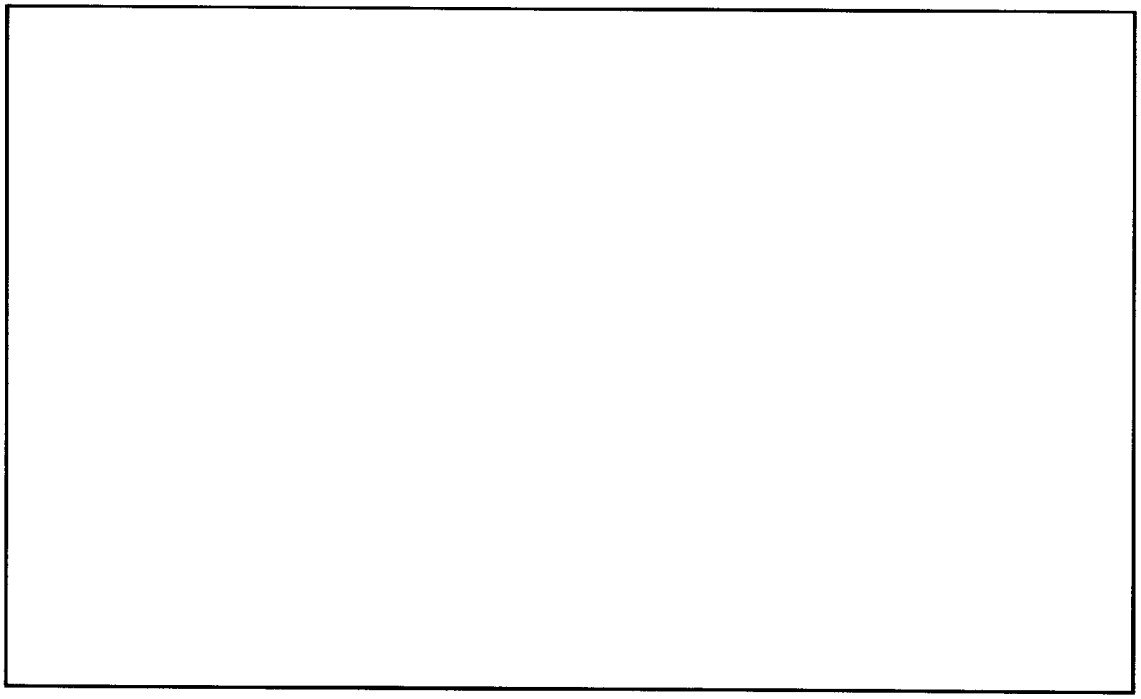
Figure 5C:
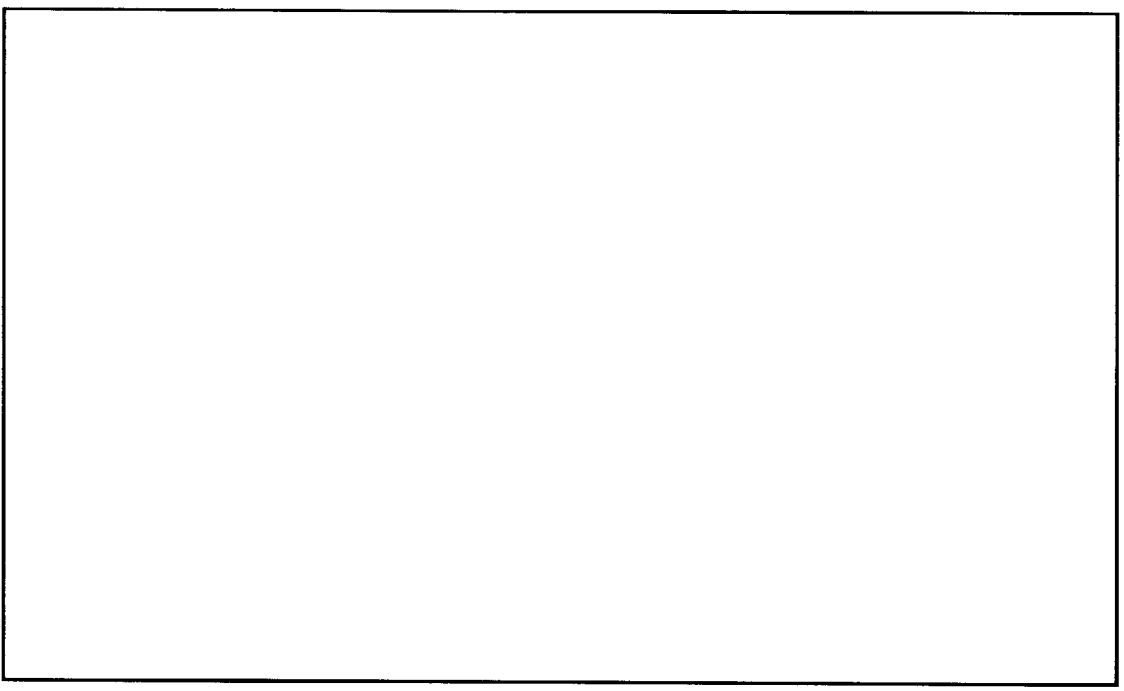

FIGS. 5B and 5C are pictures showing the respective solvent accessible surfaces of OP-1 and TGF-β2 dimers colored based on their electrostatic potential. Surface regions having an electrostatic potential of −3 kT or less are shown in red while surface regions of +3 kT or greater are shown in blue. Neutral regions are shown in green or gold to correspond to the backbone ribbons shown in 5A.

Figure 6:
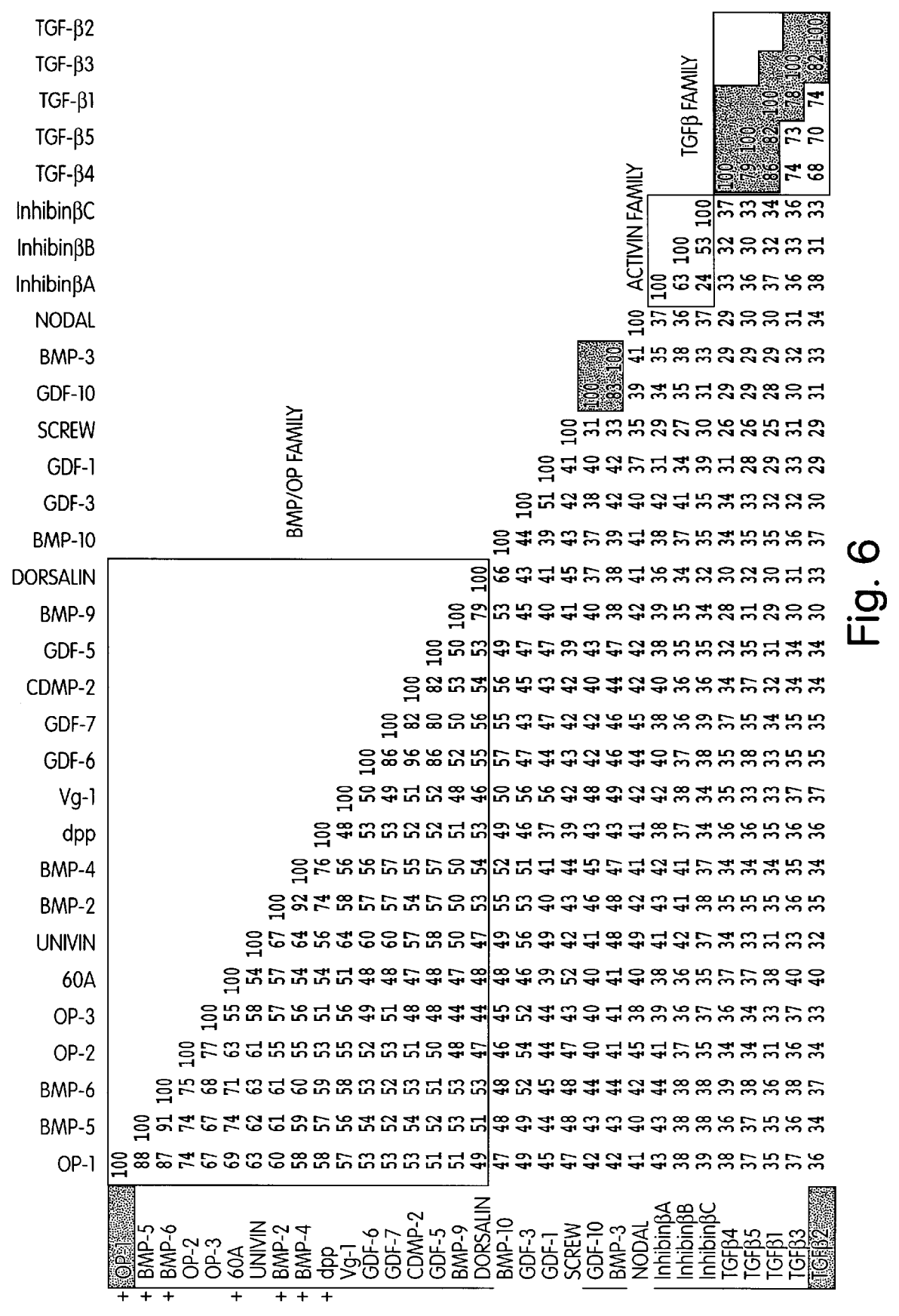

FIG. 6 is a table showing an identity matrix for the TGF-β superfamily. The matrix comprises members of the TGF-β superfamily having an amino acid sequence identity relative to OP-1 of greater than 36%. In the matrix, the TGF-β superfamily members are placed in order of decreasing amino acid identity relative to OP-1. TGF-β2 has an amino acid sequence of identity of 36% relative to OP-1 and is positioned the bottom of the matrix. Boxes enclose families of sequences having 50% or higher identity with a majority of the other members of the family; with sequences having identities of 75% or higher are shown in gray. Recombinantly expressed OP/BMP family members which have been shown to make bone are denoted by a "+" in the left margin. In the left margin, TGF-β superfamily members with three-dimensional structures determined are highlighted white on black. The sequences are referenced in Kingsley (Kingsley. (1994) *Genes and Development* 8:133–146), except for the following: (UNIVIN (Stenzel el al. (1994) *Develop. BioL* 166:149–158.), SCREW (Arora, et al. (1994) *Genes and Dev.* 8:2588–2601.), BMP-9 (Wozney, et al.(1993) PCT/WO 93/00432, SEQ. ID. NO.9), BMP-10 (Celeste el aL (1994) PCT/WO 94/26893, SEQ. ID. NO. 1), GDF-5 (Storm et al. (1994) *Nature* 368:639–643) (also called CDMP-1 (Chang et al. (1994) *J Biol. Chem.* 269: 28227–28234.), GDF-6 (Storm, et al. (1994) *Nature* 368:639–643), GDF-7 (Storm et al. (1994) *Nature* 368:639–643), CDMP-2 (Chang et al. (1994) *J Biol. Chem.* 269: 28227–28234.), OP-3 (Ozkaynak et al. (1994) PCT/WO 94/10203, SEQ. ID. NO. 1), Inhibin Be (Hotten, et al. (1995) *Bioch. Biophys. Res. Comm.* 206:608–613), and GDF-10 (Cumningham, et al. (1995) *Growth Factors* 12:99–109.). The disclosures of the aforementioned citations are incorporated herein by reference. Several sequences in the matrix have alternate names: OP-1 (BMP-7), BMP-2 (BMP-2a), BMP-4 (BMP-2b), BMP-6 (Vgr1), OP-2 (BMP-8), 60A (Vgr-D), BMP-3 (osteogenin), GDF-5 (CDMP-1, MP-52), GDF-6 (CDMP-2, BMP-13) and GDF-7 (CDMP-3, BMP-12).

Figure 7A:
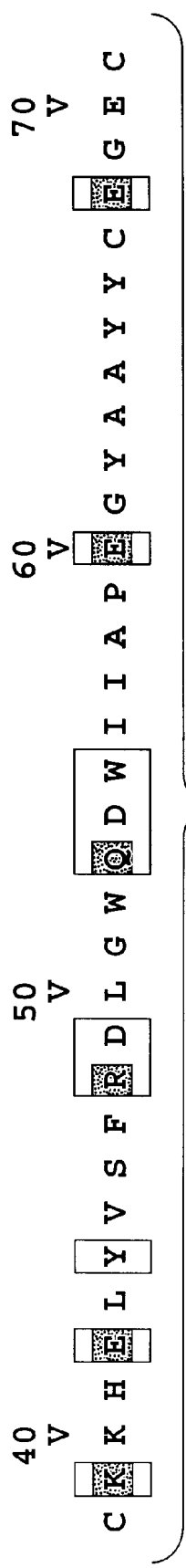
Figure 7B:
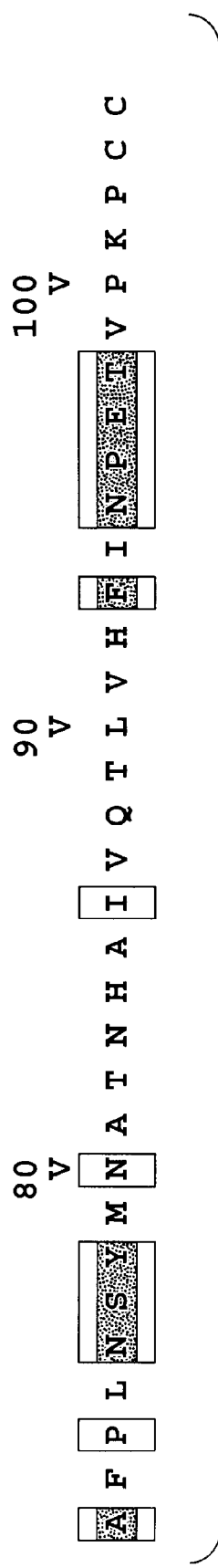
Figure 7C:
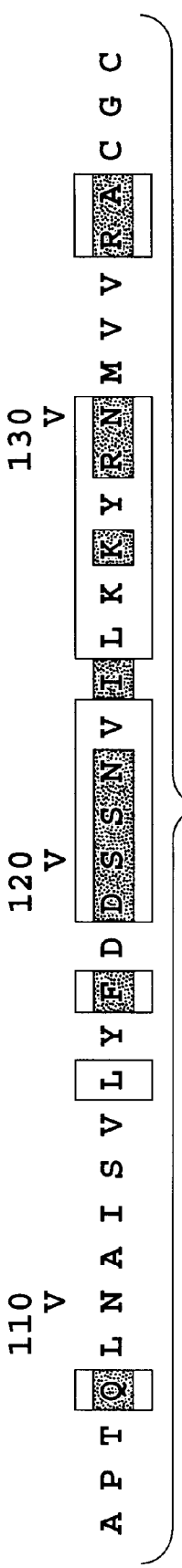

FIGS. 7A, 7B, and 7C show the amino acid sequences defining the human OP-1 finger 1, heel, and finger 2 regions, respectively. The amino acid residues having 40% or greater of their sidechain exposed to solvent are boxed, wherein the solvent accessible amino acid residues that are highly variable among the BMP/OP family of the TGF-β superfamily are identified by shaded boxes. The amino acid sequences shown in FIGS. 7A, 7B, and 7C together define the solvent accessible surfaces of dimeric hOP-1, according to the 2.8 Å resolution structure.

FIGS. 8.1–8.4 are tables, based on the 2.8 Å structure, which summarize the percentage surface accessibility of the amino acid side chains in a hOP-1 monomer subunit and in a hOP-1 dimer. Amino acid residues believed to constitute putative epitopes are designated "EPITOPE" and amino acid residues which are potential candidates as surface modifiable amino acids are marked with an asterisk. In addition, surface modifiable amino acids which are preferred candidates for enhancing solubility are marked with an asterisk.

FIG. 9 is a table, based on the 2.8 Å structure, which summarizes amino acid residues believed to define the ridge. Amino acid residues believed to constitute the receptor binding domain in the ridge are marked with an asterisk.

Figure 10:
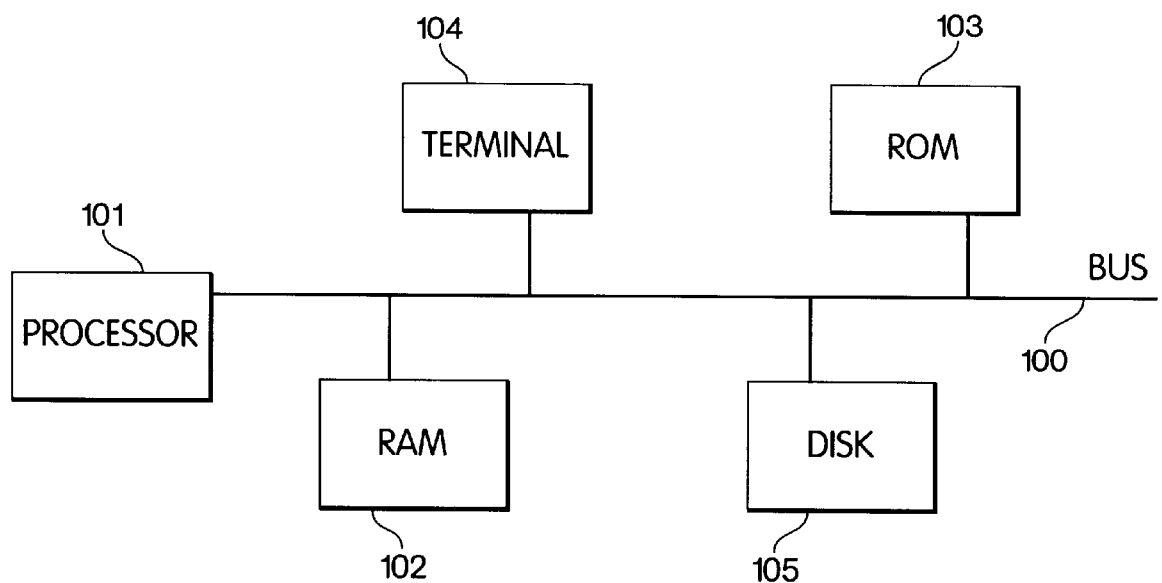

FIG. 10 is a schematic representation of a computer system useful in the practice of the invention.

FIGS. 11A and 11B are tables, produced by reference to the 2.8 Å structure, which summarize amino acid pairs believed to be useful as sites for introducing additional inter-chain (11A) or intra-chain (11B) disulfide bonds in the hOP-1 dimer.

Figure 12:
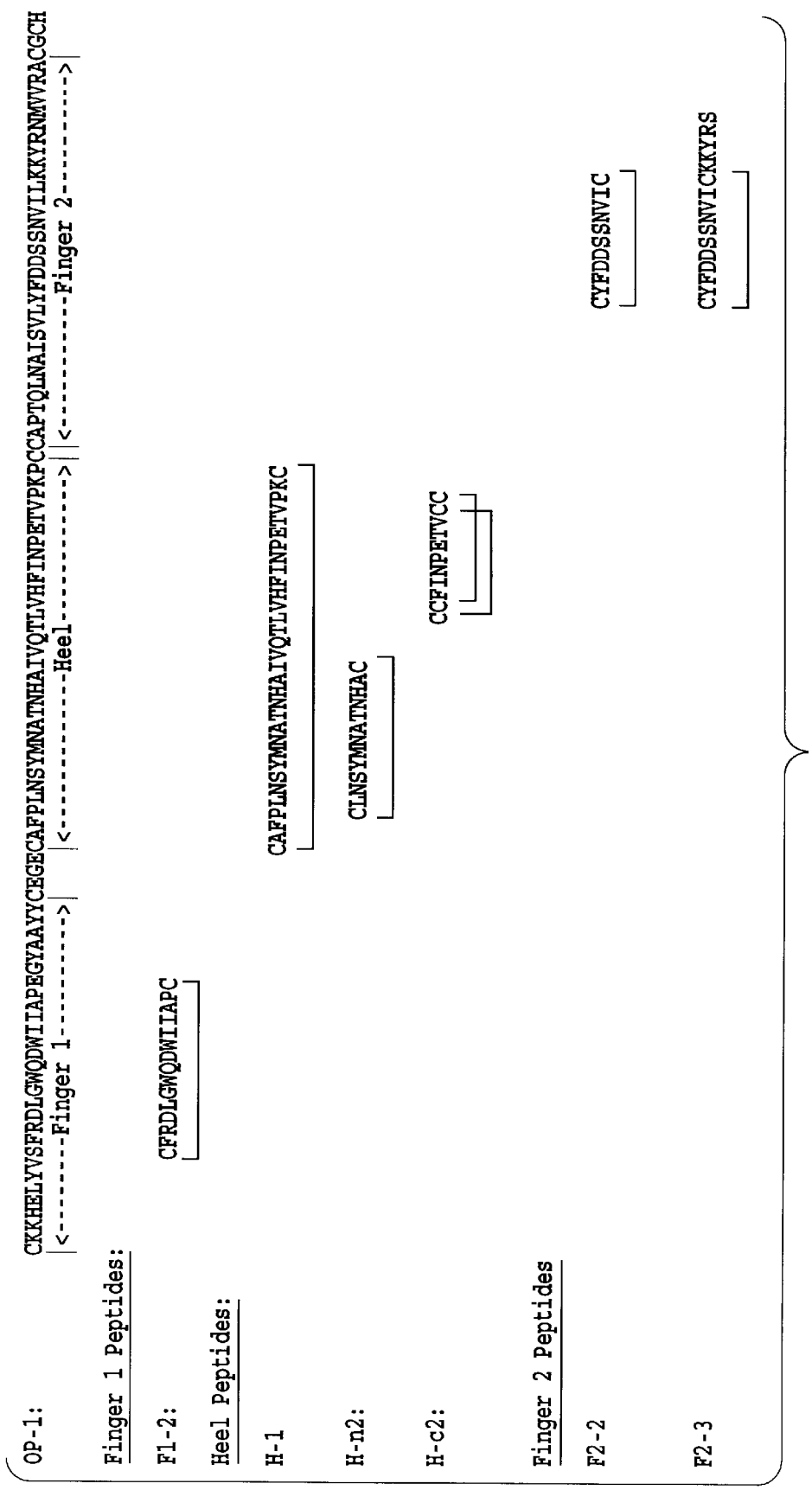

FIG. 12 is an amino acid sequence alignment showing the amino acid sequence of mature human OP-1, and peptides defining the finger-1, finger-2 and heel regions of human OP-1.

FIGS. 13A–13D are bar graphs illustrating the effect of finger-2 and heel peptides on the alkaline phosphatase activity of ROS cells incubated in either the presence or absence of soluble OP-1. FIGS. 13A, 13B, 13C, and 13D show the effect of peptides F2-2, F2-3, Hn-2 and Hn-3, respectively, on the alkaline phosphatase activity of ROS cells incubated in the presence (shaded bars) or absence of soluble OP-1 (unshaded bars).

Figure 14A:
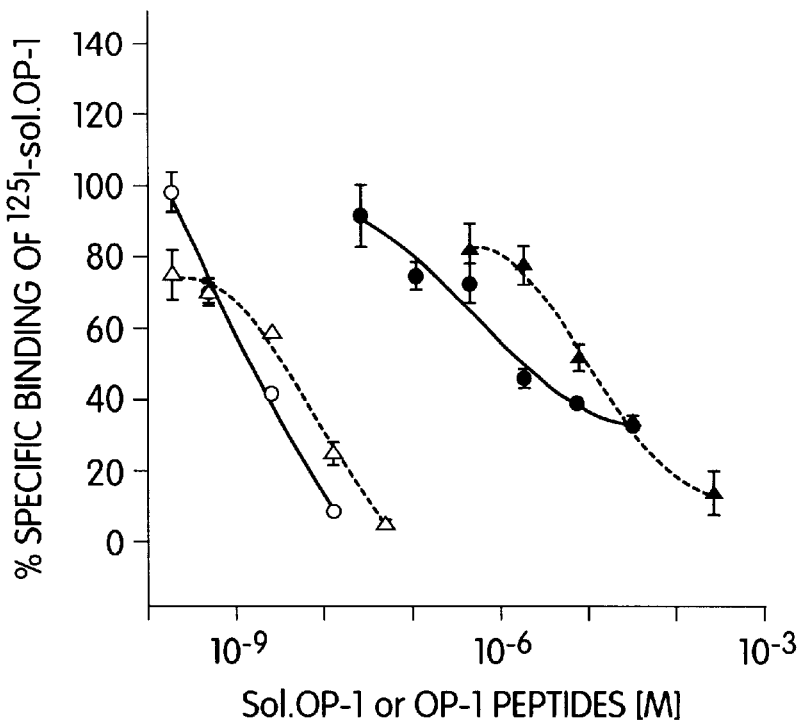
Figure 14B:
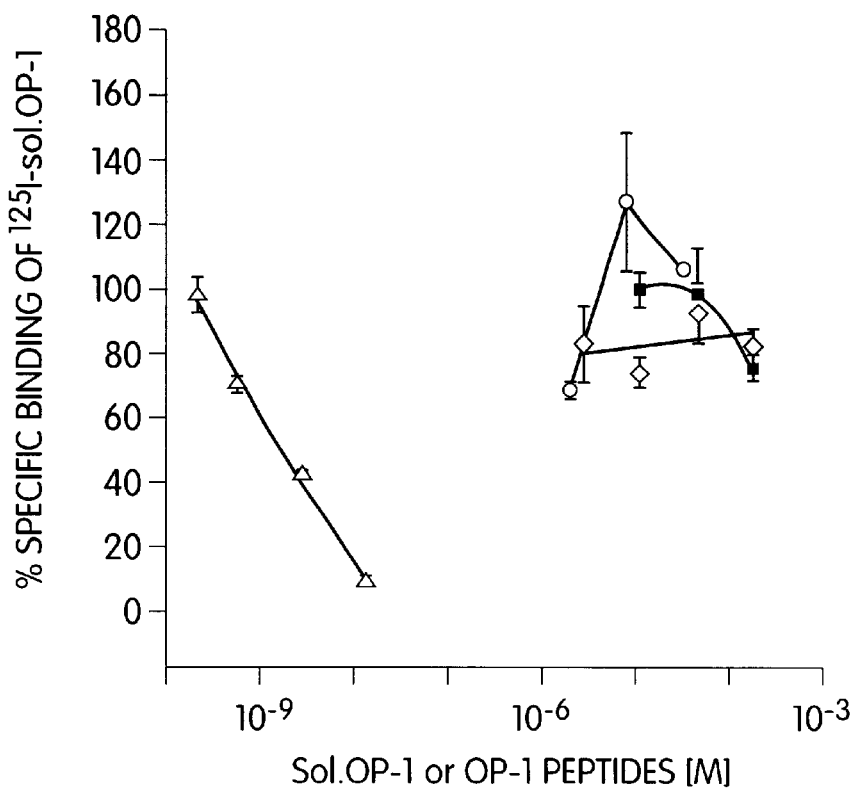

FIGS. 14A and 14B are graphs showing the displacement of radiolabelled soluble OP-1 from ROS cell membranes by finger 1, finger 2, and heel peptides. FIG. 14A shows the displacement of radiolabelled OP-1 from ROS cell membranes by unlabeled soluble OP-1 (open circles and triangles), finger 2 peptide F2-2 (closed circles) and finger 2 peptide F2-3 (closed triangles). FIG. 14B shows the displacement of radiolabelled OP-1 from ROS cell membranes by unlabeled soluble OP-1 (open triangles), finger 1 peptide F1-2 (closed boxes), heel peptide H-n2 (open diamonds) and heel peptide H-c2 (open circles).

FIGS. 15.1–15.37 are tables summarizing the atomic co-ordinates of hOP-1 resolved to 2.8 Å.

FIGS. 16\1–16\37 are tables summarizing the atomic co-ordinates of hOP-1 resolved to 2.3 Å.

Further particulars concerning the drawings are disclosed in the following description which discloses details of the three-dimensional structure of hOP-1, methods for identifying morphogen analogs, and methods for making, testing and using such morphogen analogs.

DETAILED DESCRIPTION OF PREFERRED EMBODIMENTS

I. Introduction

As described hereinbelow, the three-dimensional crystal structure of mature hOP-1 now has been solved to 2.3 Å. The disclosure provides two sets of atomic co-ordinates for hOP-1, wherein one set of co-ordinates (see FIGS. 15.1–15.37) represents the structure of hOP-1 resolved to 2.8 Å, and the other set of co-ordinates (see FIGS. 16\1–16\39) represents the structure of hOP-1 resolved to 2.3 Å. This disclosure thus provides, the atomic co-ordinates defining the relative positions, in three-dimensional space, of at least the C-terminal 104 amino acids of human OP-1 which are sufficient for imparting biological activity. The disclosure provides also an analysis of the structural features of hOP-1. The skilled artisan now can use some or all of these co-ordinates in a database for making morphogenic protein analogs, particularly OP-1 analogs. Specifically, the artisan can select part or all of the database to create templates of part, or all of the hOP-1 structure in three-dimensions, and using this template, create a desired analog or variant which may be amino acid-based, or alternatively composed, in whole or in part, by non-amino acid-based organic components.

Provided below is a detailed description of the three-dimensional crystal structure of hOP-1, along with a detailed description on how to use co-ordinates in a database to design a morphogen analog or structural variant of interest. Amino acid sequences as exemplary templates are provided as examples for designing, identifying, and producing an OP-1 analog using one of the OP-1 atomic co-ordinate databases. Specifically contemplated herein as useful analogs include: small amino molecules which mimic the receptor binding region of the protein; analogs having enhanced stability or solubility; analogs having reduced clearance rates from the body; or enhanced target tissue specificity. The reader will appreciate that these examples are merely exemplary. Given the disclosure of the co-ordinates, the three-dimensional structure, the use of the coordinates in a database, and the level of skill in the art today, still other analogs, not specifically recited herein, are contemplated and enabled by this disclosure. In particular, it will be appreciated that, given the disclosure herein, and the known amino acid sequences for other, closely related morphogens, the methods can be used to create other morphogen analogs of, for example, BMP2, BMP4, OP2, BMP5 and BMP6.

II. Structural Determination of hOP-1

A. Determination of the 2.8 Å Structure

Crystals of mature hOP-1 were grown by mixing equal volumes of purified protein (Özkaynak et al. (1990) *EMBO J.* 9:2085–20893; and Sampath et al.(1 992) *J. Biol. Chem.* 267:20352–20362) at 10 mg/ml, with 8% saturated ammonium sulfate in 50 mM sodium acetate buffer (pH 5.0) (Griffith et al. (1994) *J. Mol. Biol.* 244:657–658). The crystals have the symmetry of space group $P3_221$ with unit cell dimensions a=b=99.46 Å, and c=42.09 Å. One crystal was used to collect a complete native data set to 2.8 Å resolution at 4° C. Two heavy atom derivative data sets were collected at 4° C., one from a crystal soaked for seven days in 0.3 mM uranyl nitrate and the other from a crystal soaked for eight hours in 0.5 mM sodium gold (III) tetra chloride (Griffith et al. (1994) supra).

The native and derivative data sets were integrated and reduced with the R-AXIS-IIC software suite (Higashi (1990) A Program for Indexing and Processing R-AXIS IIC Imaging Plate Data, Rigaku Corp.) and scaled together using the CCP4 program ANSC (Collaborative Computation Project (1994) *Acta Cryst.* D50:760–763). Inspection of the Harker sections of the difference Patterson map reveals a single uranyl site. The position of the single gold site was determined by using cross-Fourier techniques using the uranyl position as the phasing site. The heavy atom x,y,z parameters and occupancy were refined with the program TENEYCK (Ten Eyck et al. (1976) *J Mol. Biol.* 100:3–11). Using these two derivatives and their anomalous signals, an initial phase set was calculated to 4.0 Å resolution with a mean figure of merit of 0.72. The phases were improved and extended to 3.5 Å resolution by cycles of solvent flattening (Wang (1985) *Meth. Enzymol.* 115:90–112) and phase combination (Reed (1986) *Acta Cryst.* A42:140–149) using the CCP4 (Collaborative Computation Project (1994) supra) crystallographic package. A completely interpretable 3.5 Å resolution electron density map permitted the unambiguous tracing of the polypeptide chain and identification of the amino acids from Gln 36 to His 139 using the graphic program "O" (Jones et al. (1991) *Acta Crystallogr.* A47:110–119). The model was refined with the program XPLOR (Brunger et al. (1987) *Science* 235:458–460) by using all reflections between 10 Å and 2.8 Å resolution for which $F_{obs}>2.0\sigma$ ($F_{obs}$). There were no water molecules included in the refinement. The root mean square (rms) deviation from ideality is 0.02 Å for bond lengths, 3.2° for bond angles. Good stereochemistry was observed for backbone torsion angles. The current R factor is 22.8%.

The atomic co-ordinates defining the 2.8 Å resolution structure are listed in FIGS. 15.1–15.37. In FIGS. 15.1–15.37, the columns entitled "Atom" denote atoms whose co-ordinates have been measured. The first letter in the column defines the element. The columns entitled "Residue" denote the amino acid residues in the hOP-1 monomer which contain an atom whose co-ordinates have been measured. The column entitled "Chain" denotes whether the atom of interest is located within the first (A) or second (B) monomer subunit of the hOP-1 dimer. The columns "X, Y, Z" are the Cartesian co-ordinates that define the atomic position of the atom measured.

B. Determination of the 2.3 Å Structure

Crystals of mature hOP-1 were produced as described in the previous section. One crystal, frozen in liquid nitrogen, was used to collect a data set to 2.3 Å resolution that was 91% complete. The data were collected on imaging plates at beam line X12C (National Synchrotron Light Source) with an oscillation range of 0.5 degrees (overlap of 0.1 degrees) and exposure times of 60–90 seconds. The digitalized data were processed, merged and scaled with DENZO and SCALEPACK (available from Molecular Structure Corporation, Tex.). An initial 2Fo-FC map, calculated after X-PLOR rigid-body refinement using the 2.8 Å model, was readily interpretable. Portions of the model were manually refitted to the electron-density map with the interactive graphics programs "O" and "Chain". Subsequent cycles of refinement (XPLOR/PROFFT) and manual rebuilding (QUANTA) rapidly converged to the present model.

The current model yielded a conventional crystallographic R factor of 23.5% for data from 10 to 2.3 Å (1.56 cutoff) and a Rfree of 27%. The refined structure was analyzed using the PROCHECK (available from Protein Data Bank, Brookhaven, N.Y.) algorithm and corrected where appropriate. The root mean square (rms) deviation from ideality is 0.015 Å for bond distances, 0.034 Å for angle distances, and 0.142 Å for planar 1–4 distances. The rms deviation from ideality is 1.7° for bond angles. The upper estimate of the error in the atomic positions from the Luzzati plots (EXPLOR) using the free R factor is 0.25–0.33 Å. The final model, comprising one monomer subunit, consists of 828 protein atoms (i.e., all non-hydrogen atoms) and 33 water molecules. The average temperature (B) factor is 33 Å$^2$ for protein atoms and 37 Å$^2$ for solvent atoms.

The atomic co-ordinates defining the 2.3 Å resolution structure are listed in FIGS. 16\1–16\39. In FIGS. 16\1–16\39, the columns entitled "Atom" denote atoms whose co-ordinates have been measured. The first letter in the column defines the element. The columns entitled "Residue" denote the amino acid residues in the hOP-1 monomer which contain an atom whose co-ordinates have been measured. The column entitled "Chain" denotes whether the atom of interest is located within the first (A) or second (B) monomer subunit of the hOP-1 dimer. The columns "X, Y, Z" are the Cartesian co-ordinates that define the atomic position of the atom measured. The column denoted "δ" represents the uncertainty in the position of the co-ordinate as derived from the temperature factor (B) of each corresponding atom. The uncertainty of each co-ordinate was derived from the formula $$\delta = \sqrt{\frac{B}{8\pi^2}}$$

(see "*Protein Crystallography*" (1976) T. L. Blundell and L. N. Johnson, Academic Press, p. 121) and is expressed in units of Å.

III. Structural Features of hOP-1 Monomer Subunits

Figure 1A:
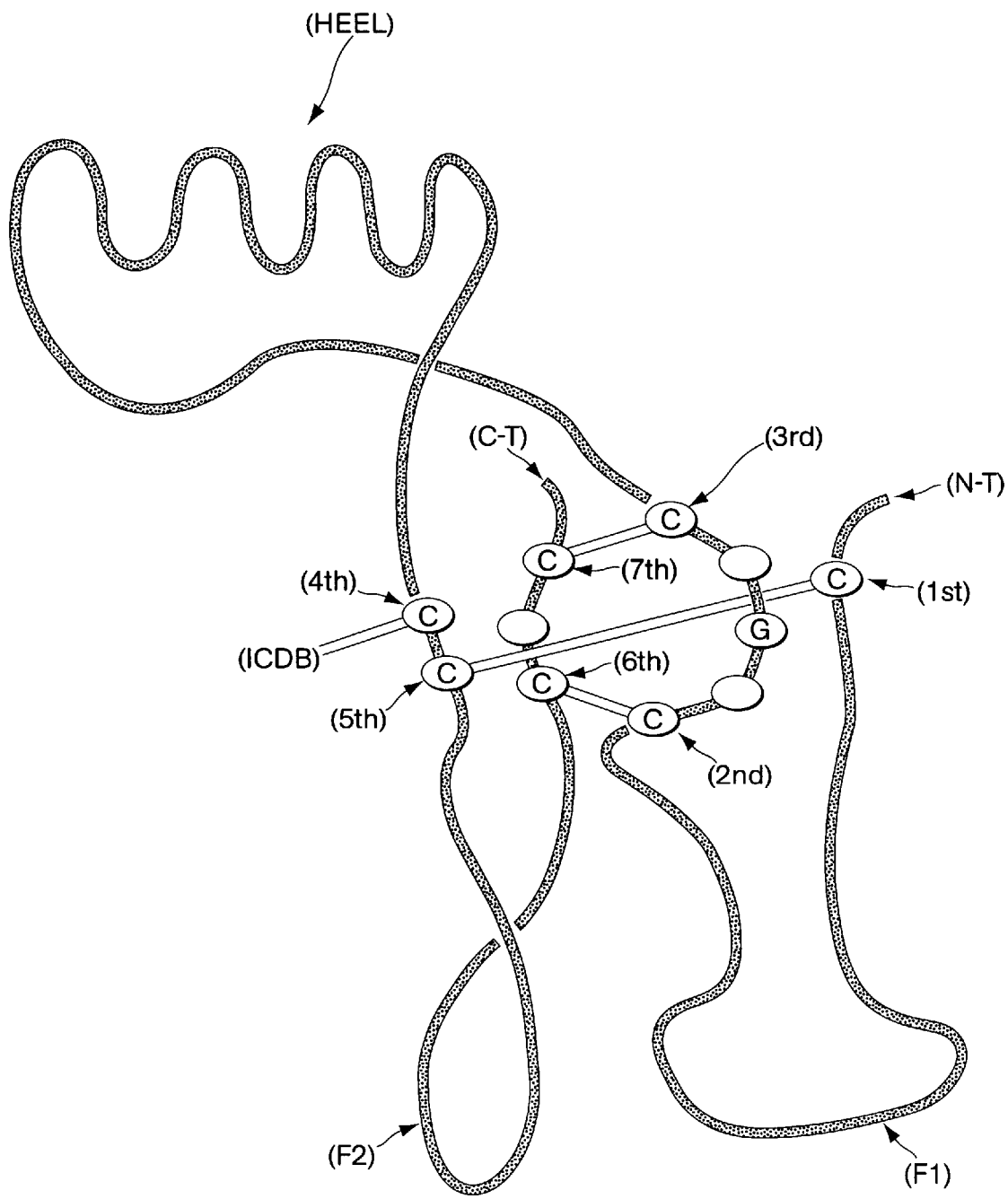
FIG. 1A is a simplified line drawing useful in describing the structure of a monomeric subunit of hOP-1. See the Summary of the Invention, infra, for explanation.

Human OP-1, like TGF-β2, is a dimeric protein having a unique folding pattern involving six of the seven C-terminal cysteine residues, as illustrated in FIG. 1A. Each of the subunits in OP-1, like TGF β2 (See Daopin et al. (1992) *Science* 257:369–373; and Schulnegger et al. (1992) *Nature* 358:430–434) have a characteristic folding pattern, illustrated schematically in FIG. 1A, that involves six of the seven C-terminal cysteine residues.

Referring to FIG. 1A, four of the cysteine residues in each subunit form two disulfide bonds which together create an eight residue ring, while two additional cysteine residues form a disulfide bond that passes through the ring to form a knot-like structure (cysteine knot). With a numbering scheme beginning with the most N-terminal cysteine of the 7 conserved cysteine residues assigned number 1, the 2nd and 6th cysteine residues are disulfide bonded to close one side of the eight residue ring while the 3rd and 7th cysteine residues are disulfide bonded to close the other side of the ring. The 1 st and 5th conserved cysteine residues are disulfide bonded through the center of the ring to form the core of the knot. Amino acid sequence alignment patterns suggest this structural motif is conserved between members of the TGF-β superfamily. The 4th cysteine is semi-conserved and when present typically forms an inter-chain disulfide bond (ICDB) with the corresponding cysteine residue in the other subunit.

Each hOP-1 monomer subunit comprises three major tertiary structural elements and an N-terminal region. The structural elements are made up of regions of contiguous polypeptide chain that possess over 50% secondary structure of the following types: (1) loop, (2) helix and (3) β-sheet. Furthermore, in these regions the N-terminal and C-terminal strands are not more than 7 Å apart.

Figure 1B:
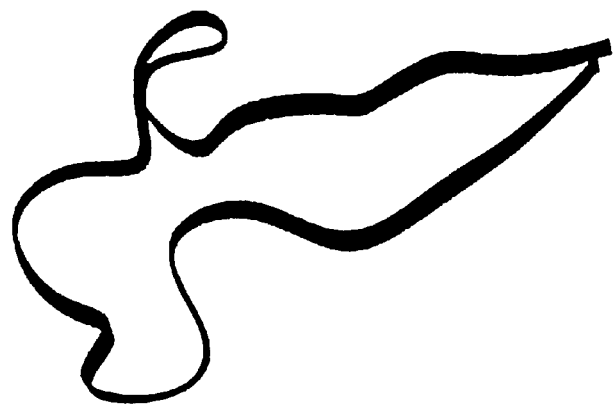
FIGS. 1B, 1C, and 1D are monovision ribbon tracings of the respective peptide backbones of hOP-1 finger-1, heel, and finger-2 regions.

The amino acid sequence between the 1st and 2nd conserved cysteines (FIG. 1A) form a structural region characterized by an anti-parallel β-sheet finger, referred to herein as the finger 1 region (F1). A ribbon trace of the human OP-1 finger 1 peptide backbone is shown in FIG. 1B. Similarly the residues between the 5th and 6th conserved cysteines in FIG. 1A also form an anti-parallel β-sheet finger, referred to herein as the finger 2 region (F2). A ribbon trace of the human OP-1 finger 2 peptide backbone is shown in FIG. 1D. A β-sheet finger is a single amino acid chain, comprising a β-strand that folds back on itself by means of a β-turn or some larger loop so that the entering and exiting strands form one or more anti-parallel β-sheet structures. The third major structural region, involving the residues between the 3rd and 4th conserved cysteines in FIG. 1A, is characterized by a three turn α-helix referred to herein as the heel region (H). A ribbon trace of the human OP-1 heel peptide backbone is shown in FIG. 1C.

The organization of the monomer structure is similar to that of a left hand (see FIG. 1E) where the knot region is located at the position equivalent to the palm (16), the finger 1 region is equivalent to the index and middle fingers (12 and 13, respectively), the α-helix, or heel region, is equivalent to the heel of the hand (17), and the finger 2 region is equivalent to the ring and small fingers (14 and 15, respectively). The N-terminal region (undefined in the 2.8 Å resolution map disclosed herein) is predicted to be located at a position roughly equivalent to the thumb (11).

Figure 1C:
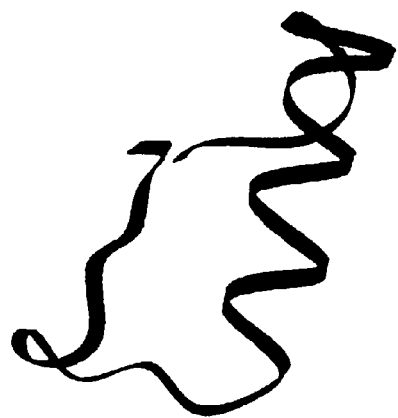
Figure 1D:
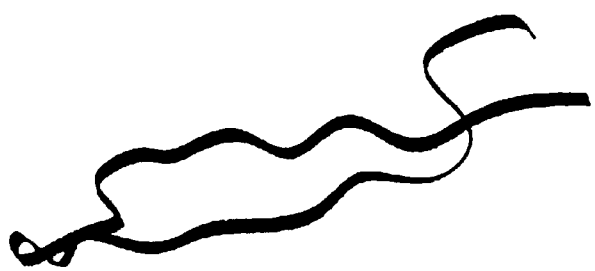
Figure 1E:
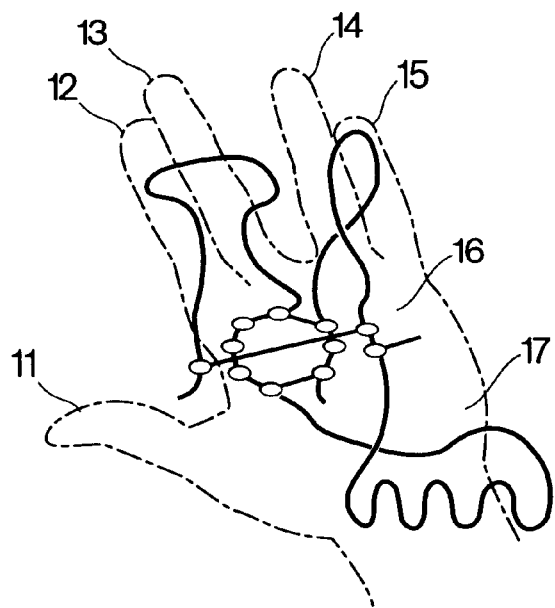
FIGS. 1E and 1F are schematic representations of monomeric and dimeric forms of hOP-1, respectively, as represented by a left hand motif.
Figure 1F:
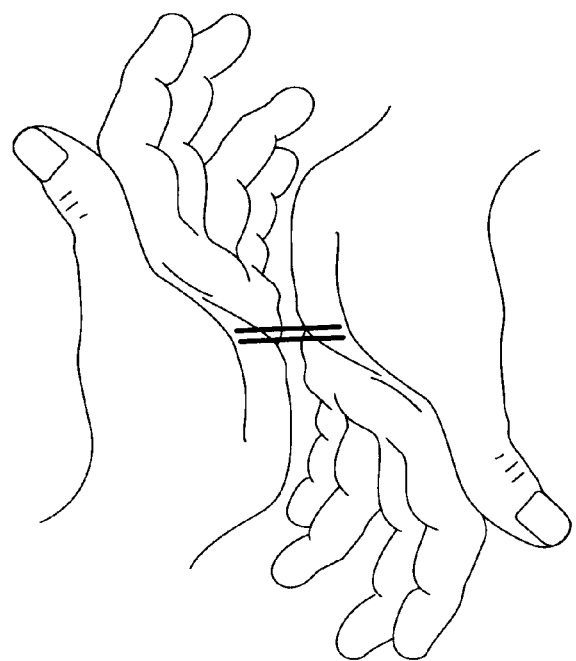

Monovision ribbon tracings illustrating the alpha carbon backbones of each of the three major independent structural elements of the monomer are illustrated in FIGS. 1B–1D. Specifically, the finger 1 region comprising the first anti-parallel β-sheet segment is shown in FIG. 1B, the heel region comprising the three turn α-helical segment is shown in FIG. 1C, and the finger 2 region comprising second and third anti-parallel β-sheet segments is shown in FIG. 1D.

For the sake of comparison, FIG. 3 shows an alignment of the amino acid sequences defining the finger 1, finger 2 and heel regions of hOP-1 and TGF-β2. In FIG. 3, the OP-1 and TGF-β2 amino acid sequences were aligned according to the corresponding regions of local structural identity in the OP-1 and TGF-β2 structures. Alignment gaps were positioned in loop regions, which is where the local conformational homology of the α-carbon traces tends to be the lowest.

The structure-based alignment of OP-1 and TGF-β2 then was used as a template for the alignment of the 7-cysteine domain sequences of other TGF-β superfamily members (other members of the TGF-β superfamily are set forth in FIG. 6). Alignment gaps were positioned in regions which are loops in both the OP-1 and TGF-β2 structures. Percent identity between pairs of sequences was calculated as the number of identical aligned sequence positions, excluding gaps, normalized to the geometric mean of the lengths of the sequences and multiplied by 100. FIG. 6 is a matrix of the resulting pair wise present identities between super family sequences so aligned. Using such principles, it is contemplated that the hOP-1 and TGF-β structures, either alone or in combination, may be used for homology modeling of other proteins belonging to the TGF-β superfamily whose three-dimensional structures have not yet been determined (see, for example, the other members of the TGF-β superfamily listed in FIG. 6). It is contemplated that such models may be useful in designing morphogen analogs for the particular candidate morphogens of interest, however, for simplicity, the disclosure hereinbelow refers specifically the design, identification, and production of morphogen analogs of hOP-1.

FIG. 3 also shows, based on an analysis of the 2.8 Å resolution structure, a comparison of interchain contact residues in OP-1 and TGF-β2. Residues were designated as contact residues if the distance between the centers of at least one non-hydrogen atom from each side chain was less than the sum of their Van der Waals radii plus 1.1 Å. Despite the low level of sequence identity between OP-1 and TGF-β2, the inter chain contacts between residues in the heel of one chain and residues in finger 1 and finger 2 of the other chain are well conserved.

Figure 2:
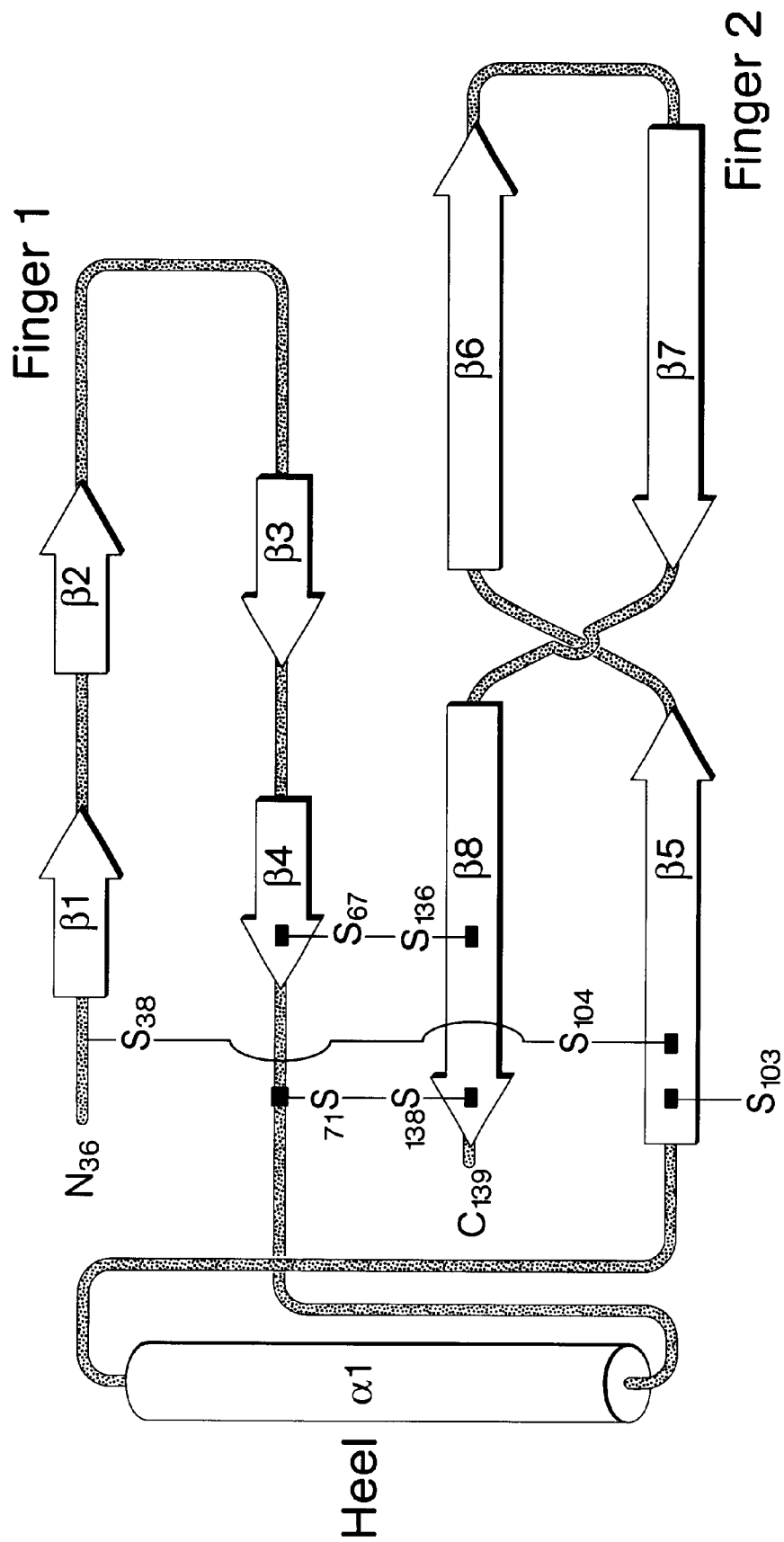
FIG. 2 is a schematic drawing of a monomeric subunit of hOP-1. The hOP-1 cysteine knot comprising three disulfide bonds constitutes the core of the hOP-1 monomer subunit. Two disulfide bonds which connect residues Cys 67-Cys 136 and Cys 71-Cys 138 produce an eight residue ring through which the third disulfide bond which connects residues Cys 38-Cys 104 passes. Four strands of antiparallel β-sheet, which emanate from the knot, form the two finger like projections. An α-helix located on the opposite end of the knot, lies perpendicular to the axis of the two fingers thereby forming the heel. The N-terminus of the monomer subunit remains unresolved. The β-sheets are displayed as arrows and labeled from β1 through β8. The α-helix is displayed as a tube and labeled 1. The intra-subunit disulfide bonds that constitute the cysteine knot are shown in solid lines. Starting from Gln 36 ("$N_{36}$"), the first residue shown in this figure, the amino acid residues which produce secondary structure in the Finger 1 region include: Lys 39-His 41 (β1), Tyr 44-Ser 46 (β2), Glu 60-Ala 63 (β3), Tyr 65-Glu 70 (β4); the amino acid residues which produce secondary structure in the Finger 2 region include: Cys 103-Asn 110 (β5); Ile 112-Asp 118 (β6); Asn 122-Tyr 128 (β7)

Upon detailed inspection of the 2.8 Å resolution structure of hOP-1, the finger 1 region of hOP-1 is an antiparallel β-sheet containing a thirteen residue omega loop (Phe 47-Glu 60) (FIG. 2). The structural alignment of the OP-1 and TGF-β2 sequences in FIG. 3 places two gaps in the omega loop. The first gap represents a deletion in hOP-1 that aligns with Arg 26 in the α2 helix of TGF-β2. This deletion results in a tighter, non-(α-helical turn in OP-1 as compared with TGF-β2. The second gap corresponds to the insertion of Gln 53 in OP-1, which has the result of directing both Gln 53 and Asp 54 side chains into the solvent. By comparison, in the corresponding region of TGF-β2, only Lys 31 is in contact with the solvent. These differences in the conformation of the omega loop also result in the conserved proline (Pro 59) adopting a trans conformation in hOP-1 rather than cis, as in TGF-β2. The conformation of the omega loop orients six non-polar residues so they can contribute to a solvent inaccessible interface with Finger 2. Of these six, four are aromatic (Phe 47, Trp 55, Tyr 62 and Tyr 65), and two are aliphatic (Ile 56 and Ile 57). In all, the conformation of the omega loop backbone places five polar residues (Arg 48, Asp 49, Gln 53, Asp 54, and Glu 60) in contact with solvent. The net surface charge in this region is −2 whereas it is +2 for TGF-β2 (FIG. 5).

According to the 2.8 Å structure, the only α helix in the monomer is located between the third and fifth cysteines (Cys 71 and Cys 104). This helix extends for three and one-half turns from residues Thr 82 to Ile 94, is amphipathic, and contains a number of hydrophobic residues which in the dimer make contact with residues from Finger 1 and Finger 2 of the other monomer (FIG. 3). Several hydrophilic residues (Thr 82, His 84, and Gln 88 ) form one wall of an internal solvent pocket near the 2-fold axis of the dimer, while others (Asn 83, His 92, and Asn 95) are in contact with the external solvent. The conformation of the loop leading from the C-terminal end of the helix back to the cysteine knot is similar in OP-1 and TGF-β2. By comparison, the loop located at the N-terminal end of the helix is 3 residues longer in OP-1, resulting in a different fold than in TGF-β2. In this loop of OP-1, it is believed that an N-linked sugar moiety is attached to Asn 80, however, no such corresponding glycosylation site exists in TGF-β2. Further, this loop is uncharged in OP-1 whereas it is negatively charged in TGF-β2.

According to the 2.8 Å structure, Finger 2 is the second antiparallel β-sheet in OP-1 (FIG. 2). The polypeptide chain reverses direction between segments β6 and β7 through a 3:5 turn (Sibanda, et al. (1991) Methods in Enzymol. 202:59–82) beginning at residue Asp 118 and ending at residue Asn 122. In contrast, TGF-β2 has one less residue in this loop and adopts a 2:2 turn (Sibanda et al. (1991) supra). Residues Arg 129 to Val 132, located between segments β7 and β8, form a peptide bridge that crosses over the C-terminal end of strand β5 and produces a 180° twist in the Finger 2 antiparallel β-structure. A similar structure is observed in other cysteine knot growth factors, however the peptide bridge length varies (McDonald el al. (1991) Nature 354:411–414). Within the monomer, Finger 2 makes intra-chain contacts with Finger 1 by contributing aromatic residues Tyr 116, Phe 117 and Tyr 128, and aliphatic residues Val 114, Leu 115, Val 123, Met 131 and Val 133 to a solvent inaccessible interface. OP-1 and TGF-β2 differ by three charges in the region of the Finger 2 turn; OP-1 has two negative charges while TGF-β2 has one positive charge. In the region between the turn and the peptide bridge, OP-1 has a net charge of +3 while TGF-β2 is neutral (FIG. 5).

The N-terminus of each monomeric subunit is believed to be highly mobile and has not been resolved in the 2.8 Å resolution structure of hOP-1. The N-terminal region can be deleted without affecting biological activity and, therefore, it is contemplated that this portion of mature hOP-1 may be removed and replaced with other protein or peptide sequences, such as antibodies, and/or radiolabel binding sites for enhancing targeting to a particular locus in vivo or for use in in vivo imaging experiments. In addition, the N-terminal region may be replaced with an ion chelating motif (e.g., $His_6$) for use in affinity purification schemes, or replaced with proteins or peptides for enhancing solubility in aqueous solvents.

IV. Structural Features of the hOP-1 Dimer

FIG. 4 shows stereo ribbon trace drawings representative of the peptide backbone of the hOP-1 dimer complex, based on the 2.8 Å structure. The two monomer subunits in the dimer complex are oriented symmetrically such that the heel region of one subunit contacts the finger regions of the other subunit with the knot regions of the connected subunits forming the core of the molecule. The 4th cysteine forms an inter-chain disulfide bond with its counterpart on the second chain thereby equivalently linking the chains at the center of the palms. The dimer thus formed is an ellipsoidal (cigar shaped) molecule when viewed from the top looking down the two-fold axis of symmetry between the subunits (FIG.

4A). Viewed from the side, the molecule resembles a bent "cigar" since the two subunits are oriented at a slight angle relative to each other (FIG. 4B).

As shown in FIG. 4, each of the structural elements which together define the native monomer subunits of the dimer are labeled 43, 43', 44, 44', 45, 45', 46, and 46', wherein, elements 43, 44, 45, and 46 are defined by one subunit and elements 43', 44', 45', and 46' belong to the other subunit. Specifically, 43 and 43' denote the finger 1 regions; 44 and 44' denote heel regions; 45 and 45' denote the finger 2 regions; and 46 and 46' denote disulfide bonds which connect the 1st and 5th conserved cysteines of each subunit to form the knot-like structure. From FIG. 4, it can be seen that the heel region from one subunit, e.g., 44, and the finger 1 and finger 2 regions, e.g., 43' and 45', respectively from the other subunit, interact with one another. These three elements are believed to cooperate with one another to define a structure interactive with the ligand binding interactive surface of the cognate receptor.

The helical axis is defined as the line equi-distant from the alpha carbons in the helical region. A sequence of four points is needed to define the dihedral angle between the axes of the helices in the dimer. The two inner points were chosen to lie on the helical axes adjacent to the α-carbon of residue His 84 in OP-1 or His 58 in TGF-β2, respectively. The two outer points were chosen to lie on their respective helical axes, but their location is arbitrary. To measure the angle between the helices, the first two points used to define the dihedral angle were translated so as to superimpose the inner points. The resulting three points define the angle.

A major difference between the OP-1 and TGF-β2 dimers is the relative orientation of the helices in the heel region. The angle between the axes of the helices in the heel region of OP-1 is 43° which is 10° larger than that measured for TGF-β2. The measured dihedral angle between the helices is −20° for OP-1 which is 14° more negative than for TGF-β2. Despite these differences in helical orientation, the same helix and finger residue positions are involved in making inter-chain contacts, as evidenced by the shaded residues in FIG. 3.

Differences in the hOP-1 Dimer Relative To Individual Monomer Subunits

During dimerization of the monomer subunits, several amino acids on the surface of each monomer subunit become buried in the hOP-1 dimer. FIGS. 8.1–8.4 highlights differences in the surface accessibility of particular amino acid residues located in the hOP-1 monomer subunit relative to those in the hOP-1 dimer, as determined from the 2.8 Å structure.

Loss of non-polar surface area during dimerization was calculated using ACCESS (version 2.1) with a 1.4 Å probe (Lee et al. (1971) *J. Mol. Biol.* 55:379–400). Non-polar surface area is defined as the contribution to the total accessible surface from carbon and sulfur atoms. The surface area measurement algorithm in ACCESS slices the structure into 0.25 Å slabs perpendicular to the Z-axis. As a consequence, the results are sensitive to the orientation of a structure relative to the Z-axis (Lee et al. (1971) supra). In order to minimize this effect, we evaluated three perpendicular and one intermediate orientations of each structure. The results of these calculations were combined by accepting, for each non-polar atom, the largest accessible area measured among the four orientations. The values for TGF-β2 reported here were calculated using coordinates from entry 2TG1 (Daopin et al. (1992) supra) and entry 1TFG (Schlunegger et al. (1992) supra) obtained from the January 1994 release of the Protein Data Bank (Bernstein et al. (1977) *J. Mol. Biol.* 112:535–542) at Brookhaven National Laboratory.

In FIG. 8, the column entitled "Residue" denotes an amino acid of interest. The column entitled "Monomer % Area" denotes the percentage of the amino acid that is exposed on the surface of the hOP-1 monomer, the column entitled "Dimer % Area" denotes the percentage of the amino acid that is exposed on the surface of the hOP-1 dimer, and the column denoted "Hidden % Area" denotes amount of surface area for each amino acid that is lost upon dimerization of each monomer subunit to produce the hOP-1 dimer. This analysis reveals amino acids which become buried during dimerization and, thus, likely are located at the interface of the two monomer subunits. For example, 70.75% of the surface area of His 84 becomes hidden upon dimerization. A review of the structure of dimeric hOP-1 reveals that His 84 is located at the interface between the two monomers.

B. Solution Electrostatic Potentials on the Surface of OP-1 and TGF-β2

The solution electrostatic potentials surrounding the OP-1 and TGF-β2 (1TFG) (Schlunegger et al (1992) supra) dimers were calculated using DELPHI (Gilson et al. (1987) *Nature* 330:84–86; and Nicholls et al. (1991) *J. Comput. Chem.* 12:435–445) (Biosym Technologies, Inc., San Diego, Calif.). The calculations were performed using a solvent dielectric constant of 80, a solvent radius of 1.4 Å, an ionic strength of 0.145M and an ionic radius of 2.0 Å. The interior of the protein was modeled using a dielectric constant of 2.0. Formal charges were used and distributed as follows: atoms OD1 and OD2 of Asp were each charged −0.5, atoms OE1 and OE2 of Glu were each charged −0.5, atoms NG1 and NE2 of His were each charged 0.25, atom NZ of Lys was charged +1.0, atoms NH1 and NH2 of Arg were each charged +0.5, and atom OXT of the C-terminal carboxyl group was charged −1.0.

The differences in charge distribution on the surfaces of OP-1 and TGF-β2 can be observed by comparing the color distributions of FIGS. 5B and 5C, respectively. Surface regions having an electrostatic potential of −3 kT or less are shown in red while surface regions of +3 kT or greater are shown in blue. Neutral regions are shown in green or gold to correspond to the backbone ribbons shown in FIG. 5A. As mentioned in the following section, the differences in electrostatic potential on the surfaces of OP-1 and TGF-β2 may play an important role in the specific interactions of the TGF-β superfamily members with their cognate receptors.

C. Receptor Binding Domain

Without wishing to be bound by theory, it is contemplated that the receptor binding regions of hOP-1 includes amino acids that are both solvent accessible and lie at positions of heterogeneous composition, as determined from the amino acid sequence of hOP-1 when aligned with other members of the TGF-β superfamily (See FIG. 3).

Divergent structural features in hOP-1, like TGF-β2, occur primarily in the external loops of finger 1 and finger 2, the loops bordering the helix in the heel region, and the residues in the N-terminal domain preceding the first cysteine of the cysteine knot. These regions are solvent accessible. In both the OP-1 and TGF-β2 dimer structures, the tip of finger 2 and the omega loop of finger 1 from one chain, and the C-terminal end of the α-helix in the heel of the other chain form a contiguous ridge approximately 40 Å long and 15 Å wide (FIG. 5A). It is contemplated that this ridge contains the primary structural features that interact with the cognate receptor, and that the binding specificity between different TGF-β superfamily members derives from conformational and electrostatic variations on the surface of this ridge.

Differences in the conformation of the finger 1 omega loop, which constitutes the mid section of the ridge, and in the turn at the end of finger 2, which forms one end of the ridge are noted. However, there are striking differences in the surface charge of the ridge in hOP-1 relative to TGF-β2 (see FIGS. 5B and 5C). In hOP-1, the ends of the finger regions are negatively charged whereas in TGF-β2, the ends of the finger regions are positively charged. This results in a net charge of −4 for the receptor binding ridge of hOP-1 versus +3 for TGF-β2. Conversely, the N-strand located C-terminal to the turn of finger 2 (β7, FIG. 2) is positively charged in OP-1 whereas it is negatively charged in TGF-β2 (FIGS. 5B and 5C). These features suggests that electrostatic charge distribution plays an important role in the specific interactions of the TGF-β superfamily members with their cognate receptors.

FIG. 9 summarizes the amino acid residues which, according to the 2.8 Å structure, are believed to constitute the ridge, and also indicates whether each amino acid residue is disposed within the heel, finger 1, or finger 2 domains. FIG. 9 also provides a list of amino acid residues which are believed to constitute at least part, if not all of the receptor binding domain of hOP-1.

V. Design of Morphogen Analogs

Although it is contemplated that the design of morphogen analogs can be facilitated by conventional ball and stick type modeling procedures, it is contemplated that the ability to design morphogen analogs is enhanced significantly using modern computer-driven modeling and design procedures.

It is contemplated that the design of morphogen analogs, as discussed in detail hereinbelow, is facilitated using conventional molecular modeling computers or workstations, commercially available from, for example, Silicon Graphics, Inc. or Evans and Sutherland Computer Corp., which implement equally conventional computer modeling programs, for example, INSIGHTII, DISCOVER, and DELPHI, commercially available from Biosym, Technologies Inc., and QUANTA, and CHARMM commercially available from Molecular Simulations, Inc.

Furthermore, it is understood that any computer system having the overall characteristics set forth in FIG. 10 may be useful in the practice of the instant invention. More specifically, FIG. 10, is a schematic representation of a typical computer work station having in electrical communication (100) with one another via, for example, an internal bus or external network, a processor (101), a RAM (102), a ROM (103), a terminal (104), and optionally an external storage device, for example, a diskette, CD ROM, or magnetic tape (105).

It is contemplated, that the co-ordinates can be used not only to provide a basis for re-engineering hOP-1 dimers by using, for example, site-directed mutagenesis methodologies, to enhance, for example, the solubility and or/stability of the active hOP-1 dimer in physiological buffers, but also to provide a starting point for the de novo design and production of peptides or other small molecules which mimic the bioactivity of hOP-1. Set forth below are illustrative examples demonstrating the usefulness of hOP-1 atomic co-ordinates in the design of morphogen analogs, however, it is understood the examples below are illustrative and not meant to be limiting in any way.

A. Engineering hOP-1 Dimers

In one aspect, the availability of the atomic co-ordinates for hOP-1, enables the artisan to perform theoretical amino acid replacements and to determine by calculation, in advance of actually making and testing the candidate molecule in a laboratory setting, whether a particular amino acid substitution disrupts the packing of the OP-1 dimer and whether a morphogen analog is likely to be more stable and/or soluble than the template OP-1 molecule. Such procedures assist the artisan to eliminate non viable replacements and to focus efforts on more promising candidate analogs.

(i) Financing the Stability of hOP-1 Dimers

It is contemplated that the skilled artisan in possession of the atomic co-ordinates defining hOP-1 can introduce additional inter- or intra-chain covalent and/or non-covalent interactions into the hOP-1 dimer to stabilize the dimer by preventing disassociation or unfolding of each monomer subunit. Preferred engineered covalent interactions include, for example, engineered disulfide bonds, and preferred engineered non-covalent interactions include, for example, hydrogen bonds, salt bridges, and hydrophobic interactions.

For example, in order to introduce additional disulfide bonds, the skilled artisan can identify sites suitable for the introduction of a pair of cysteine amino acid residues by using standard molecular modeling programs, for example, INSIGHT, DISCOVER, CHARMM and QUANTA. Another program useful in identifying pairs of amino acids as potential sites for introducing stabilizing disulfide bonds is described in U.S. Pat. No. 4,908,773, the disclosure of which is incorporated herein by reference.

For example, the skilled artisan using the INSIGHT program can screen for pairs of amino acids, where the distance between the Cβ atoms of each amino acid is in the range of about 3.0 to about 5.0, or more preferably about 3.5 to about 4.5 Å apart. For this purpose, glycines, which contain no Cβ–Cβ bond, are first converted to alanines on the computer. The possible range of Cβ–Cβ distances in a disulfide bond are 3.1 Å to 4.6 Å, but separations outside this range can be accommodated by small shifts in the neighboring atoms. Searching Cβ, rather than Cα. distances, ensures both reasonable spacing as well as proper orientation of the Cα–Cβ bond. The effects of adding such an additional linkage on protein structure are determined by mutating the two candidates residues to Cys; rotating each new Cys about the Cα–Cβ bond to bring the two γ sulfurs as close to within 2 Å as possible; creating a disulfide between the γ sulfurs; and energy minimizing structural regions within 5 Å of the disulfide bond. Any deformation of the structure caused by introduction of the additional disulfide bond is revealed by inspection when the minimized, mutated model structure is superimposed on the native structure.

It is contemplated that the introduction of additional linkages will improve solubility by preventing transient exposure of non-polar interface or buried residues. FIG. 11A lists amino acid residues, based on the 2.8 Å structure, which may be mutated to cysteine residues for introducing additional inter-chain disulfide bonds, based upon the selection criteria presented above. For reference purposes, Table 11A includes also the length of the naturally occurring interchain disulfide linkage in wild type hOP-1, that is, the disulfide linkage connecting Cys-103 of one monomer subunit with the counterpart Cys-103 of the other monomer subunit.

A preferred pair of residues suitable for modification include the residue at position 83 of one chain and the residue at position 130 of the other chain. It is contemplated that the additional inter-chain linkage stabilizes the dimeric structure by connecting the N-terminal end of the Heel helix of the first subunit to the middle of the Finger 2 region in the second subunit. A disulfide bond between position 82 on one chain and position 130 of the other chain also is geometrically feasible, but because Thr 82 is part of the NAT glycosylation site in OP-1, its modification may inhibit proper glycosylation.

FIG. 11B summarizes amino acid residues which can be mutated to cysteine residues for introducing additional intra-chain disulfide bonds, based upon the selection criteria presented above. As noted previously, the putative receptor binding region comprises at least two physically proximal, but sequentially separate regions, namely the tips of Finger 1 and Finger 2. It is contemplated that the structural integrity of the putative receptor binding ridge can be stabilized by engineering an intra-chain disulfide link between residues of Finger 1 and Finger 2. In a preferred embodiment, the residue at position 58 in Finger 1 can be disulfide bonded with the residue at position 114 in Finger 2. It is contemplated that a link between the residues at positions 58 and 115 also would be viable, however, this would move the disulfide bond nearer to the putative receptor binding region on Finger 2. Also a link between positions 65 and 133 is possible, however, this would be located near to the knot region of each chain and, thus may have little effect on stabilizing the putative receptor binding regions at the tips of Finger 1 and Finger 2. Additionally, the proximity of such a linkage to the disulfide bonds in the knot region might interfere with the proper formation of those structures.

With regard to non-covalent interactions, it is contemplated that the structural stability of the hOP-1 dimer can be enhanced by increasing inter-chain hydrogen bonding.

The electrostatic potential (due to other charges in a protein) in the region of a charged residue affects the pK of that residue. Because the pK's of both histidine and the N-terminal primary amino group are near neutrality, it may be possible to modify their pKs through the placement of charges on the surface of the molecule. It is contemplated that the buried His at position His 84 in hOP-1 helps stabilize the structure of the dimer by participating in hydrogen bonds with backbone carboxyl groups of residues Ala 64 and Tyr 65 of the other chain. Accordingly, it is contemplated that the introduction of surface charges may enhance this effect and thereby further stabilize the structure of the molecule. For example, mutating Tyr 65 or Val 132 to Asp may further polarize the carbonyl bonds of the amino acid residues at positions 64 and 65, as well as raise the pK of His 84. The pK of His 84 may further be affected by replacing residues Tyr 44, Ala 63, or Asn 110 by an Asp. It is contemplated that the preferred modification for this purpose is Tyr 65->Asp 65.

Using the same basic principles, the skilled artisan likewise can identify pairs of amino acids whose replacement can facilitate the introduction of an inter-chain salt bridge, internal hydrogen bond, or hydrophobic interaction. Such determinations are within the scope of an artisan having an ordinary level of skill in the field of molecular modeling.

Once a pair of target amino acids has been identified, the site-directed replacement of the target amino acids with the desirable replacements can be facilitated by the use of conventional site-directed mutagenesis procedures, for example, by cassette mutagenesis or oligonucleotide-directed mutagenesis. Such techniques are thoroughly documented in the art and so are not discussed herein. The effect of the site-specific replacements on the stability of resulting modified hOP-1 dimers or muteins can be measured, after production and purification, using standard methodologies well known in the art, for example, circular dicluoism, analytical centrifugation, differential scanning calorimetry, fluoresence or other spectroscopic techniques.

(ii) Enhancing Water,Solubility of hOP-1 Dimer

OP-1 has limited solubility in aqueous solvents. It is contemplated, however, that by using the hOP-1 atomic co-ordinates that the artisan can replace amino acids at the solvent accessible surface of the dimer thereby to increase the dielectric properties of dimeric hOP-1. For example, solvent accessible hydrophobic amino acid residues, such as, glycine, alanine, valine, leucine and isoleucine may be replaced by more polar residues, such as, lysine, arginine, histidine, aspartate, asparagine, glutamate and glutamine.

The solvent accessible amino acids can be identified using a computer program, such as ACCESS (version 2.1) using a 1.4 Å probe (Lee et al. (1972) supra). In FIGS. 7A–7C amino acid residues having at least 20% of their side chain areas exposed to solvent are boxed. When modifying surface residues it is important not to produce new epitopes that can be recognized as non-host especially, if the hOP-1 analogs are to be used as injectable molecules. It is believed that, amino acid side chains seen by a 10 Å spherical probe likely are part of surface epitopes. One skilled in the art can use ACCESS with a 10 Å spherical probe to identify potential epitopes, however this process can be carried out manually using a graphics package, such as, INSIGHT II. In FIG. 8, residue side chains so identified as potential epitopes are highlighted. Residue positions that are candidates for modification so as to improve the solubility of the dimer are highlighted. Preferred candidate amino acids for replacement include, for example, Ala 63, Ala 72, Ala 81, Ala 111 and Ala 135, Ile 86, Ile 112, Tyr 52, Tyr 65, and Tyr 128.

Once solvent accessible hydrophobic or non polar amino acids have been identified (see FIG. 9), these amino acids theoretically may be replaced, via a computer, with more polar amino acids. The effect of the amino acid replacements on the solution electrostatic potentials surrounding the modified hOP-1 dimer as well as the free energy of the dimer can calculated using the program DELPHI (Gilson et al (1987) supra; Nicholls et al. (1991) supra). Preferred amino acid substitutions lower the free energy of the hOP-1 dimer without introducing potential antigenic sites. As mentioned above, such antigenic sites may be detected by implementing a computer program like ACCESS (version 2.1) using a 10 Å probe. In addition, it is contemplated that preferred surface residues suitable for replacement do not constitute part of the receptor binding domain.

The resulting candidate morphogen analogs can be produced using conventional site-directed mutagenesis methodologies and the effect of the site-directed modification on the solubility of the hOP-1 dimer can be measured, for example, by comparing the partition coefficient or "salting out properties" of the modified hOP-1 dimer versus the native hOP-1 dimer. See for example, Scopes (1987) in *Protein Purification: Principles and Practice*, 2nd Edition (Springer-Verlag); and Englard et al. (1990) *Methods in Enzymology* 182: 285–300.

(iii) Engineering Glycosylation Sites

In addition to replacing single, solvent accessible amino acid residues with more polar or hydrophobic amino acid residue, one or more solvent accessible amino acid residues may be replaced so as to create a new eukaryotic glycosylation site or alternatively to eliminate or alter an existing glycosylation site. Glycosylation sites are well known and are thoroughly described in the art. Addition of a new glycosylation site or alteration of an existing site may result in the addition of one or more glycosyl groups, e.g., N-acetyl-sialic acid, which may enhance the solubility of the morphogen analog. As described herein, such sites can be introduced by site-directed mutagenesis methodologies which are well known in the art. Preferably, such sites do not create new antigenic determinants (although these may be tolerable for short duration therapeutic uses). Reference to Table 8 identifies surface accessible amino acid residues, based on the 2.8 Å structure, which likely are not part of an antigenic epitope and which may be used as candidates for introducing an additional glycosylation site.

B. Engineering Small Molecules Based Upon The hOP-1 Structure

The availability of atomic co-ordinates for hOP-1 enables the skilled artisan to design small molecules, for example, peptides or non-peptidyl based organic molecules having certain chemical features, which mimic the biological activity of hOP-1. Chemical features of interest may include, for example, the three-dimensional structure of a particular protein domain, solvent accessible surface of a particular protein domain, spatial distribution of charged and/or hydrophobic chemical moieties, electrostatic charge distribution, or a combination thereof. Such chemical features may readily be determined from the three-dimensional representation of hOP-1.

(i) Peptides

After having determined which amino acid residues contribute to the receptor binding domain (supra), it is possible for the skilled artisan to design synthetic peptides having amino acid sequences that define a pre-selected receptor binding motif. A computer program useful in designing potentially bioactive peptido-mimetics is described in U.S. Pat. No. 5,331,573, the disclosure of which is incorporated by reference herein.

In addition to choosing a desirable amino acid sequence, the skilled artisan using standard molecular modeling software packages, infra, can design specific peptides having, for example, additional cysteine amino acids located at pre-selected positions to facilitate cyclization of the peptide of interest. Oxidation of the additional cysteine residues results in cyclization of the peptide thereby constraining the peptide in a conformation which mimics the conformation of the corresponding amino acid sequence in native hOP-1. It is contemplated, that any standard covalent linkage, for example, disulfide bonds, typically used to cyclize synthetic peptides maybe useful in the practice of the instant invention. Alternative cyclization chemistries are discussed in International Application PCT/WO 95/01800, the disclosure of which is incorporated herein by reference.

In addition, it is contemplated that a single peptide containing amino acid sequences derived from separate hOP-1 subunit domains, for example, a single peptide having an amino acid sequence defining the tip of the finger 1 region linked by means of a polypeptide linker to an amino acid sequence defining the tip of the finger 2 region. The amino sequence defining each of the finger regions may further comprise a means, for example, disulfide bonds for cyclizing each finger region motif. The resulting peptide therefore comprises a single polypeptide chain having a first amino acid sequence defining a three-dimensional domain mimicking the tip of the finger 1 region and a second said sequence defining a three-dimensional domain mimicking the tip of the finger 2 region.

Such peptides may be synthesized and screened for OP-1 like activity using any of the standard protocols described below.

(ii) Organic molecules

As discussed above, upon determination of the receptor binding domain of hOP-1, it is contemplated that the skilled artisan, can design non-peptidyl based small molecules, for example, small organic molecules, whose structural and chemical features mimic the same features displayed on at least part of the surface of the receptor binding domain of hOP-1.

Because a major contribution to the receptor binding surface is the spatial arrangement of chemically interactive moieties present within the sidechains of amino acids which together define the receptor binding surface, a preferred embodiment of the present invention relates to designing and producing a synthetic organic molecule having a framework that carries chemically interactive moieties in a spatial relationship that mimics the spatial relationship of the chemical moieties disposed on the amino acid sidechains which constitute the receptor binding site of hOP-1. Preferred chemical moieties, include but are not limited to, the chemical moieties defined by the amino acid side chains of amino acids believed to constitute the receptor binding domain of hOP-1 (See FIG. 9). It is understood, therefore, that the receptor binding surface of the morphogen analog need not comprise amino acid residues but the chemical moieties disposed thereon.

For example, upon identification of relevant chemical groups, the skilled artisan using a conventional computer program can design a small molecule having the receptor interactive chemical moieties disposed upon a suitable carrier framework. Useful computer programs are described in, for example, Dixon (1992) *Tibtech* 10: 357–363; Tschinke et al. (1993) *J. Med. Chem* 36: 3863–3870; and Eisen el al. (1994) *Proteins: Structure, Function, and Genetics* 19: 199–221, the disclosures of which are incorporated herein by reference.

One particular computer program entitled "CAVEAT" searches a database, for example, the Cambridge Structural Database, for structures which have desired spatial orientations of chemical moieties (Bartlett et al. (1989) in "*Molecular Recognition: Chemical and Biological Problems*" (Roberts, S. M., ed) pp 182–196). The CAVEAT program has been used to design analogs of tendamistat, a 74 residue inhibitor of α-amylase, based on the orientation of selected amino acid side chains in the three-dimensional structure of tendamistat (Bartlett et al. (1989) supra).

Alternatively, upon identification of a series of analogs which mimic the biological activity of OP-1, as determined by in vivo or in vitro assays, the skilled artisan may use a variety of computer programs which assist the skilled artisan to develop quantitative structure activity relationships (QSAR) and further to assist in the de novo design of additional morphogen analogs. Other useful computer programs are described in, for example, Connolly-Martin (1991) *Methods in Enzymology* 203:587–613; Dixon (1992) supra; and Waszkowycz et al. (1994) *J. Med. Chenm.* 37: 3994–4002.

Thus, for example, one can begin with a portion of the three dimensional structure of OP-1 (or a related morphogen) corresponding to a region of known or suspected biological importance. One such region is the solvent accessible loop or "tip" of the finger 2 region between the β6 and β7 sheets (i.e., from approximately residues 118–122). Synthetic, cyclic peptides (i.e., F2-2 and F2-3) were produced including this region (and several flanking residues) and were shown to possess OP-1-like biological activity (see Examples below). Based upon the three-dimensional structure of this region, disclosed herein, one is now enabled to produce more effective OP-1-like (or, generally, morphogen-like) analogs. For example, as shown in great detail in FIGS. 7–9 and FIGS. 15.1–15.37, the charged y-carboxy groups of Asp 118 and Asp 119, and the relatively hydrophilic hydroxyl groups of Ser 120 and Ser 121, are solvent accessible and believed to be involved in OP-1 receptor binding. The relative positions of these groups in three dimensions in OP-1 are given in FIGS. 15.1–15.37 and FIGS. 16\1–16\39. These functional groups define a contiguous portion of the three dimensional structure of the OP-1 surface. The peptide backbone of these residues, however, is not solvent accessible and, therefore, is not believed to form a portion of the three-dimensional surface of the OP-1 molecule. Thus, one of ordinary skill in the art, when choosing or designing an OP-1 or morphogen analog, can choose or design a molecule having the same or substantially equivalent (e.g., thiol v. hydroxyl) functional groups in substantially the same (e.g., ±1–3 Å) three-dimensional conformation. The same is true for other regions of interest in the OP-1 monomers or dimers (e.g., the receptor binding domain, the finger 1, finger 2, or heel regions, or solvent accessible portions thereof). By using the three-dimensional structures disclosed herein, including the disclosure of the positions of solvent accessible and probable receptor contact residues, one of ordinary skill in the art can choose a portion of the three-dimensional structure of the OP-1 (or a related morphogen) molecule and, using this "portion" as a template select or design an analog which functionally mimics the template structure.

The molecular framework or backbone of the morphogen analog can be freely chosen by one of ordinary skill in the art so that it (1) joins the functional groups which mimic the portion of the morphogen's contiguous three-dimensional surface, including charge distribution and hydrophobicity/hydrophilicity characteristics, and (2) maintains or, at least, allows the functional groups to maintain the appropriate three-dimensional surface interaction and spatial relationships, including any hydrogen bonding and electrostatic interactions. As described above, peptides are obvious choices for the production of such morphogen analogs because they can provide all of the necessary functional groups and can assume appropriate three-dimensional structures. Several examples of peptide analogs of the finger regions are described herein, below. The peptides are cyclized to maintain hydrogen bonds and create a structure which mimics that of the template. These peptides are synthesized from a linear primary sequence of amino acids in finger 2. An alternative peptide can be created, for example, which combines portions of finger 1 and finger 2, constructed to mimic the structure of the tips of fingers 1 and 2 together as they occur in the folded OP 1 monomer. Biologically active peptides such as F2, F3 or others, then can be used as is or, more preferably, become lead compounds for iterative modification to create a compound that is more stable or more active in vivo. For example, the peptide backbone can be reduced or replaced to reduce hydrolysis in vivo. Alternatively, structural modifications can be introduced to the backbone or by amino acid substitutions which more accurately mimic the protein's structure when bound to the receptor. These second generation structures then can be tested for enhanced binding. In addition, iterative amino acid replacements with alanines, ("alanine scan") can be used to determine the minimum residue contacts required for binding.

Once these minimum functional groups are known, a fully synthetic molecule can be created which mimics the charge or electrostatic distribution of the minimum required functional groups, and provides the appropriate bulk and structure to functionally mimic a second generation molecule having the desired binding affinity.

VI. Production of Morphogen Analogs.

As mentioned above, the morphogen analogs of the invention may comprise modified hOP-1 dimeric proteins or small molecules, for example, peptides or small organic molecules. It is contemplated that any appropriate methods can be used for producing a pre-selected morphogen analog. For example, such methods may include, but are not limited to, methods of biological production from suitable host cells or synthetic production using synthetic organic chemistries.

For example, modified hOP-1 dimeric proteins or hOP-based peptides may be produced using conventional recombinant DNA technologies, well known and thoroughly documented in the art. Under these circumstances, the proteins or peptides may be produced by the preparation of nucleic acid sequences encoding the respective protein or peptide sequences, after which, the resulting nucleic acid can be expressed in an appropriate host cell. By way of example, the proteins and peptides may be manufactured by the assembly of synthetic nucleotide sequences and/or joining DNA restriction fragments to produce a synthetic DNA molecule. The DNA molecules then are ligated into an expression vehicle, for example an expression plasmid, and transfected into an appropriate host cell, for example $E.$ $coli$. The protein encoded by the DNA molecule then is expressed, purified, folded if necessary, tested in vitro for binding activity with an OP-1 receptor, and subsequently tested to assess whether the morphogen analog induces or stimulates hOP-1-like biological activity.

The processes for manipulating, amplifying, and recombining DNA which encode amino acid sequences of interest generally are well known in the art, and therefore, are not described in detail herein. Methods of identifying and isolating genes encoding hOP-1 and its cognate receptors also are well understood, and are described in the patent and other literature.

Briefly, the construction of DNAs encoding the biosynthetic constructs disclosed herein is performed using known techniques involving the use of various restriction enzymes which make sequence specific cuts in DNA to produce blunt ends or cohesive ends, DNA ligases, techniques enabling enzymatic addition of sticky ends to blunt-ended DNA, construction of synthetic DNAs by assembly of short or medium length oligonucleotides, cDNA synthesis techniques, polymerase chain reaction (PCR) techniques for amplifying appropriate nucleic acid sequences from libraries, and synthetic probes for isolating OP-1 genes or genes encoding other members of the TGF-β superfamily as well as their cognate receptors. Various promoter sequences from bacteria, mammals, or insects to name a few, and other regulatory DNA sequences used in achieving expression, and various types of host cells are also known and available. Conventional transfection techniques, and equally conventional techniques for cloning and subcloning DNA are useful in the practice of this invention and known to those skilled in the art. Various types of vectors may be used such as plasmids and viruses including animal viruses and bacteriophages. The vectors may exploit various marker genes which impart to a successfully transfected cell a detectable phenotypic property that can be used to identify which of a family of clones has successfully incorporated the recombinant DNA of the vector.

One method for obtaining DNA encoding the biosynthetic constructs disclosed herein is by assembly of synthetic oligonucleotides produced in a conventional, automated, oligonucleotide synthesizer followed by ligation with appropriate ligases. For example, overlapping, complementary DNA fragments may be synthesized using phosphoramidite chemistry, with end segments left unphosphorylated to prevent polymerization during ligation. One end of the synthetic DNA is left with a "sticky end" corresponding to the site of action of a particular restriction endonuclease, and the other end is left with an end corresponding to the site of action of another restriction endonuclease. The complementary DNA fragments are ligated together to produce a synthetic DNA construct.

After the appropriate DNA molecule has been synthesized, it may be integrated into an expression vector and transfected into an appropriate host cell for protein expression. Useful prokaryotic host cells include, but are not limited to, *E. coli*, and *B. subtilis*. Useful eukaryotic host cells include, but are not limited to, yeast cells, insect cells, myeloma cells, fibroblast 3T3 cells, monkey kidney or COS cells, chinese hamster ovary (CHO) cells, mink-lung epithelial cells, human foreskin fibroblast cells, human glioblastoma cells, and teratocarcinoma cells. Alternatively, the genes may be expressed in a cell-free system such as the rabbit reticulocyte lysate system.

The vector additionally may include various sequences to promote correct expression of the recombinant protein, including transcriptional promoter and termination sequences, enhancer sequences, preferred ribosome binding site sequences, preferred mRNA leader sequences, preferred protein processing sequences, preferred signal sequences for protein secretion, and the like. The DNA sequence encoding the gene of interest also may be manipulated to remove potentially inhibiting sequences or to minimize unwanted secondary structure formation. The morphogenic protein analogs proteins also may be expressed as fusion proteins. After being translated, the protein may be purified from the cells themselves or recovered from the culture medium and then cleaved at a specific protease site if so desired.

For example, if the gene is to be expressed in *E. coli*, it is cloned into an appropriate expression vector. This can be accomplished by positioning the engineered gene downstream of a promoter sequence such as Trp or Tac, and/or a gene coding for a leader peptide such as fragment B of protein A (FB). During expression, the resulting fusion proteins accumulate in refractile bodies in the cytoplasm of the cells, and may be harvested after disruption of the cells by French press or sonication. The isolated refractile bodies then are solubilized, and the expressed proteins folded and the leader sequence cleaved, if necessary, by methods already established with many other recombinant proteins.

Expression of the engineered genes in eukaryotic cells requires cells and cell lines that are easy to transfect, are capable of stably maintaining foreign DNA with an unrearranged sequence, and which have the necessary cellular components for efficient transcription, translation, post-translation modification, and secretion of the protein. In addition, a suitable vector carrying the gene of interest also is necessary. DNA vector design for transfection into mammalian cells should include appropriate sequences to promote expression of the gene of interest as described herein, including appropriate transcription initiation, termination, and enhancer sequences, as well as sequences that enhance translation efficiency, such as the Kozak consensus sequence. Preferred DNA vectors also include a marker gene and means for amplifying the copy number of the gene of interest. A detailed review of the state of the art of the production of foreign proteins in mammalian cells, including useful cells, protein expression-promoting sequences, marker genes, and gene amplification methods, is disclosed in Bendig (1988) *Genetic Engineering* 7:91–127.

The best characterized transcription promoters useful for expressing a foreign gene in a particular mammalian cell are the SV40 early promoter, the adenovirus promoter (AdMLP), the mouse metallothionein-I promoter (mMT-I), the *Rous sarcoma* virus (RSV) long terminal repeat (LTR), the mouse mammary tumor virus long terminal repeat (MMTV-LTR), and the human cytomegalovirus major intermediate-early promoter (hCMV). The DNA sequences for all of these promoters are known in the art and are available commercially.

The use of a selectable DHFR gene in a dhfr$^-$ cell line is a well characterized method useful in the amplification of genes in mammalian cell systems. Briefly, the DHFR gene is provided on the vector carrying the gene of interest, and addition of increasing concentrations of the cytotoxic drug methotrexate, which is metabolized by DHFR, leads to amplification of the DHFR gene copy number, as well as that of the associated gene of interest. DHFR as a selectable, amplifiable marker gene in transfected chinese hamster ovary cell lines (CHO cells) is particularly well characterized in the art. Other useful amplifiable marker genes include the adenosine deaminase (ADA) and glutamine synthetase (GS) genes.

The choice of cells/cell lines is also important and depends on the needs of the experimenter. COS cells provide high levels of transient gene expression, providing a useful means for rapidly screening the biosynthetic constructs of the invention. COS cells typically are transfected with a simian virus 40 (SV40) vector carrying the gene of interest. The transfected COS cells eventually die, thus preventing the long term production of the desired protein product but provide a useful technique for testing preliminary analogs for binding activity.

The various cells, cell lines and DNA sequences that can be used for mammalian cell expression of the single-chain constructs of the invention are well characterized in the art and are readily available. Other promoters, selectable markers, gene amplification methods and cells also may be used to express the proteins of this invention. Particular details of the transfection, expression, and purification of recombinant proteins are well documented in the art and are understood by those having ordinary skill in the art. Further details on the various technical aspects of each of the steps used in recombinant production of foreign genes in mammalian cell expression systems can be found in a number of texts and laboratory manuals in the art, such as, for example, Ausubel et al., ed., *Current Protocols in Molecular Biology*, John Wiley & Sons, New York, (1989).

Alternatively, morphogen analogs which are small peptides, usually up to 50 amino acids in length, may be synthesized using standard solid-phase peptide synthesis procedures, for example, procedures similar to those described in Merrifield (1963) *J. Am. Chem. Soc.*, 85:2149. For example, during synthesis, N-α-protected amino acids having protected side chains are added stepwise to a growing polypeptide chain linked by its C-terminal end to an insoluble polymeric support, e.g., polystyrene beads. The peptides are synthesized by linking an amino group of an N-α-deprotected amino acid to an α-carboxy group of an N-α-protected amino acid that has been activated by reacting it with a reagent such as dicyclohexylcarbodiimide. The attachment of a free amino group to the activated carboxyl leads to peptide bond formation. The most commonly used N-α-protecting groups include Boc which is acid labile and Fmoc which is base labile.

Briefly, the C-terminal N-α-protected amino acid is first attached to the polystyrene beads. Then, the N-α-protecting group is removed. The deprotected α-amino group is coupled to the activated a-carboxylate group of the next N-α-protected amino acid. The process is repeated until the desired peptide is synthesized. The resulting peptides are cleaved from the insoluble polymer support and the amino acid side chains deprotected. Longer peptides, for example greater than about 50 amino acids in length, typically are derived by condensation of protected peptide fragments. Details of appropriate chemistries, resins, protecting groups, protected amino acids and reagents are well known in the art and so are not discussed in detail herein. See for example, Atherton et al. (1963) *Solid Phase Peptide Synthesis: A Practical Approach* (IRL Press,), and Bodanszky (1993) *Peptide Chemistry, A Practical Textbook, 2nd Ed., Springer-Verlag, and Fields et al. (1990) Int. J. Peptide Protein Res.* 35:161–214, the disclosures of which are incorporated herein by reference.

Purification of the resulting peptide is accomplished using conventional procedures, such as preparative HPLC, e.g., gel permeation, partition and/or ion exchange chromatography. The choice of appropriate matrices and buffers are well known in the art and so are not described in detail herein.

With regard to the production of non-peptide small organic molecules which induce OP-1 like biological activities, these molecules can be synthesized using standard organic chemistries well known and thoroughly documented in the patent and other literatures.

VII. Screening For Binding and Biological Activity.

As a first step in determining whether a morphogen analog induces an OP-1 like biological activity, the skilled artisan can use a standard ligand-receptor assay to determine whether the morphogen analog binds preferentially to OP-1 receptor. For standard receptor-ligand assays, the artisan is referred to, for example, Legerski et al. (1992) *Biochem. Biophys. Res. Comm.* 183: 672–679; Frakar et al. (1 978) *Biochem. Biophys. Res. Comm.* 80:849–857; Chio et al. (1990) *Nature* 343: 266–269; Dahlman et al. (1988) *Biochem* 27: 1813–1817; Strader et al. (1989) *J. Biol. Chem.* 264: 13572–13578; and D'Dowd et al. (1988) *J. Biol. Chem.* 263: 15985–15992.

In a typical ligand/receptor binding assay useful in the practice of this invention, purified OP-1 having a known, quantifiable affinity for a pre-selected OP-1 receptor (see, for example, Ten Dijke et al. (1994) *Science* 264:101–103, the disclosure of which is incorporated herein by reference) is labeled with a detectable moiety, for example, a radiolabel, a chromogenic label, or a fluorogenic label. Aliquots of purified receptor, receptor binding domain fragments, or cells expressing the receptor of interest on their surface are incubated with labeled OP-1 in the presence of various concentrations of the unlabeled morphogen analog. The relative binding affinity of the morphogen analog may be measured by quantitating the ability of the candidate (unlabeled morphogen analog) to inhibit the binding of labeled OP-1 with the receptor. In performing the assay, fixed concentrations of the receptor and the OP-1 are incubated in the presence and absence of unlabeled morphogen analog. Sensitivity may be increased by pre-incubating the receptor with the candidate morphogen analog before adding labeled OP-1. After the labeled competitor has been added, sufficient time is allowed for adequate competitor binding, and then free and bound labeled OP-1 are separated from one another, and one or the other measured.

Labels useful in the practice of the screening procedures include radioactive labels (e.g., $^{125}I$, $^{131}I$, $^{111}In$ or $^{77}Br$), clromogenic labels, spectroscopic labels (such as those disclosed in Haughland (1994) *"Handbook of Fluorescent and Research Chemicals 5 ed."* by Molecular Probes, Inc., Eugene, Oreg.), or conjugated enzymes having high turnover rates, for example, horseradish peroxidase, alkaline phosphatase, or β-galactosidase, used in combination with chemiluminescent or fluorogenic substrates.

The biological activity, namely the agonist or antagonist properties of the resulting morphogen analogs subsequently may be characterized using any conventional in vivo and in vitro assays that have been developed to measure the biological activity of OP-1. A variety of specific assays believed to be useful in the practice of the invention are set forth in detail in Example 1, hereinbelow.

Furthermore, it is appreciated that many of the standard OP-1 assays may be automated thereby facilitating the screening of a large number of morphogen analogs at the same time. Such automation procedures are within the level of skill in the art of drug screening and, therefore, are not discussed herein.

Following the identification of useful morphogen analogs, the morphogenic analogs may be produced in commercially useful quantities (e.g., without limitation, gram and kilogram quantities), for example, by producing cell lines that express the morphogen analogs of interest or by producing synthetic peptides defining the appropriate amino acid sequence. It is appreciated, however, that conventional methodologies for producing the appropriate cell lines and for producing synthetic peptides are well known and thoroughly documented in the art, and so are not discussed in detail herein.

VIII. Formulation and Bioactivity.

Morphogen analogs, including OP-1 analogs, can be formulated for administration to a mammal, preferably a human in need thereof as part of a pharmaceutical composition. The composition can be administered by any suitable means, e.g., parenterally, orally or locally. Where the morphogen analog is to be administered locally, as by injection, to a desired tissue site, or systemically, such as by intravenous, subcutaneous, intramuscular, intraorbital, ophthalmic, intraventricular, intracranial, intracapsular, intraspinal, intracisternal, intraperitoneal, buccal, rectal, vaginal, intranasal or aerosol administration, the composition preferably comprises an aqueous solution. The solution preferably is physiologically acceptable, such that administration thereof to a mammal does not adversely affect the mammal's normal electrolyte and fluid volume balance. The aqueous solution thus can comprise, e.g., normal physiologic saline (0.9% NaCl, 0.1 5M), pH 7–7.4.

Useful solutions for oral or parenteral systemic administration can be prepared by any of the methods well known in the pharmaceutical arts, described, for example, in *"Remington's Pharmaceutical Sciences"* (Gennaro, A., ed., Mack Pub., 1990, the disclosure of which is incorporated herein by reference). Formulations can include, for example, polyalkylene glycols such as polyethylene glycol, oils of vegetable origin, hydrogenated naphthalenes, and the like. Formulations for direct administration, in particular, can include glycerol and other compositions of high viscosity. Biocompatible, preferably bioresorbable polymers, including, for example, hyaluronic acid, collagen, tricalcium phosphate, polybutyrate, polylactide, polyglycolide and lactide/glycolide copolymers, may be useful excipients to control the release of the morphogen analog in vivo.

Other potentially useful parenteral delivery systems for the present analogs can include ethylene-vinyl acetate copolymer particles, osmotic pumps, implantable infusion systems, and liposomes. Formulations for inhalation administration can contain as excipients, for example, lactose, or can be aqueous solutions containing, for example, polyoxyethylene-9-lauryl ether, glycocholate or deoxycholate, or oily solutions for administration in the form of nasal drops or as a gel to be applied intranasally.

Alternatively, the morphogen analogs, including OP-1 analogs, identified as described herein may be administered orally. For example, liquid formulations of morphogen analogs can be prepared according to standard practices such as those described in "*Remington's Pharmaceutical Sciences*" (supra). Such liquid formulations an then be added to a beverage or another food supplement for administration. Oral administration can also be achieved using aerosols of these liquid formulations. Alternatively, solid formulations prepared using art-recognized emulsifiers can be fabricated into tablets, capsules or lozenges suitable for oral administration.

Optionally, the analogs can be formulated in compositions comprising means for enhancing uptake of the analog by a desired tissue. For example, tetracycline and diphosphonates (bisphosphonates) are known to bind to bone mineral, particularly at zones of bone remodeling, when they are provided systemically in a mammal. Accordingly, such components can be used to enhance delivery of the present analogs to bone tissue. Alternatively, an antibody or portion thereof that binds specifically to an accessible substance specifically associated with the desired target tissue, such as a cell surface antigen, also can be used. If desired, such specific targeting molecules can be covalently bound to the present analog, e.g., by chemical crosslinking or by using standard genetic engineering techniques to create, for example, an acid labile bond such as an Asp-Pro linkage. Useful targeting molecules can be designed, for example, according to the teachings of U.S. Pat. No. 5,091,513.

It is contemplated also that some of the morphogen analogs may exhibit the highest levels of activity in vivo when combined with carrier matrices i.e., insoluble polymer matrices. See for example, U.S. Pat. No. 5,266,683 the disclosure of which is incorporated by reference herein. Currently preferred carrier matrices are xenogenic, allogenic or autogenic in nature. It is contemplated, however, that synthetic materials comprising polylactic acid, polyglycolic acid, polybutyric acid, derivatives and copolymers thereof may also be used to generate suitable carrier matrices. Preferred synthetic and naturally derived matrix materials, their preparation, methods for formulating them with the morphogen analogs of the invention, and methods of administration are well known in the art and so are not discussed in detailed herein. See for example, U.S. Pat. No. 5,266,683.

Still further, the present analogs can be administered to the mammal in need thereof either alone or in combination with another substance known to have a beneficial effect on tissue morphogenesis. Examples of such substances (herein, cofactors) include substances that promote tissue repair and regeneration and/or inhibit inflammation. Examples of useful cofactors for stimulating bone tissue growth in osteoporotic individuals, for example, include but are not limited to, vitamin $D_3$, calcitonin, prostaglandins, parathyroid hormone, dexamethasone, estrogen and IGF-I or IGF-II. Useful cofactors for nerve tissue repair and regeneration can include nerve growth factors. Other useful cofactors include symptom-alleviating cofactors, including antiseptics, antibiotics, antiviral and antifungal agents, analgesics and anesthetics.

Analogs preferably are formulated into pharmaceutical compositions by admixture with pharmaceutically acceptable, nontoxic excipients and carriers. As noted above, such compositions can be prepared for systemic, e.g., parenteral, administration, particularly in the form of liquid solutions or suspensions; for oral administration, particularly in the form of tablets or capsules; or intranasally, particularly in the form of powders, nasal drops or aerosols. Where adhesion to a tissue surface is desired, the composition can comprise a fibrinogen-thrombin dispersant or other bioadhesive such as is disclosed, for example, in PCT US91/09275, the disclosure of which is incorporated herein by reference. The composition then can be painted, sprayed or otherwise applied to the desired tissue surface.

The compositions can be formulated for parenteral or oral administration to humans or other mammals in therapeutically effective amounts, e.g., amounts which provide appropriate concentrations of the morphogen analog to target tissue for a time sufficient to induce the desired effect. Preferably, the present compositions alleviate or mitigate the mammal's need for a morphogen-associated biological response, such as maintenance of tissue-specific function or restoration of tissue-specific phenotype to senescent tissues (e.g., osteopenic bone tissue).

As will be appreciated by those skilled in the art, the concentration of the compounds described in a therapeutic composition will vary depending upon a number of factors, including the dosage of the drug to be administered, the chemical characteristics (e.g., hydrophobicity) of the compounds employed, and the route of administration. The preferred dosage of drug to be administered also is likely to depend on such variables as the type and extent of a disease, tissue loss or defect, the overall health status of the particular patient, the relative biological efficacy of the compound selected, the formulation of the compound, the presence and types of excipients in the formulation, and the route of administration. In general terms, the therapeutic molecules of this invention may be provided to an individual where typical doses range from about 10 ng/kg to about 1 g/kg of body weight per day; with a preferred dose range being from about 0.1 mg/kg to 100 mg/kg of body weight.

IX Examples

Practice of the invention will be more fully understood from the following examples, which are presented herein for illustrative purposes only, and should not be construed as limiting the invention in any way.

Example 1

Introduction of Inter-chain Disulfide Bonds to Stabilize the hOP-1 Dimer.

As discussed in section V.A.(i) it is contemplated that introduction of one or more additional inter-chain disulfide may stabilize further the hOP-1 dimer. The introduction of additional inter-chain disulfide bonds is described here.

A Sma I to Bam HI fragment of the human OP-1 cDNA as described in Ozkaynak et al. (1990) supra is cloned into Bluescript KS+ (available from Stratagene Cloning Systems, La Jolla, Calif.), previously cleaved with Eco RV and Baam HI. Upon transformation into *E. coli*, the resulting colonies are screened by a blue-white selection process wherein the desired colonies containing the OP-1 cDNA insert are blue. The correct clone may be identified by restriction screening to give the following expected restriction fragments.

| Restriction Enzyme | Fragment size (bp) |
| --- | --- |
| EcoR I | 84, 789, 3425 |
| Xho I | 161, 1223, 2914 |
| Sac II | 97, 650, 3551 |

In order to introduce two additional inter-chain disulfide bridges, a double cysteine mutant containing Asn 83 to Cys and Asn 130 to Cys replacements is produced. The cysteine mutant can be prepared by site-directed mutagenesis using synthetic oligonucleotides and either PCR or the site-directed mutagenesis methods, see for example, Kunkel el al. (1985) Proc. Natl. Acad. Sci. USA 822: 488; Kunkel et al. (1985) Meth. Enzymol. 154: 367 and U.S. Pat. No. 4,873, 192. Neither mutation causes a frameshift and, therefore, E. coli transformed with mutagenesis products that give white colonies indicate an error in the sequence. The presence of the appropriate mutation is verified by conventional dideoxy sequencing.

Then, linkers are introduced into the N- and C-termini of the mutant gene by oligonucleotide-directed mutagenesis using appropriate oligonucleotides. A preferred N terminal linker introduces a unique Not I site and a preferred C terminal linker introduces a non-suppressible stop codon TAA at the end of the mutein gene followed by a unique Bgl II site (AGATCT). Each of the resulting mutant genes are excised from the cloning vector by the restriction enzymes Nde I and Bgl II, isolated, and ligated independently into pET vector (New England Biolabs, Beverly, Mass.) previously cleaved with Nde I and Bam HI. The ligation products then are transformed into E. coli and transformants containing, and expressing each individual mutant protein are identified.

Expression of the double cysteine containing mutant analog is induced after the expression of T7 RNA polymerase (initiated through infected with λCE6 phage). During expression, the mutant analog is produced as inclusion granules which are harvested from the cell paste. Then, the mutant protein is dissolved in 6M guanidine-HCl, 0.2M Tris-HCl, pH 8.2 and 0.1 M 2-mercaptoethanol, and the mixture dialyzed exhaustively against 6M urea, 2.5 mM Tris-HCl, pH 7.5 and 1 mM EDTA. 2-mercaptoethanol is added to a final concentration of 0.1M and the solution incubated at room temperature. The mixture is dialyzed exhaustively against buffer containing 2.5 mM Tris-HCl, pH 7.5 and 1 mM EDTA. Folded mutant protein is purified by affinity chromatography on a column packed with surface immobilized OP-1 receptor. Unbound material is removed by washing as described above and the specific OP-1 receptor binding material eluted.

Following purification the stabilizing effect of the additional bond is determined by fluorescence polarization. For example, the rotational rates of morphogen analog (mutein) and natural hOP-1 are determined as a function of temperature using a fluorescence spectrophotometer modified for fluoresence anisotropy (Photon Technology International). It is anticipated that the mutein dimer will exhibit a lower rational rate upto a higher temperature than natural hOP-1 dimer, thereby indicating that the mutein dimer remains as a dimer and is more stable upto a higher temperature than is the wild type protein.

The biological activity of the resulting mutant protein or mutein can be tested using any of the bioassays developed to date for determining the biological activity of native hOP-1. A variety of such exemplary assays are described below. The assays which follow are recited for ease of testing. Specific in vivo assays for testing the efficacy of a morphogenic protein or analog in an application to repair or regenerate damaged bone, liver, kidney, or nerve tissue, periodontal tissue, including cementum and/or periodontal ligament, gastrointestinal and renal tissues, and immune-cell mediated damages tissues are disclosed in publicly available documents, which include, for example, EP 0575,555; WO93/04692; WO93/05751; WO/06399; WO94/03200; WO94/06449; and WO94/06420. The skilled artisan can test an analog in any of these assays without undue experimentation.

A. Mitogenic Effect on Rat and Human Osteoblasts

The following example is a typical assay useful in determining whether an OP-1 morphogen analog induces proliferation of osteoblasts in vitro. It is contemplated that in this, and all other examples using osteoblast cultures, preferably uses rat osteoblast-enriched primary cultures. Although these cultures are heterogeneous in that the individual cells are at different stages of differentiation, the culture is believed to more accurately reflect the metabolism and function of osteoblasts in vivo than osteoblast cultures obtained from established cell lines. Unless otherwise indicated, all chemicals referenced are standard, commercially available reagents, readily available from a number of sources, including Sigma Chemical, Co., St. Louis; Calbiochem, Corp., San Diego and Aldrich Chemical Co., Milwaukee.

Briefly, rat osteoblast-enriched primary cultures are prepared by sequential collagenase digestion of newborn rat calvaria (e.g., from 1–2 day-old animals, Long-Evans strain, Charles River Laboratories, Wilmington, Mass.), following standard procedures, such as are described, for example, in Wong et al. (1975) Proc. Natl. Acad. Sci. USA 72: 3167–3171. Rat osteoblast single cell suspensions then are plated onto a multi-well plate (e.g., a 24 well plate at a concentration of 50,000 osteoblasts per well) in alpha MEM (modified Eagle's medium, Gibco, Inc., N.Y.) containing 10% FBS (fetal bovine serum), L-glutamine and penicillin/streptomycin. The cells are incubated for 24 hours at 37° C., at which time the growth medium is replaced with alpha MEM containing 1% FBS and the cells incubated for an additional 24 hours so that cells are in serum-deprived growth medium at the time of the experiment.

The cultured cells are divided into four groups: (1) wells which receive, for example, 0.1, 1.0, 10.0, 40.0 and 80.0 ng of the OP-1 morphogen analog (mutein), (2) wells which receive 0.1, 1.0, 10.0 and 40.0 ng of wild type OP-1; (3) wells which receives 0. 1, 1.0, 10.0, and 40.0 ng of TGF-β, and (4) the control group, which receive no growth factors. The cells then are incubated for an additional 18 hours after which the wells are pulsed with 2 mCi/well of $^3$H-thymidine and incubated for six more hours. The excess label then is washed off with a cold solution of 0.15 M NaCl and then 250 ml of 10% tricholoracetic acid is added to each well and the wells incubated at room temperature for 30 minutes. The cells then are washed three times with cold distilled water, and lysed by the addition of 250 ml of 1% sodium dodecyl sulfate (SDS) for a period of 30 minutes at 37° C. The resulting cell lysates are harvested using standard means and the incorporation of $^3$H-thymidine into cellular DNA determined by liquid scintillation as an indication of mitogenic activity of the cells. In the experiment, it is contemplated that the OP-1 morphogen analog construct (mutein), like natural OP-1, will stimulate $^3$H-thymidine incorporation into DNA, and therefore promote osteoblast cell proliferation. In contrast, the effect of the TGF-β is expected to be transient and biphasic. Furthermore, it is contemplated that at higher concentrations, TGF-β will have no significant effect on osteoblast cell proliferation.

The in vitro effect of the OP-1 morphogen analog on osteoblast proliferation also may be evaluated using human primary osteoblasts (obtained from bone tissue of a normal adult patient and prepared as described above) and on human osteosarcoma-derived cell lines.

B. Progenilor Cell Stimulation.

The following example is designed to demonstrate the ability of OP-1 morphogen analogs to stimulate the proliferation of mesenchymal progenitor cells. Useful naive stem cells include pluripotent stem cells, which may be isolated from bone marrow or umbilical cord blood using conventional methodologies, (see, for example, Faradji et al. (1988) Vox Sang. 55 (3): 133–138 or Broxmeyer et al. (1989) *Proc. Natl. Acad. Sci. USA*. 86: 3828–3832), as well as naive stem cells obtained from blood. Alternatively, embryonic cells (e.g., from a cultured mesodermal cell line) may be used.

Another method for obtaining progenitor cells and for determining the ability of OP-1 morphogen analogs to stimulate cell proliferation is to capture progenitor cells from an in vivo source. For example, a biocompatible matrix material able to allow the influx of migratory progenitor cells may be implanted at an in vivo site long enough to allow the influx of migratory progenitor cells. For example, a bone-derived, guanidine-extracted matrix, formulated as disclosed for example in Sampath et al. (1983) *Proc. Natl. Acad. Sci. USA* 80: 6591–6595, or U.S. Pat. No. 4,975,526, may be implanted into a rat at a subcutaneous site, essentially following the method of Sampath et al. After three days the implant is removed, and the progenitor cells associated with the matrix dispersed and cultured.

Progenitor cells, however obtained, then are incubated in vitro with the candidate OP-1 morphogen analog under standard cell culture conditions, such as those described hereinbelow. In the absence of external stimuli, the progenitor cells do not, or only minimally, proliferate on their own in culture. However, progenitor cells cultured in the presence of a biologically active OP-1 morphogen analog, like OP-1, will proliferate. Cell growth can be determined visually or spectrophotometrically using standard methods well known in the art.

C. Morohogen-Induced Cell Differentiation.

A variety of assays also can be used to determine OP-1 based morphogen analog-induced cellular differentiation.

(1) Embryonic Mesenchyme Differentiation

As with natural OP-1, it is contemplated that the OP-1 morphogen analog (mutein) can induce cell differentiation. The ability of OP-1 morphogen analogs to induce cell differentiation can be demonstrated by culturing early mesenchymal cells in the presence of OP-1 morphogen analog and then studying the histology of the cultured cells by staining with toluidine blue using standard cell culturing and cell staining methodologies well described in the art. For example, it is known that rat mesenchymal cells destined to become mandibular bone, when separated from the overlying epithelial cells at stage 11 and cultured in vitro under standard tissue culture conditions, e.g., in a chemically defined, serum-free medium, containing for example, 67% DMEM (Dulbecco's modified Eagle's medium), 22% F-12 medium, 10 mM Hepes pH 7, 2 mM glutamine, 50 mg/ml transferrin, 25 mg/ml insulin, trace elements, 2 mg/ml bovine serum albumin coupled to oleic acid, with HAT (0.1 mM hypoxanthine, 10 mM aminopterin, 12 mM thymidine, will not continue to differentiate. However, if these same cells are left in contact with the overlying endoderm for an additional day, at which time they become stage 12 cells, they will continue to differentiate on their own in vitro to form chondrocytes. Further differentiation into osteoblasts and, ultimately, mandibular bone, requires an appropriate local environment, e.g., a vascularized environment.

It is anticipated that, as with natural OP-1, stage 11 mesenchymal cells, cultured in vitro in the presence of OP-1 morphogen analog (mutein), e.g., 10–100 ng/ml, will continue to differentiate in vitro to form chondrocytes just as they continue to differentiate in vitro if they are cultured with the cell products harvested from the overlying endodermal cells. This experiment can be performed with different mesenchymal cells to demonstrate the cell differentiation capability of OP-1 morphogen analog in different tissues.

As another example of morphogen-induced cell differentiation, the ability of OP-1 morphogen analogs to induce osteoblast differentiation can be demonstrated in vitro using primary osteoblast cultures, or osteoblast-like cells lines, and assaying for a variety of bone cell markers that are specific markers for the differentiated osteoblast phenotype, e.g., alkaline phosphatase activity, parathyroid hormone-mediated cyclic AMP (cAMP) production, osteocalcin synthesis, and enhanced mineralization rates.

(2) Induction of a Alkaline Phosphatase Activity in Osteoblasts.

Cultured osteoblasts in serum-free medium are incubated with a range of OP-1 morphogen analog concentrations, for example, 0.1, 1.0, 10.0, 40.0 or 80.0 ng OP-1 morphogen analog/ml medium; or with a similar concentration range of natural OP-1 or TGF-β. After a 72 hour incubation the cell layer is extracted with 0.5 ml of 1% Triton X-100. The resultant cell extract is centrifuged, and 100 ml of the extract is added to 90 ml of para-nitroso-phenylphosphate (PNPP)/ glycerine mixture and incubated for 30 minutes in a 37° C. water bath and the reaction stopped with 100 ml NaOH. The samples then are run through a plate reader (e.g., Dynatech MR700 plate reader, and absorbance measured at 400 nm, using p-nitrophenol as a standard) to determine the presence and amount of alkaline phosphate activity. Protein concentrations are determined by the BioRad method. Alkaline phosphatase activity is calculated in units/mg protein, where 1 unit=1 nmol p-nitrophenol liberated/30 minutes at 37° C.

It is contemplated that the OP-1 morphogen analog, like natural OP-1, will stimulate the production of alkaline phosphatase in osteoblasts thereby promoting the growth and expression of the osteoblast differentiated phenotype. The long term effect of OP-1 morphogen analog on the production of alkaline phosphatase by rat osteoblasts also can be demonstrated as follows.

Rat osteoblasts are prepared and cultured in multi-well plates as described above. In this example six sets of 24 well plates are plated with 50,000 rat osteoblasts per well. The wells in each plate, prepared as described above, then are divided into three groups: (1) those which receive, for example, 1 ng of OP-1 morphogen analog per ml of medium; (2) those which receive 40 ng of OP-1 morphogen analog per ml of medium; and (3) those which receive 80 ng of OP-1 morphogen analog per ml of medium. Each plate then is incubated for different lengths of time: 0 hours (control time), 24 hours, 48 hours, 96 hours, 120 hours and 144 hours. After each incubation period, the cell layer is extracted with 0.5 ml of 1% Triton X-100. The resultant cell extract is centrifuged, and alkaline phosphatase activity determined using para-nitroso-phenylphosphate (PNPP), as above. It is contemplated that the OP-1 morphogen analog, like natural OP-1, will stimulate the production of alkaline phosphatase in osteoblasts in a dose-dependent manner so that increasing doses of OP-1 morphogen analog will further increase the level of alkaline phosphatase production. Moreover, it is contemplated that the OP-1 morphogen analog-stimulated elevated levels of alkaline phosphatase in the treated osteoblasts will last for an extended period of time.

(3) Induction of PTH-Mediated cAMP.

This experiment is designed to test the effect of OP-1 morphogen analogs on parathyroid hormone-mediated cAMP production in rat osteoblasts in vitro. Briefly, rat osteoblasts are prepared and cultured in a multiwell plate as described above. The cultured cells then are divided into four groups: (I) wells which receive, for example, 1.0, 10.0 and 40.0 ng OP-1 morphogen analog/ml medium); (2) wells which receive for example, natural OP-1, at similar concentration ranges; (3) wells which receive for example, TGF-β, at similar concentration ranges; and (4) a control group which receives no growth factors. The plate then is incubated for another 72 hours. At the end of the 72 hours the cells are treated with medium containing 0.5% bovine serum albumin (BSA) and 1 mM 3-isobutyl-1-methylxanthine for 20 minutes followed by the addition into half of the wells of human recombinant parathyroid hormone (hPTH, Sigma, St. Louis) at a concentration of 200 ng/ml for 10 minutes. The cell layer then is extracted from each well with 0.5 ml of 1% Triton X-100. The cAMP levels then are determined using a radioimmunoassay kit (e.g., Amersham, Arlington Heights, Ill.). It is contemplated that OP-1 morphogen analog alone, like OP-1, will stimulate an increase in the PTH-mediated cAMP response, thereby promoting the growth and expression of the osteoblast differentiated phenotype.

(4) Induction of Osteocalcin Production.

Osteocalcin is a bone-specific protein synthesized by osteoblasts which plays an integral role in the rate of bone mineralization in vivo. Circulating levels of osteocalcin in serum are used as a marker for osteoblast activity and bone formation in vivo. Induction of osteocalcin synthesis in osteoblast-enriched cultures can be used to demonstrate OP-1 morphogen analog efficacy in vitro.

Rat osteoblasts are prepared and cultured in a multi-well plate as above. In this experiment the medium is supplemented with 10%FBS, and on day 2, cells are fed with fresh medium supplemented with fresh 10 mM β-glycerophosphate (Sigma, Inc.). Beginning on day 5 and twice weekly thereafter, cells are fed with a complete mineralization medium containing all of the above components plus fresh L(+)-ascorbate, at a final concentration of 50 mg/ml medium. OP-1 morphogen analog then is added to the wells directly, e.g., in 50% acetonitrile (or 50% ethanol) containing 0.1% trifluoroacetic acid (TFA), at no more than 5 ml morphogen analog/ml medium. Control wells receive solvent vehicle only. The cells then are re-fed and the conditioned medium sample diluted 1:1 in standard radioimmunoassay buffer containing standard protease inhibitors and stored at −20° C. until assayed for osteocalcin. Osteocalcin synthesis is measured by standard radioimmunoassay using a commercially available osteocalcin-specific antibody.

Mineralization is determined on long term cultures (13 day) using a modified von Kossa staining technique on fixed cell layers: cells are fixed in fresh 4% paraformaldehyde at 23° C. for 10 min, following rinsing cold 0.9% NaCl. Fixed cells then are stained for endogenous alkaline phosphatase at pH 9.5 for 10 min, using a commercially available kit (Sigma, Inc.). Purple stained cells then are dehydrated with methanol and air dried. After 30 min incubation in 3% $AgNO_3$ in the dark, $H_2O$-rinsed samples are exposed for 30 sec to 254 nm UV light to develop the black silver-stained phosphate nodules. Individual mineralized foci (at least 20 mm in size) are counted under a dissecting microscope and expressed as nodules/culture.

It is contemplated that the OP-1 morphogen analog, like natural OP-1, will stimulate osteocalcin synthesis in osteoblast cultures. Furthermore, it is contemplated that the increased osteocalcin synthesis in response to OP-1 morphogen analog will be in a dose dependent manner thereby showing a significant increase over the basal level after 13 days of incubation. Enhanced osteocalcin synthesis also can be confirmed by detecting the elevated osteocalcin mRNA message (20-fold increase) using a rat osteocalcin-specific probe. In addition, the increase in osteocalcin synthesis correlates with increased mineralization in long term osteoblast cultures as determined by the appearance of mineral nodules. It is contemplated also that OP-1 morphogen analog, like natural OP-1, will increase significantly the initial mineralization rate as compared to untreated cultures.

(5) Morphogen-Induced CAM Expression

Members of the BMP/OP family (see FIG. 6) induce CAM expression, particularly N-CAM expression, as part of their induction of morphogenesis (see copending U.S. Ser. No. 922,813). CAMs are morphoregulatory molecules identified in all tissues as an essential step in tissue development. N-CAMs, which comprise at least 3 isoforms (N-CAM-180, N-CAM-140 and N-CAM-120, where "180", "140"and "120"indicate the apparent molecular weights of the isoforms as measured by SDS polyacrylamide gel electrophoresis) are expressed at least transiently in developing tissues, and permanently in nerve tissue. Both the N-CAM- 180 and N-CAM- 140 isoforms are expressed in both developing and adult tissue. The N-CAM-120 isoform is found only in adult tissue. Another neural CAM is L1.

The ability of OP-1 based morphogen analogs to stimulate CAM expression may be demonstrated using the following protocol, using NG108-15 cells. NG108-15 is a transformed hybrid cell line (neuroblastoma x glioma, America Type Culture Collection (ATCC), Rockville, Md.), exhibiting a morphology characteristic of transformed embryonic neurons. As described in Example D, below, untreated NG108-15 cells exhibit a fibroblastic, or minimally differentiated, morphology and express only the 180 and 140 isoforms of N-CAM normally associated with a developing cell. Following treatment with members of the vg/dpp subgroup these cells exhibit a morphology characteristic of adult neurons and express enhanced levels of all three N-CAM isoforms.

In this example, NG108-15 cells are cultured for 4 days in the presence of increasing concentrations of either the OP-1 morphogen analog or natural OP-1 using standard culturing procedures, and standard Western blots are performed on whole cell extracts. N-CAM isoforms are detected with an antibody which crossreacts with all three isoforms, mAb H28.123, obtained from Sigma Chemical Co., St. Louis, the different isoforms being distinguishable by their different mobilities on an electrophoresis gel. Control NG108-15 cells (untreated) express both the 140 kDa and the 180 kDa isoforms, but not the 120 kDa, as determined by Western blot analyses using up to 100 mg of protein. It is contemplated that treatment of NG108-15 cells with OP-1 morphogen analog, like natural OP-1 may result in a dose-dependent increase in the expression of the 180 kDa and 140 kDa isoforms, as well as the induction of the 120 kDa isoform. In addition, it is contemplated that the OP-1 morphogen analog, like natural OP-1 -induced CAM expression may correlate with cell aggregation, as determined by histology.

(D) OP-1 Morphogen Analog-Induced Redifferentiation of Transformed Phenotype

It is contemplated that OP-1 morphogen analog, like natural OP-1, also induces redifferentiation of transformed cells to a morphology characteristic of untransformed cells. The examples provided below detail morphogen-induced redifferentiation of a transformed human cell line of neuronal origin (NG 108-15); as well as mouse neuroblastoma cells (N1E-1 15), and human embryo carcinoma cells, to a morphology characteristic of untransformed cells.

As described above, NG 108-15 is a transformed hybrid cell line produced by fusing neuroblastoma x glioma cells (obtained from ATCC, Rockville, Md.), and exhibiting a morphology characteristic of transformed embryonic neurons, e.g., having a fibroblastic morphology. Specifically, the cells have polygonal cell bodies, short, spike-like processes and make few contacts with neighboring cells. Incubation of NG108-15 cells, cultured in a chemically defined, serum-free medium, with 0.1 to 300 ng/ml of morphogen analog or natural OP-1 for four hours induces an orderly, dose-dependent change in cell morphology.

For example, NG108-15 cells are subcultured on poly-L-lysine coated 6 well plates. Each well contains 40–50,000 cells in 2.5 ml of chemically defined medium. On the third day, 2.5 ml of OP-1 morphogen analog or natural OP-1 in 60% ethanol containing 0.025% trifluoroacetic is added to each well. The media is changed daily with new aliquots of morphogen. It is contemplated that OP-1 morphogen analog, like OP-1, may induce a dose-dependent redifferentiation of the transformed cells, including a rounding of the soma, an increase in phase brightness, extension of the short neurite processes, and other significant changes in the cellular ultrastructure. After several days it is contemplated also that treated cells may begin to form epithelioid sheets that then become highly packed, multi-layered aggregates, as determined visually by microscopic examination.

Moreover, it is contemplated that the redifferentiation may occur without any associated changes in DNA synthesis, cell division, or cell viability, making it unlikely that the morphologic changes are secondary to cell differentiation or a toxic effect of the morphogen. In addition, it is contemplated that the morphogen analog-induced redifferentiation may not inhibit cell division, as determined by $^3$H-thymidine uptake, unlike other molecules such as butyrate, DMSO, retinoic acid or Forskolin, which have been shown to stimulate differentiation of transformed cells in analogous experiments. Thus, it is contemplated that the OP-1 morphogen analog, like natural OP-1, may maintain cell stability and viability after inducing redifferentiation.

The morphogen described herein would, therefore, provide useful therapeutic agents for the treatment of neoplasias and neoplastic lesions of the nervous system, particularly in the treatment of neuroblastomas, including retinoblastomas, and gliomas.

(E) Maintenance ofPhenotv.Ie.

OP-1 morphogen analogs, like natural OP-1, also may be used to maintain a cell's differentiated phenotype. This application is particularly useful for inducing the continued expression of phenotype in senescent or quiescent cells.

(1) In Vitro Modelfor Phenotypic Maintenance

The phenotypic maintenance capability of morphogens is determined readily. A number of differentiated cells become senescent or quiescent after multiple passages in vitro under standard tissue culture conditions well described in the art (e.g., *Culture of Animal Cells: A Manual of Basic Techniques*, C. R. Freshney, ed., Wiley, 1987). However, if these cells are cultivated in vitro in association with a morphogen such as OP-1, cells are stimulated to maintain expression of their phenotype tlrough multiple passages. For example, the alkaline phosphatase activity of cultured osteoblasts, such as cultured osteosarcoma cells and calvaria cells, is significantly reduced after multiple passages in vitro. However, if the cells are cultivated in the presence of OP-1, alkaline phosphatase activity is maintained over extended periods of time. Similarly, phenotypic expression of myocytes also is maintained in the presence of a morphogen. In the experiment, osteoblasts are cultured as described in Example A. The cells are divided into groups, incubated with varying concentrations of either OP-1 morphogen analog or natural OP-1 (e.g., 0–300 ng/ml) and passaged multiple times (e.g., 3–5 times) using standard methodology. Passaged cells then are tested for alkaline phosphatase activity, as described in Example C as an indication of differentiated cell metabolic function. It is contemplated that osteoblasts cultured in the absence of OP-1 morphogen analog may have reduced alkaline phosphatase activity, as compared to OP-1 morphogen analog, or natural OP-1-treated cells.

(2) In Vivo Model-for Phenoiylic Maintenance.

Phenotypic maintenance capability also may be demonstrated in vivo, using a standard rat model for osteoporosis. Long Evans female rats (Charles River Laboratories, Wilmington, Mass.) are sham-operated (control animals) or ovariectomized using standard surgical techniques to produce an osteoporotic condition resulting from decreased estrogen production. Following surgery, e.g., 200 days after ovariectomy, rats are systemically provided with phosphate buffered saline (PBS) or morphogen, (e.g., OP-1 morphogen analog, or natural OP-1, 1–100 mg) for 21 days (e.g., by daily tail vein injection.) The rats then are sacrificed and serum alkaline phosphatase levels, serum calcium levels, and serum osteocalcin levels are determined, using standard methodologies as described therein and above. It is contemplated that the OP-1 morphogen analog treated rats, like the OP-1 treated rats may exhibit elevated levels of osteocalcin and alkaline phosphatase activity. It is contemplated also that histomorphometric analysis on the tibial diaphyseal bone may show improved bone mass in OP-1 morphogen analog-treated animals as compared with untreated, ovariectomized rats.

F. Proliferation of Progenitor Cell Populations

Progenitor cells may be stimulated to proliferate in vivo or ex vivo. It is contemplated that cells may be stimulated in vivo by injecting or otherwise providing a sterile preparation containing the OP-1 morphogen analog into the individual. For example, the hematopoietic pluripotential stem cell population of an individual may be stimulated to proliferate by injecting or otherwise providing an appropriate concentration of OP-1 morphogen analog to the individual's bone marrow.

Progenitor cells may be stimulated ex vivo by contacting progenitor cells of the population to be enhanced with a morphogenically active OP-1 morpliogen analog under sterile conditions at a concentration and for a time sufficient to stimulate proliferation of the cells. Suitable concentrations and stimulation times may be determined empirically, essentially following the procedure described in Example A, above. It is contemplated that a OP-1 morphogen analog concentration of between about 0.1–100 ng/ml and a stimulation period of from about 10 minutes to about 72 hours, or, more generally, about 24 hours, typically should be sufficient to stimulate a cell population of about $10^4$ to $10^6$ cells. The stimulated cells then may be provided to the individual as, for example, by injecting the cells to an appropriate in vivo locus. Suitable biocompatible progenitor cells may be obtained by any of the methods known in the art or described hereinabove.

G. Regeneration of Damaged or Diseased Tissue

It is contemplated that OP-1 morphogen analogs may be used to repair diseased or damaged mammalian tissue. The tissue to be repaired preferably is assessed first, and excess necrotic or interfering scar tissue removed as needed, e.g., by ablation or by surgical, chemical, or other methods known in the medical arts.

OP-1 morphogen analog then may be provided directly to the tissue locus as part of a sterile, biocompatible composition, either by surgical implantation or injection. The morphogen analog also may be provided systemically, as by oral or parenteral administration. Alternatively, a sterile, biocompatible composition containing progenitor cells stimulated by a morphogenically active OP-1 morphogen analog may be provided to the tissue locus. The existing tissue at the locus, whether diseased or damaged, provides the appropriate matrix to allow the proliferation and tissue-specific differentiation of progenitor cells. In addition, a damaged or diseased tissue locus, particularly one that has been further assaulted by surgical means, provides a morphogenically permissive environment. Systemic provision of OP-1 morphogen analog may be sufficient for certain applications (e.g., in the treatment of osteoporosis and other disorders of the bone remodeling cycle).

In some circumstances, particularly where tissue damage is extensive, the tissue may not be capable of providing a sufficient matrix for cell influx and proliferation. In these instances, it may be necessary to provide progenitor cells stimulated by the OP-1 morphogen analog to the tissue locus in association with a suitable, biocompatible, formulated matrix, prepared by any of the means described below. The matrix preferably is in vivo biodegradable. The matrix also may be tissue-specific and/or may comprise porous particles having dimensions within the range of 70–850 $\mu$m, most preferably 150–420 Mm.

OP-1 morphogen analog also may be used to prevent or substantially inhibit immune/inflammatory response-mediated tissue damage and scar tissue formation following an injury. OP-1 morphogen analog may be provided to a newly injured tissue locus, to induce tissue morphogenesis at the locus, preventing the aggregation of migrating fibroblasts into non-differentiated connective tissue. Preferably the OP-1 morphogen analog may be provided as a sterile pharmaceutical preparation injected into the tissue locus within five hours of the injury. Where an immune/inflammatory response is unavoidably or deliberately induced, as part of, for example, a surgical or other aggressive clinical therapy, OP-1 morphogen analog preferably may be provided prophylactically to the patient prior to, or concomitant with, the therapy.

Described below is a protocol for demonstrating whether a OP-1 morphogen analog-induces tissue morphogenesis in bone.

(1) OP-1 Morphogen Analog-Induced Bone Morphogenesis.

A particularly useful mammalian tissue model system for demonstrating and evaluating the morphogenic activity of a morphogen analog is the endochondral bone tissue morphogenesis model known in the art and described, for example, in U.S. Pat. No. 4,968,590, incorporated herein by reference. The ability to induce endochondral bone formation includes the ability to induce proliferation and differentiation of progenitor cells into chondroblasts and osteoblasts, the ability to induce cartilage matrix formation, cartilage calcification, and bone remodeling, and the ability to induce formation of an appropriate vascular supply and hematopoietic bone marrow differentiation.

The local environment in which the morphogenic material is placed is important for tissue morphogenesis. As used herein, "local environment" is understood to include the tissue structural matrix and the environment surrounding the tissue. For example, in addition to needing an appropriate anchoring substratum for their proliferation, the cells stimulated by morphogens need signals to direct the tissue-specificity of their differentiation. These signals vary for the different tissues and may include cell surface markers. In addition, vascularization of new tissue requires a local environment which supports vascularization.

The following sets forth various procedures for evaluating the in vivo morphogenic utility of OP-1 morphogen analogs and OP-1 morphogen analog containing compositions. The compositions may be injected or surgically implanted in a mammal, following any of a number of procedures well known in the art. For example, surgical implant bioassays may be performed essentially following the procedure of Sampath et al. (1983) *Proc. Natl. Acad. Sci. USA* 80: 6591–6595 and U.S. Pat. No. 4,968,590.

Histological sectioning and staining is preferred to determine the extent of morphogenesis in vivo, particularly in tissue repair procedures. Excised implants are fixed in Bouins Solution, embedded in paraffin, and cut into 6–8 $\mu$m sections. Staining with toluidine blue or hemotoxylin/eosin demonstrates clearly the ultimate development of the new tissue. Twelve day implants are usually sufficient to determine whether the implants contain newly induced tissue.

Successful implants exhibit a controlled progression through the stages of induced tissue development allowing one to identify and follow the tissue-specific events that occur. For example, in endochondral bone formation the stages include: (1) leukocytes on day one; (2) mesenchymal cell migration and proliferation on days two and three; (3) chondrocyte appearance on days five and six; (4) cartilage matrix formation on day seven; (5) cartilage calcification on day eight; (6) vascular invasion, appearance of osteoblasts, and formation of new bone on days nine and ten; (7) appearance of osteoclastic cells, and the commencement of bone remodeling and dissolution of the implanted matrix on days twelve to eighteen; and (8) hematopoietic bone marrow differentiation in the resulting ossicles on day twenty-one.

In addition to histological evaluation, biological markers may be used as markers for tissue morphogenesis. Useful markers include tissue-specific enzymes whose activities may be assayed (e.g., spectrophotometrically) after homogenization of the implant. These assays may be useful for quantitation and for rapidly obtaining an estimate of tissue formation after the implants are removed from the animal. For example, alkaline phosphatase activity may be used as a marker for osteogenesis.

Incorporation of systemically provided OP-1 morphogen analog may be followed using labeled protein (e.g., radioactively labeled) and determining its localization in the new tissue, and/or by monitoring their disappearance from the circulatory system using a standard labeling protocol and pulse-chase procedure. OP-1 morphogen analog also may be provided with a tissue-specific molecular tag, whose uptake may be monitored and correlated with the concentration of OP-1 morphogen analog provided. As an example, ovary removal in female rats results in reduced bone alkaline phosphatase activity, and renders the rats predisposed to osteoporosis (as described in Example E). If the female rats now are provided with OP-1 morphogen analog, a reduction in the systemic concentration of calcium may be seen, which correlates with the presence of the provided OP-1 morphogen analog and which is anticipated to correspond with increased alkaline phosphatase activity.

Example 2

Enhancing the Solubility of a hOP-1 Dimer.

As described in section V.A.(ii), supra, it is contemplated that the solubility of the hOP-1 dimer can be enhanced by replacing hydrophobic amino acid residues located at the solvent accessible surface of hOP-1 dimer with more polar or hydrophilic amino acid residues. This example provides a description of such an approach.

A Sma I to Bam HI fragment of the human OP-1 cDNA as described in Ozkaynak et al. (1990) supra is cloned into a vector to produce a plasmid similar to the plasmid called pW24 in International Application PCT/US94/12063, the disclosure of which is incorporated herein by reference. The pW24 plasmid contains OP-1 cDNA under the transcriptional control of the CMV (cytomegalovirus) immediate early promoter. The selective marker on pW24 is the neomycin gene which provides resistance to the cytostatic drug G418. The pW24 plasmid also employs an SV40 origin of replication (ori). The early SV40 promoter is used to drive transcription of the neomycin marker gene.

Then, the alanine at position 63 is mutated to a serine by site-directed mutagenesis using, for example, synthetic oligonucleotides and either PCR or the site-directed mutagenesis methods. See, for example, Kunkel et al. (1985) *Proc. Natl. Acad. Sci. USA* 822: 488; Kunkel et al. (1985) *Meth. Enzymol.* 154: 367 and U.S. Pat. No. 4,873,192. The resulting mutation is confirmed by dideoxy sequencing.

Two additional vectors have been developed for use in a triple transfection procedure along with pW24 to enhance OP-1 expression. One of the vectors employs the adenovirus E1A gene under the VA1 gene as translation stimulation for the gene DHFR gene. The other vector employs the adenovirus E1A gene under the control of the thymidine kinase promoter as a transactivating transcription activator. Both additional vectors, known as pH1130 and pH1176, as well as preferred transfection and screening procedures are described in International Application PCT/US94/12063.

Briefly, triple transfections are performed using the calcium phosphate coprecipitation procedure. CHO cells are cultured in ccMEM, containing 5% or 10% fetal bovine serum (FBS), non-essential amino acids, glutamine and antibiotics: penicillin and streptomycin. Stable cell line transfections are carried out by seeding $1-2 \times 10^6$ cells in a 9 cm. petri dish. Following an incubation period of up to 24-hour, each petri dish is transfected with 10–30 μg total vector DNA in equimolar amounts, by calcium phosphate coprecipitation followed by glycerol shock using standard methodology. Cells are incubated at 37° C. in growth medium for 24 hours, then transferred to selection medium. All cultures are fed once or twice weekly with fresh selective medium. After 10–21 days, resistant colonies are picked and assayed for protein production.

Approximately 30 individual clones are selected, transferred to a 24-well petri dish, and allowed to grow to confluence in serum-containing media. The conditioned media from all surviving clones is screened for protein production using a standard ELISA (enzyme-linked immunosorbent assay) or Western blot. The methodologies for these assay protocols as well as for generating antibodies for use in these assays are well described in the art (see e.g., Ausubel, supra).

Under such conditions, the VA1 and E1A genes typically act synergistically to enhance OP1 expression in unamplified transfected CHO cells. Candidate cell lines identified by the screening protocol, then are seeded on ten 100 mm petri dishes at a cell density of either 50 or 100 cells per plate, and with a higher drug concentration (e.g., 1.0-μ).

After 10–21 days of growth, the clones are isolated using cloning cylinders and standard procedures, and cultured in 24-well plates. Then, clones are screened for OP-1 expression by Western immunoblots using standard procedures, and OP-1 expression levels compared to parental lines. Candidate cells showing higher protein production than cells of parental lines then are replated and grown in the presence of a still higher drug concentration (e.g., 5–20 μm). Generally, no more than 2–3 rounds of these "amplification" cloning steps are necessary to achieve cell lines with high protein productivity. Useful high producing cell lines may be further subcloned to improve cell line homogeneity and product stability.

A currently preferred method of large scale protein production e.g., at least 2 liters, is by suspension culture of the host Chinese hamster ovary (CHO) cells. CHO cells prefer attaclhent but can be adapted to grow in suspension mode of cultivation. The cells are trypsinized from a culture dish, introduced to growth media containing 10% FBS and completely suspended to produce a single cell suspension. The single cell suspension is introduced to a spinner flask and placed in a 37° C. 95% air/5% $CO_2$ humidified incubator. Over a period of time the cells are subcultured in medium with descending concentrations of serum.

Specifically, the adapted cells are introduced into a 3L spinner flask at an initial viable cell density of approximately $2 \times 10^5$ cells/ml. Preferred culture medium is DMEM/F-12 (1:1) (GIBCO, New York) supplemented with 2% FBS, and preferred agitation is approximately 50–60 rpm with a paddle impeller. After 7 days, the culture media is harvested, centrifuged at 1500 rpm and the clarified conditioned media stored at 4° C.

A representative purification scheme for purifying recombinant morphogenic protein involves three chromatographic steps (S-Sepharose, phenyl-Sepharose and C-18 HPLC) and is described in International Application PCT/US94/12063. Morphogen analog containing culture media is diluted to 6M urea, 0.05M NaCl, 13 mM HEPES, pH 7.0 and loaded onto an S-Sepharose column, which acts as a strong cation exchanger. The column subsequently is developed with two salt elutions. The first elution employs a solution containing 0.1M NaCl, and the second elution employs a buffer containing 6M urea, 0.3M NaCl, 20 mM HEPES, pH 7.0.

Ammonium sulfate is added to the 0.3M NaCl fraction to give a solution containing 6M urea, 1M $(NH_4)_2SO_4$, 0.3M NaCl, 20 mM HEPES, pH 7.0. Then, the sample is loaded onto a phenyl-Sepharose column in the presence of 1M $(NH_4)_2SO_4$). Then, the column is developed with two step elutions using decreasing concentrations of ammonium sulfate. The first elution employs 0.6M $(NH_4)_2SO_4$ and the second elution employs 6M urea, 0.3M NaCl, 20 mM HEPES, pH 7.0 buffer. The material harvested from the second elution is dialyzed against water, followed by 30% acetonitrile (0.1% TFA), and then applied to a C-18 reverse phase HPLC column. Purified morphogen analog is harvested from the HPLC column.

The enhanced solubility of the resulting morphogen analog is measured by comparing the partition coefficient of the Ala 63->Ser 63 mutein versus wild type hOP-1 dimer. It is contemplated that the Ala 63->Ser 63 mutein has a higher solubility than native hOP-1. It is contemplated that, additional muteins having multiple hydrophobic to hydrophilic substitutions can be produced and characterized using the protocols described in this Example. The biological activity of the resulting morphogen analogs can be determined using one or more of the OP-1 activity assays described Example 1.

Example 3

Biological Activity of Finger 1. Finger 2. and Heel Peptides

The hOP-1-based peptides described in this example were produced and characterized prior to determination of the three-dimensional structure of hOP-1. These peptides either agonize or antagonize the biological activity of hOP-1. It is contemplated that, further refinements based upon the hOP-1 crystal structure, for example, the choice of more suitable sites for cyclizing peptides which constrain the peptide into a conformation that more closely mimics the shape of the corresponding region in hOP-1, may be used to further enhance the agonistic or antagonistic properties of such hOP-1-based peptides.

All of the peptides used in the following experiments, as well as their relationships with the mature hOP-1 amino acid sequence, are shown in FIG. 12. The finger 1-based peptides are designated F1-2; the heel-based peptides are designated H-1, H-n2 and H-c2; and the finger 2-based peptides are designated F2-2, and F2-3. Potential intra-peptide disulfide linkages are shown for each peptide. All the peptides were synthesized on a standard peptide synthesizer in accordance with the manufacturer's instructions. The peptides were deprotected, cyclized by oxidation, and then cleaved from resin prior to use.

In a first series of experiments, increasing concentrations of peptides F2-2 (FIG. 13A), F2-3 (FIG. 13B), Hn-2 (FIG. 13C) and Hc-2(FIG. 13D) were added to ROS cells either alone (open bars) or in combination with 40ng/ml soluble OP-1 (filled bars) and their effect on alkaline phosphatase activity measured. Soluble OP-1 is the form of OP-1 in which the pro-domain is still attached to the mature portion of OP-1 (see WO94/03600). A basal alkaline phosphatase activity is shown by the line and represents the alkaline phosphatase activity of cells incubated in the absence of both soluble OP-1 and peptide.

Figure 13A:
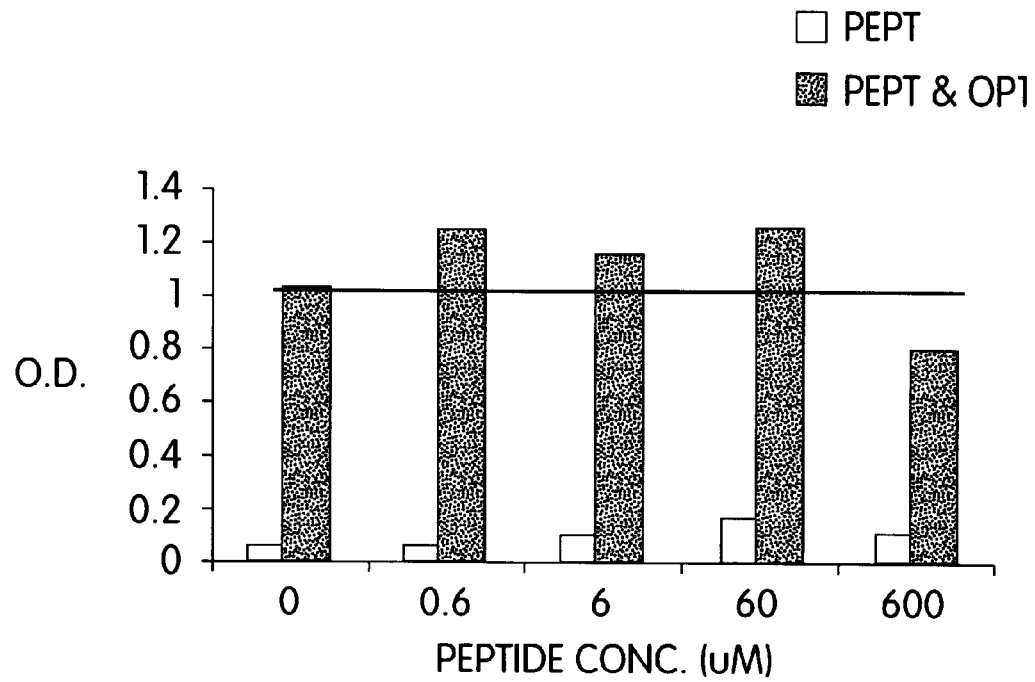
Figure 13B:
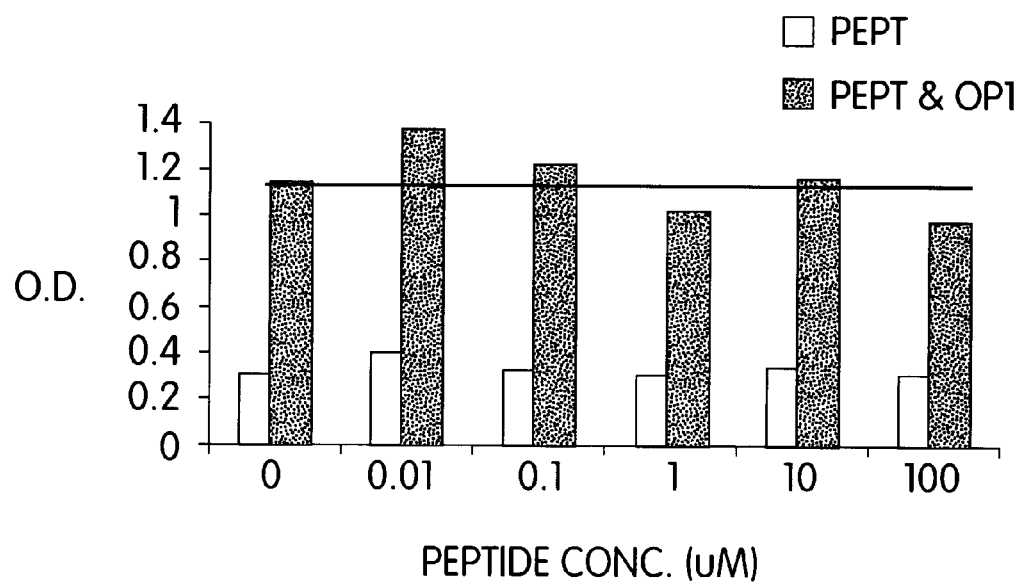

In FIG. 13A, peptide F2-2 at a concentration of about 60 $\mu$M appears to double the basal alkaline phosphatase level and, in the presence of soluble OP-1, increases alkaline phosphatase activity by about 20% relative to soluble OP-1 alone. In FIG. 13B, peptide F2-3 at a concentration of about 0.01 $\mu$M appears to increase the basal alkaline phosphatase level and, in the presence of soluble OP-1, increases alkaline phosphatase activity by about 20% relative to soluble OP-1 alone. Accordingly, both peptides F2-2 and F2-3, in the alkaline phosphatase assay, appear to act as weak OP-1 agonists.

Figure 13C:
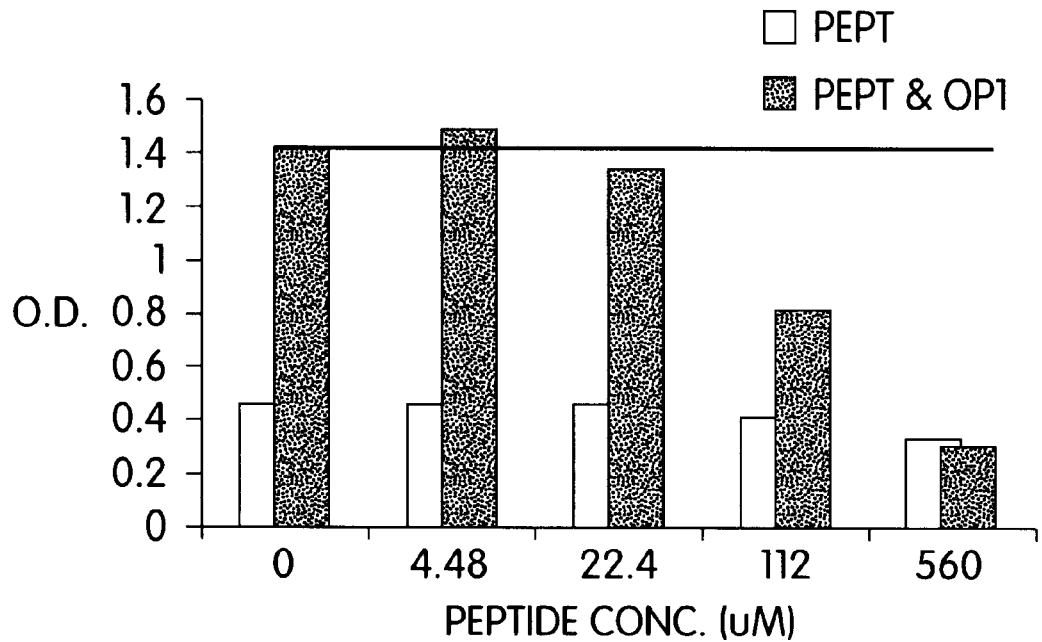
Figure 13D:
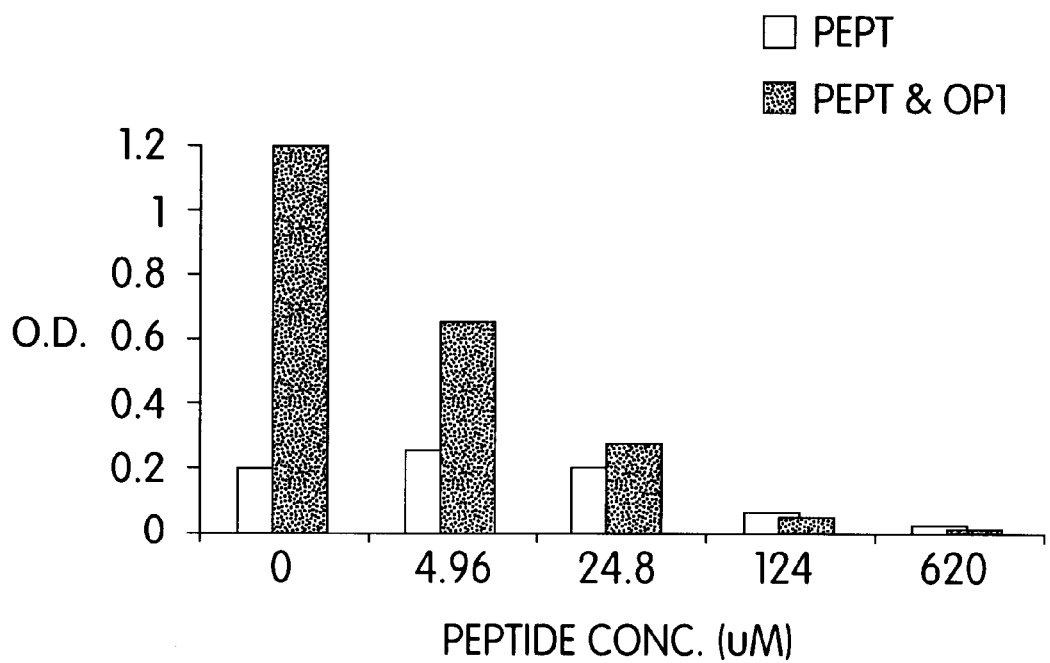

In FIG. 13C, peptide H-n2 displays little or no effect on alkaline phosphatase activity either alone or in combination with soluble OP-1. FIG. 13D, peptide H-c2, at concentrations greater than about 5 $\mu$M, appears to antagonize the activity of soluble OP-1.

In a second series of experiments, the ability of unlabeled soluble OP-1 and unlabeled peptides F1-2, F2-2, F2-3, H-n2 and H-c2 to displace $^{125}$I labeled soluble OP-1 from ROS cell membranes was measured. The activities of peptides F2-2 and F2-3 relative to soluble OP-1 are shown in FIG. 14A, and the activities of peptides F1-2, H-n2 and H-c2 relative to soluble OP-1 are shown in FIG. 14B. OP-1 receptor-enriched plasma membranes of ROS cells were incubated for 20 hrs at 4° C. with $^{125}$I-labeled soluble OP-1 and unlabeled peptide. Receptor bound material was separated from unbound material by centrifugation at 39,500×g. The resulting pellet was harvested and washed with 50 mM HEPES buffer, pH7.4 containing 5 mM MgCl$_2$ and 1 mM CaCl2 Radioactivity remaining in the pellet was determined by means of a gamma counter.

In FIG. 14A, peptide F2-2 (filled circles) soluble competes with soluble OP-1 with an Effective Dose$_{50}$ (ED$_{50}$) of about 1 $\mu$M, but cannot completely displace soluble OP-1 ED$_{50}$ is the concentration of peptide to produce half maximal displacement of labeled soluble OP-1. Peptide F2-3 (filled triangles) competes and is able to completely displace soluble OP-1 with an ED$_{50}$ of about 5 $\mu$M. In FIG. 14B, peptide F1-2 (filled boxes), peptide H-n2 (open diamonds) and peptide H-c2 (open circles) all appear to exhibit little or no ability to displace iodinated soluble OP-1 from ROS cell membranes.

Although the peptide experiments appear promising, it is contemplated that resolution of the hOP-1 structure will enable the skilled practitioner to design constrained peptides that more closely mimic the receptor binding domains of human OP-1 and which are more effective at agonizing or antagonizing an hOP-1 mediated biological effect.

Example 4

Elimination of a Binding Site on the Stirface of OP-1

α-2 macroglobulin, a protease scavenging protein known to bind proteins in serum and target them to the kidney for clearance from the body, binds OP-1. As described herein, α-2's interaction sites on the OP-1 protein have been mapped. Accordingly, using the database and structural information provided herein, one can design an analog of OP-1 which eliminates one or more α-2 macroglobulin interaction sites and provide an analog having enhanced bioavailability in the body. This same strategy can be applied for identifying and/or eliminating interaction sites for other binding proteins on the OP-1 surface.

A. Identifying α-2 macroglobulin Binding Sites

OP-1 was determined to interact specifically with α-2 macroglobulin in a standard competition binding assay, using immobilized, commercially available α-2 macroglobulin, and labeled and unlabeled OP-1 protein. Truncated mature OP-1, wherein the first 22 amino acids have been cleaved from the mature form of OP-1 in a standard trypsin digest, bound α-2 with 10-fold less affinity, indicating that the N terminal portion of the mature protein is involved in binding. This N-terminal portion of the protein, which is not part of the crystal structure, is positively charged and likely is highly flexible in solution. Elimination of this sequence does not interfere with OP-1 activity. Two cyclized peptides to all or a portion of the heel region, H-n2 and H1 (Cys$_{71}$-Pro$_{102}$, where Pro$_{102}$ has been changed to a cysteine to allow a disulfide bond between the two cysteines) also compete for binding; while peptides to the finger regions (F2-2, F2-3) do not compete.

α-2 macroglobulin was determined not to interfere with OP-1's ability to stimulate alkaline phosphatase activity in a ROS cell assay. Accordingly, α-2 macroglobulin binding does not appear to sterically inhibit OP-1 receptor binding.

B. Design of Modified OP-1 Analog

The precise α-2 macroglobulin interaction sites on OP-1 now can be mapped and an analog designed using the structure information provided herein. For example, the exact contact residues can be identified by creating model peptides like H-N2 and/or H1 in conjunction with an "alanine scan" mutagenesis program, wherein each residue is individually changed to an alanine in turn, and the constructs then tested for their ability to compete for binding. Once the contact residues are mapped, an analog can be designed which eliminates the contact residues without altering the overall structure of the heel region. Specifically, a template of the region can be called up on the computer from the database, and candidate replacement residues tested. The information in Table 8 identifies particularly useful candidate residues in the heel region which are solvent accessible, which likely are not available as epitopes and make good candidates for modification.

Equivalents

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes that come within the meaning and range of equivalency of the claims are intended to be embraced therein.

---

What is claimed is:

1. A computer system comprising:
   (a) a memory comprising atomic X-ray crystallographic coordinates defining at least a portion of human OP-1; and
   (b) a processor in electrical communication with the memory; wherein the processor generates a molecular model having a three dimensional shape representative of at least a portion of human OP-1.

2. The system of claim 1, wherein the processor further comprises a processor which generates the molecular model having a solvent accessible surface representative of at least a portion of human OP-1.

3. The system of claim 1, wherein said coordinates are stored on a computer readable diskette.

4. The system of claim 1, wherein the molecular model is representative of at least a portion of human OP-1 finger 1 region.

5. The system of claim 1 or 4, wherein the molecular model is representative of at least a portion of the human OP-1 heel region.

6. The system of claim 1 or 4, wherein the molecular model is representative of at least a portion of the human OP-1 finger 2 region.

7. The system of claim 6, wherein the molecular model is representative of at least a portion of the human OP-1 heel region.

8. The system of claim 1, wherein the processor further identifies a morplhogenic analog having a three-dimensional shape and a solvent accessible surface corresponding to at least a portion of the three-dimensional shape and the solvent accessible surface of human OP-1.

9. The system of claim 1, wherein the processor further identifies at least one candidate amino acid defined by the co-ordinates, which upon modification enhances water solubility or stability of human OP-1.

10. A method of producing a morphogenic analog having osteogenic protein-1 (OP-1) like biological activity, the method comprising the steps of:
    (a) providing a molecular model comprising X-ray crystallograhic coordinates defining a three dimensional shape representative of at least a portion of human OP-1;
    (b) identifying a candidate analog having a three dimensional shape corresponding to the three dimensional shape representative of at least a portion of human OP-1; and
    (c) producing the candidate analog identified in step (b).

11. The method of claim 10, further comprising the step of determining whether the compound produced in step (c) has an OP-1-like biological activity.

12. The method of claim 10, wherein the molecular model provided in step (a) is representative of at least a portion of a finger 1 region of human OP-1.

13. The method of claim 10 or 12, wherein the molecular model provided in step (a) is representative of at least a portion of a heel region of human OP-1.

14. The method of claim 10 or 12, wherein the model provided in step (a) is representative of at least a portion of a finger 2 region of human OP-1.

15. The method of claim 14, wherein the molecular model provided in step (a) is representative of at least a portion of a heel region of human OP-1.

16. The method of claim 10, wherein the analog comprises a plurality of charged moieties spaced about the solvent accessible surface thereof and disposed in a spaced-apart relation corresponding to charged moieties spaced about a portion of the solvent accessible surface of human OP-1.

17. The method of claim 10, wherein steps (a) and (b) are performed by means of an electronic processor.

18. The method of claim 17, wherein step (a) comprises storing a representation of at least a portion of the atomic co-ordinates of human OP-1 in a computer memory.

19. A method of producing a morphogen analog that modulates an osteogenic protein-1 (OP-1) mediated biological effect, the method comprising the steps of:
    (a) providing in a computer memory atomic X-ray crystallographic co-ordinates defining at least a portion of human OP-1;
    (b) generating with a processor a molecular model having a three-dimensional shape and a solvent accessible surface representative of at least a portion of human OP-1,
    (c) identifying a candidate morphogen analog having a three-dimensional structure shape and a solvent accessible surface corresponding to the three-dimensional shape and the solvent accessible surface of at least a portion of human OP-1;
    (d) producing the candidate morphogen analog identified in step (c); and
    (e) determining whether the candidate morphogen analog produced in step (d) modulates the OP-1 mediated biological effect.

20. The method of claim 11 or 19, further comprising the additional step of producing the compound in a commercially useful quantity.

21. The method of claim 11 or 19, wherein said compound is a peptide.

* * * * *

UNITED STATES PATENT AND TRADEMARK OFFICE
CERTIFICATE OF CORRECTION

PATENT NO. : 6,273,598 B1
DATED : August 14, 2001
INVENTOR(S) : Peter C. Keck et al.

It is certified that error appears in the above-identified patent and that said Letters Patent is hereby corrected as shown below:

<u>Title page,</u>
Item [73], Assignee, insert:
-- ; Brandeis University, Waltham, MA (US) --
after "Boston, MA (US)".

Signed and Sealed this

First Day of July, 2003

JAMES E. ROGAN
*Director of the United States Patent and Trademark Office*